(12) United States Patent
Buchanan et al.

(10) Patent No.: US 10,174,129 B2
(45) Date of Patent: *Jan. 8, 2019

(54) REGIOSELECTIVELY SUBSTITUTED CELLULOSE ESTERS PRODUCED IN A CARBOXYLATED IONIC LIQUID PROCESS AND PRODUCTS PRODUCED THEREFROM

(71) Applicant: EASTMAN CHEMICAL COMPANY, Kingsport, TN (US)

(72) Inventors: Charles Michael Buchanan, Bluff City, TN (US); Norma Lindsey Buchanan, Bluff City, TN (US); Robert Thomas Hembre, Johnson City, TN (US); Juanelle Little Lambert, Gray, TN (US); Michael Eugene Donelson, Kingsport, TN (US); Maryna Grigorievna Gorbunova, Kingsport, TN (US); Thauming Kuo, Kingsport, TN (US); Bin Wang, Kingport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,058

(22) Filed: Feb. 6, 2017

(65) Prior Publication Data

US 2017/0204201 A1  Jul. 20, 2017

Related U.S. Application Data

(63) Continuation-in-part of application No. 12/539,800, filed on Aug. 12, 2009, now Pat. No. 9,834,516, which is a continuation-in-part of application No. 12/030,387, filed on Feb. 13, 2008, now Pat. No. 8,148,518.

(60) Provisional application No. 60/901,615, filed on Feb. 14, 2007, provisional application No. 61/088,423, filed on Aug. 13, 2008.

(51) Int. Cl.
| | |
|---|---|
| C08B 3/16 | (2006.01) |
| C08L 1/14 | (2006.01) |
| G02B 1/14 | (2015.01) |
| C08J 5/18 | (2006.01) |
| C08B 1/00 | (2006.01) |
| C08B 3/28 | (2006.01) |
| C07D 233/54 | (2006.01) |
| G02B 5/30 | (2006.01) |
| G02B 1/10 | (2015.01) |

(52) U.S. Cl.
CPC ............. *C08B 3/16* (2013.01); *C07D 233/54* (2013.01); *C08B 1/003* (2013.01); *C08B 3/28* (2013.01); *C08J 5/18* (2013.01); *C08L 1/14* (2013.01); *G02B 1/14* (2015.01); *G02B 5/3083* (2013.01); *C08J 2301/10* (2013.01); *C08J 2301/12* (2013.01); *C08J 2301/14* (2013.01); *G02B 1/105* (2013.01)

(58) Field of Classification Search
CPC  C08B 3/16; C08L 1/14; G02B 5/3083; G02B 1/14; C08J 5/18
See application file for complete search history.

(56) References Cited

U.S. PATENT DOCUMENTS

| | | |
|---|---|---|
| 1,924,238 A | 8/1933 | Graenacher |
| 1,943,176 A | 1/1934 | Graenacher |
| 1,996,754 A | 4/1935 | Dreyfus et al. |
| 2,563,506 A | 8/1951 | Werntz |
| 3,505,313 A | 4/1970 | Ichiro |
| 4,028,132 A | 6/1977 | Litt et al. |
| 4,189,761 A | 2/1980 | Finkelstein et al. |
| 4,278,790 A | 7/1981 | McCormick et al. |
| 4,501,888 A | 2/1985 | Schmidt |
| 4,557,951 A | 12/1985 | Verbanac |
| 4,592,885 A | 6/1986 | Ichino et al. |
| 4,597,798 A | 7/1986 | Kamata et al. |
| 5,093,486 A | 3/1992 | Diamantoglou |
| 5,360,902 A | 11/1994 | Oke et al. |
| 5,610,233 A | 3/1997 | Sharma |
| 5,876,567 A | 3/1999 | Yamamoto et al. |
| 5,929,229 A | 7/1999 | Edgar et al. |
| 5,977,347 A | 11/1999 | Shuto et al. |
| 6,500,215 B1 | 12/2002 | Login et al. |

(Continued)

FOREIGN PATENT DOCUMENTS

| | | |
|---|---|---|
| CN | 1417407 A | 5/2003 |
| CN | 1491974 A | 4/2004 |

(Continued)

OTHER PUBLICATIONS

JPO English machine translation of JP 2007-332292 A, https://dossier1.jplatpat.inpit.go.jp, accessed online on Apr. 11, 2017. (Year: 2017).*

Ritter et al., Industrial & Engineering Chemistry Analytical Edition, 1929, 1(1), p. 52-54. (Year: 1929).*

Acemoglu, Murat, et al.; "Synthesis of regioselectively substituted cellulose derivatives and applications in chiral chromatography"; Chirality (1998), 10(4), 294-306.

Avalos, Martin et al.; "Grünere Medien für chemische Synthesen und Verfahren"; Angew. Chem. 2006, 118, 4008-1012 (Citation for English version is: Angewandte Chemie International Edition, 2006, 45(24), 3904-3908).

(Continued)

*Primary Examiner* — Jonathan S Lau
(74) *Attorney, Agent, or Firm* — Steven A. Owen; Polly C. Owen

(57) ABSTRACT

This invention relates to novel compositions comprising regioselectively substituted cellulose esters. One aspect of the invention relates to processes for preparing regioselectively substituted cellulose esters from cellulose dissolved in ionic liquids. Another aspect of the invention relates to the utility of regioselectively substituted cellulose esters in applications such as protective and compensation films for liquid crystalline displays.

17 Claims, 39 Drawing Sheets

(56) References Cited

U.S. PATENT DOCUMENTS

| | | |
|---|---|---|
| 6,596,130 B2 | 7/2003 | Westman |
| H2083 H | 10/2003 | Bogard et al. |
| 6,808,557 B2 | 10/2004 | Holbrey et al. |
| 6,824,599 B2 | 11/2004 | Swatloski et al. |
| 6,827,773 B2 | 12/2004 | Cuculo et al. |
| 6,872,766 B2 | 3/2005 | Schunk et al. |
| 6,939,974 B2 | 9/2005 | Earle et al. |
| 7,122,660 B1 | 10/2006 | Nakanishi et al. |
| 7,172,713 B2 | 2/2007 | Arai et al. |
| 7,208,605 B2 | 4/2007 | Davis, Jr. |
| 7,252,791 B2 | 8/2007 | Wasserscheid et al. |
| 7,351,339 B2 | 4/2008 | Maase et al. |
| 7,501,522 B2 | 3/2009 | Maase et al. |
| 7,550,520 B2 | 6/2009 | Daly et al. |
| 7,605,271 B2 | 10/2009 | Uchimura et al. |
| 7,754,002 B2 | 7/2010 | Maase |
| 7,879,994 B2 | 2/2011 | Buchanan et al. |
| 7,919,631 B2 | 4/2011 | Buchanan et al. |
| 8,148,518 B2 | 4/2012 | Buchanan et al. |
| 8,158,777 B2 | 4/2012 | Buchanan et al. |
| 8,188,267 B2 | 5/2012 | Buchanan et al. |
| 8,354,525 B2 | 1/2013 | Buchanan et al. |
| 2003/0036493 A1 | 2/2003 | Alam et al. |
| 2003/0094380 A1 | 5/2003 | Moulton |
| 2004/0035293 A1 | 2/2004 | Davis, Jr. |
| 2004/0059106 A1 | 3/2004 | Yamada et al. |
| 2004/0181009 A1 | 9/2004 | Shelton et al. |
| 2004/0233362 A1 | 11/2004 | Kashima |
| 2005/0020857 A1 | 1/2005 | Volland et al. |
| 2005/0133953 A1 | 6/2005 | Yamazaki et al. |
| 2005/0192434 A1 | 9/2005 | Buchanan et al. |
| 2005/0288484 A1 | 12/2005 | Holbrey et al. |
| 2006/0004192 A1 | 1/2006 | Oya et al. |
| 2006/0062749 A1 | 3/2006 | Shelton et al. |
| 2006/0094615 A1 | 5/2006 | Hecht et al. |
| 2006/0149074 A1 | 7/2006 | Maase et al. |
| 2006/0221280 A1 | 10/2006 | Oka et al. |
| 2006/0226396 A1 | 10/2006 | Majumdar et al. |
| 2006/0241287 A1 | 10/2006 | Hecht et al. |
| 2006/0268207 A1* | 11/2006 | Tan ..................... G02B 5/3083 349/117 |
| 2007/0006774 A1 | 1/2007 | Rogers et al. |
| 2007/0010688 A1 | 1/2007 | Ko et al. |
| 2007/0035682 A1 | 2/2007 | Ito et al. |
| 2007/0054216 A1 | 3/2007 | Habu |
| 2007/0073051 A1 | 3/2007 | Myllymaki et al. |
| 2007/0093462 A1 | 4/2007 | Rogers et al. |
| 2007/0093655 A1 | 4/2007 | Oya et al. |
| 2007/0112185 A1 | 5/2007 | Myllymaki et al. |
| 2007/0142642 A1 | 6/2007 | Szarvas et al. |
| 2007/0142646 A1 | 6/2007 | Maase et al. |
| 2007/0200987 A1 | 8/2007 | Yoda et al. |
| 2007/0215300 A1 | 9/2007 | Upfal et al. |
| 2007/0222927 A1 | 9/2007 | Uehara et al. |
| 2007/0225190 A1 | 9/2007 | Scheibel et al. |
| 2007/0225191 A1 | 9/2007 | Scheibel et al. |
| 2007/0255064 A1 | 11/2007 | Szarvas et al. |
| 2007/0259134 A1 | 11/2007 | Nozoe et al. |
| 2007/0285603 A1 | 12/2007 | Nakayama et al. |
| 2007/0290168 A1 | 12/2007 | Fukagawa et al. |
| 2008/0003444 A1 | 1/2008 | Oya |
| 2008/0023162 A1 | 1/2008 | Myllymaki et al. |
| 2008/0033187 A1 | 2/2008 | Zhao et al. |
| 2008/0164440 A1 | 7/2008 | Maase et al. |
| 2008/0188636 A1 | 8/2008 | Argyropoulos et al. |
| 2008/0190321 A1 | 8/2008 | Maase et al. |
| 2008/0192192 A1 | 8/2008 | Toyama et al. |
| 2008/0194807 A1 | 8/2008 | Buchanan et al. |
| 2008/0194808 A1 | 8/2008 | Buchanan et al. |
| 2008/0194834 A1 | 8/2008 | Buchanan et al. |
| 2008/0227162 A1 | 9/2008 | Varanasi et al. |
| 2008/0241536 A1 | 10/2008 | Luo et al. |
| 2008/0269477 A1 | 10/2008 | Stegmann et al. |
| 2008/0287684 A1 | 11/2008 | Exner et al. |
| 2009/0002605 A1 | 1/2009 | Imai et al. |
| 2009/0011473 A1 | 1/2009 | Varanasi et al. |
| 2009/0012297 A1 | 1/2009 | Pagoria et al. |
| 2009/0020112 A1 | 1/2009 | Massonne et al. |
| 2009/0021673 A1 | 1/2009 | Fukagawa et al. |
| 2009/0032015 A1 | 2/2009 | Myllymaki et al. |
| 2009/0033839 A1 | 2/2009 | Fukuda |
| 2009/0043088 A1 | 2/2009 | Shimamoto et al. |
| 2009/0050842 A1 | 2/2009 | Shelby et al. |
| 2009/0053429 A1 | 2/2009 | Sasada |
| 2009/0054638 A1 | 2/2009 | Shelby et al. |
| 2009/0062524 A1 | 3/2009 | Massonne et al. |
| 2009/0084509 A1 | 4/2009 | Luo et al. |
| 2009/0088564 A1 | 4/2009 | Luo et al. |
| 2009/0096962 A1 | 4/2009 | Shelton et al. |
| 2009/0097117 A1 | 4/2009 | Coleman |
| 2009/0111981 A1 | 4/2009 | Kuwabara et al. |
| 2009/0171079 A1 | 7/2009 | Higuchi |
| 2009/0181232 A1 | 7/2009 | Wang et al. |
| 2009/0182138 A1 | 7/2009 | Massonne et al. |
| 2009/0187016 A1 | 7/2009 | Massone et al. |
| 2009/0198046 A1 | 8/2009 | Fanselow et al. |
| 2009/0203899 A1 | 8/2009 | Buchanan et al. |
| 2009/0221813 A1 | 9/2009 | Moellmann et al. |
| 2009/0326216 A1 | 12/2009 | Stegmann et al. |
| 2010/0029927 A1 | 2/2010 | Buchanan et al. |
| 2010/0055356 A1 | 3/2010 | Takeda et al. |
| 2010/0267942 A1 | 10/2010 | Buchanan et al. |
| 2010/0305249 A1 | 12/2010 | Buchanan et al. |
| 2011/0021842 A1 | 1/2011 | Nishimoto et al. |
| 2011/0166340 A1 | 7/2011 | Shibata et al. |
| 2012/0003403 A1 | 1/2012 | Wang et al. |
| 2012/0238741 A1 | 9/2012 | Bucnanan et al. |
| 2012/0238742 A1 | 9/2012 | Buchanan et al. |
| 2012/0262650 A1 | 10/2012 | Buchanan et al. |
| 2012/0263889 A1 | 10/2012 | Buchanan et al. |
| 2012/0263890 A1 | 10/2012 | Buchanan et al. |
| 2014/0343271 A1 | 11/2014 | Buchanan et al. |

FOREIGN PATENT DOCUMENTS

| | | |
|---|---|---|
| CN | 1804161 | 7/2006 |
| CN | 1958616 A | 5/2007 |
| CN | 1978433 A | 6/2007 |
| CN | 101085838 | 12/2007 |
| CN | 101234197 | 8/2008 |
| CN | 101240085 A | 8/2008 |
| CN | 101284913 | 10/2008 |
| CN | 101285213 | 10/2008 |
| CN | 101289817 | 10/2008 |
| CN | 100471843 C | 2/2009 |
| DE | 10 2006 028 165 A1 | 12/2007 |
| DE | 10 2007 035 322 A1 | 1/2009 |
| DE | 22 62 829 A1 | 7/2017 |
| EP | 911656 A2 | 4/1999 |
| EP | 1 215 216 A1 | 6/2002 |
| EP | 1 860 201 A | 11/2007 |
| EP | 1 911 792 A1 | 4/2008 |
| EP | 1 911 829 A1 | 4/2008 |
| EP | 2 072 530 A1 | 6/2009 |
| FR | 2831171 A1 | 4/2003 |
| GB | 572 017 A | 9/1945 |
| GB | 581 046 A | 9/1946 |
| GB | 611 665 A | 11/1948 |
| GB | 689 194 A | 3/1953 |
| GB | 736 964 A | 9/1955 |
| GB | 1 519 648 A | 8/1978 |
| JP | 6-329603 | 11/1994 |
| JP | 2002-179701 | 6/2002 |
| JP | 2002-265501 | 9/2002 |
| JP | 2002-275132 A | 9/2002 |
| JP | 2004-175785 A | 6/2004 |
| JP | 2005-089689 | 4/2005 |
| JP | 2005-281645 | 10/2005 |
| JP | 2005-307055 | 11/2005 |
| JP | 2006-265544 | 5/2006 |
| JP | 2006-137677 | 6/2006 |
| JP | 2006-213778 | 8/2006 |
| JP | 2006-232959 | 9/2006 |
| JP | 2006328298 A | 12/2006 |

(56) References Cited

FOREIGN PATENT DOCUMENTS

| | | |
|---|---|---|
| JP | 2007-332292 A | 12/2007 |
| JP | 2008-156623 A | 7/2008 |
| JP | 2008-248217 | 10/2008 |
| JP | 2008-266625 A | 11/2008 |
| JP | 2008-303319 A | 12/2008 |
| JP | 2009-091542 A | 4/2009 |
| WO | WO 99/14160 A1 | 3/1999 |
| WO | WO 01/77081 A1 | 10/2001 |
| WO | WO 03/029329 A2 | 4/2003 |
| WO | WO 2004/083253 A1 | 9/2004 |
| WO | WO 2005/054297 A2 | 6/2005 |
| WO | WO 2005/070896 A1 | 8/2005 |
| WO | WO 2006/013869 A1 | 2/2006 |
| WO | WO 2006/021302 A1 | 3/2006 |
| WO | WO 2006/027069 A1 | 3/2006 |
| WO | WO 2006/027070 A1 | 3/2006 |
| WO | WO 2006/038013 A2 | 4/2006 |
| WO | WO 2007/049485 A1 | 5/2007 |
| WO | WO 2007/101813 A1 | 9/2007 |
| WO | WO 2007/111339 A1 | 10/2007 |
| WO | WO 2007/144282 A1 | 12/2007 |
| WO | WO 2007/147813 A1 | 12/2007 |
| WO | WO 2008/000666 A1 | 1/2008 |
| WO | WO 2008/043837 A1 | 4/2008 |
| WO | WO 2008/062209 A2 | 5/2008 |
| WO | WO 2008/090156 A1 | 7/2008 |
| WO | WO 2008/098037 A2 | 8/2008 |
| WO | WO 2008/100566 A1 | 8/2008 |
| WO | WO 2008/100569 A1 | 8/2008 |
| WO | WO 2008/100577 A1 | 8/2008 |
| WO | WO 2008/102747 A1 | 8/2008 |
| WO | WO 2008/114584 | 9/2008 |
| WO | WO 2008/119770 A1 | 10/2008 |
| WO | WO 2008/133269 A1 | 11/2008 |
| WO | WO 2008/143765 A2 | 11/2008 |
| WO | WO 2009/027250 A2 | 3/2009 |
| WO | WO 2009/029220 A1 | 3/2009 |
| WO | WO 2009/030950 A1 | 3/2009 |
| WO | WO 2009/062723 A1 | 5/2009 |
| WO | WO 2009/077452 A1 | 6/2009 |
| WO | WO 2009/101111 A1 | 8/2009 |
| WO | WO 2009/102305 A1 | 8/2009 |
| WO | WO 2009/102306 A1 | 8/2009 |
| WO | WO 2009/102307 A1 | 8/2009 |
| WO | WO 2010/120268 A1 | 10/2010 |
| WO | WO 2010/120269 A1 | 10/2010 |

OTHER PUBLICATIONS

Barthel et al.; "Acylation and carbanilation of cellulose in ionic liquids"; Green Chem., 2006, 8, pp. 301-306.
Bicak, Niyazi; "A new ionic liquid: 2-hydroxy ethylammonium formate"; Journal of Molecular Liquids 116 (2005) 15-18.
Buchanan, Charles M., et al.; "Preparation and Characterization of Cellulose Monoacetates: The Relationship between Structure and Water Solubility"; Macromolecules 1991, 24, 3060-3064.
Buchanan, Charles M., et al.; "Preparation of Cellulose [1-$^{13}$C] Acetates and Determination of Monomer Compositions by NMR Spectroscopy"; Macromolecules 1991, 3050-3059.
Cao et al.; "Acetone-soluble cellulose acetates prepared by one-step homogeneous acetylation of cornhusk cellulose in an ionic liquid 1-allyl-3-methylimidazolium chloride (AmimCl)"; Elsevier, Carbohydrate Polymers, vol. 69, Issue 4, (2007), pp. 665-672.
Co-pending U.S. Appl. No. 12/030,387, titled "Cellulose Esters and Their Production in Carboxylated Ionic Liquids", filed Feb. 13, 2008; Now published as US 2008-0194808 A1 cited above, Buchanan et al Aug. 2008.
Co-pending U.S. Appl. No. 12/030,425, titled "Production of Ionic Liquids", filed Feb. 13, 2008; Now published as US 2008-0194834 A1 cited above, Buchanan et al Aug. 2008.
Co-Pending U.S. Appl. No. 12/030,434, titiled "Reformation of Ionic Liquids", filed Feb. 13, 2008; Now published as US 2008-0194807 A1 cited above, Buchanan et al Aug. 2008.
Co-pending U.S. Appl. No. 12/189,415, titled "Cellulose Esters and Their Production in Halogenated Ionic Liquids", filed Aug. 11, 2008.
Co-pending U.S. Appl. No. 12/189,421, titled "Treatment of Cellulose Esters", filed Aug. 11, 2008.
Co-pending U.S. Appl. No. 12/189,753, titled "Production of Cellulose Esters in the Presence of a Cosolvent", filed Aug. 11, 2008.
Crosthwaite et al.; "Phase transition and decomposition temperatures, heat capacities and viscosities of pyridinium ionic liquids"; Elsevier; J. Chem. Thermodynamics 37 (2005), pp. 559-568.
Edgar, Kevin J., et al.; "Advances in cellulose ester performance and application"; Prog. Polym. Sci. 26 (2001) 1605-1688.
El Seoud et al.; "Applications of Ionic Liquids in Carbohydrate Chemistry: A Window of Opportunities"; Biomacromolecules, Sep. 2007, Published by the American Chemical Society, vol. 8, No. 9, pp. 2629-2640, pp. 3752-3758.
Fujimoto, et al.; "13C NMR spectral studies on the distribution of substituents in some cellulose derivatives"; J. Polym. Sci.: Part A: Polymer Chemistry Edition, 1986, 24, 2981-2993.
Fukaya et al.; "Superior Solubility of Polysaccharides in Low Viscosity, Polar, and Halogen-Free 1,3-Dialkylimidazolium Formates"; Biomacromolecules, Dec. 2006, Published by the American Chemical Society, vol. 7, No. 12, pp. 3295-3297.
Fukaya et al.; "Supporting Information—Superior Solubility of Polysaccharides in Low Viscosity, Polar and Halogen-Free 1,3-Dialkylimidazolium Formates"; Department of Biotechnology, Tokyo University of Agriculture and Technology; pp. 1-4, Nov. 14, 20116.
Heinze et al.; "Ionic Liquids as Reaction Medium in Cellulose Functionalization"; Macromolecular Bioscience 2005, 5, pp. 520-525.
Heinze, et al.; "Synthesis and carboxymethylation of organo-soluble trifluoroacetates and ormats of cellulose"; J.M.S.—Pure Appl. Chem. 1996, A33(5), 613-626.
Heinze, et al.; "Synthesis path versus distribution of functional groups in cellulose esters"; Macromol. Symp. 1998, 130, 271-283.
Heinze, Thomas, et al.; "Synthesis and subsequent reactions of cellulose-p-toluenesulfonic acid esters. Pool for new functional polymers."; Papier (Darmstadt) (1996), 50(12), 721-729.
Heinze, Thomas et al.; "Interactions of Ionic Liquids with polysaccharides—2: Cellulose"; Macromol. Symp; 2008; pp. 8-22; 262.
Heinze, Thomas et al.; "Interactions of Ionic Liquids with Polysaccharides 1. Unexpected Acetylation of Cellulose with 1-Ethyl-3-methylimidazolium"; Macromolecular Journals; 2007; 28; pp. 2311-2317.
Huddleston et al.; "Characterization and comparison of hydrophilic and hydrophobic room temperature ionic liquids incorporating the imidazolium cation"; The Royal Society of Chemistry 2001; Green Chemistry, 2001, 3, pp. 156-164.
Husemann, E. et al.; "N-Äthyl-pyridinium-chlorid als Lösungsmittel und Reaktionsmedium fur Cellulose"; Makromolekulare Chemie, 128 (1969) 288-291 (nr. 3178).
Iwata, Tadahisa, et al.; "Conformational analysis of regioselectively substituted cellulose esters"; Sen'i Gakkaishi (1991), 47(8), 379-83.
Iwata, Tadahisa, et al.; "Preparation and NMR assignments of cellulose mixed esters regioselectively substituted by acetyl and propanoyl groups"; Carbohydrate Research (1992), 224, 277-83.
Kametani et al.; "Novel Methylation. III (1a). Methylation of Tertiary Amines such as Pyridine and Isoquinoline with Alkyl Carboxylates (1b)."; J. Heterocycl. Chem., 1966, 3, pp. 129-136.
Kasuya, Natsuki, et al.; "Chiral discrimination with regioselectively substituted cellulose esters as chiral stationary phases"; Chirality (2000), 12(9), 670-674.
Klemm, D., et al.; "New procedures for regioselective synthesis and modification of trialkylsilylcelluloses"; Cellulosics: Materials for Selective Separations and Other Technologies, 1993, Chapter 26, 221-226.
Klemm, D., et al.; "Polyglucane derivatives with regular substitutent distribution"; Macromol. Symp. 1995, 99, 129-140.
Klemm, D., et al.; "Readily hydrolyzable cellulose esters as intermediates for the regioselective derivatization of cellulose"; Die Angewandte Makromolekulare Chemie 1992, 198, 155-164.

(56) References Cited

OTHER PUBLICATIONS

Klemm, D., et al.; "Readily hydrolyzable cellulose esters as intermediates for the regioselective derivatization of cellulose"; Cellulose Chem. Technol. 1990, 24, 667-678.
Klemm, D.O., et al.; "Silylated Cellulose Materials in Design of Supramolecular Structure of Ultrathin Films"; J.M.S.—Pure Appl. Chem. 1995, A32, 899-904.
Klemm, D.O.; "Regiocontrol in Cellulose Chemistry: Principles and Examples of Etherification and Esterification"; Cellulose Derivatives: Modification, Characterization, and Nanostructures, ACS Symposium Series 688, T.J. Heinze and W.G. Glasser, Editors, 1998, Oxford University Press, 19-37.
Kondo, T.; "Preparation of 6-O-alkylcelluloses"; Carbohydr. Res. 1993, 238, 231-240.
Laus et al.; "Ionic Liquids: Current Developments, Potential and Drawbacks for Industrial Applications"; Lenzinger Berichte, 84 (2005), pp. 71-85.
Liebert et al.; "Click Chemistry with Polysaccharides"; Macromolecular Rapid Communications, 2006, 27, pp. 208-213.
Liebert, Tim, et al.; "Readily hydrolyzable cellulose esters as intermediates for the regioselective derivatization of cellulose. Part II Soluble, highly substituted cellulose trifluoroacetates."; Cellulose (London) (1994), 1(4), 249-258.
MacFarlane, et al.; "Lewis base ionic liquids"; The Royal Society of Chemistry 2006; Chem. Commun., 2006, 1905-1917.
Mayumi, Ayaka, et al.; "Partial substitution of cellulose by ring-opening esterification of cyclic esters in a homogeneous system"; Journal of Applied Polymer Science (2006), 102(5), 4358-4364.
Moulthrop et al.; "High-resolution $^{13}$C NMR studies of cellulose and cellulose oligomers in ionic liquid solutions"; The Royal Society of Chemistry 2005; Chem. Commun., 2005, pp. 1557-1559.
Murugesan et al.; "Benzoate-based room temperature ionic liquids—thermal properties and glycosaminoglycan dissolution"; Elsevier; Carbohydrate Polymers 63 (2006), pp. 268-271.
Nishio, Naotaka, et al.; "Preparation of high regioselectively monosubstituted carboxymethyl celluloses"; Cellulose Chemistry and Technology (2005), 39(5-6), 377-387.
Notification of Transmittal of the International Search Report and the Written Opinion of the International Searching Authority, or the Declaration dated Jun. 20, 2008; International Application No. PCT/US2008/001952.
Notification of Transmittal of the International Search Report and the Written Opinion of the International Searching Authority, or the Declaration dated Jun. 27, 2008; International Application No. PCT/US2008/001958.
Notification of Transmittal of the International Search Report and the Written Opinion of the International Searching Authority, or the Declaration dated Jul. 4, 2008; International Application No. PCT/US2008/001975.
Philipp, B., et al.; "Regioselective esterification and etherification of cellulose and cellulose derivatives. Part 2. Synthesis of regioselective cellulose esters."; Papier (Bingen, Germany) (1995), 49(2), 58-64.
Philipp, Burkart, et al.; "Regioselective derivatization of cellulose. Routes of synthesis, effects on properties, and areas of application."; Polymer News (1996), 21(5), 155-161.
Philipp, Burkart, et al.; "Regioselective esterification and etherification of cellulose and cellulose derivatives. Part 1. Problems and descriptions of the reaction systems."; Papier (Bingen, Germany) (1995), 49(1), 3-7.
Philipp, Burkhart, et al.; "Untersuchungen Zur Sulfatierung Von Celluloseformiat Im Vergleich Zu Cellulose-Acetat Unter Homogenen Reaktionsbedingungen"; [Investigations on Sulfation of Cellulose Formate in Comparison with Cellulose Acetate under Homogeneous reaction conditions]; Cellulose Chemistry and Technology, 24, 667-678 (1990).
Potthast et al.; "Hydrolytic processes and condensation reactions in the cellulose solvent system N,N-dimethylacetamide/lithium chloride. Part 2: degradation of cellulose"; Elsevier; Polymer 44 (2003), pp. 7-17.

Ramos et al.; "Carboxymethylation of cellulose in the new solvent dimethyl sulfoxide/tetrabutylammonium fluoride"; Elsevier; Carbohydrate Polymers 60 (2005), pp. 259-267.
Remsing et al.; "Mechanism of cellulose dissolution in the ionic liquid 1-n-butyl-3-methylimidazolium chloride: a $^{13}$C and $^{35/37}$Cl NMR relaxation study on model systems"; The Royal Society of Chemistry 2006; Chem. Commun., 2006, pp. 1271-1273.
Richardson, Sara and Gorton, LO; "Characterisation of the Substituent Distribution in Starch and Cellulose Derivatives"; Analytica Chimica Acta; 2003; pp. 27-65; 497.
Rosenau et al.; "Hydrolytic Processes and Condensation Reactions in the Cellulose Solvent System N,N-Dimethylacetamide/Lithium Chloride. Part 1."; Holzforschung 55 (2001), pp. 661-666.
Saalwächter et al.; "Cellulose Solutions in Water Containing Metal Complexes"; Macromolecules 2000, 33, pp. 4094-4107.
Schlufter et al.; "Efficient Homogeneous Chemical Modification of Bacterial Cellulose in the Ionic Liquid 1-N-Butyl-3-methylimidazolium Chloride"; Macromolecular Rapid Communications, 2006, 27, pp. 1670-1676.
Swatloski et al.; "Dissolution of Cellulose with Ionic Liquids"; J. Am. Chem. Soc., 2002, 124, pp. 4974-4975.
Varma et al.; "An expeditious solvent-free route to ionic liquids using microwaves"; The Royal Society of Chemistry 2001; Chem. Commun., 2001, pp. 643-644.
Wagenknecht, W., et al.; "Regioselective homogeneous sulfaction of cellulose via unstable intermediates"; Cellulosics: Materials for Selective Separations and Other Technologies, 1993, Chapter 24, 205-211.
Wagenknecht, Wolfgang; "Regioselectively substituted cellulose derivatives by modification of commercial cellulose acetates"; Papier (Darmstadt) (1996), 50(12), 712-720.
Wenz, G., et al.; "Synthesis, control of substitution pattern and phase transitions of 2,3-di-O-methylcellulose"; Carbohydrate Research, 2000, 326, 67-79.
Wu et al.; "Homogeneous Acetylation of Cellulose in a New Ionic Liquid"; Biomacromolecules 2004, 5, pp. 266-268.
Xie, Jiangbing, et al.; "Enzyme-catalyzed transesterification of vinyl ester on cellulose and its regioselectivity"; Abstracts of Paper, 221$^{st}$ ACS National Meeting, San Diego, CA, United States, Apr. 1-5, 2001 (2001), CELL-068.
Xie, Jiangbing, et al.; "Modification of cellulose solids by enzyme-catalyzed transesterification with vinyl esters in anhydrous organic solvents"; ACS Symposium Series (2003), 840(Biocatalysis in Polymer Science), 217-230.
Xie, Jiangbing, et al.; "Regioselectivity of enzyme catalyzed transesterification of cellulose"; Polymer Preprints (American Chemical Society, Division of Polymer Chemistry) (2001), 42(1), 512-513.
Yoshida et al.; "Preparation of polymer brush-type cellulose β-ketoesters using LiCl/1,3-dimethyl-2-imidazolidinone as a solvent"; Elsevier; Polymer 46 (2005), pp. 2548-2557.
Zhang et al.; "1-Allyl-3-methylimidazolium Chloride Room Temperature Ionic Liquid: A New and Powerful Nonderivatizing Solvent for Cellulose"; Macromolecules 2005, 38, pp. 8272-8277.
Zhu et al.; "Dissolution of cellulose with ionic liquids and its application: a mini-review"; Green Chem., 2006, 8, pp. 325-327.
Notification of Transmittal of the International Search Report and the Written Opinion of the International Searching Authority, or the Declaration dated Nov. 7, 2008; International Application No. PCT/US2008/009624.
Notification of Transmittal of the International Search Report and the Written Opinion of the International Searching Authority, or the Declaration dated Nov. 5, 2008; International Application No. PCT/US2008/009625.
Notification of Transmittal of the International Search Report and the Written Opinion of the International Searching Authority, or the Declaration dated Nov. 18, 2008; International Application No. PCT/US2008/009622.
Co-pending U.S. Appl. No. 12/539,814, titled "Cellulose Solutions Comprising Tetraalkylammonium Alkylphosphate and Products Produced Therefrom", filed Aug. 12, 2009, Buchanan et al.

(56) References Cited

OTHER PUBLICATIONS

Co-pending U.S. Appl. No. 12/539,800, titled "Regioselectively Substituted Cellulose Esters Produced in a Carboxylated Ionic Liquid Process and Products Produced Therefrom", filed Aug. 12, 2009, Buchanan et al.
Co-pending U.S. Appl. No. 12/539,812, titled "Regioselectively Substituted Cellulose Esters Produced in a Halogenated Ionic Liquid Process and Products Produced Therefrom", filed Aug. 12, 2009, Buchanan et al.
Co-pending U.S. Appl. No. 12/539,817, titled "Regioselectively Substituted Cellulose Esters Produced in a Tetraalkylammonium Alkylphosphate Ionic Liquid Process and Products Produced Therefrom", filed Aug. 12, 2009, Buchanan et al.
Notification of Transmittal of the International Search Report and the Written Opinion of the International Searching Authority, or the Declaration dated Nov. 20, 2009; International Application No. PCT/US2009/004637.
Cao, et al.; "Room temperature ionic liquid (RTILs): A new and versatile platform for cellulose processing and derivation"; Chemical Engineering Journal 147 (2009) 13-21.
Notification of Transmittal of the International Search Report and the Written Opinion of the International Searching Authority, or the Declaration dated Nov. 13, 2009; International Application No. PCT/US2009/004638.
Ren, et al.; "Acetylation of wheat straw hemicelluloses in ionic liquid using iodine as a catalyst"; Carbohydrate Polymers 70(2007) 406-414.
Granstrom, et al.; "Tosylation and acylation of cellulose in 1-allyl-3-methylimidazolium chloride"; Springer Science + Business Media B.V. 2008; Cellulose (2008) 15:481-488.
Kohler, et al.; "Efficient synthesis of cellulose furoates in 1-N-butyl-3-methylimidazolium chloride"; Springer Science + Business Media B.V. 2007; Cellulose (2007) 14:489-495.
Meng, et al.; "Graft copolymers prepared by atom transfer radical polymerization (ATRP) from cellulose"; Polymer 50 (2009) 447-454.
Notification of Transmittal of the International Search Report and the Written Opinion of the International Searching Authority, or the Declaration dated Dec. 28, 2009; International Application No. PCT/US2009/004624.
Notification of Transmittal of the International Search Report and the Written Opinion of the International Searching Authority, or the Declaration dated Dec. 28, 2009; International Application No. PCT/US2009/004626.
Kern et al., "Synthesis, Control of Substitution Pattern and Phase Transitions of 2,3-di-O-methylcellulose," Carbohydrate Research, 2000, 326, pp. 67-79.
USPTO Office Action dated Mar. 2, 2011 for copending U.S. Appl. No. 12/030,387.
Murugesan, S. et al., "Dialkyl Imidazolium Benzoates—Room Temperature Ionic Liquids Useful in the Peracetylation and Perbenzoylation of Simple and Sulfated Saccharides," Synlett, 2003, pp. 1283-1286, No. 9, Georg Thieme Verlag Stuttgart, New York.
Kohler, S. et al., "Interactions of Ionic Liquids with Polysaccharides 1. Unexpected Acetylation of Cellulose with 1-Ethyl-3-methylimidazolium Acetate," Macromolecular Rapid Communications, published online Oct. 22, 2007, pp. 2311-2317, 28, Wiley InterScience.
Ruben S. et al., "Tracer Studies with Radioactive Carbon. The Exchange between Acetic Anhydride and Sodium Acetate," J. Am. Chem. Soc., 1942, p. 3050, vol. 64.
Avicel for Solid Dose Forms, FMC Biopolymer website, http://www.bmcbiopolymer.com/; Feb. 24, 2011.
Abbott, A. et al., "O-Acetylation of cellulose and monosaccharides using a based ionic liquid," Green Chemistry, 2005, pp. 705-707, vol. 7.
USPTO Office Action dated Jun. 22, 2011 for copending U.S. Appl. No. 12/189,421.

USPTO Office Action dated Jun. 9, 2011 for copending U.S. Appl. No. 12/189,415.
USPTO Office Action dated May 27, 2011 for copending U.S. Appl. No. 12/189,753.
USPTO Office Action dated Jun. 21, 2011 for copending U.S. Appl. No. 12/030,434.
New copending U.S. Appl. No. 13/217,326, filed Aug. 25, 2011, Charles Buchanan et al.
USPTO Office Action dated Sep. 14, 2011 for copending U.S. Appl. No. 12/539,817.
USPTO Office Action dated Dec. 12, 2010 for copending U.S. Appl. No. 12/539,814.
USPTO Office Action dated May 7, 2010 for copending U.S. Appl. No. 12/030,425.
USPTO Notice of Allowance dated Dec. 10, 2010 for copending U.S. Appl. No. 12/030,425.
USPTO Notice of Allowance dated Nov. 21, 2011 for copending U.S. Appl. No. 12/189,421.
USPTO Office Action dated Jan. 5, 2012 for copending U.S. Appl. No. 13/217,326.
USPTO Notice of Allowance dated Nov. 16, 2011 for copending U.S. Appl. No. 12/030,387.
Tsunashima et al., "Substituent Distribution in Cellulose Acetates: Its Control and the Effect on Structure Formation in Solution," Journal of Colloid and Interface Science (2000) vol. 228, pp. 279-286.
New copending U.S. Appl. No. 13/278,796, filed Oct. 21, 2011, Charles Michael Buchanan et al.
New copending U.S. Appl. No. 13/330,828, filed Dec. 20, 2011, Charles Michael Buchanan et al.
New copending U.S. Appl. No. 13/339,814, filed Dec. 29, 2011, Charles Michael Buchanan et al.
New copending U.S. Appl. No. 13/357,636, filed Jan. 25, 2012, Charles Michael Buchanan et al.
New copending U.S. Appl. No. 13/357,635, filed Jan. 25, 2012, Charles Michael Buchanan et al.
USPTO Notice of Allowance dated Jan. 27, 2012 for copending U.S. Appl. No. 12/189,753.
USPTO Notice of Allowance dated Feb. 8, 2012 for copending U.S. Appl. No. 12/030,387.
USPTO Notice of Allowance dated Jan. 30, 2012 for copending U.S. Appl. No. 12/189,415.
USPTO Notice of Allowance dated Feb. 15, 2012 for copending U.S. Appl. No. 12/030,434.
New copending U.S. Appl. No. 13/396,700, filed Feb. 15, 2012, Charles Michael Buchanan.
Wasserscheid, P., et al., "Synthesis and Purification of Ionic Liquids," Ionic Liquids in Synthesis, (2002), pp. 7-40, Wiley—VCH Verlag GmbH & Co.
USPTO Office Action dated Feb. 29, 2012 for copending U.S. Appl. No. 12/539,800.
Takaragi, A. et al., "Reaction Characteristics of Cellulose in the LiCl/1,3-dimethyl-2-imidazolidininone Solvent System," Cellulose, 1999, vol. 6, pp. 93-102, Kluwar Academic Publishers.
New copending U.S. Appl. No. 13/409,724, filed Mar. 1, 2012, Charles Michael Buchanan, et al.
New copending U.S. Appl. No. 13/409,735, filed Mar. 1, 2012, Charles Michael Buchanan, et al.
New copending U.S. Appl. No. 13/409,743, filed Mar. 1, 2012, Charles Michael Buchanan, et al.
New copending U.S. Appl. No. 13/409,747, filed Mar. 1, 2012, Charles Michael Buchanan, et al.
Buchanan, C., "Two-Dimensional NMR of Polysaccharides: Spectral Assignments of Cellulose Triesters," Macromolecules, 1987, pp. 2750-2754, vol. 20, American Chemical Society.
USPTO Office Action dated Mar. 9, 2012 for copending U.S. Appl. No. 12/539,812.
USPTO Notice of Allowance dated Mar. 15, 2012 for copending U.S. Appl. No. 12/189,421.
USPTO Office Action dated Apr. 2, 2012 for copending U.S. Appl. No. 12/539,817.

(56) References Cited

OTHER PUBLICATIONS

Notification of Transmittal of the International Search Report dated Jul. 26, 2012 for International Application No. PCT/US2012/031069.
Notification of Transmittal of the International Search Report dated Jul. 26, 2012 for International Application No. PCT/US2012/031062.
Notification of Transmittal of the International Search Report dated Jul. 26, 2012 for International Application No. PCT/US2012/031064.
Notification of Transmittal of the International Search Report dated Jul. 26, 2012 for International Application No. PCT/US2012/031077.
USPTO Notice of Allowance dated Jul. 24, 2012 for U.S. Appl. No. 13/217,326.
USPTO Office Action dated Jul. 2, 2012 for copending application U.S. Appl. No. 13/330,828.
UPSTO Notice of Allowance and Fees Due dated Oct. 15, 2012 received in co-pending U.S. Appl. No. 12/539,812.
Office Action notification dated Nov. 5, 2012 received in co-pending U.S. Appl. No. 13/339,814.
Office Action notification dated Nov. 5, 2012 received in co-pending U.S. Appl. No. 13/396,700.
Office Action notification dated Nov. 7, 2012 received in co-pending U.S. Appl. No. 12/539,800.
Office Action notification dated Dec. 21, 2012 received in co-pending U.S. Appl. No. 13/278,796.
Notice of Allowance and Fees Due dated Oct. 15, 2012 received in co-pending U.S. Appl. No. 12/539,812.
Notice of Allowance dated Jan. 24, 2013 for copending U.S. Appl. No. 13/330,828.
Office Action notification dated Jun. 6, 2013 received in co-pending U.S. Appl. No. 13/357,635.
Office Action notification dated Jun. 18, 2013 received in co-pending U.S. Appl. No. 13/409,724.
Office Action notification dated Jul. 19, 2013, 2013 received in co-pending U.S. Appl. No. 13/409,743.
Office Action notification dated Aug. 29, 2013 received in co-pending U.S. Appl. No. 13/396,700.
Office Action notification dated Sep. 9, 2013 received in co-pending U.S. Appl. No. 13/409,747.
Office Action notification dated Sep. 9, 2013 received in co-pending U.S. Appl. No. 13/357,636.
Edgar et al., "Long-Chain Cellulose Esters: Preparation, Properties, and Perspective," in Cellulose Derivatives, Heinze t. et al., ACS Symposium Series 688: Washington, DC, 1998, pp. 38-60.
Heinz et al., "Unconventional Methods in Cellulose Functionalization," Prog. Polym. Sci., 2001, 26, pp. 1689-1762.
Reier, G.E. Avicel PH Microcrystalline Cellulose, 2000, pp. 1-27, FMC biopolymers website, www.fmcbiopolyner.com/Portals/bio/content/Docs/PS-Section%2011.pdf accessed on Aug. 13, 2013.
Spurlin, H.M., "Arrangement of Substituents in Cellulose Derivatives," J. Am. Chem. Soc., 1939, 61, pp. 2222-2227.
Office Action notification dated Feb. 24, 2014 received in co-pending U.S. Appl. No. 13/357,635.
Notice of Allowance and Fees Due dated Mar. 24, 2014 received in co-pending U.S. Appl. No. 13/409,724.
Office Action notification dated May 6, 2014 received in co-pending U.S. Appl. No. 13/409,735.
Office Action notification dated May 20, 2014 received in co-pending U.S. Appl. No. 13/357,636.
Notice of Allowance and Fees Due dated Jun. 11, 2014 received in co-pending U.S. Appl. No. 13/357,635.
Office Action notification dated Jul. 3, 2014 received in co-pending U.S. Appl. No. 12/539,800.
Okubo, JP 2006328298 A, English Machine Translation: http://dossier1.ipdl.inpit.go.jp/AIPN/odse_top_dn.ipdl?N000=7400.
Notice of Allowance and Fees Due dated Jul. 25, 2014 received in co-pending U.S. Appl. No. 13/357,635.
New copending application U.S. Appl. No. 14/447,704, dated Jul. 31, 2014, Charles Buchanan et al.
Office Action notification dated Sep. 23, 2014 received in co-pending U.S. Appl. No. 13/486,042.
Luo et al., J. Appl. Polym. Sci., 2005 100(4), Acetylation of Cellulose Using Recyclable Polymeric, p. 3288-3296, Article first published online Feb. 27, 2006.
Edgar, K.J., Cellulose Esters, Organic. Encyclopedia of Polymer Science and Technology, 2004, vol. 9, p. 129-159.
Zhu et al., Dissolution of Cellulose with Ionic and its Applications: A Mini-Review, Green Chemistry, 2006, 8, p. 325-327.
Office Action notification dated Aug. 19, 2014 received in co-pending U.S. Appl. No. 13/409,743.
Office Action notification dated Aug. 25, 2014 received in co-pending U.S. Appl. No. 13/449,978.
Office Action notification dated Sep. 11, 2014 received in co-pending U.S. Appl. No. 13/409,747.
Office Action notification dated Sep. 23, 2014 received in co-pending U.S. Appl. No. 13/486,043.
Office Action notification dated Nov. 6, 2014 received in co-pending U.S. Appl. No. 13/409,735.
Office Action notification dated Nov. 13, 2014 received in co-pending U.S. Appl. No. 13/396,700.
Office Action notification dated Dec. 10, 2014 received in co-pending U.S. Appl. No. 13/706,684.
Office Action notification dated Feb. 4, 2015 received in co-pending U.S. Appl. No. 13/449,978.
Notice of Allowance and Fees Due dated Mar. 27, 2015 received in co-pending U.S. Appl. No. 12/539,800.
Office Action notification dated Mar. 27, 2015 recieved in co-pending U.S. Appl. No. 13/409,747.
Office Action notification dated May 8, 2015 received in co-pending U.S. Appl. No. 13/409,735.
Notice of Allowance and Fees Due dated May 8, 2015 received in co-pending U.S. Appl. No. 13/409,743.
Notice of Allowance and Fees Due dated May 22, 2015 received in co-pending U.S. Appl. No. 13/706,684.
Notice of Allowance and Fees Due dated Jun. 19, 2015 received in co-pending U.S. Appl. No. 13/409,743.
Notice of Allowance and Fees Due dated Jun. 22, 2015 received in co-pending U.S. Appl. No. 13/706,684.
Office Action notification dated Jul. 6, 2015 received in co-pending U.S. Appl. No. 14/447,704.
Office Action notification dated Sep. 11, 2015 received in co-pending U.S. Appl. No. 13/409,747.
New copending U.S. Appl. No. 14/858,450, filed Sep. 18, 2015, Charles Buchanan et al.
Office Action notification dated Nov. 4, 2015 received in co-pending U.S. Appl. No. 13/409,735.
Office Action notification dated Feb. 2, 2016 received in co-pending U.S. Appl. No. 13/409,747.
USPTO Notice of Allowance dated Feb. 11, 2016 for copending U.S. Appl. No. 14/447,704.
Office Action notification dated Apr. 21, 2016 received in co-pending U.S. Appl. No. 12/539,800.
Office Action notification dated Jul. 7, 2016 received in co-pending U.S. Appl. No. 14/447,704.
Office Action notification dated Sep. 16, 2016 received in co-pending U.S. Appl. No. 13/409,735.
Office Action notification dated Sep. 30, 2016 received in co-pending U.S. Appl. No. 13/409,747.
USPTO Notice of Allowance dated Nov. 15, 2016 for copending U.S. Appl. No. 12/539,800.
Office Action notification dated Jan. 10, 2017 received in co-pending U.S. Appl. No. 14/858,450.
Office Action notification dated Feb. 3, 2017 received in co-pending U.S. Appl. No. 14/447,704.
Co-pending U.S. Appl. No. 15/425,085, titled "Regioselectively Substituted Cellulose Esters Produced in a Carboxylated Ionic Liquid Process and Products Produced Therefrom", filed Feb. 6, 2017.
Office Action notification dated Apr. 18, 2017 received in co-pending U.S. Appl. No. 12/539,800.

(56) References Cited

OTHER PUBLICATIONS

Office Action notification dated May 22, 2017 received in co-pending U.S. Appl. No. 13/409,735.
USPTO Notice of Allowance dated May 24, 2017 for copending U.S. Appl. No. 13/409,747.
Office Action notification dated Jun. 28, 2017 received in co-pending U.S. Appl. No. 14/447,704.
USPTO Notice of Allowance dated Aug. 15, 2017 for copending U.S. Appl. No. 14/858,450.
USPTO Notice of Allowance dated Aug. 31, 2017 for copending U.S. Appl. No. 13/409,747.
USPTO Notice of Allowance dated Oct. 3, 2017 for copending U.S. Appl. No. 12/539,800.
European Search Report—Application No. 17169625.5-1302 dated Aug. 7, 2017.
USPTO Notice of Allowance dated Jan. 26, 2018 for copending U.S. Appl. No. 14/447,704.
USPTO Notice of Allowance dated Nov. 15, 2017 for copending U.S. Appl. No. 13/409,735.
New copending U.S. Appl. No. 15/974,795, filed May 9, 2018, Charles Buchanan et al.

* cited by examiner

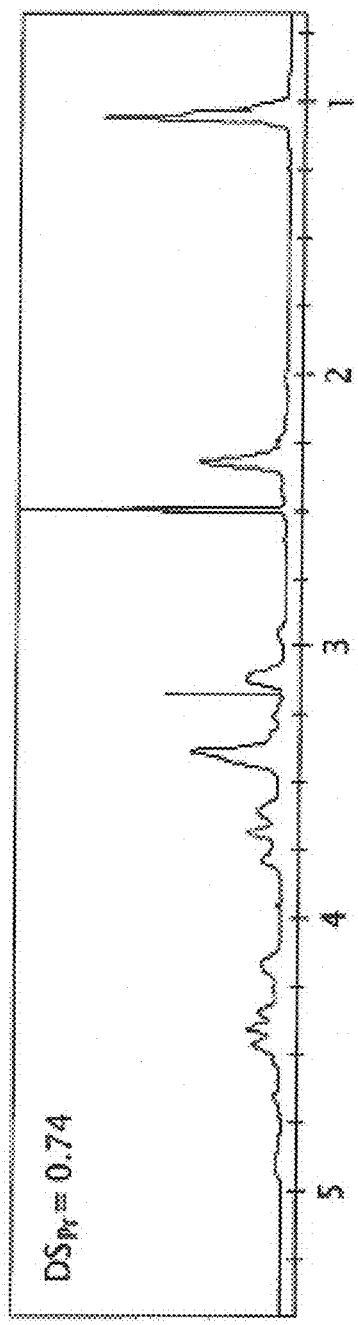
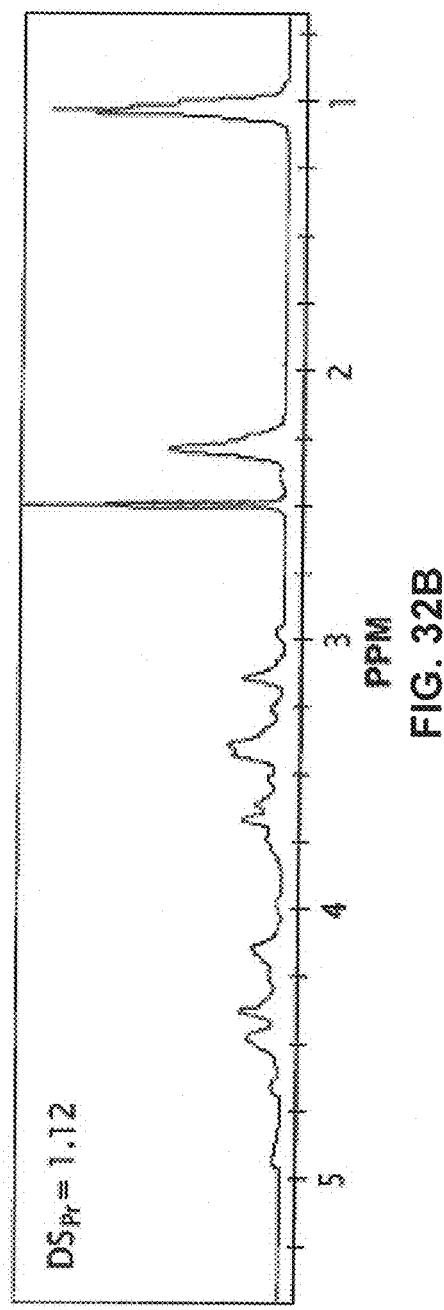
FIG. 32A
FIG. 32B

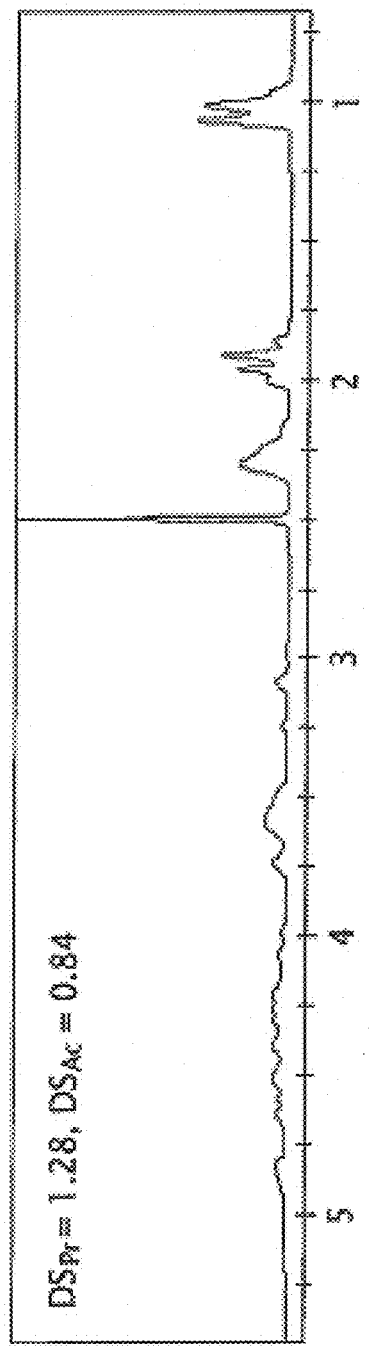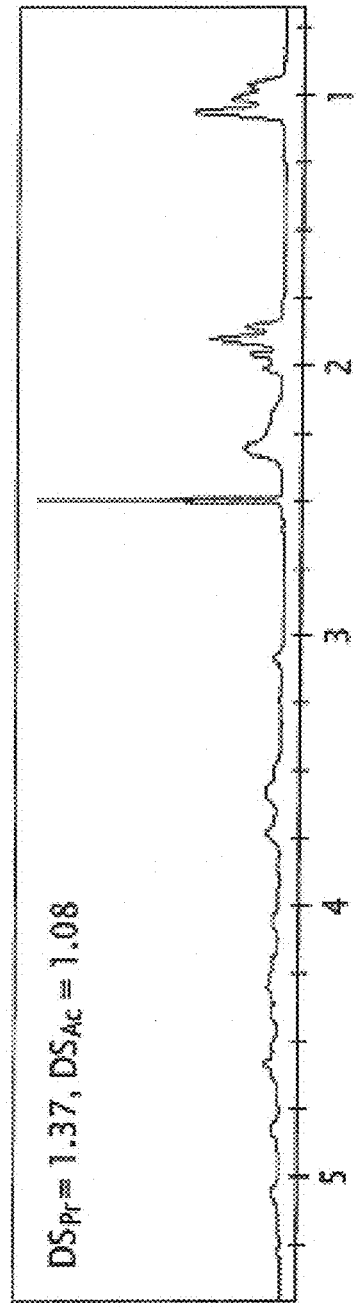

REGIOSELECTIVELY SUBSTITUTED CELLULOSE ESTERS PRODUCED IN A CARBOXYLATED IONIC LIQUID PROCESS AND PRODUCTS PRODUCED THEREFROM

CROSS REFERENCE TO RELATED APPLICATIONS

This application is a continuation-in-part of U.S. application Ser. No. 12/539,800 filed on Aug. 12, 2009, now U.S. Publication No. 2010-0029927, which is a continuation-in-part of U.S. application Ser. No. 12/030,387, filed Feb. 13, 2008, now U.S. Pat. No. 8,148,518, which claims priority to U.S. Provisional Application Ser. No. 60/901,615, filed Feb. 14, 2007; U.S. application Ser. No. 12/539,800 also claims priority to U.S. Provisional Application 61/088,423 filed Aug. 13, 2008, the disclosures of which are herein incorporated by reference in their entirety to the extent they do not contradict the statements herein.

BACKGROUND

1. Field of the Invention

The present invention relates generally to cellulose esters and/or ionic liquids. One aspect of the invention concerns processes for producing cellulose esters in ionic liquids.

2. Description of the Related Art

Cellulose is a β-1,4-linked polymer of anhydroglucose. Cellulose is typically a high molecular weight, polydisperse polymer that is insoluble in water and virtually all common organic solvents. The use of unmodified cellulose in wood or cotton products, such as in the housing or fabric industries, is well known. Unmodified cellulose is also utilized in a variety of other applications usually as a film (e.g., cellophane), as a fiber (e.g., viscose rayon), or as a powder (e.g., microcrystalline cellulose) used in pharmaceutical applications. Modified cellulose, including cellulose esters, are also utilized in a wide variety of commercial applications. Cellulose esters can generally be prepared by first converting cellulose to a cellulose triester, then hydrolyzing the cellulose triester in an acidic aqueous media to the desired degree of substitution ("DS"), which is the average number of ester substituents per anhydroglucose monomer. Hydrolysis of cellulose triesters containing a single type of acyl substituent under these conditions can yield a random copolymer that can consist of up to 8 different monomers depending upon the final DS.

Ionic liquids ("ILs") are liquids containing substantially only anions and cations. Room temperature ionic liquids ("RTILs") are ionic liquids that are in liquid form at standard temperature and pressure. The cations associated with ILs are structurally diverse, but generally contain one or more nitrogens that are part of a ring structure and can be converted to a quaternary ammonium. Examples of these cations include pyridinum, pyridazinium, pyrimidinium, pyrazinium, imidazolium, pyrazolium, oxazolium, triazolium, thiazolium, piperidinium, pyrrolidinium, quinolinium, and isoquinolinium. The anions associated with ILs can also be structurally diverse and can have a significant impact on the solubility of the ILs in different media. For example, ILs containing hydrophobic anions such as hexafluorophosphates or triflimides have very low solubilities in water while ILs containing hydrophilic anions such chloride or acetate are completely miscible in water.

The names of ionic liquids can generally be abbreviated. Alkyl cations are often named by the letters of the alkyl substituents and the cation, which are given within a set of brackets, followed by the abbreviation for the anion. Although not expressively written, it should be understood that the cation has a positive charge and the anion has a negative charge. For example, [BMIm]OAc indicates 1-butyl-3-methylimidazolium acetate, [AMIm]Cl indicates 1-allyl-3-methylimidazolium chloride, and [EMIm]OF indicates 1-ethyl-3-methylimidazolium formate.

Ionic liquids can be costly; thus, their use as solvents in many processes may not be feasible. Despite this, methods and apparatus for reforming and/or recycling ionic liquids have heretofore been insufficient. Furthermore, many processes for producing ionic liquids involve the use of halide and/or sulfur intermediates, or the use of metal oxide catalysts. Such processes can produce ionic liquids having high levels of residual metals, sulfur, and/or halides.

SUMMARY OF THE INVENTION

In one embodiment of the invention, a regioselectively substituted cellulose ester is provided having a $C_6/C_3$ relative degree of substitution (RDS) ratio greater than one or a $C_6/C_2$ RDS ratio greater than 1.

In another embodiment of the invention, a regioselectively substituted cellulose ester is provided wherein the RDS is $C_6 > C_2 > C_3$.

In another embodiment of the invention, a process for making a regioselectively substituted cellulose ester is provided. The process comprises:
   (a) dissolving cellulose in a carboxylated ionic liquid to thereby form a cellulose solution;
   (b) contacting the cellulose solution with at least two acylating reagents to thereby provide an acylated cellulose solution comprising a cellulose ester, wherein the cellulose ester comprises at least one acyl group donated by the carboxylated ionic liquid; wherein the acylating reagents are contacted consecutively in stages with the cellulose solution;
   (c) contacting the acylated cellulose solution with a non-solvent to cause at least a portion of the cellulose ester to precipitate and thereby provide a slurry comprising precipitated cellulose ester and the carboxylated ionic liquid;
   (d) separating at least a portion of the precipitated cellulose ester from the carboxylated ionic liquid to thereby provide a recovered cellulose ester and a separated carboxylated ionic liquid; and
   (e) optionally, recycling at least a portion of the separated carboxylated ionic liquid for use in dissolving additional cellulose.

In another embodiment of the invention, a process of making a regioselectively substituted cellulose ester is provided. The process comprises:
   (a) dissolving cellulose in a carboxylated ionic liquid to thereby form a cellulose solution;
   (b) contacting the cellulose solution with at least two acylating reagents to thereby provide an acylated cellulose solution comprising a cellulose ester, wherein the cellulose ester comprises at least one acyl group donated by the carboxylated ionic liquid; wherein the acylating reagents are added simultaneously to cellulose solution;
   (c) contacting the acylated cellulose solution with a non-solvent to cause at least a portion of the cellulose ester to precipitate and thereby provide a slurry comprising precipitated cellulose ester and the carboxylated ionic liquid;

(d) separating at least a portion of the precipitated cellulose ester from the carboxylated ionic liquid to thereby provide a recovered cellulose ester and a separated carboxylated ionic liquid; and (e) optionally, recycling at least a portion of the separated carboxylated ionic liquid for use in dissolving additional cellulose.

In another embodiment of the invention, photographic film, protective film, or compensation film is provided.

In yet another embodiment of the invention, a compensation film is provided comprising at least one regioselectively substituted cellulose ester wherein the compensation film has an $R_{th}$ range from about −400 to about +100 nm.

In yet another embodiment, articles are provided comprising the regioselectively substituted cellulose ester, such articles include, but are not limited to, thermoplastic molded products, coatings, personal care products, and drug delivery products.

In yet another embodiment, A cellulose ester comprising at least two different acyl groups, wherein at least one of said acyl groups comprises an aromatic compound, wherein said cellulose ester is regioselectively substituted with a RDS ratio of C6>C2>C3

BRIEF DESCRIPTION OF THE DRAWINGS

FIGS. 32A-32E show the proton NMR spectra for the samples removed during the contact period following the staged addition of Pr$_2$O (1$^{st}$) and Ac$_2$O (2$^{nd}$).

DETAILED DESCRIPTION

Figure 1:
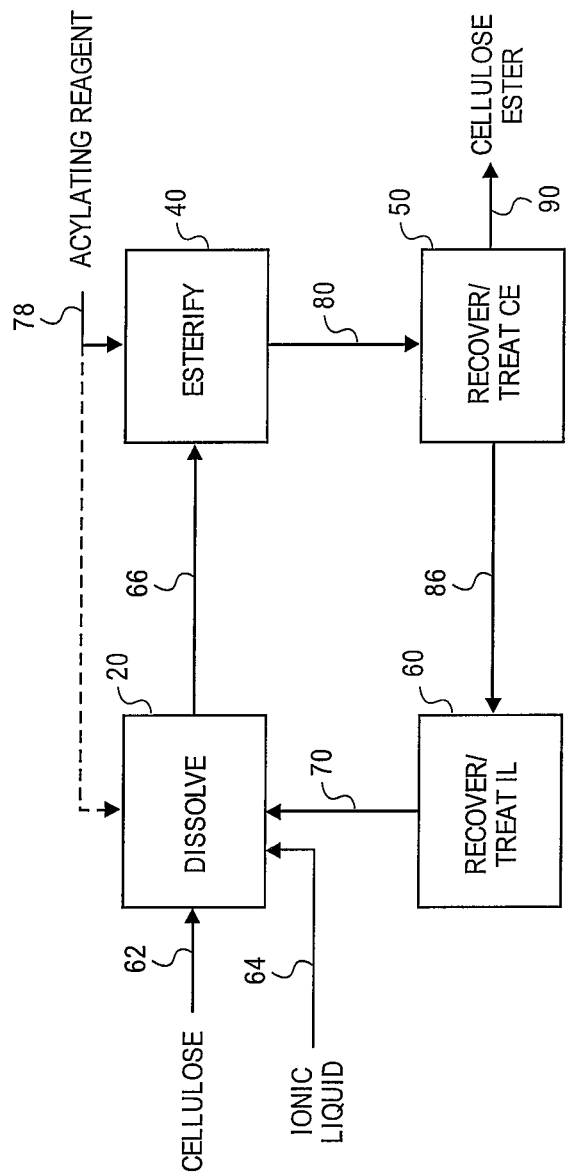
FIG. 1 is a simplified diagram depicting the majors steps involved in a process for producing cellulose esters in ionic liquids.

FIG. 1 depicts a simplified system for producing cellulose esters. The system of FIG. 1 generally includes a dissolution zone 20, an esterification zone 40, a cellulose ester recovery/treatment zone 50, and an ionic liquid recovery/treatment zone 60.

As shown in FIG. 1, cellulose and an ionic liquid ("IL") can be fed to dissolution zone 20 via lines 62 and 64, respectively. In dissolution zone 20, the cellulose can be dissolved to form an initial cellulose solution comprising the cellulose and the ionic liquid. The initial cellulose solution can then be transported to esterification zone 40. In esterification zone 40, a reaction medium comprising the dissolved cellulose can be subjected to reaction conditions sufficient to at least partially esterify the cellulose, thereby producing an initial cellulose ester. An acylating reagent can be added to esterification zone 40 and/or dissolution zone 20 to help facilitate esterification of the dissolved cellulose in esterification zone 40.

As illustrated in FIG. 1, an esterified medium can be withdrawn from esterification zone 40 via line 80 and thereafter transported to cellulose ester recovery/treatment zone 50 where the initial cellulose ester can be recovered and treated to thereby produce a final cellulose ester that exits recovery/treatment zone 50 via line 90. A recycle stream is produced from cellulose ester recovery/treatment zone 50 via line 86. This recycle stream can comprise an altered ionic liquid derived from the ionic liquid originally introduced into dissolution zone 20. The recycle stream in line 86 can also include various other compounds including byproducts of reactions occurring in upstream zones 20,40, 50 or additives employed in upstream zones 20,40,50. The recycle stream in line 86 can be introduced into ionic liquid recovery/treatment zone 60 where it can be subjected to separation and/or reformation processes. A recycled ionic liquid can be produced from ionic liquid recovery/treatment zone 60 and can be routed back to dissolution zone 20 via line 70. Additional details of the streams, reactions, and steps involved in the cellulose ester production system of FIG. 1 are provided immediately below.

The cellulose fed to dissolution zone 20 via line 62 can be any cellulose known in the art that is suitable for use in the production of cellulose esters. In one embodiment, the cellulose suitable for use in the present invention can be obtained from soft or hard woods in the form of wood pulps, or from annual plants such as cotton or corn. The cellulose can be a β-1,4-linked polymer comprising a plurality of anhydroglucose monomer units. The cellulose suitable for use in the present invention can generally comprise the following structure:

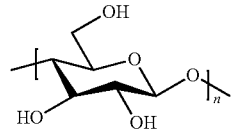

Additionally, the cellulose employed in the present invention can have an α-cellulose content of at least about 90 percent by weight, at least about 95 percent by weight, or at least 98 percent by weight.

The cellulose fed to dissolution zone 20 via line 62 can have a degree of polymerization ("DP") of at least about 10, at least about 250, at least about 1,000, or at least 5,000. As used herein, the term "degree of polymerization," when referring to cellulose and/or cellulose esters, shall denote the average number of anhydroglucose monomer units per cellulose polymer chain. Furthermore, the cellulose can have a weight average molecular weight in the range of from about 1,500 to about 850,000, in the range of from about 40,000 to about 200,000, or in the range of from 55,000 to about 160,000. Additionally, the cellulose suitable for use in the present invention can be in the form of a sheet, a hammer milled sheet, fiber, or powder. In one embodiment, the cellulose can be a powder having an average particle size of less than about 500 micrometers ("μm"), less than about 400 μm, or less than 300 μm.

The ionic liquid fed to dissolution zone 20 via line 64 can be any ionic liquid capable of at least partially dissolving cellulose. As used herein, the term "ionic liquid" shall denote any substance containing substantially only ions, and which has a melting point at a temperature of 200° C. or less. In one embodiment, the ionic liquid suitable for use in the present invention can be a cellulose dissolving ionic liquid. As used herein, the term "cellulose dissolving ionic liquid" shall denote any ionic liquid capable of dissolving cellulose in an amount sufficient to create an at least 0.1 weight percent cellulose solution. In one embodiment, the ionic liquid fed to dissolution zone 20 via line 64 can have a temperature at least 10° C. above the melting point of the ionic liquid. In another embodiment, the ionic liquid can have a temperature in the range of from about 0 to about 100° C., in the range of from about 20 to about 80° C., or in the range of from 25 to 50° C.

In one embodiment, the ionic liquid fed to dissolution zone 20 via line 64 can comprise water, nitrogen-containing bases, alcohol, or carboxylic acid. The ionic liquid in line 64 can comprise less than about 15 weight percent of each of water, nitrogen-containing bases, alcohol, and carboxylic acid; less than about 5 weight percent of each of water, nitrogen-containing bases, alcohol, and carboxylic acid; or less than 2 weight percent of each of water, nitrogen-containing bases, alcohol, and carboxylic acid.

As mentioned above, an ionic liquid comprises ions. These ions include both cations (i.e., positively charged ions) and anions (i.e., negatively charged ions). In one embodiment, the cations of the ionic liquid suitable for use in the present invention can include, but are not limited to, imidazolium, pyrazolium, oxazolium, 1,2,4-triazolium, 1,2,3-triazolium, and/or thiazolium cations, which correspond to the following structures:

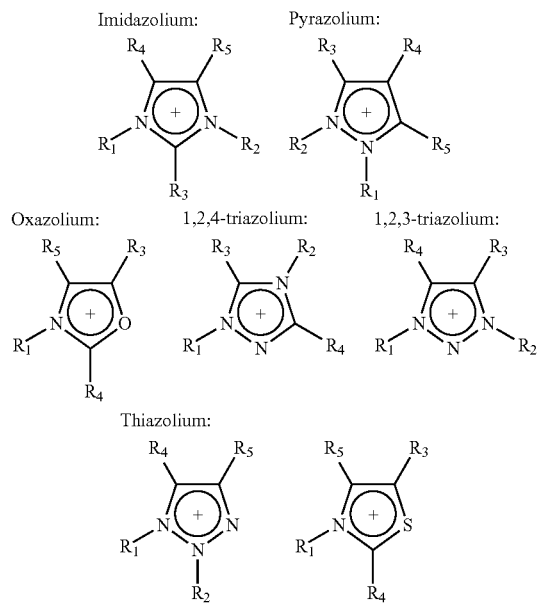

In the above structures, $R_1$ and $R_2$ can independently be a $C_1$ to $C_8$ alkyl group, a $C_2$ to $C_8$ alkenyl group, or a $C_1$ to $C_8$ alkoxyalkyl group. $R_3$, $R_4$, and $R_5$ can independently be a hydrido, a $C_1$ to $C_8$ alkyl group, a $C_2$ to $C_8$ alkenyl group, a $C_1$ to $C_8$ alkoxyalkyl group, or a $C_1$ to $C_8$ alkoxy group. In one embodiment, the cation of the ionic liquid used in the present invention can comprise an alkyl substituted imidazolium cation, where $R_1$ is a $C_1$ to $C_4$ alkyl group, and $R_2$ is a different $C_1$ to $C_4$ alkyl group.

In one embodiment of the present invention, the cellulose dissolving ionic liquid can be a carboxylated ionic liquid. As used herein, the term "carboxylated ionic liquid" shall denote any ionic liquid comprising one or more carboxylate anions. Carboxylate anions suitable for use in the carboxylated ionic liquids of the present invention include, but are not limited to, $C_1$ to $C_{20}$ straight- or branched-chain carboxylate or substituted carboxylate anions. Examples of suitable carboxylate anions for use in the carboxylated ionic liquid include, but are not limited to, formate, acetate, propionate, butyrate, valerate, hexanoate, lactate, oxalate, or chloro-, bromo-, fluoro-substituted acetate, propionate, or butyrate and the like. In one embodiment, the anion of the carboxylated ionic liquid can be a $C_2$ to $C_6$ straight-chain carboxylate. Furthermore, the anion can be acetate, propionate, butyrate, or a mixture of acetate, propionate, and/or butyrate.

Examples of carboxylated ionic liquids suitable for use in the present invention include, but are not limited to, 1-ethyl-3-methylimidazolium acetate, 1-ethyl-3-methylimidazolium propionate, 1-ethyl-3-methylimidazolium butyrate, 1-butyl-3-methylimidazolium acetate, 1-butyl-3-methylimidazolium propionate, 1-butyl-3-methylimidazolium butyrate, or mixtures thereof.

In one embodiment of the present invention, the carboxylated ionic liquid can contain sulfur in an amount less than 200 parts per million by weight ("ppmw"), less than 100 ppmw, less than 50 ppmw, or less than 10 ppmw based on the total ion content of the carboxylated ionic liquid. Additionally, the carboxylated ionic liquid can contain a total halide content of less than 200 ppmw, less than 100 ppmw, less than 50 ppmw, or less than 10 ppmw based on the total ion content of the carboxylated ionic liquid. Furthermore, the carboxylated ionic liquid can contain a total metal content of less than 200 ppmw, less than 100 ppmw, less than 50 ppmw, or less than 10 ppmw based on the total ion content of the carboxylated ionic liquid. In one embodiment, carboxylated ionic liquid can contain transition metals in an amount less than 200 ppmw, less than 100 ppmw, less than 50 ppmw, or less than 10 ppmw. Sulfur, halide, and metal content of the carboxylated ionic liquid can be determined by x-ray fluorescence ("XRF") spectroscopy.

The carboxylated ionic liquid of the present invention can be formed by any process known in the art for making ionic liquids having at least one carboxylate anion. In one embodiment, the carboxylated ionic liquid of the present invention can be formed by first forming an intermediate ionic liquid. The intermediate ionic liquid can be any known ionic liquid that can participate in an anion exchange reaction.

In one embodiment, the intermediate ionic liquid can comprise a plurality of cations such as, for example, imidazolium, pyrazolium, oxazolium, 1,2,4-triazolium, 1,2,3-triazolium, and/or thiazolium cations, which correspond to the following structures:

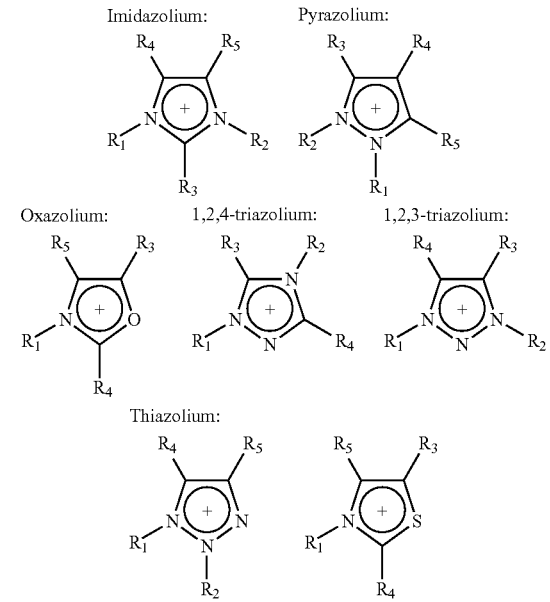

In the above structures, $R_1$ and $R_2$ can independently be a $C_1$ to $C_8$ alkyl group, a $C_2$ to $C_8$ alkenyl group, or a $C_1$ to $C_8$ alkoxyalkyl group. $R_3$, $R_4$, and $R_5$ can independently be a hydrido, a $C_1$ to $C_8$ alkyl group, a $C_2$ to $C_8$ alkenyl group, a $C_1$ to $C_8$ alkoxyalkyl group, or a $C_1$ to $C_8$ alkoxy group. In one embodiment, the cation of the intermediate ionic liquid used in the present invention can comprise an alkyl substituted imidazolium cation, where $R_1$ is a $C_1$ to $C_4$ alkyl group, and $R_2$ is a different $C_1$ to $C_4$ alkyl group. In one embodiment, the cation of the intermediate ionic liquid can comprise 1-ethyl-3-methylimidazolium or 1-butyl-3-methylimidazolium.

Additionally, the intermediate ionic liquid can comprise a plurality of anions. In one embodiment, the intermediate ionic liquid can comprise a plurality of carboxylate anions, such as, for example, formate, acetate, and/or propionate anions.

In one embodiment, the intermediate ionic liquid can comprise an alkyl amine formate. The amine cation of the alkyl amine formate can comprise any of the above-described substituted or unsubstituted imidazolium, pyrazolium, oxazolium, 1,2,4-triazolium, 1,2,3-triazolium, and/or thiazolium cations. In one embodiment, the amine of the alkyl amine formate can be an alkyl substituted imidazolium, alkyl substituted pyrazolium, alkyl substituted oxazolium, alkyl substituted triazolium, alkyl substituted thiazolium, and mixtures thereof. In one embodiment, the amine of the alkyl amine formate can be an alkyl substituted imidazolium. Examples of alkyl amine formates suitable for use in the present invention include, but are not limited to, 1-methyl-3-methylimidazolium formate, 1-ethyl-3-methylimidazolium formate, 1-propyl-3-methylimidazolium formate, 1-butyl-3-methylimidazolium formate, 1-pentyl-3-methylimidazolium formate, and/or 1-octyl-3-methylimidazolium formate.

The intermediate ionic liquid useful in the present invention can be formed by contacting at least one amine with at least one alkyl formate. Amines suitable for use in the present invention include, but are not limited to, substituted or unsubstituted imidazoles, pyrazoles, oxazoles, triazoles, and/or thiazoles. In one embodiment, the alkyl amine formate can be formed by contacting at least one alkyl substituted imidazole with at least one alkyl formate. Examples of alkyl substituted imidazoles suitable for use in forming the intermediate ionic liquid include, but are not limited to, 1-methylimidazole, 1-ethylimidazole, 1-propylimidazole, 1-butylimidazole, 1-hexylimidazole, and/or 1-octylimidazole. Examples of alkyl formates suitable for use in forming the intermediate ionic liquid include, but are not limited to, methyl formate, ethyl formate, propyl formate, isopropyl formate, butyl formate, isobutyl formate, tert-butyl formate, hexyl formate, octyl formate, and the like. In one embodiment, the alkyl formate used in forming the intermediate ionic liquid can comprise methyl formate.

Once the intermediate ionic liquid has been formed, the intermediate ionic liquid can be contacted with one or more carboxylate anion donors at a contact time, pressure, and temperature sufficient to cause the at least partial conversion of the intermediate ionic liquid to at least one of the above-mentioned carboxylated ionic liquids. Such interconversion can be accomplished via anion exchange between the carboxylate anion donor and the intermediate ionic liquid. In one embodiment, at least a portion of the formate of the alkyl amine formate can be replaced via anion exchange with a carboxylate anion originating from one or more carboxylate anion donors.

Carboxylate anion donors useful in the present invention can include any substance capable of donating at least one carboxylate anion. Examples of carboxylate anion donors suitable for use in the present invention include, but are not limited to, carboxylic acids, anhydrides, and/or alkyl carboxylates. In one embodiment, the carboxylate anion donor can comprise one or more $C_2$ to $C_{20}$ straight- or branched-chain alkyl or aryl carboxylic acids, anhydrides, or methyl esters. Additionally, the carboxylate anion donor can comprise one or more $C_2$ to $C_{12}$ straight-chain alkyl carboxylic acids, anhydrides, or methyl esters. Furthermore, the carboxylate anion donor can comprise one or more $C_2$ to $C_4$ straight-chain alkyl carboxylic acids, anhydrides, or methyl esters. In one embodiment, the carboxylate anion donor can comprise at least one anhydride, which can comprise acetic anhydride, propionic anhydride, butyric anhydride, isobutyric anhydride, valeric anhydride, hexanoic anhydride, 2-ethylhexanoic anhydride, nonanoic anhydride, lauric anhydride, palmitic anhydride, stearic anhydride, benzoic anhydride, substituted benzoic anhydrides, phthalic anhydride, isophthalic anhydride, and mixtures thereof.

The amount of carboxylate anion donor useful in the present invention can be any amount suitable to convert at least a portion of the intermediate ionic liquid to a carboxylated ionic liquid. In one embodiment, the carboxylate anion donor can be present in a molar ratio with the intermediate ionic liquid in the range of from about 1:1 to about 20:1 carboxylate anion donor-to-intermediate ionic liquid anion content, or in the range of from 1:1 to 6:1 carboxylate anion donor-to-intermediate ionic liquid anion content. In one embodiment, when alkyl amine formate is present as the intermediate ionic liquids, the carboxylate anion donor can be present in an amount in the range of from 1 to 20 molar equivalents per alkyl amine formate, or in the range of from 1 to 6 molar equivalents per alkyl amine formate.

The anion exchange between the intermediate ionic liquid and the carboxylate anion donor can be accomplished in the presence of at least one alcohol. Alcohols useful in the present invention include, but are not limited to, alkyl or aryl alcohols such as methanol, ethanol, n-propanol, i-propanol, n-butanol, i-butanol, t-butanol, phenol, and the like. In one embodiment, the alcohol can be methanol. The amount of alcohol present in the contact mixture during interconversion of the intermediate ionic liquid can be in the range of from about 0.01 to about 20 molar equivalents of the ionic liquid, or in the range of from 1 to 10 molar equivalents of the ionic liquid.

In one embodiment, water can be present in the contact mixture during the anion exchange between the intermediate ionic liquid and the carboxylate anion donor. The amount of water present in the contact mixture during interconversion of the intermediate ionic liquid can be in the range of from about 0.01 to about 20 molar equivalents of the ionic liquid, or in the range of from 1 to 10 molar equivalents of the ionic liquid.

As mentioned above, the interconversion of the intermediate ionic liquid to the carboxylated ionic liquid can be performed at a contact time, pressure, and temperature sufficient to cause the at least partial conversion of the intermediate ionic liquid to the carboxylated ionic liquid. In one embodiment, the interconversion can be performed for a time in the range of from about 1 minute to about 24 hours, or in the range of from 30 minutes to 18 hours. Additionally, the interconversion can be performed at a pressure up to 21,000 kPa, or up to 10,000 kPa. In one embodiment, the interconversion can be performed at a pressure in the range of from about 100 to about 21,000 kPa, or in the range of from 100 to 10,000 kPa. Furthermore, the interconversion can be performed at a temperature in the range of from about 0 to about 200° C., or in the range of from 25 to 170° C.

In one embodiment, the resulting carboxylated ionic liquid can comprise carboxylate anions comprising substituted or non-substituted $C_1$ to $C_{20}$ straight- or branched-chain carboxylate anions. In one embodiment, the carboxylate anion can comprise a $C_2$ to $C_6$ straight-chain carboxylate anion. Additionally, the carboxylated ionic liquid can comprise carboxylate anions such as, for example, formate, acetate, propionate, butyrate, valerate, hexanoate, lactate, and/or oxalate. In one embodiment, the carboxylated ionic liquid can comprise at least 50 percent carboxylate anions, at least 70 percent carboxylate anions, or at least 90 percent carboxylate anions. In another embodiment, the carboxylated ionic liquid can comprise at least 50 percent acetate anions, at least 70 percent acetate anions, or at least 90 percent acetate anions.

In an alternative embodiment of the present invention, the above-mentioned cellulose dissolving ionic liquid can be a halide ionic liquid. As used herein, the term "halide ionic liquid" shall denote any ionic liquid that contains at least one halide anion. In one embodiment, the halide anion of the halide ionic liquid can be fluoride, chloride, bromide, and/or iodide. In another embodiment, the halide anion can be chloride and/or bromide. Additionally, as mentioned above, the cation of the cellulose dissolving ionic liquid can comprise, but is not limited to, imidazolium, pyrazolium, oxazolium, 1,2,4-triazolium, 1,2,3-triazolium, and/or thiazolium cations. Any method known in the art suitable for making a halide ionic liquid can be employed in the present invention.

Examples of halide ionic liquids suitable for use in the present invention include, but are not limited to, 1-butyl-3-methylimidazolium chloride, 1-propyl-3-methylimidazolium chloride, 1-ethyl-3-methylimidazolium chloride, 1-allyl-3-methylimidazolium chloride, or mixtures thereof.

Referring again to FIG. 1, the weight percent of the amount of cellulose fed to dissolution zone 20 to the cumulative amount of ionic liquid (including recycled ionic liquid) fed to dissolution zone 20 can be in the range of from about 1 to about 40 weight percent, in the range of from about 5 to about 25 weight percent, or in the range of from 10 to 20 weight percent based on the combined weight of cellulose and ionic liquid. In one embodiment, the resulting medium formed in dissolution zone 20 can comprise other components, such as, for example, water, alcohol, acylating reagent, and/or carboxylic acids. In one embodiment, the medium formed in dissolution zone 20 can comprise water in an amount in the range of from about 0.001 to about 200 weight percent, in the range of from about 1 to about 100 weight percent, or in the range of from 5 to 15 weight percent based on the entire weight of the medium. Additionally, the medium formed in dissolution zone 20 can comprise a combined concentration of alcohol in an amount in the range of from about 0.001 to about 200 weight percent, in the range of from about 1 to about 100 weight percent, or in the range of from 5 to 15 weight percent based on the entire weight of the medium.

The medium formed in dissolution zone 20 can optionally comprise one or more carboxylic acids. The medium formed in dissolution zone 20 can comprise a total concentration of carboxylic acids in the range of from about 0.01 to about 25 weight percent, in the range of from about 0.05 to about 15 weight percent, or in the range of from 0.1 to 5 weight percent based on the total concentration of ionic liquid in the medium formed in dissolution zone 20. Examples of suitable carboxylic acids useful in this embodiment include, but are not limited to, acetic acid, propionic acid, butyric acid, isobutyric acid, valeric acid, hexanoic acid, 2-ethylhexanoic acid, nonanoic acid, lauric acid, palmitic acid, stearic acid, benzoic acid, substituted benzoic acids, phthalic acid, and isophthalic acid. In one embodiment, the carboxylic acid in the medium formed in dissolution zone 20 can comprise acetic acid, propionic acid, and/or butyric acid.

As is described in more detail below with reference to FIG. 2, at least a portion of the carboxylic acids present in the medium formed in dissolution zone 20 can originate from a recycled carboxylated ionic liquid introduced via line 70. Though not wishing to be bound by theory, the inventors have unexpectedly found that the use of carboxylic acid in the medium formed in dissolution zone 20 can reduce the viscosity of the cellulose/ionic liquid solution, thereby enabling easier processing of the solution. Additionally, the presence of carboxylic acid in the medium in dissolution zone 20 appears to reduce the melting points of the ionic liquids employed, thereby allowing processing of the ionic liquids at lower temperatures than predicted.

The medium formed in dissolution zone 20 can optionally comprise an acylating reagent, as is discussed in more detail below. The optional acylating reagent can be introduced into dissolution zone 20 via line 78. In one embodiment, the medium formed in dissolution zone 20 can comprise acylating reagent in an amount in the range of from about 0.01 molar equivalents to about 20 molar equivalents, in the range of from about 0.5 molar equivalents to about 10 molar equivalents, or in the range of from 1.8 molar equivalents to about 4 molar equivalents based on the total amount of cellulose in the medium in dissolution zone 20.

The medium formed in dissolution zone 20 can also comprise recycled ionic liquid, as is discussed in more detail below with reference to FIG. 2. The recycled ionic liquid can be introduced into dissolution zone 20 via line 70. The medium formed in dissolution zone 20 can comprise recycled ionic liquid in an amount in the range of from about 0.01 to about 99.99 weight percent, in the range of from about 10 to about 99 weight percent, or in the range of from 90 to 98 weight percent based on the total amount of ionic liquid in dissolution zone 20.

In one embodiment, the medium can optionally comprise immiscible or substantially immiscible co-solvents. Such co-solvents can comprise one or more co-solvents that are immiscible or sparingly soluble with the cellulose-ionic liquid mixture. Surprisingly, the addition of an immiscible or sparingly soluble co-solvent does not cause precipitation of the cellulose upon contacting the cellulose-ionic liquid mixture. However, upon contact with an acylating reagent, as will be discussed in more detail below, the cellulose can be esterified which can change the solubility of the now cellulose ester-ionic liquid solution with respect to the formerly immiscible or sparingly soluble co-solvent. Accordingly, subsequent to esterification, the contact mixture can become a single phase or highly dispersed mixture of cellulose ester-ionic liquid in the co-solvent. The resulting single phase or dispersed phase has much lower solution viscosity than the initial cellulose-ionic liquid solution.

This discovery is significant in that heretofore highly viscous cellulose solutions can now be used to make cellulose esters while still maintaining the ability to mix and process the solution. The discovery also provides a viable method to process highly viscous cellulose-ionic liquid solutions at lower contact temperatures.

Immiscible or sparingly soluble co-solvents suitable for use in the present invention can comprise alkyl or aryl esters, ketones, alkyl halides, hydrophobic ionic liquids, and the like. Specific examples of immiscible or sparingly soluble co-solvents include, but are not limited to, methyl acetate, ethyl acetate, isopropyl acetate, methyl propionate, methyl butyrate, acetone, methyl ethyl ketone, chloroform, methylene chloride, alkyl imidazolium hexafluorophosphate, alkyl imidazolium triflimide, and the like. In one embodiment, the immiscible or sparingly soluble co-solvents can comprise methyl acetate, methyl propionate, methyl butyrate, methyl ethyl ketone, and/or methylene chloride. The weight ratio of immiscible or sparingly soluble co-solvents to cellulose-ionic liquid mixture can be in the range of from about 1:20 to about 20:1, or in the range of from 1:5 to 5:1.

In one embodiment, the cellulose entering dissolution zone 20 via line 62 can initially be dispersed in the ionic liquid. Dispersion of the cellulose in the ionic liquid can be achieved by any mixing means known in the art. In one embodiment, dispersion of the cellulose can be achieved by mechanical mixing, such as mixing by one or more mechanical homogenizers.

After the cellulose has been dispersed in the ionic liquid, dissolution of the cellulose in dissolution zone 20, along with removal of at least a portion of any volatile components in the mixture, can be achieved using any method known in the art. For example, dissolution of the cellulose can be achieved by lowering the pressure and/or raising the temperature of the cellulose/ionic liquid dispersion initially formed in dissolution zone 20. Accordingly, after the cellulose is dispersed in the ionic liquid, the pressure can be lowered in dissolution zone 20. In one embodiment, the pressure in dissolution zone 20 can be lowered to less than about 100 millimeters mercury ("mm Hg"), or less than 50 mm Hg. Additionally, the cellulose/ionic liquid dispersion can be heated to a temperature in the range of from about 60 to about 100° C., or in the range of from 70 to about 85° C. After dissolution, the resulting solution can be maintained at the above-described temperatures and pressures for a time in the range of from about 0 to about 100 hours, or in the range of from about 1 to about 4 hours. The cellulose solution formed in dissolution zone 20 can comprise cellulose in an amount in the range of from about 1 to about 40 weight percent, or in the range of from 5 to 20 weight percent, based on the entire weight of the solution. In another embodiment, the cellulose solution formed in dissolution zone 20 can comprise dissolved cellulose in an amount of at least 10 weight percent based on the entire weight of the solution.

After dissolution, at least a portion of the resulting cellulose solution can be removed from dissolution zone 20 via line 66 and routed to esterification zone 40. In one embodiment, at least one acylating reagent can be introduced into esterification zone 40 to esterify at least a portion of the cellulose. As mentioned above, in another embodiment, at least one acylating reagent can be introduced into dissolution zone 20. Additionally, the acylating reagent can be added after the cellulose has been dissolved in the ionic liquid. Optionally, at least a portion of the acylating reagent can be added to the ionic liquids prior to dissolution of the cellulose in the ionic liquid. Regardless of where the acylating reagent is added, at least a portion of the cellulose in esterification zone 40 can undergo esterification subsequent to being contacted with the acylating reagent.

As used herein, the term "acylating reagent" shall denote any chemical compound capable of donating at least one acyl group to a cellulose. As used herein, the term "acyl group" shall denote any organic radical derived from an organic acid by the removal of a hydroxyl group. Acylating reagents useful in the present invention can be one or more $C_1$ to $C_{20}$ straight- or branched-chain alkyl or aryl carboxylic anhydrides, carboxylic acid halides, diketene, or acetoacetic acid esters. Examples of carboxylic anhydrides suitable for use as acylating reagents in the present invention include, but are not limited to, acetic anhydride, propionic anhydride, butyric anhydride, isobutyric anhydride, valeric anhydride, hexanoic anhydride, 2-ethylhexanoic anhydride, nonanoic anhydride, lauric anhydride, palmitic anhydride, stearic anhydride, benzoic anhydride, substituted benzoic anhydrides, phthalic anhydride, and isophthalic anhydride. Examples of carboxylic acid halides suitable for use as acylating reagents in the present invention include, but are not limited to, acetyl, propionyl, butyryl, hexanoyl, 2-ethylhexanoyl, lauroyl, palmitoyl, benzoyl, substituted benzoyl, and stearoyl chlorides. Examples of acetoacetic acid esters suitable for use as acylating reagents in the present invention include, but are not limited to, methyl acetoacetate, ethyl acetoacetate, propyl acetoacetate, butyl acetoacetate, and tert-butyl acetoacetate. In one embodiment, the acylating reagents can be $C_2$ to $C_9$ straight- or branched-chain alkyl carboxylic anhydrides selected from the group consisting of acetic anhydride, propionic anhydride, butyric anhydride, 2-ethylhexanoic anhydride, and nonanoic anhydride.

The reaction medium formed in esterification zone 40 can comprise cellulose in an amount in the range of from about 1 to about 40 weight percent, in the range of from about 5 to about 25 weight percent, or in the range of from 10 to 20 weight percent, based on the weight of the ionic liquid in the reaction medium. Additionally, the reaction medium formed in esterification zone 40 can comprise ionic liquid in an amount in the range of from about 20 to about 98 weight percent, in the range of from about 30 to about 95 weight percent, or in the range of from 50 to 90 weight percent based on the total weight of the reaction medium. Furthermore, the reaction medium formed in esterification zone 40 can comprise acylating reagent in an amount in the range of from about 1 to about 50 weight percent, in the range of from about 5 to about 30 weight percent, or in the range of from 10 to 20 weight percent based on the total weight of the reaction medium. Furthermore, the reaction medium formed in esterification zone 40 can have a cumulative concentration of nitrogen containing bases and carboxylic acids in an amount less than 15 weight percent, less than 5 weight percent, or less than 2 weight percent.

In one embodiment, the weight ratio of cellulose-to-acylating reagent in esterification zone 40 can be in the range of from about 90:10 to about 10:90, in the range of from about 60:40 to about 25:75, or in the range of from 45:55 to 35:65. In one embodiment, the acylating reagent can be present in esterification zone 40 in an amount less than 5, less than 4, less than 3, or less than 2.7 molar equivalents per anhydroglucose unit.

In one embodiment of the present invention, when a halide ionic liquid is employed as the cellulose dissolving ionic liquid, a limited excess of acylating reagent can be employed in the esterification of the cellulose to achieve a cellulose ester with a particular DS. Thus, in one embodiment, less than 20 percent molar excess, less than 10 percent molar excess, less than 5 percent molar excess, or less than 1 percent excess of acylating reagent can be employed during esterification.

In a preferred embodiment of the present invention when 2 or more acylating reagents are employed in the esterification of cellulose, the 2 or more acylating reagents can be added as a mixture or the addition can be staged. In a staged addition, the acylating reagents are added consecutively.

Preferably, in a staged addition at least about 80 molar percent of the first acylating reagent is allowed to react with the cellulose prior to adding the next acylating reagent.

Optionally, one or more catalysts can be introduced into esterification zone 40 to aid in esterification of the cellulose. The catalyst employed in the present invention can be any catalyst that increases the rate of esterification in esterification zone 40. Examples of catalysts suitable for use in the present invention include, but are not limited to, protic acids of the type sulfuric acid, alkyl sulfonic acids, aryl sulfonic acids, functional ionic liquids, and weak Lewis acids of the type MXn, where M is a transition metal exemplified by B, Al, Fe, Ga, Sb, Sn, As, Zn, Mg, or Hg, and X is halogen, carboxylate, sulfonate, alkoxide, alkyl, or aryl. In one embodiment, the catalyst is a protic acid. The protic acid catalysts can have a pKa in the range of from about −5 to about 10, or in the range of from −2.5 to 2.0. Examples of suitable protic acid catalysts include methane sulfonic acid ("MSA"), p-toluene sulfonic acid, and the like. In one embodiment, the one or more catalysts can be Lewis acids. Examples of Lewis acids suitable for use as catalysts include $ZnCl_2$, $Zn(OAc)_2$, and the like. When a catalyst is employed, the catalyst can be added to the cellulose solution prior to adding the acylating reagent. In another embodiment the catalyst can be added to the cellulose solution as a mixture with the acylating reagent.

Additionally, functional ionic liquids can be employed as catalysts during esterification of the cellulose. Functional ionic liquids are ionic liquids containing specific functional groups, such as hydrogen sulfonate, alkyl or aryl sulfonates, and carboxylates, that effectively catalyze the esterification of cellulose by the acylating reagent. Examples of functional ionic liquids include 1-alkyl-3-methylimidazolium hydrogen sulfate, methyl sulfonate, tosylate, and trifluoroacetate, where the alkyl can be a $C_1$ to $C_{10}$ straight-chain alkyl group. Additionally, suitable functional ionic liquids for use in the present invention are those in which the functional group is covalently linked to the cation. Thus, functional ionic liquids can be ionic liquids containing functional groups, and are capable of catalyzing the esterification of cellulose with an acylating reagent.

An example of a covalently-linked functional ionic liquid suitable for use in the present invention includes, but is not limited to, the following structure:

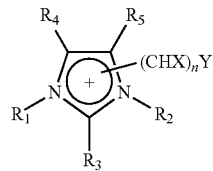

where at least one of the $R_1$, $R_2$, $R_3$, $R_4$, $R_5$ groups are replaced with the group $(CHX)_nY$, where X is hydrogen or halide, n is an integer in the range of from 1 to 10, and Y is sulfonic or carboxylate and the remainder $R_1$, $R_2$, $R_3$, $R_4$, $R_5$ groups are those previously described in relation to the cations suitable for use as the cellulose dissolving ionic liquid. Examples of cations suitable for use in the functional ionic liquids to be used in the present invention include, but are not limited to, 1-alkyl-3-(1-carboxy-2,2-difluoroethyl) imidazolium, 1-alkyl-3-(1-carboxy-2,2-difluoropropyl)imidazolium, 1-alkyl-3-(1-carboxy-2,2-difluoro-butyl)imidazolium, 1-alkyl-3-(1-carboxy-2,2-difluorohexyl)imidazolium, 1-alkyl-3-(1-sulfonylethyl)imidazolium, 1-alkyl-3-(1-sulfonylpropyl)imidazolium, 1-alkyl-3-(1-sulfonylbutyl)imidazolium, and 1-alkyl-3-(1-sulfonylhexyl)imidazolium, where the alkyl can be a $C_1$ to $C_{10}$ straight-chain alkyl group.

The amount of catalyst used to catalyze the esterification of cellulose may vary depending upon the type of catalyst employed, the type of acylating reagent employed, the type of ionic liquid, the contact temperature, and the contact time. Thus, a broad concentration of catalyst employed is contemplated by the present invention. In one embodiment, the amount of catalyst employed in esterification zone 40 can be in the range of from about 0.01 to about 30 mol percent catalyst per anhydroglucose unit ("AGU"), in the range of from about 0.05 to about 10 mol percent catalyst per AGU, or in the range of from 0.1 to 5 mol percent catalyst per AGU. In one embodiment, the amount of catalyst employed can be less than 30 mol percent catalyst per AGU, less than 10 mol percent catalyst per AGU, less than 5 mol percent catalyst per AGU, or less than 1 mol percent catalyst per AGU. In another embodiment, when a catalyst is employed as a binary component, the amount of binary component employed can be in the range of from about 0.01 to about 100 mol percent per AGU, in the range of from about 0.05 to about 20 mol percent per AGU, or in the range of from 0.1 to 5 mol percent per AGU.

The inventors have discovered a number of surprising and unpredictable advantages apparently associated with employing a catalyst as a binary component during the esterification of cellulose. For example, the inventors have discovered that the inclusion of a binary component can accelerate the rate of esterification. Very surprisingly, the binary component can also serve to improve solution and product color, prevent gellation of the esterification mixture, provide increased DS values in relation to the amount of acylating reagent employed, and/or help to decrease the molecular weight of the cellulose ester product. Though not wishing to be bound by theory, it is believed that the use of a binary component acts to change the network structure of the ionic liquid containing the dissolved cellulose ester. This change in network structure may lead to the observed surprising and unpredicted advantages of using the binary component.

As mentioned above, at least a portion of the cellulose can undergo an esterification reaction in esterification zone 40. The esterification reaction carried out in esterification zone 40 can operate to convert at least a portion of the hydroxyl groups contained on the cellulose to ester groups, thereby forming a cellulose ester. As used herein, the term "cellulose ester" shall denote a cellulose polymer having at least one ester substituent. Furthermore, the term "mixed cellulose ester" shall denote a cellulose ester having at least two different ester substituents on a single cellulose ester polymer chain. In one embodiment, at least a portion of the ester groups on the resulting cellulose ester can originate from the above-described acylating reagent. The cellulose esters thus prepared can comprise the following structure:

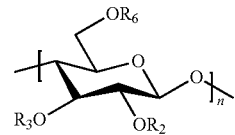

where $R_2$, $R_3$, and $R_6$ can independently be hydrogen, so long as $R_2$, $R_3$, and $R_6$ are not all hydrogen simultaneously, or a $C_1$ to $C_{20}$ straight- or branched-chain alkyl or aryl groups bound to the cellulose via an ester linkage.

In one embodiment, when the ionic liquid employed is a carboxylated ionic liquid, one or more of the ester groups on the resulting cellulose ester can originate from the ionic liquid in which the cellulose is dissolved. The amount of ester groups on the resulting cellulose ester that originate from the carboxylated ionic liquid can be at least 10 percent, at least 25 percent, at least 50 percent, or at least 75 percent.

Additionally, the ester group on the cellulose ester originating from the carboxylated ionic liquid can be a different ester group than the ester group on the cellulose ester that originates from the acylating reagent. Though not wishing to be bound by theory, it is believed that when an acylating reagent is introduced into a carboxylated ionic liquid, an anion exchange can occur such that a carboxylate ion originating from the acylating reagent replaces at least a portion of the carboxylate anions in the carboxylated ionic liquid, thereby creating a substituted ionic liquid. When the carboxylate ion originating from the acylating reagent is of a different type than the carboxylate anions of the ionic liquid, then the substituted ionic liquid can comprise at least two different types of carboxylate anions. Thus, so long as the carboxylate anion from the carboxylated ionic liquid comprises a different acyl group than is found on the acylating reagent, at least two different acyl groups are available for esterification of the cellulose. By way of illustration, if cellulose was dissolved in 1-butyl-3-methyl-imidazolium acetate ("[BMIm]OAc" or "[BMIm]acetate") and a propionic anhydride ("Pr$_2$O") acylating reagent were added to the carboxylated ionic liquid, the carboxylated ionic liquid can become a substituted ionic liquid, comprising a mixture of [BMIm]acetate and [BMIm]propionate. Thus, the process of forming a cellulose ester via this process can be illustrated as follows:

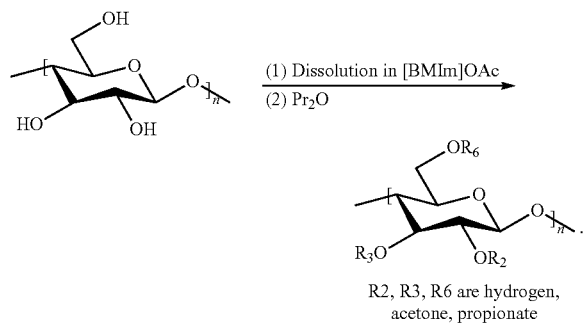

R2, R3, R6 are hydrogen, acetone, propionate

As illustrated, contacting a solution of cellulose dissolved in [BMIm]acetate with a propionic anhydride can result in the formation of a cellulose ester comprising both acetate ester substituents and propionate ester substituents. Thus, at least a portion of the ester groups on the cellulose ester can originate from the ionic liquid, and at least a portion of the ester groups can originate from the acylating reagent. Additionally, at least one of the ester groups donated by the ionic liquid can be an acyl group. In one embodiment, all of the ester groups donated by the ionic liquid can be acyl groups.

Therefore, in one embodiment, the cellulose ester prepared by methods of the present invention can be a mixed cellulose ester. In one embodiment, the mixed cellulose ester of the present invention can comprise a plurality of first pendant acyl groups and a plurality of second acyl groups, where the first pendant acyl groups originate from the ionic liquid, and the second pendant acyl groups originate from the acylating reagent. In one embodiment, the mixed cellulose ester can comprise a molar ratio of at least two different acyl pendant groups in the range of from about 1:10 to about 10:1, in the range of from about 2:8 to about 8:2, or in the range of from 3:7 to 7:3. Additionally, the first and second pendant acyl groups can comprise acetyl, propionyl, and/or butyryl groups.

In one embodiment, at least one of the first pendant acyl groups can be donated by the ionic liquid or at least one of the second pendant acyl groups can be donated by the ionic liquid. As used herein, the term "donated," with respect to esterification, shall denote a direct transfer of an acyl group. Comparatively, the term "originated," with respect to esterification, can signify either a direct transfer or an indirect transfer of an acyl group. In one embodiment of the invention, at least 50 percent of the above-mentioned first pendant acyl groups can be donated by the ionic liquid, or at least 50 percent of the second pendant acyl groups can be donated by the ionic liquid. Furthermore, at least 10 percent, at least 25 percent, at least 50 percent, or at least 75 percent of all of the pendant acyl groups on the resulting cellulose ester can result from donation of an acyl group by the ionic liquid.

In one embodiment, the above-described mixed cellulose ester can be formed by a process where a first portion of the first pendant acyl groups can initially be donated from the acylating reagent to the carboxylated ionic liquid, and then the same acyl groups can be donated from the carboxylated ionic liquid to the cellulose (i.e., indirectly transferred from the acylating reagent to the cellulose, via the ionic liquid). Additionally, a second portion of the first pendant acyl groups can be donated directly from the acylating reagent to the cellulose.

In a further embodiment of the present invention when 2 or more acylating reagents are employed in the esterification of cellulose, the 2 or more acylating reagents can be added as a mixture or the addition can be staged. In a mixed addition, 2 or more acylating reagents are added to the cellulose solution simultaneously. In the case of carboxylated ionic liquids, where one of the acyl groups are donated by the ionic liquid, addition of one or more acylating reagents constitutes a mixed addition. In a staged addition, the acylating reagents are added consecutively. In one embodiment of the staged addition process, at least about 80 mol percent of the first acylating reagent is allowed to react with the cellulose prior to adding the next acylating reagent.

In one aspect of the present invention, when contacting one or more acylating reagents with the cellulose solution reaction kinetics, the amount of acylating reagent that is added, and the order of which they are added can also significantly influence substituent distribution or regioselectivity when the total DS is less than about 2.95.

Regioselectivity is most easily measured by determining the relative degree of substitution (RDS) at $C_6$, $C_3$, and $C_2$ in the cellulose ester by carbon 13 NMR (Macromolecules, 1991, 24, 3050-3059). In the case of one acyl substituent or when a second acyl substituent is present in a minor amount (DS≤0.2), the RDS can be most easily determined directly by integration of the ring carbons. When 2 or more acyl substituents are present in more equal amounts, in addition to determining the ring RDS it is sometimes necessary to fully substitute the cellulose ester with an additional substituent in order to independently determine the RDS of each substituent by integration of the carbonyl carbons. In conventional cellulose esters, regioselectivity is generally not observed, and the RDS ratio of $C_6/C_3$, $C_6/C_2$, or $C_3/C_2$ is generally near 1. In essence, conventional cellulose esters are random copolymers.

In the present invention, we found that when adding one or more acylating reagents, the $C_6$ position of cellulose was acylated much faster than $C_2$ and $C_3$. Consequentially, the $C_6/C_3$ and $C_6/C_2$ RDS ratios are greater than 1 which is characteristic of a regioselectively substituted cellulose ester. The degree of regioselectivity depends upon at least one of the following factors: type of acyl substituent, contact temperature, ionic liquid interaction, equivalents of acyl reagent, order of additions, and the like. Typically, the larger the number of carbon atoms in the acyl substituent, the $C_6$ position of the cellulose is acylated preferentially over the $C_2$ and $C_3$ position. In addition, as the contact temperature is lowered in the esterification zone 40, the $C_6$ position of the cellulose can be acylated preferentially over the $C_2$ or $C_3$ position. As mentioned previously, the type of ionic liquid and its interaction with cellulose in the process can affect the regioselectivity of the cellulose ester. For example, when carboxylated ionic liquids are utilized, a regioselectively substituted cellulose ester is produced where the RDS ratio is $C_6>C_2>C_3$. When halide ionic liquids are utilized, a regioselectively substituted cellulose ester is produced where the RDS ratio is $C_6>C_3>C_2$. This is significant in that regioselective placement of substituents in a cellulose ester leads to regioselectively substituted cellulose esters with different physical properties relative to conventional cellulose esters.

In one embodiment of this invention, no protective groups are utilize to prevent reaction of the cellulose with the acylating reagent.

In one embodiment of the present invention, the ring RDS ratio for $C_6/C_3$ or $C_6/C_2$ is at least 1.05. In another embodiment, the ring RDS ratio for $C_6/C_3$ or $C_6/C_2$ is at least 1.1. Another embodiment of the present invention is when the ring $R_{DS}$ ratio for $C_6/C_3$ or $C_6/C_2$ is at least 1.3.

In another embodiment of the present invention, the product of the ring RDS ratio for $C_6/C_3$ or $C_6/C_2$ times the total DS $[(C_6/C_3)*DS$ or $(C_6/C_2)*DS]$ is at least 2.9. In another embodiment, the product of the ring RDS ratio for $C_6/C_3$ or $C_6/C_2$ times the total DS is at least 3.0. In another embodiment, the product of the ring RDS ratio for $C_6/C_3$ or $C_6/C_2$ times the total DS is at least 3.2.

In another embodiment of the present invention, the ring RDS ratio for $C_6/C_4$ or $C_6/C_2$ is at least 1.05, and the product of the ring RDS ratio for $C_6/C_3$ or $C_6/C_2$ times the total DS is at least 2.9. In another embodiment, the ring RDS ratio for $C_6/C_3$ or $C_6/C_2$ is at least 1.1, and the product of the ring RDS ratio for $C_6/C_3$ or $C_6/C_2$ times the total DS is at least 3.0. In yet another embodiment, the ring RDS ratio for $C_6/C_3$ or $C_6/C_2$ is at least 1.3, and the product of the ring RDS ratio for $C_6/C_3$ or $C_6/C_2$ times the total DS is at least 3.2.

As noted previously, when 2 or more acyl substituents are present in more equal amounts, it is sometimes desirable to integrate the carbonyl carbons in order to determine the RDS of each substituent independently. Hence, in one embodiment of the present invention, the carbonyl RDS ratio of at least one acyl substituent for $C_6/C_3$ or $C_6/C_2$ is at least 1.3. In another embodiment, the carbonyl RDS ratio of at least one acyl substituent for $C_6/C_3$ or $C_6/C_2$ is at least 1.5. In another embodiment, the carbonyl RDS ratio of at least one acyl substituent for $C_6/C_3$ or $C_6/C_2$ is at least 1.7.

In another embodiment of the present invention, the product of the carbonyl RDS ratio of at least one acyl substituent for $C_6/C_3$ or $C_6/C_2$ times the DS of the acyl substituent $[(C_6/C_3)*DS_{acyl}$ or $(C_6/C_2)*DS_{acyl}]$ is at least 2.3. In another embodiment, the product of the carbonyl RDS ratio for $C_6/C_3$ or $C_6/C_2$ times the DS of the acyl substituent is at least 2.5. In another embodiment, the product of the carbonyl RDS ratio for $C_6/C_3$ or $C_6/C_2$ times the DS of the acyl substituent is at least 2.7. In another embodiment of the present invention, the carbonyl RDS ratio of at least one acyl substituent for $C_6/C_3$ or $C_6/C_2$ is at least 1.3, and the product of the carbonyl RDS ratio for $C_6/C_3$ or $C_6/C_2$ times the acyl DS is at least 2.3. In another embodiment, the carbonyl RDS ratio for $C_6/C_3$ or $C_6/C_2$ is at least 1.5, and the product of the carbonyl RDS ratio for $C_6/C_3$ or $C_6/C_2$ times the acyl DS is at least 2.5. In yet another embodiment, the carbonyl RDS ratio for $C_6/C_3$ or $C_6/C_2$ is at least 1.7 and the product of the carbonyl RDS ratio for $C_6/C_3$ or $C_6/C_2$ times the acyl DS is at least 2.7.

Surprisingly, in one embodiment of the invention, staged additions of the acylating reagent gave a relative degree of substitution (RDS) different from that obtained in the mixed addition of acylating reagent Moreover, both the staged and mixed additions of the present invention provide a different RDS relative to other means known in the prior art for making mixed cellulose esters which generally provide cellulose esters with a RDS at $C_6$, $C_3$, and $C_2$ of about 1:1:1. In some cases, the prior art methods provide a RDS where the RDS at $C_6$ is less than that of $C_2$ and $C_3$.

Referring still to FIG. 1, the temperature in esterification zone 40 during the above-described esterification process can be in the range of from about 0 to about 120° C., in the range of from about 20 to about 80° C., or in the range of from 25 to 50° C. Additionally, the cellulose can have a residence time in esterification zone 40 in the range of from about 1 minute to about 48 hours, in the range of from about 30 minutes to about 24 hours, or in the range of from 1 to 5 hours.

Subsequent to the above-described esterification process, an esterified medium can be withdrawn from esterification zone 40 via line 80. The esterified medium withdrawn from esterification zone 40 can comprise an initial cellulose ester. The initial cellulose ester in line 80 can be a regioselectively substituted cellulose ester. Additionally, as mentioned above, the initial cellulose ester in line 80 can be a mixed cellulose ester.

The initial cellulose ester can have a degree of substitution ("DS") in the range of from about 0.1 to about 3.5; about 0.1 to about 3.08, about 0.1 to about 3.0, about 1.8 to about 2.9, or in the range of from 2.0 to 2.6. In another embodiment, the initial cellulose ester can have a DS of at least 2. Additionally, the initial cellulose ester can have a DS of less than 3.0, or less than 2.9.

Furthermore, the degree of polymerization ("DP") of the cellulose esters prepared by the methods of the present invention can be at least 10, at least 50, at least 100, or at least 250. In another embodiment, the DP of the initial cellulose ester can be in the range of from about 5 to about 1,000, or in the range of from 10 to 250.

The esterified medium in line 80 can comprise the initial cellulose ester in an amount in the range of from about 2 to about 80 weight percent, in the range of from about 10 to about 60 weight percent, or in the range of from 20 to 40 weight percent based on weight of ionic liquid. In addition to the initial cellulose ester, the esterified medium withdrawn from esterification zone 40 via line 80 can also comprise other components, such as, for example, altered ionic liquid, residual acylating reagent, and/or one or more carboxylic acids. In one embodiment, the esterified medium in line 80 can comprise a ratio of altered ionic liquid to initial ionic liquid introduced into dissolution zone 20 in an amount in the range of from about 0.01 to about 99.99 weight percent, in the range of from about 10 to about 99 weight percent, or in the range of from 90 to 98 weight percent based on the total amount of initial ionic liquid. Additionally, the esterified medium in line 80 can comprise residual acylating reagent in an amount less than about 20 weight percent, less than about 10 weight percent, or less than 5 weight percent.

Furthermore, the esterified medium in line 80 can comprise a total concentration of carboxylic acids in an amount in the range of from about 0.01 to about 40 weight percent, in the range of from about 0.05 to about 20 weight percent, or in the range of from 0.1 to 5 weight percent. In another embodiment, the esterified medium in line 80 can comprise a total concentration of carboxylic acids in an amount less than 40, less than 20, or less than 5 weight percent. Carboxylic acids that can be present in the esterified medium in line 80 include, but are not limited to, formic acid, acetic acid, propionic acid, butyric acid, isobutyric acid, valeric acid, hexanoic acid, 2-ethyihexanoic acid, nonanoic acid, lauric acid, palmitic acid, stearic acid, benzoic acid, substituted benzoic acids, phthalic acid, and/or isophthalic acid.

The esterified medium in line 80 can be routed to cellulose ester recovery/treatment zone 50. As is discussed in more detail below with reference to FIG. 2, at least a portion of the cellulose ester can optionally be subjected to at least one randomization process in recovery/treatment zone 50, thereby producing a randomized cellulose ester. Additionally, as is discussed in more detail below with reference to FIG. 2, at least a portion of the cellulose ester can be caused to precipitate out of the esterified medium, at least a portion of which can thereafter be separated from the resulting mother liquor.

Referring still to FIG. 1, at least a portion of the cellulose ester precipitated and recovered in recovery/treatment zone 50 can be withdrawn via line 90 as a final cellulose ester. The final cellulose ester exiting recovery/treatment zone 50 via line 90 can have a number average molecular weight ("Mn") in the range of from about 1,200 to about 200,000, in the range of from about 6,000 to about 100,000, or in the range of from 10,000 to 75,000. Additionally, the final cellulose ester exiting recovery/treatment zone 50 via line 90 can have a weight average molecular weight ("Mw") in the range of from about 2,500 to about 420,000, in the range of from about 10,000 to about 200,000, or in the range of from 20,000 to 150,000. Furthermore, the final cellulose ester exiting recovery/treatment zone 50 via line 90 can have a Z average molecular weight ("Mz") in the range of from about 4,000 to about 850,000, in the range of from about 12,000 to about 420,000, or in the range of from 40,000 to 330,000. The final cellulose ester exiting recovery/treatment zone 50 via line 90 can have a polydispersity in the range of from about 1.3 to about 7, in the range of from about 1.5 to about 5, or in the range of from 1.8 to 3. Additionally, the final cellulose ester in line 90 can have a DP and DS as described above in relation to the initial cellulose ester in line 80. Furthermore, the cellulose ester can be random or non-random, as is discussed in more detail below with reference to FIG. 2. Moreover, the final cellulose ester in line 90 can comprise a plurality of ester substituents as described above. Also, the final cellulose ester in line 90 can optionally be a mixed cellulose ester as described above.

In one embodiment, the cellulose ester in line 90 can be in the form of a wet cake. The wet cake in line 90 can comprise a total liquid content of less than 99, less than 50, or less than 25 weight percent. Furthermore, the wet cake in line 90 can comprise a total ionic liquid concentration of less than 1, less than 0.01, or less than 0.0001 weight percent. Additionally, the wet cake in line 90 can comprise a total alcohol content of less than 100, less than 50, or less than 25 weight percent. Optionally, as is discussed in greater detail below with reference to FIG. 2, the final cellulose ester can be dried to produce a dry final cellulose ester product.

The cellulose esters prepared by the methods of this invention can be used in a variety of applications. Those skilled in the art will understand that the specific application will depend upon various characteristics of the cellulose ester, such as, for example, the type of acyl substituent, DS, molecular weight, and type of cellulose ester copolymer.

In one embodiment of the invention, the cellulose esters can be used in thermoplastic applications in which the cellulose ester is used to make film or molded objects. Examples of cellulose esters suitable for use in thermoplastic applications include cellulose acetate, cellulose propionate, cellulose butyrate, cellulose acetate propionate, cellulose acetate butyrate, or mixtures thereof.

In yet another embodiment of the invention, the cellulose esters can be used in coating applications. Examples of coating applications include but, are not limited to, automotive, wood, plastic, or metal coating processes. Examples of cellulose esters suitable for use in coating applications include cellulose acetate, cellulose propionate, cellulose butyrate, cellulose acetate propionate, cellulose acetate butyrate, or mixtures thereof.

In still another embodiment of the invention, the cellulose esters can be used in personal care applications. In personal care applications, cellulose esters can be dissolved or suspended in appropriate solvents. The cellulose ester can then act as a structuring agent, delivery agent, and/or film forming agent when applied to skin or hair. Examples of cellulose esters suitable for use in personal care applications include cellulose acetate, cellulose propionate, cellulose butyrate, cellulose acetate propionate, cellulose acetate butyrate, cellulose hexanoate, cellulose 2-ethylhexanoate, cellulose laurate, cellulose palmitate, cellulose stearate, or mixtures thereof.

In still another embodiment of the invention, the cellulose esters can be used in drug delivery applications. In drug delivery applications, the cellulose ester can act as a film former such as in the coating of tablets or particles. The cellulose ester can also be used to form amorphous mixtures of poorly soluble drugs, thereby improving the solubility and bioavailability of the drugs. The cellulose esters can also be used in controlled drug delivery, where the drug can be released from the cellulose ester matrix in response to external stimuli such as a change in pH. Examples of preferred cellulose esters suitable for use in drug delivery applications include cellulose acetate, cellulose propionate, cellulose butyrate, cellulose acetate propionate, cellulose acetate butyrate, cellulose acetate phthalate, or mixtures thereof.

In still another embodiment of the invention, the cellulose esters of the present invention can be used in applications involving solvent casting of film. Examples of such applications include photographic film, protective film, and compensation film for liquid crystalline displays. Examples of cellulose esters suitable for use in solvent cast film applications include, but are not limited to, cellulose triacetate, cellulose acetate, cellulose propionate, and cellulose acetate propionate.

In an embodiment of the invention, films are produced comprising cellulose esters of the present invention and are used as protective and compensation films for liquid crystalline displays (LCD). These films can be prepared by solvent casting as described in US application 2009/0096962 or by melt extrusion as described in US application 2009/0050842, both of which are incorporated in their entirety in this invention to the extent they do not contradict the statements herein.

When used as a protective film, the film is typically laminated to either side of an oriented, iodinated polyvinyl alcohol (PVOH) polarizing film to protect the PVOH layer from scratching and moisture, while also increasing structural rigidity. When used as compensation films (or plates), they can be laminated with the polarizer stack or otherwise included between the polarizer and liquid crystal layers. These compensation films can improve the contrast ratio, wide viewing angle, and color shift performance of the LCD. The reason for this important function is that for a typical set of crossed polarizers used in an LCD, there is significant light leakage along the diagonals (leading to poor contrast ratio), particularly as the viewing angle is increased. It is known that various combinations of optical films can be used to correct or "compensate" for this light leakage. These compensation films must have certain well-defined retardation (or birefringence) values, which vary depending on the type of liquid crystal cell or mode used because the liquid crystal cell itself will also impart a certain degree of undesirable optical retardation that must be corrected.

Compensation films are commonly quantified in terms of birefringence, which is, in turn, related to the refractive index n. For cellulose esters, the refractive index is approximately 1.46 to 1.50. For an unoriented isotropic material, the refractive index will be the same regardless of the polarization state of the entering light wave. As the material becomes oriented, or otherwise anisotropic, the refractive index becomes dependent on material direction. For purposes of the present invention, there are three refractive indices of importance denoted $n_x$, $n_y$, and $n_z$, which correspond to the machine direction (MD), the transverse direction (TD), and the thickness direction, respectively. As the material becomes more anisotropic (e.g. by stretching), the difference between any two refractive indices will increase. This difference in refractive index is referred to as the birefringence of the material for that particular combination of refractive indices. Because there are many combinations of material directions to choose from, there are correspondingly different values of birefringence. The two most common birefringence parameters are the planar birefringence defined as $\Delta_e = n_x - n_y$, and the thickness birefringence ($\Delta_{th}$) defined as: $\Delta_{th} = n_z - (n_x + n_y)/2$. The birefringence $\Delta_e$ is a measure of the relative in-plane orientation between the MD and TD and is dimensionless. In contrast, $\Delta_{th}$ gives a measure of the orientation of the thickness direction, relative to the average planar orientation.

Optical retardation (R) is related the birefringence by the thickness (d) of the film: $R_e = \Delta_e d = (n_x - n_y)d$; $R_{th} = \Delta_{th} d = [n_z - (n_x + n_y)/2]$. Retardation is a direct measure of the relative phase shift between the two orthogonal optical waves and is typically reported in units of nanometers (nm). Note that the definition of $R_{th}$ varies with some authors, particularly with regards to the sign (±).

Compensation films or plates can take many forms depending upon the mode in which the LCD display device operates. For example, a C-plate compensation film is isotropic in the x-y plane, and the plate can be positive (+C) or negative (−C). In the case of +C plates, $n_x = n_y < n_z$. In the case of −C plates, $n_x = n_y > n_z$. Another example is A-plate compensation film which is isotropic in the y-z direction, and again, the plate can be positive (+A) or negative (−A). In the case of +A plates, $n_x > n_y = n_z$. In the case of −A plates, $n_x < n_y = n_z$.

In general, aliphatic cellulose esters provide values of $R_{th}$ ranging from about 0 to about −350 nm at a film thickness of 60 μm. The most important factors that influence the observed $R_{th}$ is type of substituent and the degree of substitution of hydroxyl ($DS_{OH}$). Film produced using cellulose mixed esters with very low $DS_{OH}$ in Shelby et al. (US 2009/0050842) had $R_{th}$ values ranging from about 0 to about −50 nm. By significantly increasing $DS_{OH}$ of the cellulose mixed ester, Shelton et al. (US 2009/0096962) demonstrated that larger absolute values of $R_{th}$ ranging from about −100 to about −350 nm could be obtained. Cellulose acetates typically provide $R_{th}$ values ranging from about −40 to about −90 nm depending upon $DS_{OH}$.

One aspect of the present invention relates to compensation film comprising regioselectively substituted cellulose esters wherein the compensation film has an $R_{th}$ range from about −400 to about +100 nm. In another embodiment of the invention, compensation films are provided comprising regioselectively substituted cellulose esters having a total DS from about 1.5 to about 2.95 of a single acyl substituent (DS≤0.2 of a second acyl substituent) and wherein the compensation film has an $R_{th}$ value from about −400 to about +100 nm.

In one embodiment of the invention, the regioselectively substituted cellulose esters utilized for producing films are selected from the group consisting of cellulose acetate, cellulose propionate, and cellulose butyrate wherein the regioselectively substituted cellulose ester has a total DS from about 1.6 to about 2.9. In another embodiment of the invention, the compensation film has $R_{th}$ values from about −380 to about −110 nm and is comprised of a regioselectively substituted cellulose propionate having a total DS of about 1.7 to about 2.5. In yet another embodiment, the compensation film has $R_{th}$ values from about −380 to about −110 nm and is comprised of a regioselectively substituted cellulose propionate having a total DS of about 1.7 to about 2.5 and a ring RDS ratio for $C_6/C_3$ or $C_6/C_2$ of at least 1.05. In another embodiment, the compensation film has $R_{th}$ values from about −60 to about +100 nm and is comprised of regioselectively substituted cellulose propionate having a total DS of about 2.6 to about 2.9. In yet another embodiment, the compensation film has $R_{th}$ values from about −60 to about +100 nm and is comprised of regioselectively substituted cellulose propionate having a total DS of about 2.6 to about 2.9 and a ring RDS ratio for $C_6/C_3$ or $C_6/C_2$ of at least 1.05. In another embodiment, the compensation film has $R_{th}$ values from about 0 to about +100 nm and is comprised of a regioselectively substituted cellulose propionate having a total DS of about 2.75 to about 2.9. In yet another embodiment, the compensation film has $R_{th}$ values from about 0 to about +100 nm and is comprised of a regioselectively substituted cellulose propionate having a total DS of about 2.75 to about 2.9 and a ring RDS ratio for $C_6/C_3$ or $C_6/C_2$ of at least 1.05. In yet another embodiment, the compensation film has $R_{th}$ values from about 0 to about +100 nm, or $R_{th}$ values from about 160 to about +270 nm, or $R_{th}$ values from about 0 to about +350 nm, or $R_{th}$ values from about 0 to about +100 nm, $R_{th}$ values from about −60 to about 100 nm, or $R_{th}$ values from about −400 to 100 nm.

Another aspect of the present invention relates to compensation film with an $R_{th}$ range from about −160 to about +270 nm comprised of regioselectively substituted cellulose esters having a total DS from about 1.5 to about 3.0 of a plurality of 2 or more acyl substituents. In one embodiment of this invention, the cellulose esters can be selected from the group consisting of cellulose acetate propionate, cellulose acetate butyrate, cellulose benzoate propionate, and cellulose benzoate butyrate; wherein the regioselectively substituted cellulose ester has a total DS from about 2.0 to about 3.0. In another embodiment, the compensation film has $R_{th}$ values from about −160 to about 0 nm and is comprised of a regioselectively substituted cellulose acetate propionate having a total DS of about 2.0 to about 3.0, a ring RDS ratio for $C_6/C_3$ or $C_6/C_2$ of at least 1.05, and a carbonyl RDS ratio for at least one acyl substituent for $C_6/C_3$ or $C_6/C_2$ of at least about 1.3. In another embodiment, the compensation film has $R_{th}$ values from about +100 to about +270 nm and is comprised of a regioselectively substituted cellulose benzoate propionate having a total DS of about 2.0 to about 3.0, a ring RDS ratio for $C_6/C_3$ or $C_6/C_2$ of at least 1.05, and a carbonyl RDS ratio for at least one acyl substituent for $C_6/C_3$ or $C_6/C_2$ of at least about 1.3. In another embodiment, the compensation film has $R_{th}$ values from about +100 to about +270 nm and is comprised of a regioselectively substituted cellulose benzoate propionate having a total DS of about 2.0 to about 3.0, a ring RDS ratio for $C_6/C_3$ or $C_6/C_2$ of at least 1.05, a carbonyl RDS ratio for at least one acyl substituent for $C_6/C_3$ or $C_6/C_2$ of at least about 1.3, and the benzoate substituent is located primarily at C2 or C3.

Referring still to FIG. 1, at least a portion of the mother liquor produced in cellulose ester recovery/treatment zone 50 can be withdrawn via line 86 and routed to ionic liquid recovery/treatment zone 60. As will be discussed in further detail below with reference to FIG. 2, the mother liquor can undergo various treatments in ionic liquid recovery/treatment zone 60. Such treatment can include, but is not limited to, volatiles removal and reformation of the ionic liquid. Reformation of the ionic liquid can include, but is not limited to, (1) anion homogenization, and (2) anion exchange. Accordingly, a recycled ionic liquid can be formed in ionic liquid recovery/treatment zone 60.

In one embodiment, at least a portion of the recycled ionic liquid can be withdrawn from ionic liquid recovery/treatment zone 60 via line 70. The recycled ionic liquid in line 70 can have a composition such as described above in relation to the ionic liquid in line 64 of FIG. 1. The production and composition of the recycled ionic liquid will be discussed in greater detail below with reference to FIG. 2. As mentioned above, at least a portion of the recycled ionic liquid in line 70 can be routed back to dissolution zone 20. In one embodiment, at least about 80 weight percent, at least about 90 weight percent, or at least 95 weight percent of the recycled ionic liquid produced in ionic liquid recovery/treatment zone 60 can be routed to dissolution zone 20.

Figure 2:
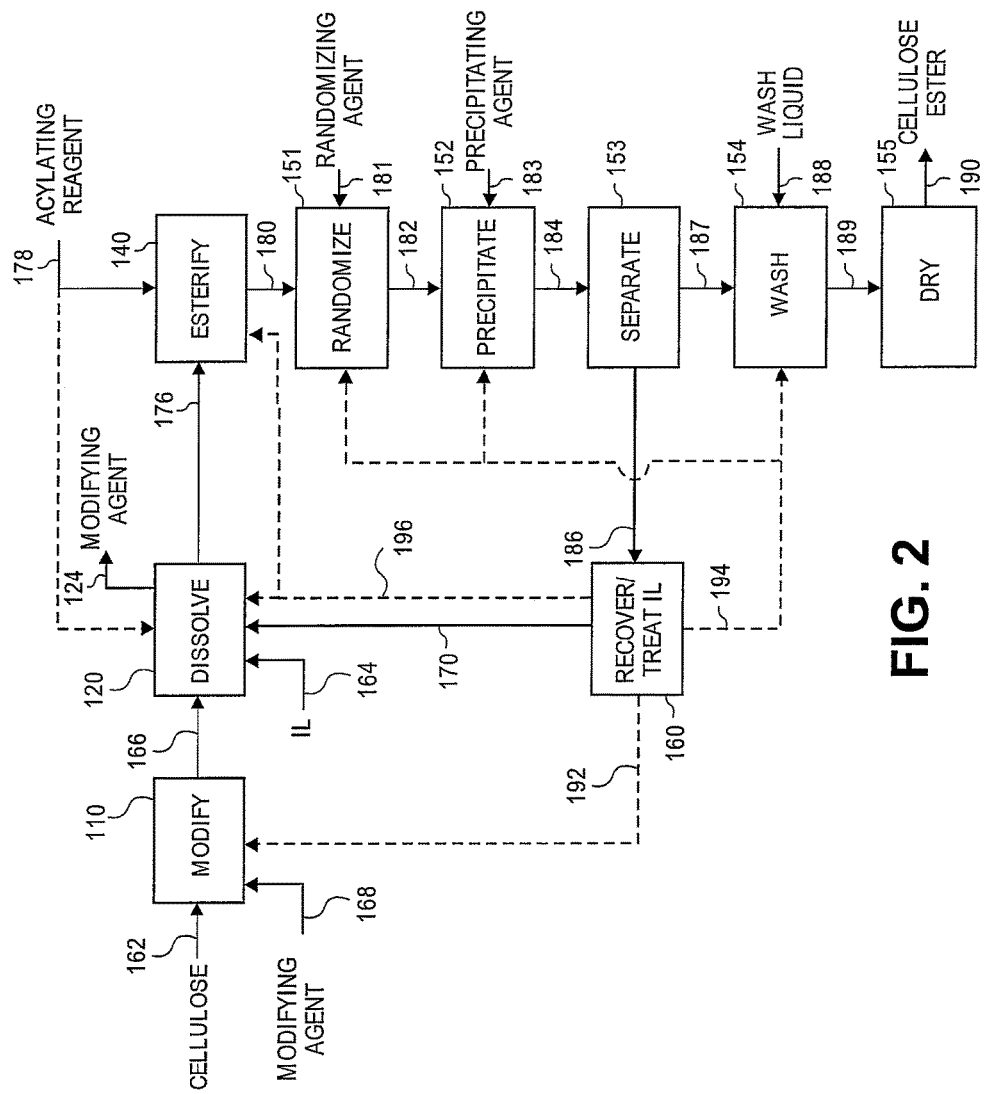
FIG. 2 is a more detailed diagram of a process for producing cellulose esters, depicting a number of additional/optional steps for enhancing to overall efficacy and/or efficiency of the process.

Referring now to FIG. 2, a more detailed diagram for the production of cellulose esters is depicted, including optional steps for improving the overall efficacy and/or efficiency of the esterification process. In the embodiment depicted in FIG. 2, a cellulose can be introduced into an optional modification zone 110 via line 162. The cellulose fed to optional modification zone 110 can be substantially the same as the cellulose in line 62 described above with reference to FIG. 1. In optional modification zone 110, the cellulose can be modified employing at least one modifying agent.

As mentioned above, water may be employed as the modifying agent. Thus, in one embodiment of the present invention, a water-wet cellulose can be withdrawn from optional modification zone 110 and added to one or more ionic liquids in dissolution zone 120. In one embodiment, the cellulose can be mixed with water then pumped into one or more ionic liquids as a slurry. Alternatively, excess water can be removed from the cellulose, and thereafter the cellulose can be added to the one or more ionic liquids in the form of a wet cake. In this embodiment, the cellulose wet cake can contain associated water in an amount in the range of from about 10 to about 95 weight percent, in the range of from about 20 to about 80 weight percent, or in the range of from 25 to 75 weight percent, based on the combined weight of the cellulose and associated water.

Though not wishing to be bound by theory, the addition of water wet cellulose has unexpectedly and unpredictably been found to provide at least three heretofore unknown benefits. First, water can increase dispersion of the cellulose in the one or more ionic liquids so that when removal of water is initiated while heating the cellulose, the cellulose rapidly dissolves in the one or more ionic liquids. Secondly, water appears to reduce the melting points of ionic liquids that are normally solids at room temperature, thus allowing processing of ionic liquids at ambient temperatures. A third benefit is that the molecular weight of cellulose esters prepared using initially water wet cellulose is reduced during the above-discussed esterification in esterification zone 40 when compared to cellulose esters prepared using initially dry cellulose.

This third benefit is particularly surprising and useful. Under typical cellulose ester processing conditions, the molecular weight of cellulose is not reduced during dissolution or during esterification. That is, the molecular weight of the cellulose ester product is directly proportionate to the molecular weight of the initial cellulose. Typical wood pulps used to prepare cellulose esters generally have a DP in the range of from about 1,000 to about 3,000. However, the desired DP range of cellulose esters can be from about 10 to about 500. Thus, in the absence of molecular weight reduction during esterification, the cellulose must be specially treated prior to dissolving the cellulose in the ionic liquid or after dissolving in the ionic liquid but prior to esterification. However, when employing water as at least one of the optional modifying agents, pretreatment of the cellulose is not required since molecular weight reduction can occur during esterification. Accordingly, in one embodiment of the present invention, the DP of the modified cellulose subjected to esterification can be within about 10 percent of, within about 5 percent of, within 2 percent of, or substantially the same as the DP of the initial cellulose subjected to modification. However, the DP of the cellulose ester produced in accordance with embodiments of the present invention can be less than about 90 percent, less than about 70 percent, or less than 50 percent of the DP of the modified cellulose subjected to esterification.

Referring still to FIG. 2, the optionally modified cellulose in line 166 can be introduced into dissolution zone 120. Once in dissolution zone 120, the optionally modified cellulose can be dispersed in one or more ionic liquids, as described above with reference to dissolution zone 20 in FIG. 1. Subsequently, at least a portion of the modifying agent in the resulting cellulose/ionic liquid mixture can be removed. In one embodiment, at least 50 weight percent of all modifying agents can be removed, at least 75 weight percent of all modifying agents can be removed, at least 95 weight percent of all modifying agents can be removed, or at least 99 weight percent of all modifying agents can be removed from the cellulose/ionic liquid mixture. Removal of one or more modifying agents in dissolution zone 120 can be accomplished by any means known in the art for liquid/liquid separation, such as, for example, distillation, flash vaporization, and the like. Removed modifying agent can be withdrawn from dissolution zone 120 via line 124.

After removal of the modifying agent, dissolution zone 120 can produce a cellulose solution in substantially the same manner as dissolution zone 20, as described above with reference to FIG. 1. Thereafter, a cellulose solution can be withdrawn from dissolution zone 120 via line 176. The cellulose solution in line 176 can comprise ionic liquid, cellulose, and a residual concentration of one or more optional modifying agents. The cellulose solution in line 176 can comprise cellulose in an amount in the range of from about 1 to about 40 weight percent, in the range of from about 5 to about 30 weight percent, or in the range of from 10 to 20 weight percent, based on the weight of the ionic liquid. Furthermore, the cellulose solution in line 176 can comprise a cumulative amount of residual modifying agents in an amount of less than about 50 weight percent, less than about 25 weight percent, less than about 15 weight percent, less than about 5 weight percent, or less than 1 weight percent.

In the embodiment of FIG. 2, at least a portion of the cellulose solution in line 176 can be introduced into esterification zone 140. Esterification zone 140 can be operated in substantially the same manner as esterification zone 40, as described above with reference to FIG. 1. For example, an acylating reagent can be introduced into esterification zone 140 via line 178. As in esterification zone 40, the acylating reagent can esterify at least a portion of the cellulose in esterification zone 140. Additionally, as described above, at least a portion of the resulting cellulose ester can comprise one or more ester substituents that originated from and or were donated by the ionic liquid.

After esterification in esterification zone 140, an esterified medium can be withdrawn via line 180. The esterified medium in line 180 can be substantially the same as the esterified medium in line 80, as described above with reference to FIG. 1. Thus, the esterified medium in line 180 can comprise an initial cellulose ester and other components, such as, for example, altered ionic liquid, residual acylating reagent, one or more carboxylic acids, and/or one or more catalysts. The concentrations of the initial cellulose ester and other components in the esterified medium in line 180 can be substantially the same as the esterified medium in line 80 described above with reference to FIG. 1.

Referring still to FIG. 2, as mentioned above, the initial cellulose ester produced in esterification zone 140 can be a non-random cellulose ester. In one embodiment, at least a portion of the initial cellulose in line 180 can optionally be introduced into randomization zone 151 to undergo randomization, thereby creating a random cellulose ester. Randomization of the initial cellulose can comprise introducing at least one randomizing agent into randomization zone 151 via line 181. Additionally, as will be discussed in further detail below, at least a portion of the randomization agent introduced into randomization zone 151 can be introduced via line 194.

The randomization agent employed in the present invention can be any substance capable lowering the DS of the cellulose ester via hydrolysis or alcoholysis, and/or by causing migration of at least a portion of the acyl groups on the cellulose ester from one hydroxyl to a different hydroxyl, thereby altering the initial monomer distribution. Examples of suitable randomizing agents include, but are not limited to water and/or alcohols. Alcohols suitable for use as the randomizing agent include, but are not limited to methanol, ethanol, n-propanol, i-propanol, n-butanol, i-butanol, t-butanol, phenol and the like. In one embodiment, methanol can be employed as the randomizing agent introduced via line 181.

The amount of randomizing agent introduced into randomization zone 151 can be in the range of from about 0.5 to about 20 weight percent, or in the range of from 3 to 10 weight percent, based on the total weight of the resulting randomization medium in randomization zone 151. The randomization medium can have any residence time in randomization zone 151 suitable to achieve the desired level of randomization. In one embodiment, the randomization medium can have a residence time in randomization zone 151 in the range of from about 1 min. to about 48 hours, in the range of from about 30 min. to about 24 hours, or in the range of from 2 to 12 hours. Additionally, the temperature in randomization zone 151 during randomization can be any temperature suitable to achieve the desired level of randomization. In one embodiment, the temperature in randomization zone 151 during randomization can be in the range of from about 20 to about 120° C., in the range of from about 30 to about 100° C., or in the range of from 50 to 80° C.

Those skilled in the art will understand that the DS and DP of the cellulose ester random copolymer might be less than that of the cellulose ester non-random copolymer. Accordingly, in this embodiment the non-random cellulose ester entering randomization zone 151 may optionally have a greater DS and/or DP than the target DS and/or DP of the randomized cellulose ester.

In one embodiment of the present invention, it may be desirable to produce cellulose esters that are at least partially soluble in acetone. Accordingly, the initial cellulose ester produced in esterification zone 140 can bypass optional randomization zone 151, thereby producing a final non-random cellulose ester. Non-random cellulose esters prepared by the methods of the present invention can be at least partially soluble in acetone when they have a DS in the range of from about 2.1 to about 2.4, in the range of from about 2.28 to about 2.39 or in the range of from 2.32 to 2.37.

After optional randomization, an optionally randomized medium can be withdrawn from randomization zone 151 via line 182. The optionally randomized medium can comprise randomized cellulose ester and residual randomizing agent. In one embodiment, the optionally randomized medium in line 182 can comprise randomized cellulose ester in an amount in the range of from about 2 to about 80 weight percent, in the range of from about 10 to about 60 weight percent, or in the range of from 20 to 40 weight percent based on the weight of the ionic liquid. Additionally, the optionally randomized medium can comprise residual randomizing agent in the range of from about 0.5 to about 20 weight percent, or in the range of from 3 to 10 weight percent, based on the total weight of the resulting randomized medium.

Additionally, the optionally randomized medium in line 182 can comprise other components, such as those described above with reference to the esterified medium in line 180 and with reference to the esterified medium in line 80 of FIG. 1. Such components include, but are not limited to, altered ionic liquid, residual acylating reagent, one or more carboxylic acids, and/or one or more catalysts.

Following optional randomization, at least a portion of the esterified and optionally randomized medium in line 182 can be introduced into precipitation zone 152. Precipitation zone 152 can operate to cause at least a portion of the cellulose ester from the esterified and optionally randomized medium to precipitate. Any methods known in the art suitable for precipitating a cellulose ester can be employed in precipitation zone 152. In one embodiment, a precipitating agent can be introduced into precipitation zone 152, thereby causing at least a portion of the cellulose ester to precipitate.

In one embodiment, the precipitating agent can be a non-solvent for the cellulose ester. Examples of suitable non-solvents that can be employed as the precipitating agent include, but are not limited to, $C_1$ to $C_8$ alcohols, water, or a mixture thereof. In one embodiment, the precipitating agent introduced into precipitation zone 152 can comprise methanol.

The amount of precipitating agent introduced into precipitation zone 152 can be any amount sufficient to cause at least a portion of the cellulose ester to precipitate. In one embodiment, the amount of precipitating agent introduced into precipitation zone 152 can be at least about 20 volumes, at least 10 volumes, or at least 4 volumes, based on the total volume of the medium entering precipitation zone 152. The resulting precipitation medium can have any residence time in precipitation zone 152 suitable to achieve the desired level of precipitation. In one embodiment, the precipitation medium can have a residence time in precipitation zone 152 in the range of from about 1 to about 300 min., in the range of from about 10 to about 200 min., or in the range of from 20 to 100 min. Additionally, the temperature in precipitation zone 152 during precipitation can be any temperature suitable to achieve the desired level of precipitation. In one embodiment, the temperature in precipitation zone 152 during precipitation can be in the range of from about 0 to about 120° C., in the range of from about 20 to about 100° C., or in the range of from 25 to 50° C. The amount of cellulose ester precipitated in precipitation zone 152 can be at least 50 weight percent, at least 75 weight percent, or at least 95 weight percent, based on the total amount of cellulose ester in precipitation zone 152.

After precipitation in precipitation zone 152, a cellulose ester slurry can be withdrawn via line 184 comprising a final cellulose ester. The cellulose ester slurry in line 184 can have a solids content of less than about 50 weight percent, less than about 25 weight percent, or less than 1 weight percent.

At least a portion of the cellulose ester slurry in line 184 can be introduced into separation zone 153. In separation zone 153, at least a portion of the liquid content of the cellulose ester slurry can be separated from the solids portion. Any solid/liquid separation technique known in the art for separating at least a portion of a liquid from a slurry can be used in separation zone 153. Examples of suitable solid/liquid separation techniques suitable for use in the present invention include, but are not limited to, centrifugation, filtration, and the like. In one embodiment, at least 50 weight percent, at least 70 weight percent, or at least 90 weight percent of the liquid portion of the cellulose ester slurry can be removed in separation zone 153.

Furthermore, separation zone 153 can have any temperature or pressure suitable for solid liquid separation. In one embodiment, the temperature in separation zone 153 during separation can be in the range of from about 0 to about 120° C., in the range of from about 20 to about 100° C., or in the range of from 25 to 50° C.

After separation in separation zone 153, a cellulose ester wet cake can be withdrawn from separation zone 153 via line 187. The cellulose ester wet cake in line 187 can have a total solids content of at least 1 weight percent, at least 50 weight percent, or at least 75 weight percent. Additionally, the cellulose ester wet cake in line 187 can comprise cellulose ester in an amount of at least 70 weight percent, at least 80 weight percent, or at least 90 weight percent. Additionally, as will be discussed in greater detail below, at least a portion of the separated liquids from separation zone 153 can be withdrawn via line 186.

Once removed from separation zone 153, at least a portion of the cellulose ester solids from the cellulose ester wet cake can be washed in wash zone 154. Any method known in the art suitable for washing a wet cake can be employed in wash zone 154. An example of a washing technique suitable for use in the present invention includes, but is not limited to, a multi-stage counter-current wash. In one embodiment, a wash liquid that is a non-solvent for cellulose ester can be introduced into wash zone 154 via line 188 to wash at least a portion of the cellulose ester solids. Such wash liquids include, but are not limited to, a $C_1$ to $C_8$ alcohol, water, or a mixture thereof. In one embodiment, the wash liquid can comprise methanol. Additionally, as will be described in greater detail below, at least a portion of the wash liquid can be introduced into wash zone 154 via line 194.

In one embodiment, washing of the cellulose ester solids in wash zone 153 can be performed in such a manner that at least a portion of any undesired by-products and/or color bodies are removed from the cellulose ester solids and/or ionic liquid. In one embodiment, the non-solvent wash liquid can contain a bleaching agent in the range of from about 0.001 to about 50 weight percent, or in the range of from 0.01 to 5 weight percent based on the total weight of the wash fluid. Examples of bleaching agents suitable for use in the present invention include, but are not limited to, chlorites, such as sodium chlorite ($NaClO_2$); hypohalites, such as NaOCl, NaOBr and the like; peroxides, such as hydrogen peroxide and the like; peracids, such as peracetic acid and the like; metals, such as Fe, Mn, Cu, Cr and the like; sodium sulfites, such as sodium sulfite ($Na_2SO_3$), sodium metabisulfite ($Na_2S_2O_5$), sodium bisulfite ($NaHSO_3$) and the like; perborates, such as sodium perborate ($NaBO_3 \cdot nH_2O$ where n=1 or 4); chlorine dioxide ($ClO_2$); oxygen; and ozone. In one embodiment, the bleaching agent employed in the present invention can include hydrogen peroxide, NaOCl, sodium chlorite and/or sodium sulfite. Washing in wash zone 153 can be sufficient to remove at least 50, at least 70, or at least 90 percent of the total amount of byproducts and/or color bodies.

After washing in wash zone 154, a washed cellulose ester product can be withdrawn via line 189. The washed cellulose ester product in line 189 can be in the form of a wet cake, and can comprise solids in an amount of at least 1, at least 50, or at least 75 weight percent. Additionally, the washed cellulose ester product in line 189 can comprise cellulose ester in an amount of at least 1, at least 50, or at least 75 weight percent.

The washed cellulose ester product can optionally be dried in drying zone 155. Drying zone 155 can employ any drying methods known in the art to remove at least a portion of the liquid content of the washed cellulose ester product. Examples of drying equipment suitable for use in drying zone 155 include, but are not limited to, rotary dryers, screw-type dryers, paddle dryers, and/or jacketed dryers. In one embodiment, drying in drying zone 155 can be sufficient to produce a dried cellulose ester product comprising less than 5, less than 3, or less than 1 weight percent liquids.

After drying in drying zone 155, a final cellulose ester product can be withdrawn via line 190. The final cellulose ester product in line 190 can be substantially the same as the final cellulose ester product in line 90, as described above with reference to FIG. 1.

Referring still to FIG. 2, as mentioned above at least a portion of the separated liquids generated in separation zone 153 can be withdrawn via line 186 as a recycle stream. The recycle stream in line 186 can comprise altered ionic liquid, one or more carboxylic acids, residual modifying agent, residual catalyst, residual acylating reagent, residual randomizing agent, and/or residual precipitation agent. As used herein, the term "altered ionic liquid" refers to an ionic liquid that has previously passed through a cellulose esterification step wherein at least a portion of the ionic liquid acted as acyl group donor and/or recipient. As used herein, the term "modified ionic liquid" refers to an ionic liquid that has previously been contacted with another compound in an upstream process step. Therefore, altered ionic liquids are a subset of modified ionic liquids, where the upstream process step is cellulose esterification.

In one embodiment, the recycle stream in line 186 can comprise altered ionic liquid, one or more carboxylic acids, one or more alcohols, and/or water. In one embodiment, the recycle stream in line 186 can comprise altered ionic liquid in an amount in the range of from about 10 to about 99.99 weight percent, in the range of from about 50 to about 99 weight percent, or in the range of from 90 to 98 weight percent, based on the total weight of the recycle stream in line 186. In one embodiment, the altered ionic liquid can comprise an ionic liquid having at least two different anions: primary anions and secondary anions. At least a portion of the primary anions in the altered ionic liquid originate from the initial ionic liquid introduced into dissolution zone 120 via line 164, as described above. Additionally, at least a portion of the secondary anions in the altered ionic liquid originate from the acylating reagent introduced into esterification zone 140, as described above. In one embodiment, the altered ionic liquid can comprise primary anions and secondary anions in a ratio in the range of from about 100:1 to about 1:100, in the range of from about 1:10 to about 10:1, or in the range of from 1:2 to about 2:1. Additionally, the altered ionic liquid can comprise a plurality of cations, such as those described above with reference to the initial ionic liquid in line 68 of FIG. 1.

The recycle stream in line 186 can comprise a total amount of carboxylic acids in an amount in the range of from about 5 to about 60 weight percent, in the range of from about 10 to about 40 weight percent, or in the range of from 15 to 30 weight percent based on the total weight of ionic liquid in the recycle stream in line 186. Examples of suitable carboxylic acids the recycle stream in line 186 can comprise include, but are not limited to, acetic acid, propionic acid, butyric acid, isobutyric acid, valeric acid, hexanoic acid, 2-ethylhexanoic acid, nonanoic acid, lauric acid, palmitic acid, stearic acid, benzoic acid, substituted benzoic acids, phthalic acid, and isophthalic acid. In one embodiment, at least 50 weight percent, at least 70 weight percent, or at least 90 weight percent of the carboxylic acids in the recycle stream in line 186 are acetic, propionic, and/or butyric acids.

Furthermore, the recycle stream in line 186 can comprise a total concentration of alcohols in an amount of at least 20 volumes, at least 10 volumes, or at least 4 volumes, based on the total volume of the recycle stream. Examples of suitable alcohols the recycle stream in line 186 can comprise include, but are not limited to, $C_1$ to $C_8$ straight- or branched-chain alcohols. In one embodiment, at least 50 weight percent, at least 70 weight percent, or at least 90 weight percent of the alcohol in the separated ionic liquids in line 186 comprises methanol. Moreover, the recycle stream in line 186 can comprise water in an amount of at least 20 volumes, at least 10 volumes, or at least 4 volumes, based on the total volume of the recycle stream.

As depicted in FIG. 2, at least a portion of the recycle stream in line 186 can be introduced into ionic liquid recovery/treatment zone 160. Ionic liquid recovery/treatment zone 160 can operate to segregate and/or reform at least a portion of the recycle stream from line 186. In one embodiment, at least a portion of the recycle stream can undergo at least one flash vaporization and/or distillation process to remove at least a portion of the volatile components in the recycle stream. At least 40 weight percent, at least 75 weight percent, or at least 95 weight percent of the volatile components in the recycle stream can be removed via flash vaporization. The volatile components removed from the recycle stream can comprise one or more alcohols. In one embodiment, the volatile components can comprise methanol. After vaporization, the resulting volatiles-depleted recycle stream can comprise a total amount of alcohols in the range of from about 0.1 to about 60 weight percent, in the range of from about 5 to about 55 weight percent, or in the range of from 15 to 50 weight percent.

In one embodiment, at least a portion of the carboxylic acids can be removed from the recycle stream. This can be accomplished by first converting at least a portion of the carboxylic acids to carboxylate esters. In this embodiment, at least a portion of the recycle stream can be placed into a pressurized reactor where the recycle stream can be treated at a temperature, pressure, and time sufficient to convert the at least a portion of the carboxylic acid to methyl esters, by reacting the carboxylic acids with the alcohol present in the recycle stream. During the esterification, the pressurized reactor can have a temperature in the range of from 100 to 180° C., or in the range of from 130 to 160° C. Additionally, the pressure in the pressurized reactor during esterification can be in the range of from about 10 to about 1,000 pounds per square inch gauge ("psig"), or in the range of from 100 to 300 psig. The recycle stream can have a residence time in the pressurized reactor in the range of from about 10 to about 1,000 minutes, or in the range of from 120 to 600 minutes. Prior to the above-described esterification, the alcohol and carboxylic acid can be present in the recycle stream in a molar ratio in the range of from about 1:1 to about 30:1, in the range of from about 3:1 to about 20:1, or in the range of from 5:1 to 10:1 alcohol-to-carboxylic acid. In one embodiment, at least 5, at least 20, or at least 50 mole percent of the carboxylic acids can be esterified during the above-described esterification.

As mentioned above, at least a portion of the carboxylic acids can be acetic, propionic, and/or butyric acids. Additionally, as mentioned above, the alcohol present in the recycle stream can be methanol. Accordingly, the above-described esterification process can operate to produce methyl acetate, methyl propionate, and/or methyl butyrate. Subsequent to esterification, at least 10, at least 50, or at least 95 weight percent of the resulting carboxylate esters can be removed from the recycle stream by any methods known in the art. As depicted in FIG. 2, at least a portion of the carboxylate esters produced by the above described esterification can be routed to esterification zone 140 via line 196. Carboxylate esters introduced into esterification zone 140 can be employed as immiscible cosolvents, as described above. In another embodiment, at least a portion of the carboxylate esters can be converted to anhydrides by CO insertion.

In another embodiment of the present invention, at least a portion of the altered ionic liquid present in the recycle stream can undergo reformation. Reformation of the altered ionic liquid can optionally be performed simultaneously with the esterification of the carboxylic acids in the recycle stream. Alternatively, reformation of the altered ionic liquid can be performed subsequently to the esterification of the carboxylic acids in the recycle stream. Reformation of the altered ionic liquid can comprise at least one anion exchange process.

In one embodiment, reformation of the altered ionic liquid can comprise anion homogenization via anion exchange, such that substantially all of the anions of the altered ionic liquid are converted to the same type of anion. In this embodiment, at least a portion of the altered ionic liquid can be contacted with at least one alkyl formate. Alkyl formates suitable for use in the present invention include, but are not limited to, methyl formate, ethyl formate, propyl formate, isopropyl formate, butyl formate, isobutyl formate, tert-butyl formate, hexyl formate, octyl formate, and the like. In one embodiment, the alkyl formate can comprise methyl formate. Additionally, reformation of the altered ionic liquid can be performed in the presence of one or more alcohols. Alcohols suitable for use in this embodiment of the invention include, but are not limited to, alkyl or aryl alcohols such as methanol, ethanol, n-propanol, i-propanol, n-butanol, i-butanol, t-butanol, phenol and the like. In one embodiment, the alcohol present during reformation can comprise methanol.

The temperature during reformation of the altered ionic liquid can be in the range of from about 100 to about 200° C., or in the range of from 130 to about 170° C. Additionally, the pressure during reformation of the altered ionic liquid can be at least 700 kPa, or at least 1,025 kPa. Furthermore, the reaction time of the reformation of the altered ionic liquid can be in the range of from about 10 min. to about 24 hours, or in the range of from 3 to 18 hours.

As mentioned above, reformation of the altered ionic liquid can comprise anion homogenization. In one embodiment, the resulting reformed ionic liquid can have an at least 90, at least 95, or at least 99 percent uniform anion content. Additionally, the reformed ionic liquid can comprise an alkyl amine formate. In one embodiment, the amine of the alkyl amine formate can be an imidazolium. Examples of alkyl amine formates suitable for use as the reformed ionic liquid include, but are not limited to, 1-methyl-3-methylimidazolium formate, 1-ethyl-3-methylimidazolium formate, 1-propyl-3-methylimidazolium formate, 1-butyl-3-methylimidazolium formate, 1-hexyl-3-methylimidazolium formate, and/or 1-octyl-3-methylimidazolium formate.

Following reformation, at least a portion of the volatile components of the reformed ionic liquid can optionally be removed via any methods known in the art for removing volatile components. Volatile components removed from the reformed ionic liquid can include, for example, carboxylate esters, such as those formed via the above described carboxylic acid esterification process. Thereafter, at least a portion of the reformed ionic liquid can undergo at least one anion exchange process to replace at least a portion of the anions of the reformed ionic liquid thereby forming a carboxylated ionic liquid. In one embodiment, the reformed ionic liquid can be contacted with at least one carboxylate anion donor to at least partially effect the anion exchange. Carboxylate anion donors suitable for use in this embodiment include, but are not limited to, one or more carboxylic acids, anhydrides, or alkyl carboxylates. Additionally, the carboxylate anion donors can comprise one or more $C_2$ to $C_{20}$ straight- or branched-chain alkyl or aryl carboxylic acids, anhydrides, or methyl esters. Furthermore, the carboxylate anion donor can be one or more $C_2$ to $C_{12}$ straight-chain alkyl carboxylic acids, anhydrides, or methyl esters. Moreover, the carboxylate anion donor can be one or more $C_2$ to $C_4$ straight-chain alkyl carboxylic acids, anhydrides, or methyl esters. The resulting carboxylated ionic liquid can be substantially the same as the carboxylated ionic liquid described above with reference to the carboxylated ionic liquid in line 64 of FIG. 1.

When contacting the reformed ionic liquid with one or more carboxylate anion donors, the contacting can be carried out in a contact mixture further comprising alcohol or water. In one embodiment, the alcohol or water can be present in the contact mixture in the range of from 0.01 to 20 molar equivalents per alkyl amine formate, or in the range of from 1 to 10 molar equivalents per alkyl amine formate. In one embodiment, methanol can be present in the contact mixture in the range of from 1 to 10 molar equivalents per alkyl amine formate.

Referring still to FIG. 2, in one embodiment at least a portion of the carboxylated ionic liquid produced in ionic liquid recovery/treatment zone 160 can be in a treated ionic liquid mixture further comprising at least one alcohol, at least one residual carboxylic acid, and/or water. The one or more alcohols and/or residual carboxylic acids can be substantially the same as described above with reference to the recycle stream in line 186. The treated ionic liquid mixture can be subjected to at least one liquid/liquid separation process to remove at least a portion of the one or more alcohols. Such separation process can comprise any liquid/liquid separation process known in the art, such as, for example, flash vaporization and/or distillation. Additionally, the treated ionic liquid mixture can be subjected to at least one liquid/liquid separation process to remove at least a portion of the water. Such separation process can comprise any liquid/liquid separation process known in the art, such as, for example, flash vaporization and/or distillation.

In one embodiment, at least 50, at least 70, or at least 85 weight percent of the alcohols and/or water can be removed from the treated ionic liquid mixture thereby producing a recycled carboxylated ionic liquid. At least a portion of the alcohol separated from the treated ionic liquid mixture can optionally be removed from ionic liquid recovery/treatment zone 160 via line 194. The one or more alcohols in line 194 can thereafter optionally be routed to various other points depicted in FIG. 2. In one embodiment, at least 50, at least 70, or at least 90 weight percent of the alcohols removed from the treated ionic liquid mixture can be routed to various other points in the process depicted in FIG. 2. In one optional embodiment, at least a portion of the alcohols in line 194 can be routed to randomization zone 151 to be employed as a randomizing agent. In another optional embodiment, at least a portion of the alcohols in line 194 can be routed to precipitation zone 152 to be employed as a precipitating agent. In yet another optional embodiment, at least a portion of the alcohols in line 194 can be routed to wash zone 154 to be employed as a wash liquid.

In one embodiment, at least a portion of the water separated from the treated ionic liquid mixture can optionally be removed from ionic liquid recovery/treatment zone 160 via line 192. Optionally, at least a portion of the water removed from ionic liquid recovery/treatment zone 160 can be routed to modification zone 110 to be employed as a modifying agent. At least about 5, at least about 20, or at least 50 weight percent of the water separated from the treated ionic liquid mixture can optionally be routed to modification zone 110. Additionally, at least a portion of the water in line 192 can optionally be routed to a waste water treatment process.

After alcohol and/or water removal, the above-mentioned recycled carboxylated ionic liquid can comprise residual carboxylic acid in an amount in the range of from about 0.01 to about 25 weight percent, in the range of from about 0.05 to about 15 weight percent, or in the range of from 0.1 to 5 weight percent based on the entire weight of the recycled carboxylated ionic liquid. Additionally, the recycled carboxylated ionic liquid can comprise sulfur in an amount of less than 200 ppmw, less than 100 ppmw, less than 50 ppmw, or less than 10 ppmw. Furthermore, the recycled carboxylated ionic liquid can comprise halides in an amount less than 200 ppmw, less than 100 ppmw, less than 50 ppmw, or less than 10 ppmw. Moreover, the carboxylated ionic liquid can comprise transition metals in an amount less than 200 ppmw, less than 100 ppmw, less than 50 ppmw, or less than 10 ppmw.

In one embodiment, at least a portion of the recycled carboxylated ionic liquid produced in ionic liquid recovery/treatment zone 160 can optionally be routed to dissolution zone 120. At least 50 weight percent, at least 70 weight percent, or at least 90 weight percent of the recycled carboxylated ionic liquid produced in ionic liquid recovery/treatment zone 160 can be routed to dissolution zone 120.

In dissolution zone 120, the recycled carboxylated ionic liquid can be employed either individually or combined with the carboxylated ionic liquid entering dissolution zone 120 via line 164 to thereby form the above-described cellulose dissolving ionic liquid. In one embodiment, the recycled carboxylated ionic liquid can make up in the range of from about 10 to about 99.99 weight percent, in the range of from about 50 to about 99 weight percent, or in the range of from about 90 to about 98 weight percent of the cellulose dissolving ionic liquid in dissolution zone 120.

Further information concerning ionic liquids, their use in the production of cellulose esters and cellulose derivatives, the use of cosolvents with ionic liquids in processes to produce cellulose esters and cellulose derivatives, and treatment of cellulose esters are disclosed in U.S. Patent application entitled "Cellulose Esters and Their Production In Carboxylated Ionic Liquids" filed on Feb. 13, 2008 and having Ser. No. 12/030,387; U.S. Patent application entitled "Cellulose Esters and Their Production in Halogenated Ionic Liquids filed on Aug. 11, 2008 and having Ser. No. 12/189, 415 and its Continuation-In-Part application entitled "Regioselectively Substituted Cellulose Esters Produced In A Halogenated Ionic Liquid Process and Products Produced Therefrom" filed on Sep. 12, 2009; U.S. Patent application "Production of Ionic Liquids" filed on Feb. 13, 2008 having Ser. No. 12/030,425; and U.S. Patent application entitled "Reformation of Ionic Liquids" filed on Feb. 13, 2008 having Ser. No. 12/030,424; U.S. Patent application entitled "Treatment of Cellulose Esters" filed on Aug. 11, 2008, having Ser. No. 12/189,421; U.S. Patent application entitled "Production of Cellulose Esters In the Presence of A Cosolvent" filed on Aug. 11, 2008 having Ser. No. 12/189,753; U.S. application entitled "Cellulose Solutions Comprising Tetraalkylammonium Alkylphosphates and Products Produced Therefrom" filed on Sep. 12, 2009; U.S. application entitled "Regioselectively Substituted Cellulose Esters Produced In A Tetraalkylammonium Alkylphosphate Ionic Liquid Process and Products Produced Therefrom" filed on Sep. 12, 2009; and U.S. Provisional application entitled "Regioselectively Substituted Cellulose Esters and Their Production in Ionic Liquids" filed on Aug. 13, 2008 having Ser. No. 61/088,423; and U.S. Provisional application entitled "Tetraalkylammoinium Alkylphosphates" filed on Apr. 15, 2009 having Ser. No. 61/169,560; all of which are incorporated by reference to the extent they do not contradict the statements herein.

This invention can be further illustrated by the following examples of embodiments thereof, although it will be understood that these examples are included merely for purposes of illustration and are not intended to limit the scope of the invention unless otherwise specifically indicated.

EXAMPLES

Materials Used in Examples

Commercial grades of ionic liquids employed in the following examples were manufactured by BASF and were obtained through Fluka. These ionic liquids were used both as received and after purification as described in the examples. Experimental alkyl imidazolium carboxylates were also prepared as described in the examples. Cellulose was obtained from Aldrich. The degree of polymerization of the Aldrich cellulose (DP ca. 335) was determined capillary viscometry using copper ethylenediamine (Cuen) as the solvent. Prior to dissolution in ionic liquids, the cellulose was typically dried for 14-18 h at 50° C. and 5 mm Hg, except in cases where the cellulose was modified with water prior to dissolution.

The relative degree of substitution (RDS) at $C_6$, $C_3$, and $C_2$ in the cellulose ester of the present invention was determined by carbon 13 NMR following the general methods described in "Cellulose Derivatives", ACS Symposium Series 688, 1998, T. J. Heinze and W. G. Glasser, Editors, herein incorporated by reference to the extent it does not contradict the statements herein. Briefly, the carbon 13 NMR data was obtained using a JEOL NMR spectrometer operating at 100 MHz or a Bruker NMR spectrometer operating at 125 MHz. The sample concentration was 100 mg/mL of DMSO-$d_6$. Five mg of $Cr(OAcAc)_3$ per 100 mg of sample were added as a relaxation agent. The spectra were collected at 80° C. using a pulse delay of 1 second. Normally, 15,000 scans were collected in each experiment. Conversion of a hydroxyl to an ester results in a downfield shift of the carbon bearing the hydroxyl and an upfield shift of a carbon gamma to the carbonyl functionality. Hence, the RDS of the $C_2$ and $C_6$ ring carbons were determined by direct integration of the substituted and unsubstituted $C_1$ and $C_6$ carbons. The RDS at $C_3$ was determined by subtraction of the sum of the $C_6$ and $C_2$ RDS from the total DS. The carbonyl RDS was determined by integration of the carbonyl carbons using the general assignments described in Macromolecules, 1991, 24, 3050-3059, herein incorporated by reference to the extent it does not contradict the statements herein. In the case of cellulose mixed esters containing a plurality of acyl groups, the cellulose ester was first converted to fully substituted cellulose mixed p-nitrobenzoate ester. The position of the p-nitrobenzoate esters indicate the location of the hydroxyls in the cellulose mixed ester.

Color measurements were made following the general protocol of ASTM D1925. Samples for color measurements were prepared by dissolving 1.7 g of cellulose ester in 41.1 g of n-methylpyrrolidone (NMP). A HunterLab ColorQuest XE colorimeter with a 20 mm pathlength cell operating in transmittance mode was used for the measurements. The colorimeter was interfaced to a standard computer running EasyMatch QC Software (HunterLab). Values (L*; white to black, a*; + red to − green, b*; + yellow to − blue) were obtained for NMP (no cellulose ester) and for the cellulose ester/NMP solutions. Color difference (E*) between the solvent and the sample solutions were then calculated (E*= $[(\Delta a^*)^2+(\Delta b^*)^2+(\Delta L^*)^2]^{0.5}$ where $\Delta$ is the value for the sample solutions minus the value for the solvent). As the value for E* approaches zero, the better the color.

Viscosity measurements were made using an AR2000 rheometer (TA Instruments LTD) interfaced with a computer running TA Instruments Advantage Software. The 25 mm aluminum stage for the rheometer was enclosed in a plastic cover with a nitrogen purge to ensure that the samples did not pick up moisture during the measurements. The ionic liquid-cellulose solutions were prepared by the general methods disclosed in the examples.

Solvent casting of film was performed according to the following general procedure: Cellulose ester solids and 10 wt % plasticizer were added to a 90/10 wt % solvent mixture of $CH_2Cl_2$/methanol (or ethanol) to give a final concentration of 5-30 wt % based on cellulose ester+plasticizer. The mixture was sealed, placed on a roller, and mixed for 24 hours to create a uniform solution. After mixing, the solution was cast onto a glass plate using a doctor blade to obtain a film with the desired thickness. Casting was conducted in a fume hood with relative humidity controlled at 50%. After casting, the film and glass were allowed to dry for one hour under a cover pan (to minimize rate of solvent evaporation). After this initial drying, the film was peeled from the glass and annealed in a forced air oven for 10 minutes at 100° C. After annealing at 100° C., the film was annealed at a higher temperature (120° C.) for another 10 minutes.

Film optical retardation measurements were made using a J. A. Woollam M-2000V Spectroscopic Ellipsometer having a spectral range of 370 to 1000 nm. RetMeas (Retardation Measurement) program from J. A. Woollam Co., Inc. was used to obtain optical film in-plane ($R_e$) and out-of-plane ($R_{th}$) retardations. Values are reported at 589 or 633 nm at a film thickness of 60 μm.

Example 1—Preparation of Cellulose Ester (Comparative)

A 3-neck 100 mL round bottom flask, fitted with two double neck adapters giving five ports, was equipped for mechanical stirring, with an iC10 diamond tipped IR probe (Mettler-Toledo AutoChem, Inc., Columbia, Md., USA), and with an $N_2$/vacuum inlet. To the flask was added 61 g of 1-butyl-3-methylimidazolium chloride. Prior to adding the [BMIm]Cl, the ionic liquid was melted at 90° C. then stored in a desiccator; during storage, the [BMIm]Cl remained a liquid. While stirring rapidly, began adding 3.21 g of previously dried microcrystalline cellulose (DP ca. 335) in small portions (3 min addition). The slurry was stirred for 5 min before applying vacuum. After ca. 3 h 25 min, most of the cellulose had dissolved except for a few small pieces and 1 large piece stuck to the probe. After 5.5 h, the oil bath temperature was increased to 105° C. to speed up dissolution of the remaining cellulose. The solution was maintained at 105° C. for 1.5 h (47 min heat up) before allowing the solution to cool to room temperature (6 h 25 min from the start of the cellulose addition) and stand overnight at ambient temperature.

After standing overnight, the cellulose/[BMIm]Cl solution was clear and the IR spectra indicated that all of the cellulose was dissolved. The solution was heated to 80° C. before adding 10.11 g (5 eq) $Ac_2O$ drop wise (26 min addition). The reaction was sampled throughout the reaction period by removing 6-10 g aliquots of the reaction mixture and precipitating in 100 mL of MeOH. The solid from each aliquot was washed 2× with 100 mL portions of MeOH then 2× with 100 mL of MeOH containing 8% of 35 wt % $H_2O_2$ before drying at 60° C., 5 mm Hg. The $1^{st}$ sample was white, the $2^{nd}$ sample was tan, and the $3^{rd}$ sample was brown. During the course of the reaction, the solution became progressively darker. Approximately 2 h 45 min after the start of the $Ac_2O$ addition, the viscosity of the reaction mixture abruptly increased then the reaction mixture completely gelled. The oil bath was lowered and the contact solution was allowed to cool to room temperature.

Figure 3:
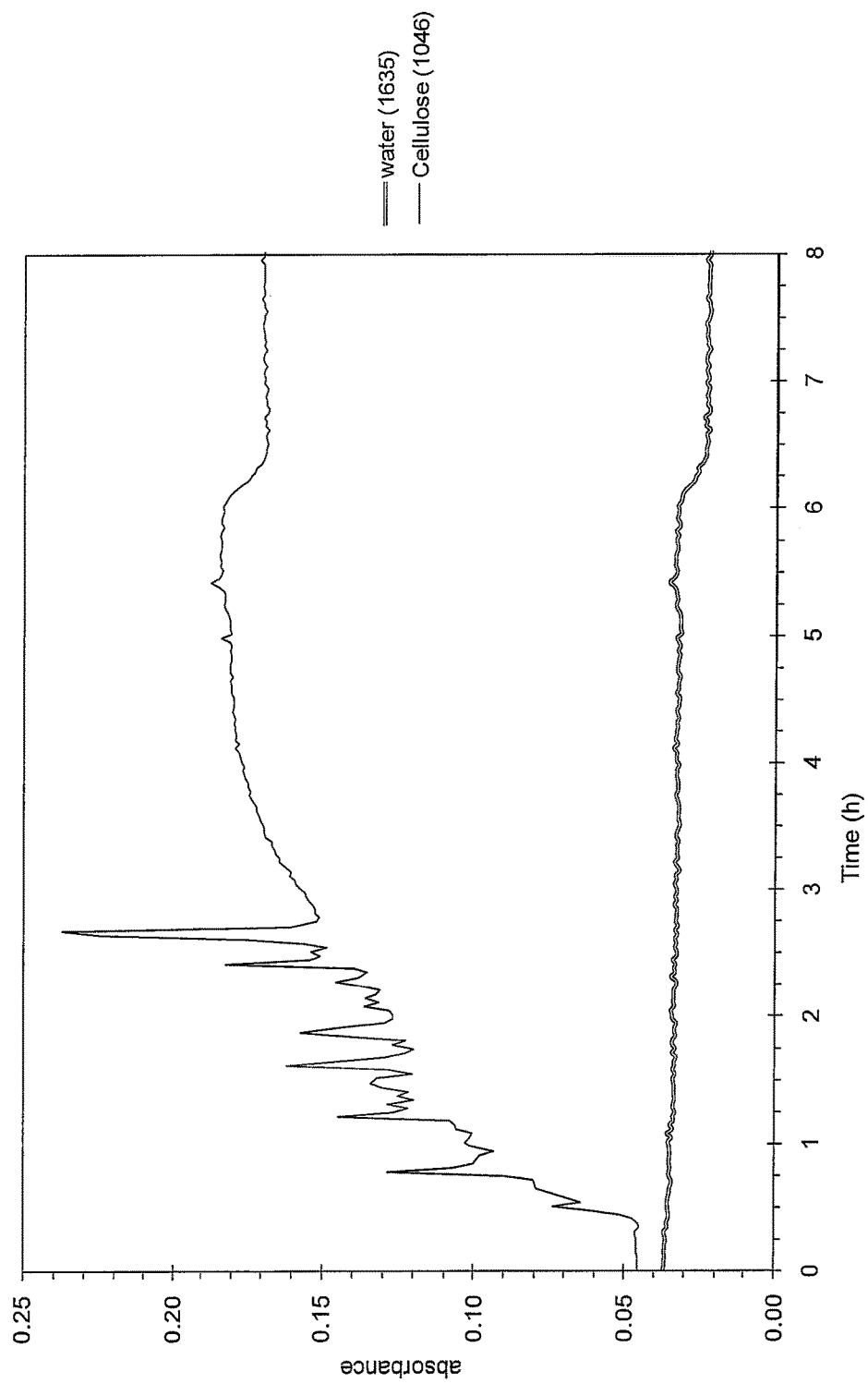
FIG. 3 is a plot of absorbance versus time showing the dissolution of 5 weight percent cellulose in 1-butyl-3-methylimidazolium chloride.

FIG. 3 is a plot of absorbance versus time for Example 1 and it shows the dissolution of cellulose (1046 $cm^{-1}$) and the removal of residual water (1635 $cm^{-1}$) from the mixture during the course of the dissolution. The spikes in the cellulose trend line are due to large cellulose gel particles sticking to the probe which, are removed by the stirring action. Clumping occurs because the surfaces of the cellulose particles become partially dissolve before dispersion is obtained leading to clumping and large gel particles. The dip in the trend lines near 6 h result from the temperature increase from 80 to 105° C. This figure illustrates that ca. 6 h is required to fully dissolve the cellulose when the cellulose is added to the ionic liquid that is preheated to 80° C.

Figure 4:
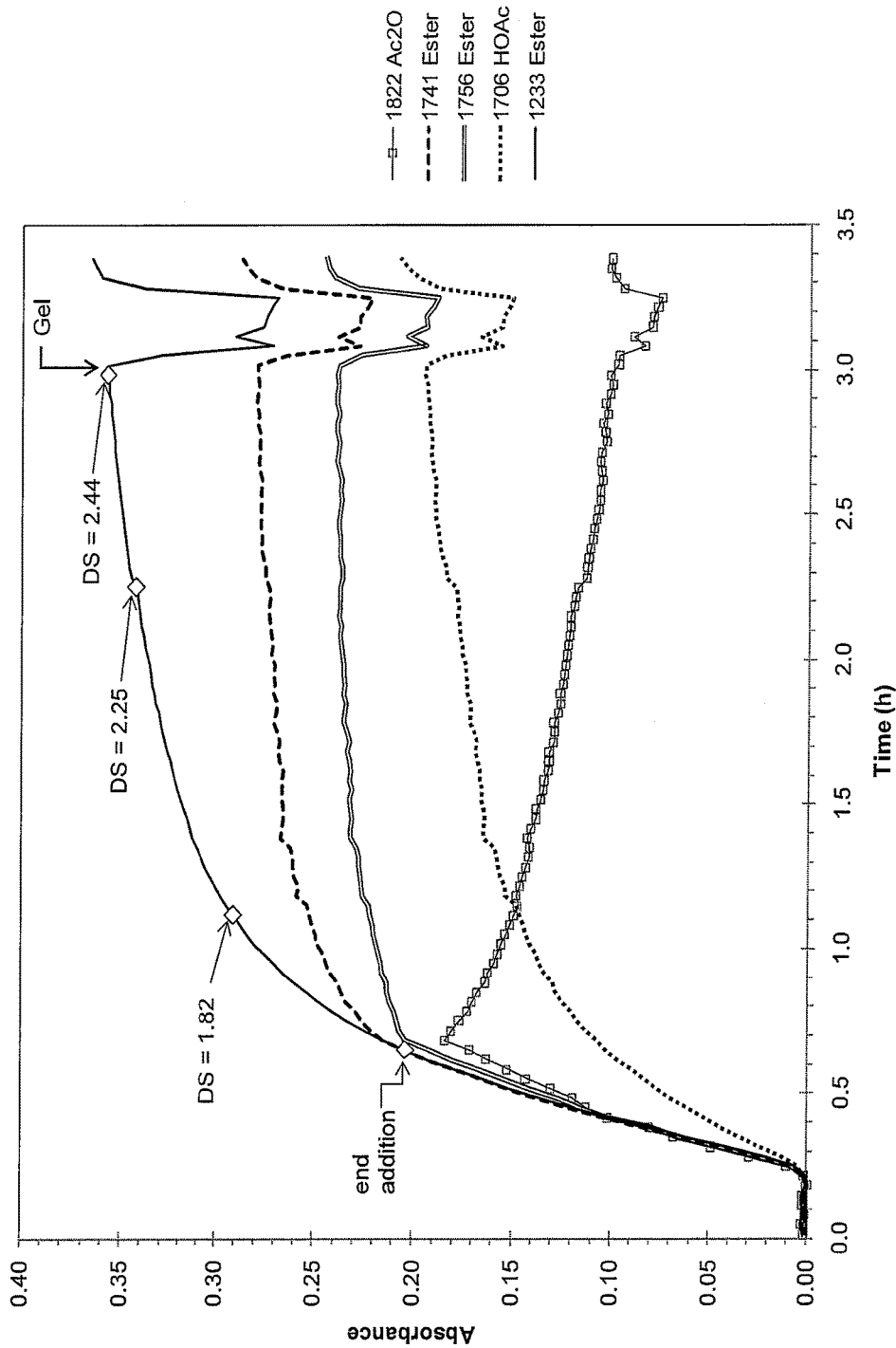
FIG. 4 is a plot of absorbance versus time showing the acetylation of cellulose dissolved in 1-butyl-3-methylimidazolium chloride with 5 molar equivalents of acetic anhydride.

FIG. 4 is a plot of absorbance versus time for Example 1 and it illustrates the acetylation of cellulose (1756, 1741, 1233 $cm^{-1}$), the consumption of $Ac_2O$ (1822 $cm^{-1}$), and the coproduction of acetic acid (1706 $cm^{-1}$) during the experiment. The DS values shown in FIG. 4 were determined by NMR spectroscopy and correspond to the samples removed during the course of the contact period. As illustrated, ca. 75% of the acetylation occurred during the first hour after which the reaction rates slowed. Approximately 2 h 45 from beginning the $Ac_2O$ addition (DS=2.45), the solution viscosity suddenly increased followed by gellation of the contact mixture. At this point, no further reaction occurred and the remaining contact solution was processed as described above. It should be noted that there was still a large excess of $Ac_2O$ at the point of gellation. Furthermore, during the course of the contact period, the solution became progressively darker and the final product color was dark brown. Color measurements of the final sample dissolved in NMP gave a L* value of 82.74, an a* value of 2.23, a b* value of 56.94, and an E* value of 59.55. In addition to determining the DS of each sample, the molecular weight of each sample was determined by GPC (Table 1, below). In general, Mw was approximately 55,000 and the polydispersity ranged from 3-4. Based on the DP of the starting cellulose, this analysis indicates that the molecular weight of the cellulose polymer remained essentially intact during the contact period.

Example 2—Modification of Cellulose with Water

A 3-neck 100 mL round bottom flask, fitted with two double neck adapters giving five ports, was equipped for mechanical stirring, with an iC10 diamond tipped IR probe, and with an $N_2$/vacuum inlet. To the flask was added 64.3 g of 1-butyl-3-methylimidazolium chloride. Prior to adding the [BMIm]Cl, the IL was melted at 90° C. then stored in a desiccator; the [BMIm]Cl remained a liquid during storage. To the ionic liquid was added 3.4 g (5 wt %) of microcrystalline cellulose (DP ca. 335) at ambient temperature while stirring rapidly to disperse the cellulose. Approximately 12 min after adding the cellulose, a preheated 80° C. oil bath was raised to the flask. After ca. 17 min in the 80° C. oil bath, visually, all of the cellulose appeared to be dissolved. After ca. 22 min in the 80° C. oil bath, began applying vacuum. To insure complete removal of water, 50 min after applying vacuum, the oil bath setting was increased to 105° C. and the solution was stirred for 2 h 25 min before the oil bath was allowed to cool to room temperature.

The temperature of the clear, amber cellulose solution was adjusted to 80° C. before adding 6.42 g of $Ac_2O$ (3 eq) drop wise (5 min addition). The contact mixture was sampled throughout the reaction period by removing 6-10 g aliquots of the contact mixture and precipitating in 100 mL of MeOH. The solid from each aliquot was washed 1× with 100 mL of MeOH then 2× with MeOH containing 8 wt % 35% $H_2O_2$. The samples were then dried at 60° C., 5 mm Hg overnight. During the course of the contact period, the color of the solution became darker ultimately becoming dark brown. Approximately 2 h 10 min from the start of $Ac_2O$ addition, the solution viscosity began to increase significantly; 10 min later the solution completely gelled out and started climbing the stir shaft. The experiment was aborted and MeOH was added to the flask to precipitate the remaining product.

The precipitation and the wash liquids from each aliquot were combined and concentrated invacuo at 68° C. until the vacuum dropped to 24 mm Hg which provided 54.2 g of recovered [BMIm]Cl. Analysis by $^1H$ NMR revealed that the ionic liquid contained 4.8 wt % acetic acid when measured by this technique.

Figure 5:
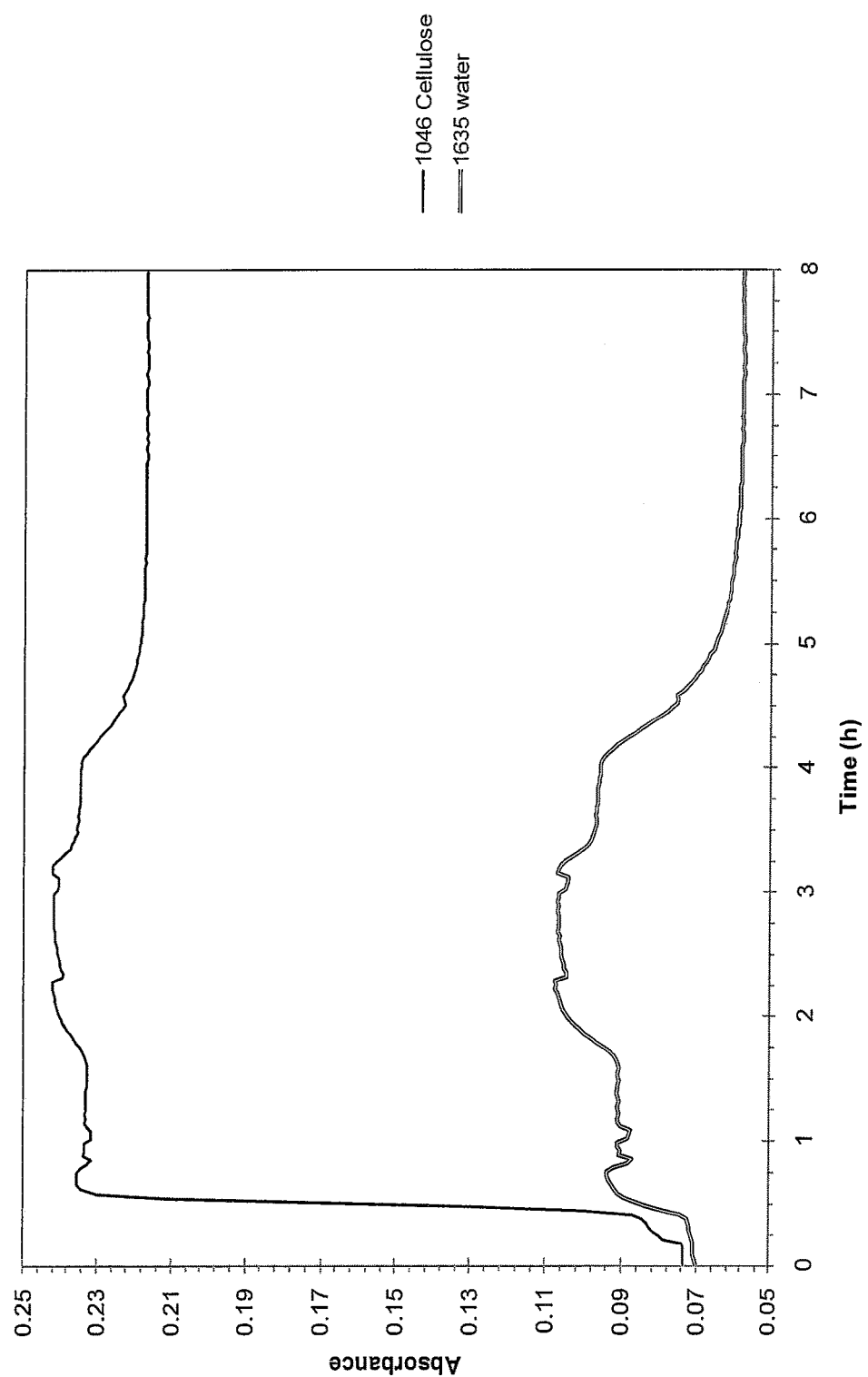
FIG. 5 is a plot of absorbance versus time showing the dissolution of 5 weight percent cellulose in 1-butyl-3-methylimidazolium chloride.

FIG. 5 is a plot of absorbance versus time for Example 2 and it shows the dissolution of cellulose (1046 $cm^{-1}$) and the removal of residual water (1635 $cm^{-1}$) from the mixture during the course of the dissolution. As can be seen, the dissolution of the cellulose was very rapid (17 min versus 360 min in Example 1). This was due to adding the cellulose to the ionic liquid at room temperature, stirring to get a good dispersion (higher surface area), then heating to effect dissolution. Normally, [BMIm]Cl is a solid that melts at ca. 70° C. However, if water or a carboxylic acid is allowed to mix with [BMIm]Cl, the [BMIm]Cl will remain a liquid at room temperature thus allowing introduction of the cellulose at ambient temperature. As can be seen from the water loss in FIG. 5, the [BMIm]Cl contained significant water. This example illustrates that the addition of water to an ionic liquid followed by cellulose addition and good mixing to get a good dispersion provides rapid dissolution of cellulose.

Figure 6:
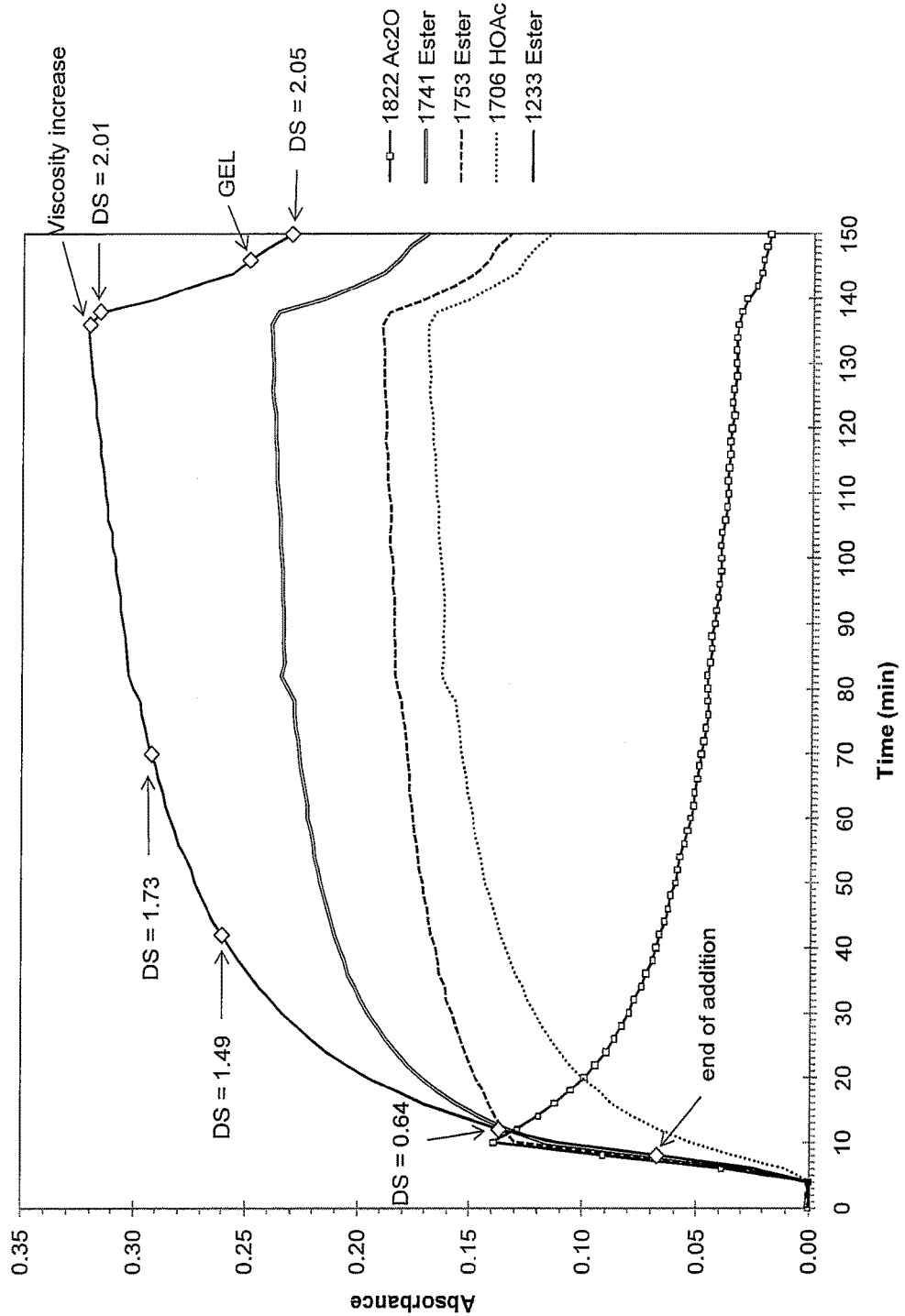
FIG. 6 is a plot of absorbance versus time showing the acetylation of cellulose dissolved in 1-butyl-3-methylimidazolium chloride with 3 molar equivalents of acetic anhydride at 80° C.

FIG. 6 is a plot of absorbance versus time for Example 2 and it illustrates the acetylation of cellulose (1756, 1741, 1233 $cm^{-1}$), the consumption of $Ac_2O$ (1822 $cm^{-1}$), and the coproduction of acetic acid (1706 $cm^{-1}$) during the experiment. The DS values shown in FIG. 6 were determined by NMR spectroscopy and correspond to the samples removed during the course of the contact period. Relative to Example 1, the reaction rate was slower (Example 1, DS=2.44 @ 165 min; Example 2, DS=2.01 @ 166 min, cf. Table 1, below). As was observed in Example 1, the solution viscosity suddenly increased followed by gellation of the contact mixture, but in Example 2, gellation occurred at a lower DS. Both the slower reaction rate and gellation at a lower temperature can be attributed to the use of less $Ac_2O$. However, it should be noted that there was still a large excess of $Ac_2O$ at the point of gellation. As with Example 1, during the course of the contact period, the solution became progressively darker and the final product color was dark brown. Color measurements of the final sample dissolved in NMP gave a L value of 67.30, an a* value of 17.53, a b* value of 73.35, and an E* value of 82.22. In addition to determining the DS of each sample, the molecular weight of each sample was determined by GPC (Table 1, below). In general, Mw was approximately 55,000 and the polydispersity ranged from 3-6. Based on the DP of the starting cellulose, this analysis indicates that the molecular weight of the cellulose polymer remained essentially intact during the contact period.

Example 3—MSA Secondary Component, No Modification with Water

Cellulose (3.58 g, 5 wt %) was dissolved in 68 g of [BMIm]Cl in a manner similar to Example 2. To the cellulose solution (contact temperature=80° C.) was added a mixture of 433 mg MSA and 6.76 g of $Ac_2O$ (3 eq) drop wise (8 min). The reaction was sampled throughout the reaction period by removing 6-10 g aliquots of the reaction mixture and precipitating in 100 mL of MeOH. The solid from each aliquot was washed 2× with 100 mL portions of MeOH then dried at 60° C., 5 mm Hg. The solid samples were snow white. After ca. 2 h, all of the $Ac_2O$ appeared to be consumed by IR. The experiment was aborted and the remaining sample was processed as above.

The precipitation and the wash liquids from each aliquot were combined and concentrated invacuo at 68° C. until the vacuum dropped to 24 mm Hg which provided 64 g of recovered [BMIm]Cl. Unlike Example 2, analysis by $^1H$ NMR revealed that the ionic liquid did not contain any acetic acid when measured by this technique. This result indicates that MSA aids in the removal of residual acetic acid from the ionic liquid, probably by conversion of the residual acetic acid to methyl acetate.

Figure 7:
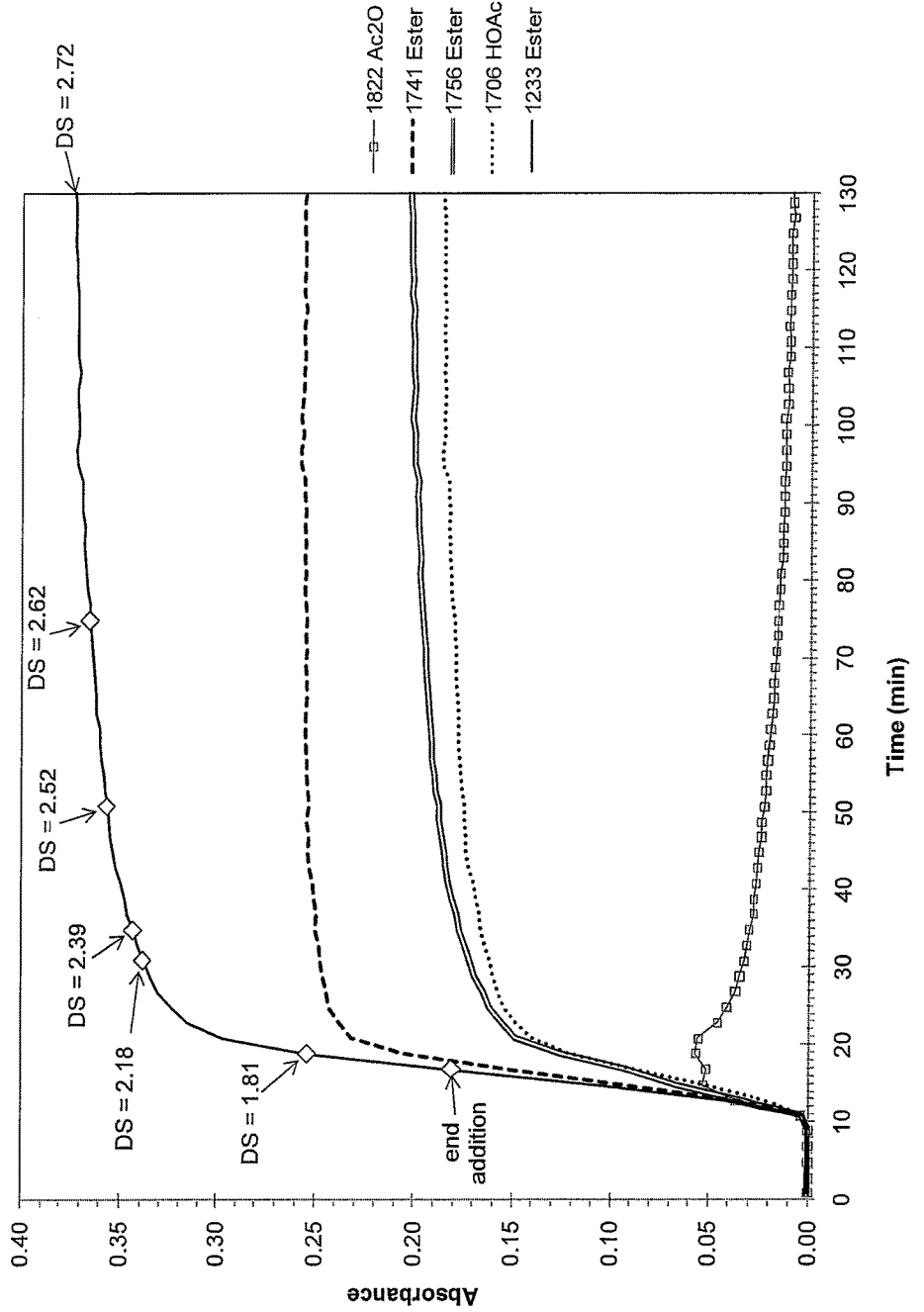
FIG. 7 is a plot of absorbance versus time showing the acetylation of cellulose dissolved in 1-butyl-3-methylimidazolium chloride with 3 molar equivalents of acetic anhydride and 0.2 molar equivalents of methane sulfonic acid at 80° C.

FIG. 7 is a plot of absorbance versus time for Example 3 and it illustrates the acetylation of cellulose (1756, 1741, 1233 $cm^{-1}$), the consumption of $Ac_2O$ (1822 $cm^{-1}$), and the coproduction of acetic acid (1706 $cm^{-1}$) during the experiment. The DS values shown in FIG. 7 were determined by NMR spectroscopy and correspond to the samples removed during the course of the contact period. What is apparent from FIG. 7 is that the rates of reaction are much faster compared to Examples 2 and 3. For example, 55 min was required to reach a DS of 1.82 in Example 1-1 (Table 1, below) while only 10 min was required to reach a DS of 1.81 in Example 3-1. Similarly, 166 min was required to reach a DS of 2.01 in Example 2-4 (Table 1, below) while only 20 min was required to reach a DS of 2.18 in Example 3-2. Additionally, FIG. 7 shows that no gellation occurred during the course of the experiment. In fact, throughout the experiment, there was not any increase in solution viscosity, the solution color was essentially unchanged from the initial solution color, and the products isolated from the contact mixture were all white. Color measurements of the final sample dissolved in NMP gave a L* value of 97.65, an a* value of −2.24, a b* value of 11.07, and an E* value of 11.54. Comparison of these values to those obtained in Example 1 and 2 (E*=59.55 and 82.22, respectively) shows that inclusion of a secondary component such as MSA in the contact mixture significantly improves solution and product color. This effect is particularly pronounced in view of the fact that the samples in Examples 1 and 2 were bleached and the samples in this Example were not bleached. As discussed in Example 36, bleaching can significantly improve product color for cellulose esters prepared from cellulose dissolved in ionic liquids. Finally, it should be noted in Table 1, below, that the Mw (ca. 40,000) for the samples of Example 3 are less than those for Examples 1 and 2 and that the polydispersity (Mw/Mn) is lower and more narrow (2-3) than those for Examples 1 and 2 (3-6). When compared to Examples 1 and 2, Example 3 shows that inclusion of a secondary component such as MSA in the contact mixture accelerates the rates of reaction, significantly improves solution and product color, prevents gellation of the contact mixture, allows the achievement of high DS values while using less acylating reagent, and helps to promote lowering of the cellulose ester molecular weight.

TABLE 1

Properties of Cellulose Acetates Prepared Without Water Modification

| Example | Time (min) | DS | Mw | Mw/Mn |
|---|---|---|---|---|
| 1-1 | 55 | 1.82 | 59243 | 3.29 |
| 1-2 | 122 | 2.25 | 61948 | 4.34 |
| 1-3 | 165 | 2.44 | 51623 | 3.73 |
| 2-1 | 6 | 0.64 | 50225 | 2.93 |
| 2-2 | 34 | 1.49 | 56719 | 3.48 |
| 2-3 | 56 | 1.73 | 64553 | 5.4 |
| 2-4 | 166 | 2.01 | 66985 | 5.7 |
| 2-5 | 176 | 2.05 | 63783 | 5.83 |
| 3-1 | 10 | 1.81 | 41778 | 1.92 |
| 3-2 | 20 | 2.18 | 43372 | 2.01 |
| 3-3 | 27 | 2.39 | 41039 | 2.22 |
| 3-4 | 43 | 2.52 | 41483 | 2.4 |
| 3-5 | 66 | 2.62 | 40412 | 2.54 |
| 3-6 | 124 | 2.72 | 39521 | 2.55 |

Example 4—Modification with Water, MSA Secondary Component

A 3-neck 100 mL round bottom flask, fitted with two double neck adapters giving five ports, was equipped for mechanical stirring, with an iC10 diamond tipped IR probe, and with an $N_2$/vacuum inlet. To the flask added 58.07 g of 1-butyl-3-methylimidazolium chloride. Prior to adding the [BMIm]Cl, the IL was melted at 90° C. then stored in a desiccator. The flask was placed in an oil bath and heated to 80° C.

To 3.06 g (5 wt %) of microcrystalline cellulose (DP ca. 335), was added 3.06 g of water. The slurry was hand mixed and allowed to stand for ca. 30 min before adding the slurry in small portions to the [BMIm]Cl (5 min addition). This gave a hazy solution in which the cellulose was surprisingly well dispersed. The slurry was stirred for 27 min, before applying vacuum. Visually, after 28 min under vacuum all of the cellulose had dissolved which was confirmed by IR. By IR, there was still ca. 3 wt % water in the [BMIm]Cl when all of the cellulose was dissolved. The system was maintained under vacuum at 80° C. to remove the remaining water. The sample was allowed to cool to room temperature and left standing until the next step.

The cellulose solution was heated to 80° C. before adding a mixture of 5.78 g $Ac_2O$ (3 eq) and 368 mg MSA drop wise (8 min). The reaction was sampled throughout the reaction period by removing 6-10 g aliquots of the reaction mixture and precipitating in 100 mL of MeOH. The solid from each aliquot was washed 2× with 100 mL portions of MeOH then dried at 60° C., 5 mm Hg. The isolated samples were snow white. The solution color was excellent throughout the experiment and there was no indication of a viscosity increase. After ca. 2 h 25 min, infrared spectroscopy indicated that all of the $Ac_2O$ was consumed. The experiment was aborted and the remaining sample was processed as above.

Figure 8:
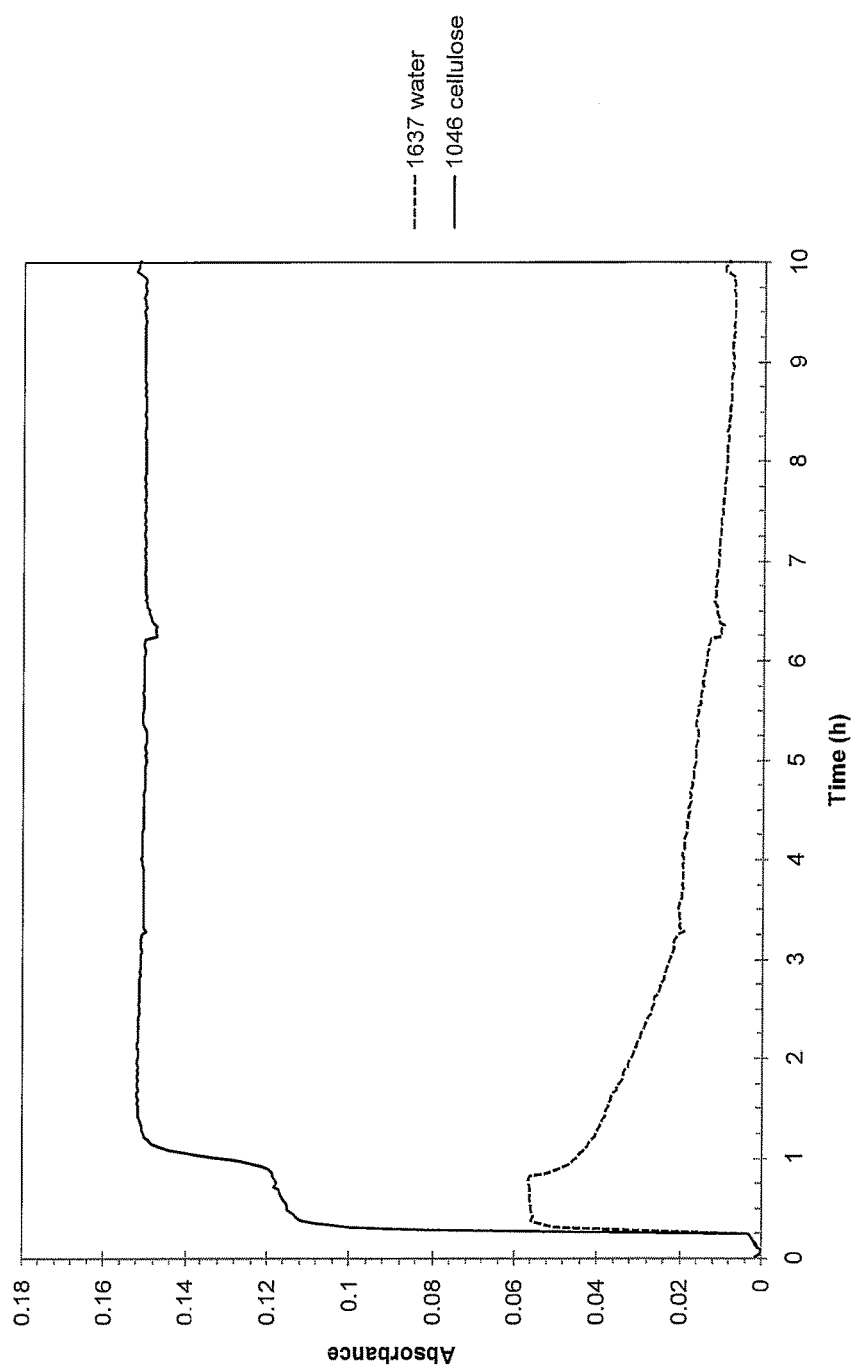
FIG. 8 is a plot of absorbance versus time showing the dissolution of 5 weight percent cellulose in 1-butyl-3-methylimidazolium chloride.

FIG. 8 is a plot of absorbance versus time for Example 4 and it shows the dissolution of cellulose (1046 $cm^{-1}$) and the removal of residual water (1635 $cm^{-1}$) from the mixture during the course of the dissolution. As can be seen, the dissolution of the water wet (activated) cellulose was very rapid (28 min) despite the presence of a significant amount of water. This is surprising in view of the conventional teachings. The addition of water wet cellulose to the ionic liquid enables one to obtain a good dispersion of cellulose with little clumping. Upon application of a vacuum to remove the water, the cellulose rapidly dissolves without clumping to form large particles.

Figure 9:
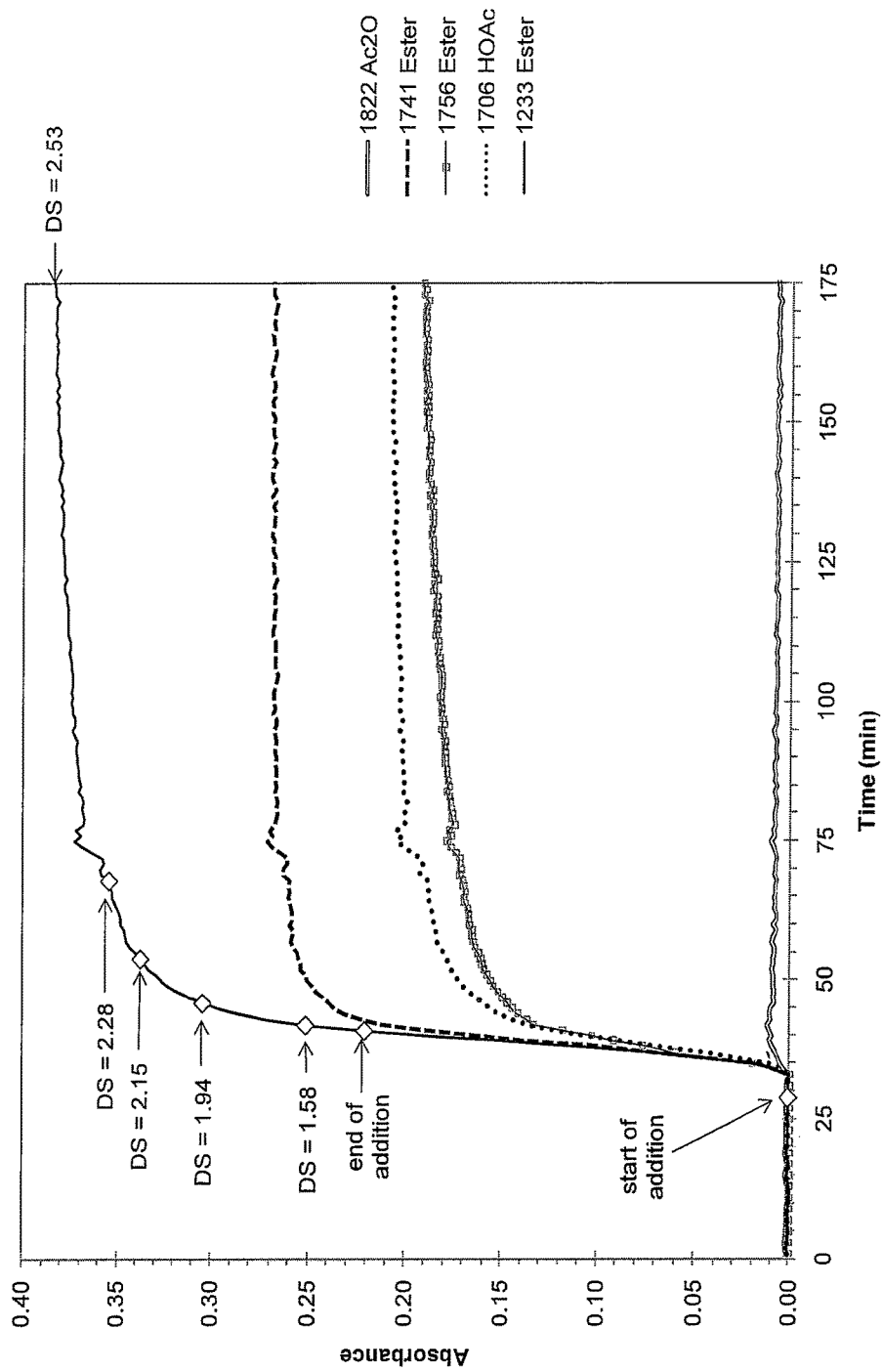
FIG. 9 is a plot of absorbance versus time showing the acetylation of cellulose dissolved in 1-butyl-3-methylimidazolium chloride with 3 molar equivalents of acetic anhydride and 0.2 molar equivalents of methane sulfonic acid at 80° C.

FIG. 9 is a plot of absorbance versus time for Example 4 and it illustrates the acetylation of cellulose (1756, 1741, 1233 $cm^{-1}$), the consumption of $Ac_2O$ (1822 $cm^{-1}$), and the coproduction of acetic acid (1706 $cm^{-1}$) during the experiment. The DS values shown in FIG. 9 were determined by NMR spectroscopy and correspond to the samples removed during the course of the contact period. Relative to Example 3, the reaction rate to produce cellulose acetate was similar. However, the molecular weights (ca. 33,000) of the cellulose acetate samples (Table 2, below) were notably lower that that observed in Example 3 and much lower than that observed in Examples 1 and 2 (Table 1, above). Additionally, the polydispersities for the samples of Example 4 are all less than 2, less than that observed for the samples of Examples 1, 2, and 3.

This example illustrates that water wet cellulose leads to good cellulose dispersion in the ionic liquid and rapid cellulose dissolution. The reaction rate for formation of cellulose acetate is rapid. Surprisingly, water wet cellulose leads to lower molecular weight cellulose acetate with low polydispersities relative to dry cellulose. The cellulose acetate made from water wet cellulose has better acetone solubility relative to when dry cellulose is utilized.

Example 5—Modification with Water, MSA Secondary Component

A 3-neck 100 mL round bottom flask, fitted with two double neck adapters giving five ports, was equipped for mechanical stirring, with a iC10 diamond tipped IR probe, and with an $N_1$/vacuum inlet. To the flask added 67.33 g of 1-butyl-3-methylimidazolium chloride. Prior to adding the [BMIm]Cl, the IL was melted at 90° C. then stored in a desiccator. The flask was placed in an oil bath and heated to 80° C. To 7.48 g (10 wt %) of microcrystalline cellulose (DP ca. 335), was added 7.08 g of water. The cellulose slurry was hand mixed and allowed to stand for ca. 60 min before adding the slurry in small portions to the [BMIm]Cl (8 min addition). This gave a hazy solution in which the cellulose was surprisingly well dispersed. The slurry was stirred for 10 min, before applying vacuum. The cellulose dissolution was left stirring overnight.

Infrared spectroscopy indicated that essentially all of the cellulose was dissolved within 50 min after applying vacuum; ca. 3.5 h was required to remove the water. To the cellulose solution was added a mixture of 14.13 g of $Ac_2O$ (3 eq) and 884 mg (0.2 eq) of MSA drop wise (11 min). The reaction was sampled throughout the reaction period by removing 6-10 g aliquots of the reaction mixture and precipitating in 100 mL of MeOH. The solid from each aliquot was washed 2× with 100 mL portions of MeOH then dried at 60° C., 5 mm Hg. The isolated samples were snow white. The solution color was excellent through out the experiment and there was no indication of a viscosity increase. After ca. 2 h 10 min, all of the $Ac_2O$ appeared to be consumed by IR. The experiment was aborted and the remaining sample was processed as above.

Figure 10:
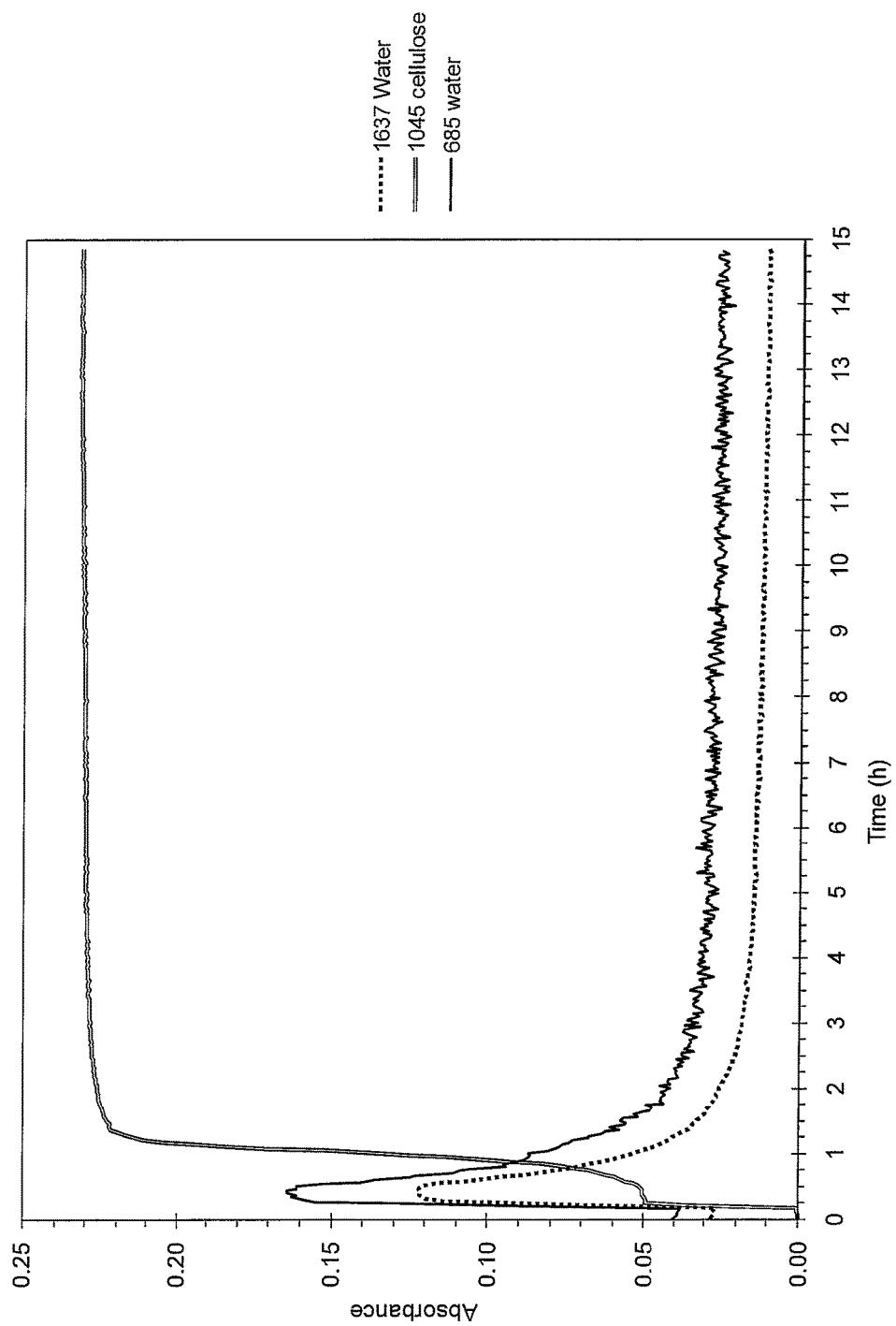
FIG. 10 is a plot of absorbance versus time showing the dissolution of 10 weight percent cellulose in 1-butyl-3-methylimidazolium chloride.

FIG. 10 is a plot of absorbance versus time for Example 5 and it shows the dissolution of cellulose (1046 $cm^{-1}$) and the removal of residual water (1635 $cm^{-1}$) from the mixture during the course of the dissolution. As can be seen, the dissolution of the water wet (activated) cellulose was very rapid (50 min) despite the presence of a significant amount of water and the increase in cellulose concentration relative to Example 4.

Figure 11:
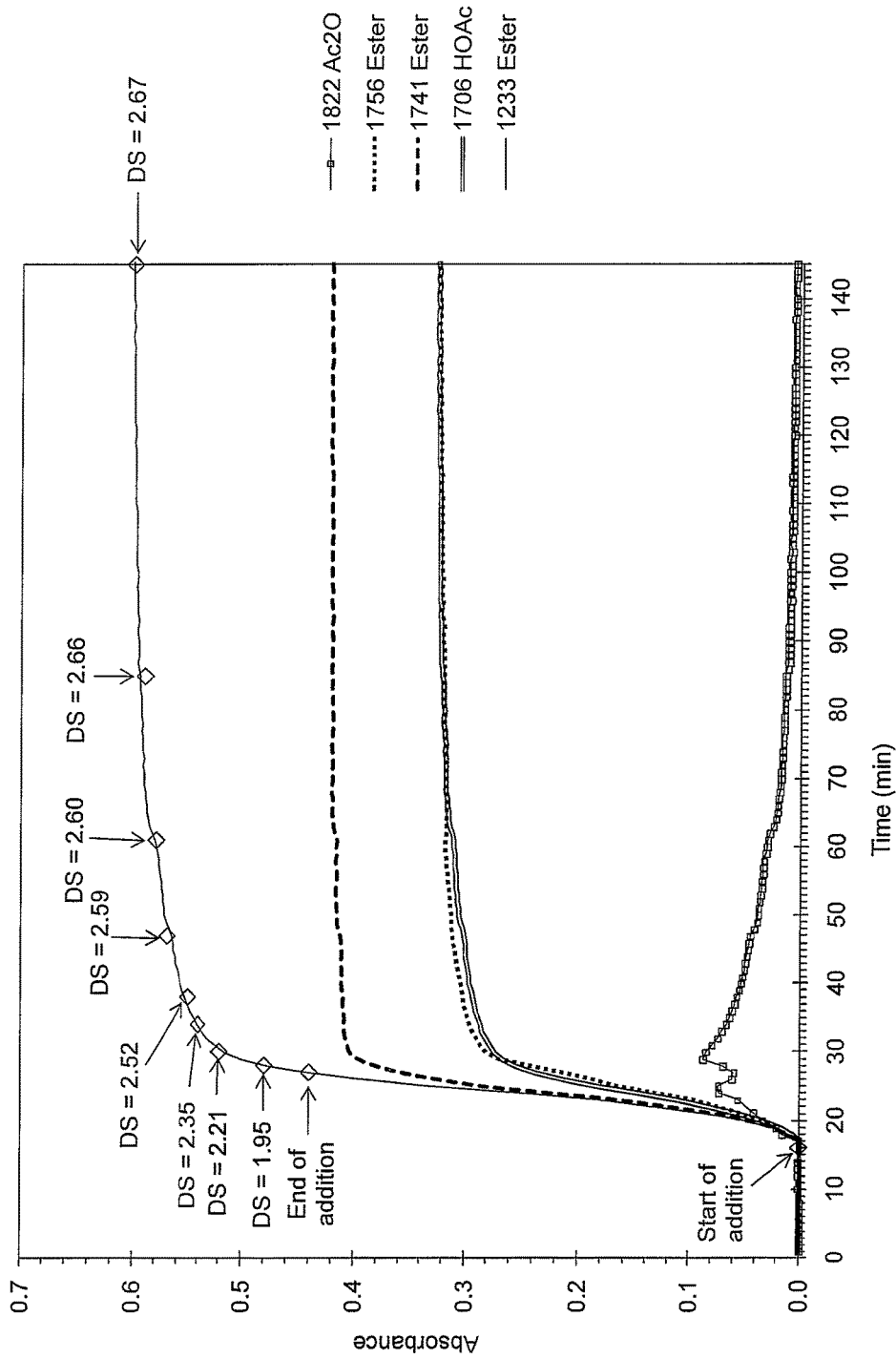
FIG. 11 is a plot of absorbance versus time showing the acetylation of cellulose dissolved in 1-butyl-3-methylimidazolium chloride with 3 molar equivalents of acetic anhydride and 0.2 molar equivalents of methane sulfonic acid at 80° C.

FIG. 11 is a plot of absorbance versus time for Example 5 and it illustrates the acetylation of cellulose (1756, 1741, 1233 cm$^{-1}$), the consumption of Ac$_2$O (1822 cm$^{-1}$), and the coproduction of acetic acid (1706 cm$^{-1}$) during the experiment. The DS values shown in FIG. 11 were determined by NMR spectroscopy and correspond to the samples removed during the course of the contact period. Despite the increase in cellulose concentration, relative to Examples 3 and 4, the reaction rate to produce cellulose acetate was similar. The molecular weights (ca. 22,000) of the cellulose acetate samples (Table 2, below) were notably lower that that observed in Example 4 and much lower than that observed in Examples 1, 2, and 3 (Table 1, above). As was observed for Example 4, the polydispersities for the samples of Example 5 are all less than 2, less than that observed for the samples of Examples 1, 2, and 3.

This example illustrates that water wet cellulose leads to good cellulose dispersion in the ionic liquid and rapid cellulose dissolution even when the cellulose concentration is increased to 10 wt %. The reaction rate for formation of cellulose acetate is rapid. Surprisingly, water wet cellulose at this concentrations leads to even lower molecular weight cellulose acetates with low polydispersities relative to dry cellulose. The cellulose acetate made from water wet cellulose has better acetone solubility relative to when dry cellulose is utilized.

Example 6—Modification with Water, MSA Secondary Component

A 3-neck 100 mL round bottom flask, fitted with two double neck adapters giving five ports, was equipped for mechanical stirring, with an iC10 diamond tipped IR probe, and with an N$_2$/vacuum inlet. To the flask added 51.82 g of 1-butyl-3-methylimidazolium chloride. Prior to adding the [BMIm]Cl, the IL was melted at 90° C. then stored in a desiccator. The flask was placed in an oil bath and heated to 80° C. To 9.15 g (15 wt %) of microcrystalline cellulose (DP ca. 335), added 53.6 g of water. After hand mixing, the cellulose was allowed to stand in the water for 50 min before filtering which gave 18.9 g of a wet cellulose cake. The water wet cellulose was then added in small portions to the [BMIm]Cl (5 min addition). Within 2 min, the cellulose was finely dispersed in the ionic liquid. Ten minutes after adding the cellulose to the [BMIm]Cl, the flask was placed under vacuum. After ca. 1 h, there were no visible cellulose particles; the solution viscosity was very high and the solution started climbing the stir rod. The solution was left stirring overnight at 80° C. under vacuum.

Infrared spectroscopy indicated that ca. 1 h was required for cellulose dissolution and 2 h was required to strip the water to the initial value. The cellulose solution was heated to 100° C. prior to adding a mixture of 17.28 g Ac$_2$O (3 eq) and 1.087 g (0.2 eq) of MSA drop wise (8 min). The reaction was sampled throughout the reaction period by removing 6-10 g aliquots of the reaction mixture and precipitating in 100 mL of MeOH. The solid from each aliquot was washed 1× with 100 mL of MeOH then 2× with MeOH containing 8 wt % 35% H$_2$O$_2$. The solid samples were then dried at 60° C., 5 mm Hg. After ca. 65 min, all of the Ac$_2$O appeared to be consumed by IR. The experiment was aborted and the remaining sample was processed as above.

Figure 12:
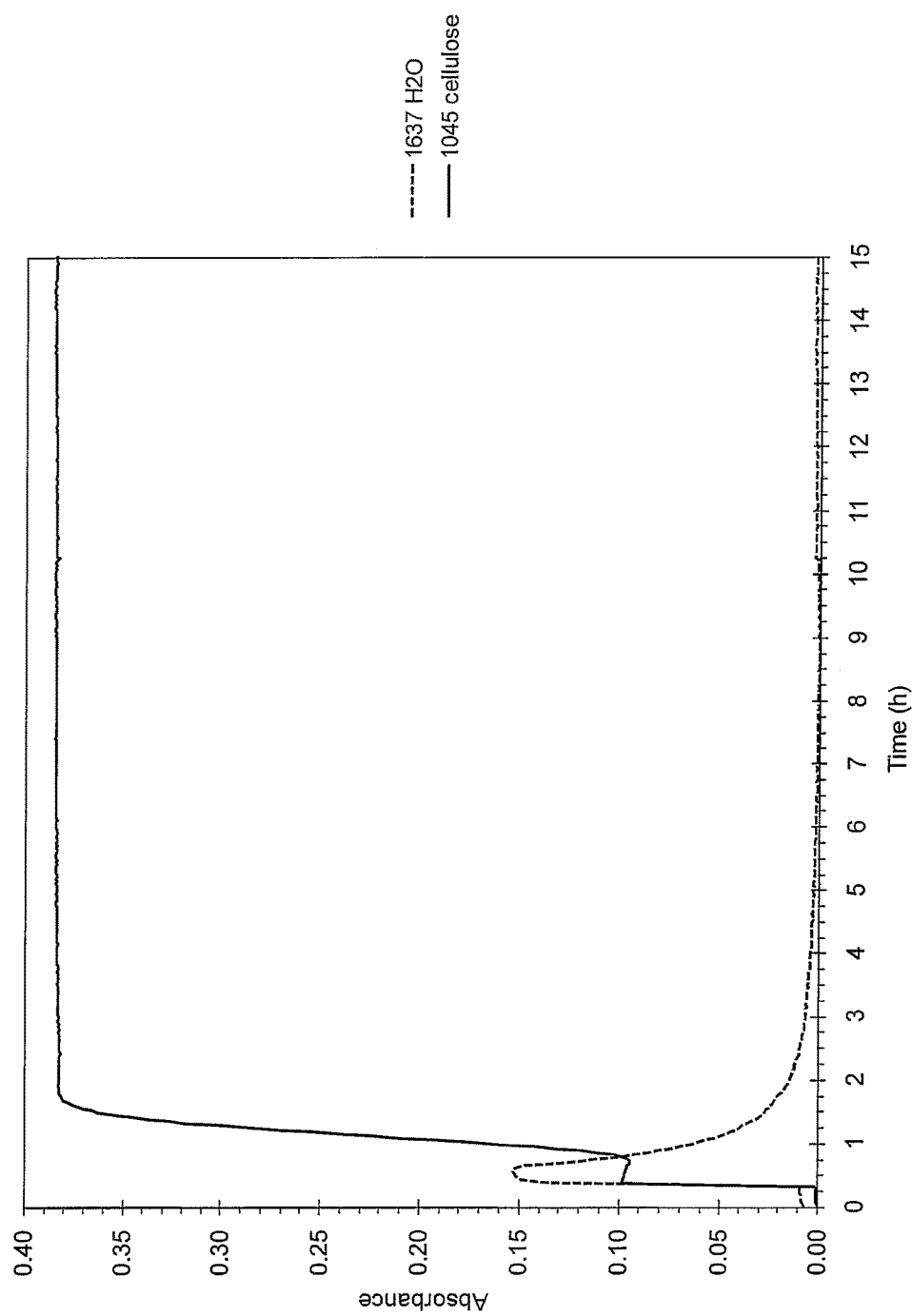
FIG. 12 is a plot of absorbance versus time showing the dissolution of 15 weight percent cellulose in 1-butyl-3-methylimidazolium chloride.

FIG. 12 is a plot of absorbance versus time for Example 6 and it shows the dissolution of presoaked water wet cellulose (1046 cm$^{-1}$) and the removal of residual water (1635 cm$^{-1}$) from the mixture during the course of the dissolution. As can be seen, the dissolution of the water wet (activated) cellulose was very rapid (60 min) despite the presence of a significant amount of water and the use of 15 wt % cellulose. Even more surprising was the rapid removal of water (ca. 2 h) at this high cellulose concentration.

Figure 13:
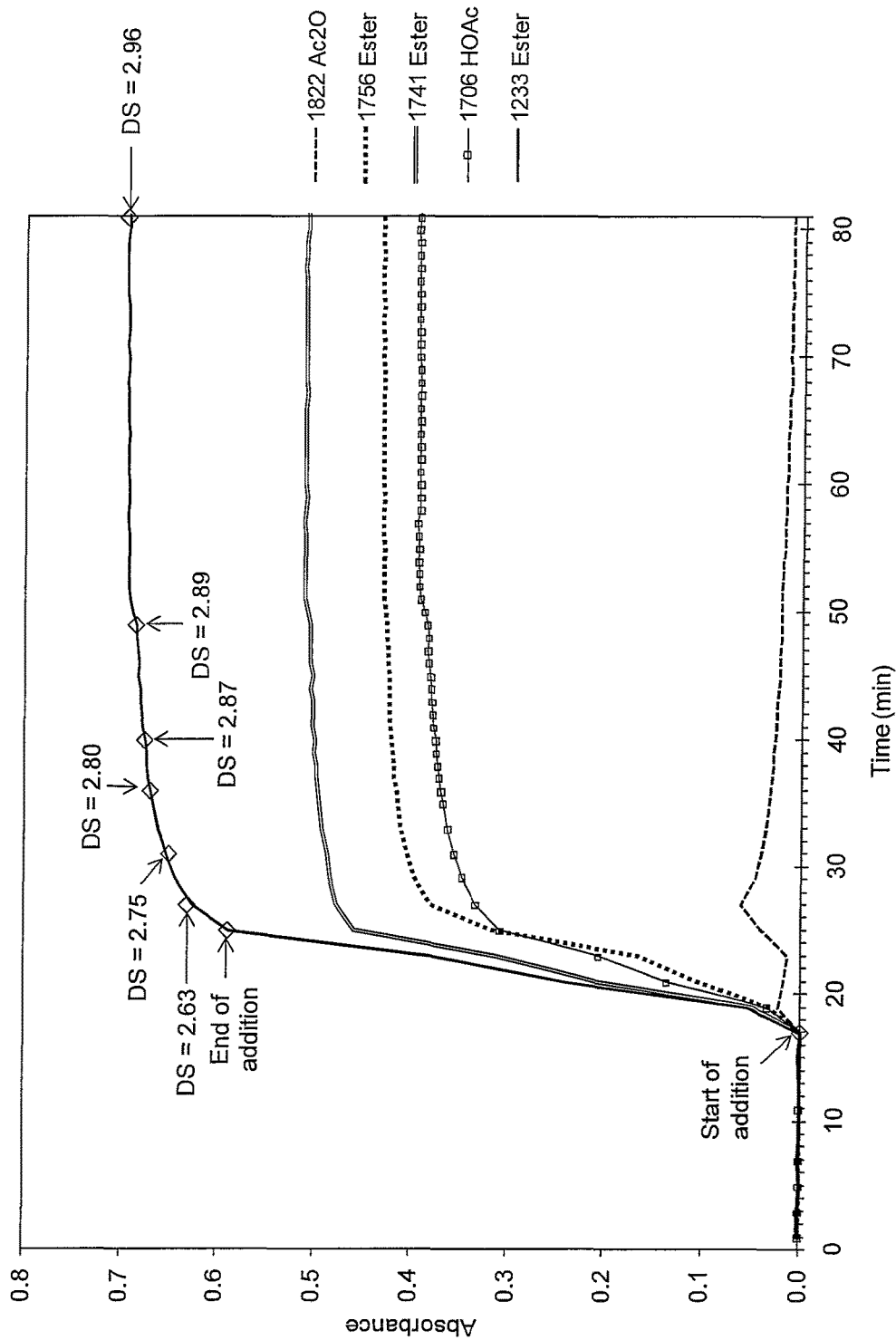
FIG. 13 is a plot of absorbance versus time showing the acetylation of cellulose dissolved in 1-butyl-3-methylimidazolium chloride with 3 molar equivalents of acetic anhydride and 0.2 molar equivalents of methane sulfonic acid at 100° C.

FIG. 13 is a plot of absorbance versus time for Example 6 and it illustrates the acetylation of cellulose (1756, 1741, 1233 cm$^{-1}$), the consumption of Ac$_2$O (1822 cm$^{-1}$), and the coproduction of acetic acid (1706 cm$^{-1}$) during the experiment. The DS values shown in FIG. 13 were determined by NMR spectroscopy and correspond to the samples removed during the course of the contact period. Despite the increase in cellulose concentration (15 wt %), acetic anhydride could be easily mixed into the cellulose solution at 100° C. The higher reaction temperature led to an increase in reaction rate. Again, the molecular weights (ca. 20,000) of the cellulose acetate samples (Table 2, below) were notably lower that that observed in Examples 1, 2, and 3 (Table 1, above) were the cellulose was dried prior to use; the polydispersities for the samples of Example 6 are also less than 2.

This example illustrates that water wet cellulose leads to good cellulose dispersion in the ionic liquid and rapid cellulose dissolution even when the cellulose concentration is increased to 15 wt %. This example also shows that higher temperature (100° C.) increases reaction rates for formation of cellulose acetate. Surprisingly, water wet cellulose at this concentrations leads to even lower molecular weight cellulose acetates with low polydispersities relative to dry cellulose. The cellulose acetate made from water wet cellulose has better acetone solubility relative to when dry cellulose is utilized.

TABLE 2

Effect of Water Modification on Properties of Cellulose Acetates

| Example | Time (min) | DS | Mw | Mw/Mn |
| --- | --- | --- | --- | --- |
| 4-1 | 9 | 1.58 | 31732 | 1.73 |
| 4-2 | 13 | 1.94 | 33559 | 1.64 |
| 4-3 | 21 | 2.15 | 34933 | 1.63 |
| 4-4 | 35 | 2.28 | 31810 | 1.77 |
| 4-5 | 150 | 2.63 | 30771 | 1.89 |
| 5-1 | 11 | 1.95 | 24522 | 1.6 |
| 5-2 | 14 | 2.21 | 23250 | 1.67 |
| 5-3 | 18 | 2.35 | 22706 | 1.76 |
| 5-4 | 22 | 2.52 | 22692 | 1.79 |
| 5-5 | 31 | 2.59 | 21918 | 1.86 |
| 5-6 | 45 | 2.60 | 21628 | 1.89 |
| 5-7 | 70 | 2.66 | 19708 | 1.97 |
| 5-8 | 130 | 2.67 | 20717 | 1.99 |
| 6-1 | 10 | 2.63 | 20729 | 1.67 |
| 6-2 | 14 | 2.75 | 19456 | 1.78 |
| 6-3 | 18 | 2.80 | 19658 | 1.84 |
| 6-4 | 23 | 2.87 | 18966 | 1.84 |
| 6-5 | 32 | 2.89 | 20024 | 1.88 |
| 6-6 | 65 | 2.96 | 18962 | 1.85 |

Example 7—Miscible Cosolvent

Figure 14:
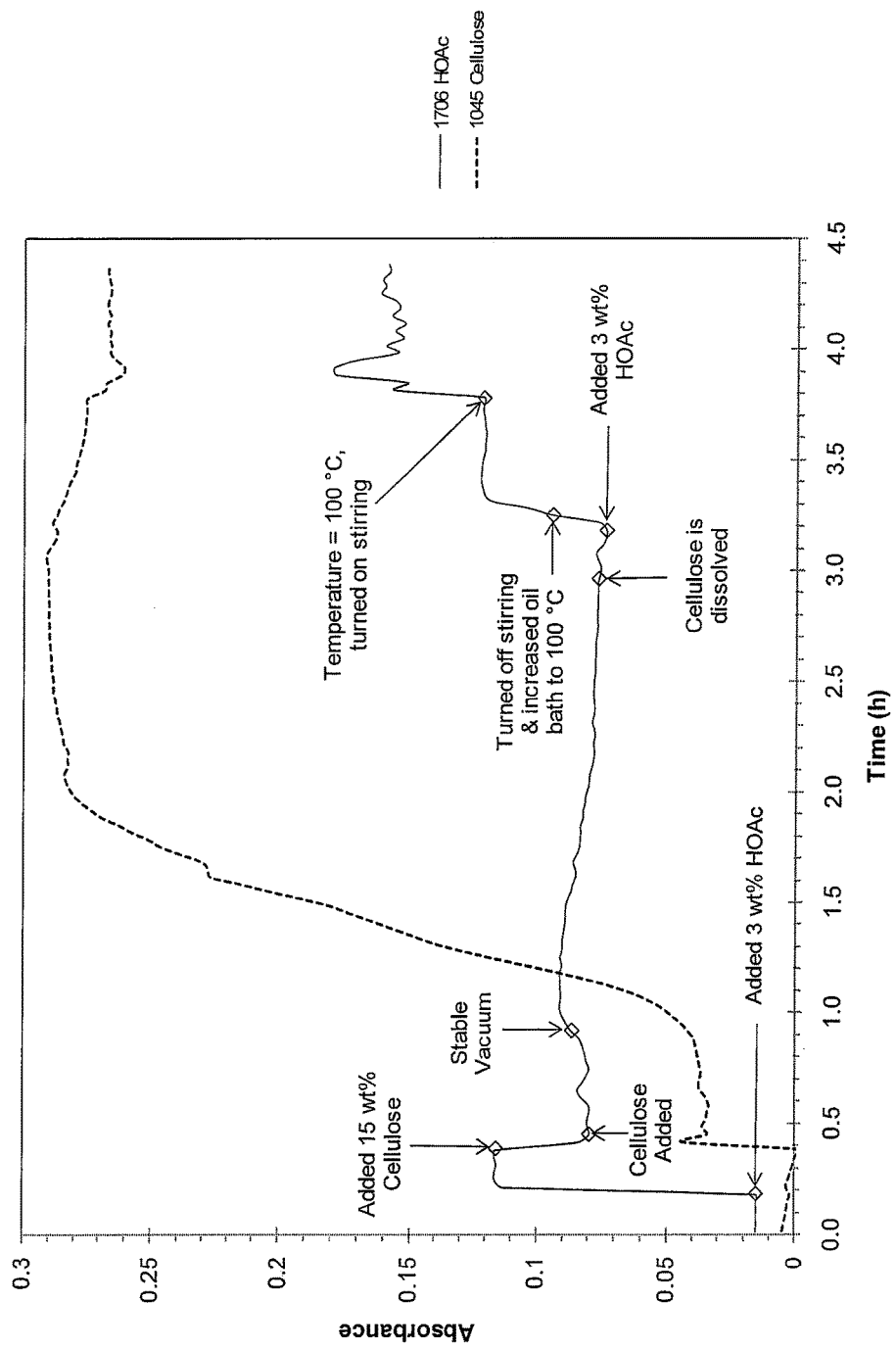
FIG. 14 is a plot of absorbance versus time showing the dissolution of 15 weight percent cellulose in 1-butyl-3-methylimidazolium chloride.

A 3-neck 100 mL round bottom flask, fitted with two double neck adapters giving five ports, was equipped for mechanical stirring, with an iC10 diamond tipped IR probe, and with an N$_2$/vacuum inlet. To the flask added 58.79 g of 1-butyl-3-methylimidazolium chloride. Prior to adding the [BMIm]Cl, the IL was melted at 90° C. then stored in a desiccator. The flask was placed in an oil bath and heated to 80° C. After reaching 80° C., began collecting IR spectra before adding 1.82 g (3 wt %) of glacial acetic acid. The mixture was stirred for 12 min before adding 10.38 g (15 wt %) cellulose (DP ca. 335) as a water wet cellulose cake (10.29 g water, prepared by soaking the cellulose for 50 min in excess water, 9 min addition). The mixture was stirred for ca. 9 min to allow the cellulose to disperse before applying a vacuum. After ca. 65 min, infrared spectroscopy indicated that all of the cellulose was dissolved (FIG. 14). Stirring was continued for an additional 70 min before adding 1.82 g of glacial acetic acid (6 wt % total). In order to reduce the solution viscosity, the stirring was turned off 8 min after adding the acetic acid and the oil bath temperature was increased to 100° C. After reaching 100° C. (45 min) stirring was resumed. Infrared spectroscopy indicated that upon resuming stirring, the acetic acid mixed well with the cellulose solution. The final solution was clear and no cellulose particles were observed. After standing for 10 days, the cellulose solution was still clear and could be hand stirred at room temperature which one cannot do with a 15 wt % cellulose solution in [BMIm]Cl in the absence of acetic acid.

This example shows that significant amount of a miscible cosolvent such as a carboxylic acid compatible with cellulose acylation can be mixed with a cellulose-ionic liquid sample while still maintaining cellulose solubility. A cosolvent has the added benefit of reducing solution viscosity.

Example 8—Randomization

A 3-neck 250 mL round bottom flask, fitted with two double neck adapters giving five ports, was equipped for mechanical stirring, with an iC10 diamond tipped IR probe, and with an $N_2$/vacuum inlet. To the flask added 149.7 g of 1-butyl-3-methylimidazolium chloride. The flask was placed in an oil bath and heated to 80° C. Microcrystalline cellulose (12.14 g, 7.5 wt %, DP ca. 335) was added to 68.9 g of water. After hand mixing, the cellulose was allowed to stand in the water for 45 min at 60° C. before filtering which gave 24.33 g of a wet cellulose cake. The water wet cellulose was then added in small portions to the [BMIm]Cl (5 min addition). Approximately 15 min after adding the cellulose to the [BMIm]Cl, the flask was placed under vacuum by gradually lowering the vacuum starting at ca. 120 mm Hg to ca. 1.4 mm Hg. After ca. 85 min, there were no visible cellulose particles; IR spectroscopy indicated that all of the cellulose was dissolved. The solution was left stirring overnight at 80° C. under vacuum.

To the cellulose solution heated to 80° C. was added a mixture of 22.93 g $Ac_2O$ (3 eq) and 1.427 g (0.2 eq) of MSA drop wise (15 min). The reaction was sampled throughout the reaction period by removing 6-10 g aliquots of the reaction mixture and precipitating in 100 mL of MeOH. The solid from each aliquot was washed 3× with 100 mL portions of MeOH then dried at 60° C., 5 mm Hg. After removing an aliquot 192 min from the start of the $Ac_2O$ addition, 1.21 g of MeOH was added to the contact mixture. The contact mixture was stirred for an addition 120 min before adding 1.95 g of water. The contact mixture was then stirred overnight at 80° C. (14 h 40 min) at which time, the experiment was aborted and the remaining sample was processed as above.

The contact times, DS and molecular weights for isolated samples removed from the contact mixture are summarized below in Table 3.

TABLE 3

Effect of Randomization on Cellulose Acetates

| Example | Time (min) | DS | Mw | Mw/Mn |
|---|---|---|---|---|
| 8-1 | 16 | 1.95 | 26492 | 1.54 |
| 8-2 | 18 | 2.15 | 24838 | 1.57 |
| 8-3 | 21 | 2.24 | 23973 | 1.63 |
| 8-4 | 25 | 2.33 | 23043 | 1.7 |
| 8-5 | 32 | 2.42 | 23499 | 1.79 |
| 8-6 | 57 | 2.56 | 21736 | 1.82 |
| 8-7 | 190 | 2.73 | 20452 | 2.08 |
| 8-8 | After MeOH Addition | 2.73 | 20478 | 2.00 |
| 8-10 | After $H_2O$ Addition | 2.59 | 21005 | 1.89 |

With increasing contact time, the DS increased (until water was added) and the Mw decreased. Fifty-seven minutes after starting the contact period, the cellulose acetate sample had a DS of 2.56 and a Mw of 21,736. Prior to adding the MeOH/water, the DS was 2.73 and the Mw was 20,452. After the water contact period, the isolated cellulose acetate had a DS of 2.59 and a Mw of 21,005 indicating that the DS was reduced but the Mw was unchanged.

Figure 15:
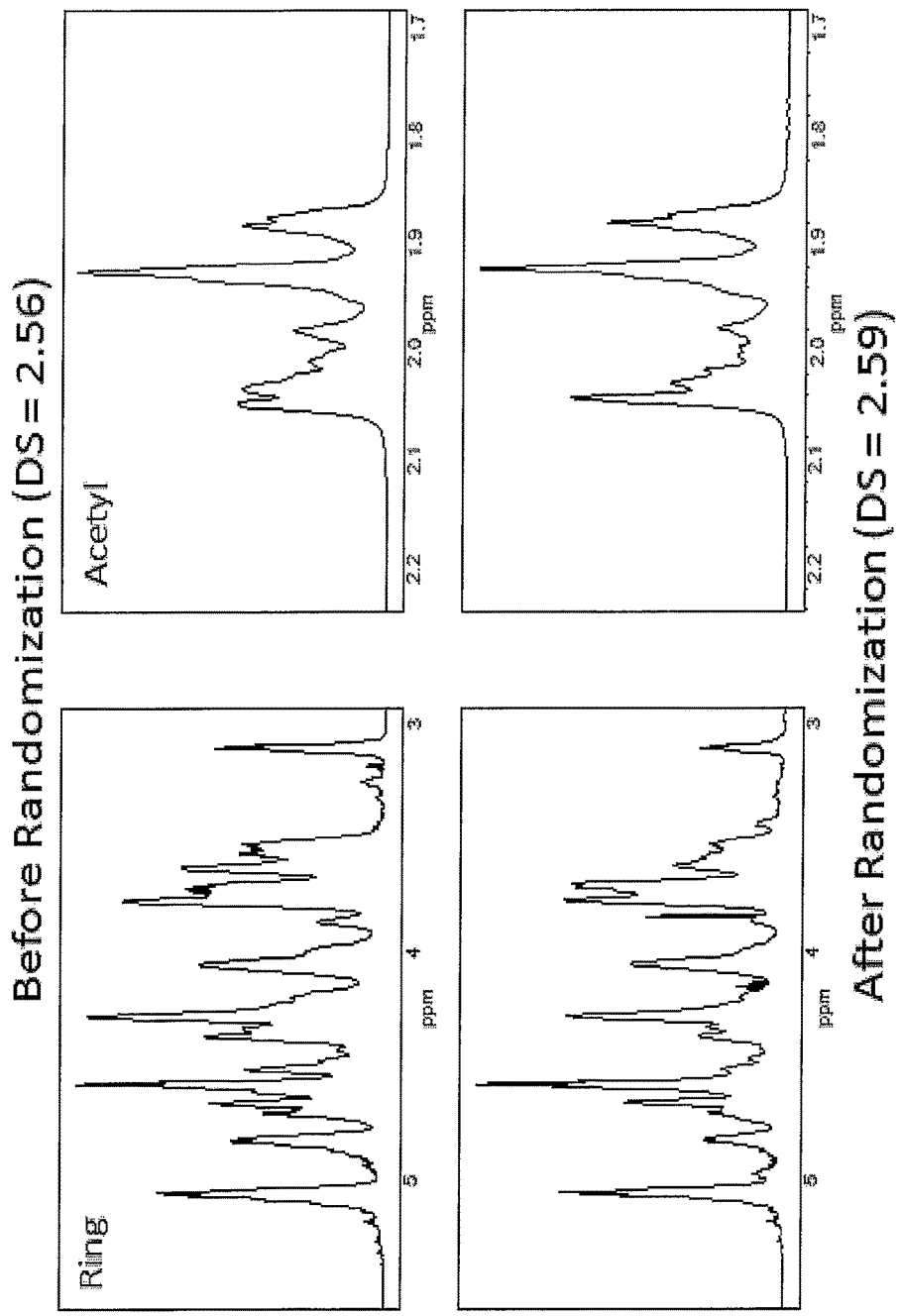
FIG. 15 is an NMR spectra showing the proton NMR spectra of a cellulose acetate prepared by direct acetylation.

FIG. 15 shows the proton NMR spectra of a cellulose acetate prepared by direct acetylation (DS=2.56) and after randomization (DS=2.59). Both the ring protons attached to the anhydroglucose monomers and acetyl protons attached to the acetyl substituents are shown. FIG. 15 demonstrates that even though these two cellulose acetates have much essentially the same DS, they have a much different monomer content.

Example 9—MSA Secondary Component, Minimal Acylating Reagent

A 3-neck 100 mL round bottom flask, fitted with two double neck adapters giving five ports, was equipped for mechanical stirring, with an iC10 diamond tipped IR probe, and with an $N_2$/vacuum inlet. To the flask added 60.47 g of 1-allyl-3-methylimidazolium chloride. The flask was placed in an oil bath and heated to 80° C. Microcrystalline cellulose (9.15 g, 7 wt %, DP ca. 335) was added to 27.3 g of water. After hand mixing, the cellulose was allowed to stand in the water for 50 min at 60° C. before filtering which gave 9.44 g of a wet cellulose cake. The water wet cellulose was then added in small portions to the [AMIm]Cl (5 min addition). Approximately 15 min after adding the cellulose to the [AMIm]Cl, the flask was placed under vacuum by gradually lowering the vacuum starting at ca. 120 mm Hg. After ca. 40 min, there were no visible cellulose particles; IR spectroscopy indicated that all of the cellulose was dissolved. The solution was left stirring overnight at 80° C. under vacuum.

To the cellulose solution heated to 80° C. was added a mixture of 8.58 g $Ac_2O$ (3 eq) and 537 mg (0.2 eq) of MSA drop wise (5 min). The reaction was sampled throughout the reaction period by removing 6-10 g aliquots of the reaction mixture and precipitating in 100 mL of MeOH. The solid from each aliquot was washed 3× with 100 mL portions of MeOH then dried at 60° C., 5 mm Hg. After all of the $Ac_2O$ appeared to be consumed by IR, the experiment was aborted and the remaining sample was processed as above.

The contact times, DS and molecular weights for isolated samples removed from the contact mixture are summarized below in Table 4.

TABLE 4

Contact Times and Properties of Cellulose Acetate Prepared in [AMIm]Cl.

| Example | Time (min) | DS | Mw | Mw/Mn |
|---|---|---|---|---|
| 9-1 | 5 | 1.74 | 36192 | 1.69 |
| 9-2 | 8 | 2.24 | 35734 | 1.84 |
| 9-3 | 11 | 2.38 | 32913 | 1.9 |
| 9-4 | 15 | 2.48 | 31811 | 1.99 |
| 9-5 | 24 | 2.60 | 31970 | 2.14 |
| 9-6 | 50 | 2.74 | 31302 | 2.36 |
| 9-7 | 109 | 2.82 | 30808 | 2.48 |

Five minutes after starting the reaction, the first cellulose acetate sample had a DS of 1.74 and a Mw of 36,192. With increasing contact time, the DS increased and the Mw decreased. After 109 min, the DS was 2.82 and the Mw was 30,808. This example shows that, compared to the conventional method of Example 11 (5 eq $Ac_2O$, 6.5 h contact time), the method of Example 9 provides for a higher DS and a significant reduction in cellulose acetate molecular weight. For example, the conventional method of Example 11 requires 6.5 h to provide a cellulose acetate with a DS of 2.42 and a Mw of 50,839 while in Example 9, a cellulose acetate with a DS of 2.48 and a Mw of 31,811 was achieved in 15 min.

Example 10—Conventional Cellulose Ester Preparation (Comparative)

A solution of cellulose (5 wt %) dissolved in 29.17 g of [BMIm]Cl was heated to 80° C. with an oil bath. The solution was held under vacuum (ca. 7 mm Hg) while stirring for 2 h. To the cellulose solution was added 4.6 g (5 eq) of $Ac_2O$ (5 min addition). During the course of the reaction, the solution color became gradually darker (brown). After 2.5 h, the solution had gelled so the contact solution was allowed to cool to room temperature. The product was isolated by adding the solution to water then homogenizing to give a dispersed gel/powder. The mixture was filtered and washed extensively with water. After drying the solid invacuo at 50° C., 2.04 g of a pink powder was obtained that was insoluble in acetone. Analysis by $^1H$ NMR indicated that the sample had a DS of 2.52 and a Mw of 73,261.

Example 11—Conventional Cellulose Ester Preparation (Comparative)

To a 3-neck 100 mL round bottom flask equipped for mechanical stirring and with an $N_2$/vacuum inlet added 33.8 g of 1-allyl-3-methylimidazolium chloride. While stirring rapidly, added 1.78 g of dry cellulose powder (DP ca. 335). The flask was placed under vacuum (2 mm Hg) and the mixture was stirred at room temperature to insure that the cellulose was well dispersed. After 15 min, the cellulose was well dispersed and the solution viscosity was rising. The flask was placed in an oil bath which was heated to 80° C. After 40 min, all of the cellulose was dissolved. The solution was maintained at 80° C. for 6.5 h before allowing the solution to cool to room temperature and stand overnight.

The viscous solution was heated to 80° C. before adding 5.6 g (5 eq) of $Ac_2O$ drop wise (15 min). After 5 h, the product was isolated by pouring the mixture into 300 mL of MeOH. The MeOH/solid slurry was stirred for ca. 30 min before filtering to remove the liquids. The solid was then taken up in two 200 mL portions of MeOH and the slurry was stirred for ca. 30 min before filtering to remove the liquids. The solids were dried overnight at 55° C. (6 mm Hg) which gave 2.27 g of a powder that gave a hazy acetone solution. Analysis by $^1H$ NMR and by GPC indicated that the sample had a DS of 2.42 and a Mw of 50,839.

Example 12—MSA Secondary Component, Long Chain Aliphatic Cellulose Esters

A solution of cellulose (5 wt %) dissolved in [BMIm]Cl was heated to 80° C. with an oil bath. The solution was held under vacuum (ca. 2.5 mm Hg) while stirring for 4 h. To the cellulose solution was added a mixture of 10.88 g (5 eq) of nonanoic anhydride and 141 mg of MSA (25 min addition). After 18.5 h, the solution was allowed to cool to room temperature before it was poured into a solution of 80:20 MeOH:$H_2O$. After filtering the solid was washed extensively with 85:15 MeOH:$H_2O$ then with 95:5 MeOH:$H_2O$. The sample was dried invacuo which gave 3.7 g of a white powder soluble in isododecane. Analysis by $^1H$ NMR indicated that the product was cellulose nonanoate with a DS of 2.49.

Obtainment of a cellulose nonanoate with a high degree of substitution by the method of this example is surprising in view of conventional teachings that long chain aliphatic cellulose esters with a DS greater than ca. 1.5 cannot be prepared in ionic liquids.

Example 13—MSA Secondary Component, C3 and C4 Alphatic Cellulose Esters

A solution of cellulose (5 wt %) dissolved in [BMIm]Cl was heated to 80° C. with an oil bath. The solution was held under vacuum (ca. 6 mm Hg) while stirring overnight. To the cellulose solution was added a mixture of 7.91 g (5 eq) of butyric anhydride and 190 mg of MSA (25 min addition). After 2.6 h, the solution was allowed to cool to room temperature before it was poured into water. The solid was washed extensively with water before drying invacuo which gave 2.62 g of a white powder soluble in acetone and 90:10 $CHCl_3$:MeOH. Analysis by $^1H$ NMR indicated that the product was cellulose butyrate with a DS of 2.59.

This example shows that C3 and C4 aliphatic cellulose esters with high degrees of substitution can be prepared by the methods of this example.

Example 14—Homogenization of Cellulose Solution

To a 1 L flat bottom kettle was added 193.6 g of solid [BMIm]Cl. A 3 neck top was placed on the kettle and the kettle was fitted with a $N_2$/vacuum inlet and for mechanical stirring. The kettle was then placed in an 80° C. oil bath and the [BMIm]Cl was melted while stirring under a 6 mm Hg vacuum. After the [BMIm]Cl was completely melted, 10.2 g of previously dried cellulose (DP ca. 335) was added and the mixture was homogenized with a Heidolph Silent Crusher. After ca. 3 min of homogenization, essentially all of the cellulose was dissolved. The solution was stirred under vacuum (6 mm Hg) for an additional 1.5 h at which time, all of the cellulose was dissolved.

This example illustrates that high intensity mixing can be used to disperse the cellulose (increased surface area) which leads to rapid cellulose dissolution.

Example 15—Acetone Solubility

The solubilities of cellulose acetate in acetone were evaluated as follows: Acetone (Burdick & Jackson high purity grade) was dried prior to use using 4 A molecular sieves (purchased from Aldrich and stored in an oven at 125° C.). All of the cellulose acetates were dried prior to use in a vacuum oven (Eurotherm 91e) at 60° C., 5 mm Hg for at least 12 h. Each cellulose acetate was weighed into a 2 Dram vial (100 mg±1 mg) and 1 mL±5 µL of dry acetone was then added to the vial (vials were obtained from VWR). The vials were then placed in an ultrasonic bath (VWR, model 75HT) and ultrasonicated at room temperature for 30-120 min then removed and vortexed (VWR minivortexer) at room temperature using a speed setting of 10. If the cellulose acetate appeared to be dissolving but the rate of dissolution appeared to be slow, the vial was placed on a roller and mixed (ca. 15 revolutions per min) overnight at ambient temperature. Following the mixing period, the solubility of each cellulose acetate was rated as follows:

| Rating | Description |
|---|---|
| 1 | Soluble, transparent with no visible particles |
| 2 | Partially soluble, hazy |
| 3 | Partially soluble, very hazy, visible particles |
| 4 | Gel |
| 5 | Swollen solid |
| 6 | Insoluble |

Cellulose acetates with a rating of 1 are very useful in all applications in which acetone solubility or solubility in related solvents (e.g. diethyl phthalate) is a critical factor (e.g. solvent spinning of acetate fiber or melt processing of plasticized cellulose acetate). Cellulose acetates with a rating of 2 or 3 would require additional filtration to remove insoluble particles and/or the use of co-solvents before they would have utility. Cellulose acetates with a rating of 4-6 would not have utility in these applications. Hence, cellulose acetates with a rating of 1 are highly desired.

The solubility in acetone of cellulose acetates prepared in Examples 3-6, 8, 9 are compared (Table 5, below) to the solubilities of the cellulose acetates in Examples 1, 2 and to cellulose acetates (Examples 15-1 to 15-6) prepared by traditional methods. The cellulose acetates prepared by traditional methods were prepared by acetylation of cellulose to make cellulose triacetate followed by $H_2SO_4$ catalyzed reduction of DS, a process know to yield cellulose acetates that are random copolymers. In the absence of water (dry acetone), the acetone solubility of these cellulose acetates is known to be limited to a narrow range (from about 2.48 to about 2.52).

TABLE 5

Solubility of Cellulose Acetate in Acetone (100 mg/mL).

| Example | DS | Solubility |
|---|---|---|
| 1-1 | 1.82 | 5 |
| 1-2 | 2.25 | 4 |
| 1-3 | 2.44 | 4 |
| 2-1 | 0.64 | 5 |
| 2-2 | 1.49 | 5 |
| 2-3 | 1.73 | 5 |
| 2-4 | 2.01 | 5 |
| 2-5 | 2.05 | 5 |
| 3-1 | 1.81 | 5 |
| 3-2 | 2.18 | 1 |
| 3-3 | 2.39 | 1 |
| 3-4 | 2.52 | 2 |
| 3-5 | 2.62 | 3 |
| 3-6 | 2.72 | 3 |
| 4-1 | 1.58 | 6 |
| 4-2 | 1.94 | 2 |
| 4-3 | 2.15 | 1 |
| 4-4 | 2.28 | 1 |
| 4-5 | 2.63 | 2 |
| 5-1 | 1.95 | 2 |
| 5-2 | 2.21 | 1 |
| 5-3 | 2.35 | 1 |
| 5-4 | 2.52 | 2 |
| 5-5 | 2.59 | 2 |
| 5-6 | 2.60 | 2 |
| 5-7 | 2.66 | 3 |
| 5-8 | 2.67 | 3 |
| 6-1 | 2.63 | 2 |
| 6-2 | 2.75 | 3 |
| 6-3 | 2.80 | 3 |
| 6-4 | 2.87 | 3 |
| 6-5 | 2.89 | 3 |
| 6-6 | 2.96 | 3 |
| 8-1 | 1.95 | 3 |
| 8-2 | 2.15 | 1 |
| 8-3 | 2.24 | 1 |
| 8-4 | 2.33 | 1 |
| 8-5 | 2.42 | 1 |
| 8-6 | 2.56 | 2 |
| 8-7 | 2.73 | 2 |
| 9-1 | 1.74 | 5 |
| 9-2 | 2.24 | 1 |
| 9-3 | 2.38 | 1 |
| 9-4 | 2.48 | 2 |
| 9-5 | 2.60 | 3 |
| 9-6 | 2.74 | 3 |
| 9-7 | 2.82 | 3 |
| 15-1 | 2.48 | 1 |
| 15-2 | 2.46 | 2 |
| 15-3 | 2.16 | 3 |
| 15-4 | 1.99 | 5 |
| 15-5 | 1.96 | 5 |
| 15-6 | 1.80 | 6 |

Careful examination of Table 5 reveals that the cellulose acetates having a DS from about 2.42 to about 2.15 that were produced by acetylation of cellulose dissolved in ionic liquids in the presence of a secondary component (Examples 3-6, 8, 9) all have a acetone solubility rating of 1. That is, all of these samples yield transparent acetone solutions in which there are no visible particles. In contrast, cellulose acetates produced by acetylation of cellulose dissolved in ionic liquids in the absence of a secondary component (Examples 1 and 2) have acetone solubility ratings of 4-5 regardless of DS. For example, Example 1-2 (no secondary component) has a DS of 2.25 and this cellulose acetate forms a gel in acetone while Examples 8-3 and 9-2 (includes secondary component) have a DS of 2.24 and these cellulose acetates yield transparent acetone solutions. In agreement with what is known about cellulose acetates prepared by traditional methods, only one of the cellulose acetates examined (15-1, DS=2.48) has an acetone solubility rating of 1. Example 15-3 (DS=2.16) has an acetone solubility rating of 3 as opposed to Examples 4-3 and 8-2 (DS=2.15) which have acetone solubility ratings of 1.

This example shows that cellulose acetates produced by acetylation of cellulose dissolved in ionic liquids in the presence of a secondary component having a DS of about 2.4 to about 2.1 yield transparent acetone solutions. In the absence of a secondary component, none of the cellulose acetates yield transparent acetone solutions. Furthermore, the DS range that yield transparent acetone solutions when using cellulose acetates produced by acetylation of cellulose dissolved in ionic liquids in the presence of a secondary component is broader and lower relative to cellulose acetates produced by traditional methods. Without wishing to be bound by theory, the evidence indicates that these solubility differences reflect a difference in copolymer compositions.

Example 16—Purification of [BMIm]Acetate

To a 1 L 3-neck round bottom flask was added 360 mL of water, 1.30 g of acetic acid, and 5.68 g of Ba(OH)$_2$.H$_2$O. The mixture was heated to 80° C. giving a translucent solution. To this solution was added 300 g of commercial [BMIm] OAc dropwise (1 h addition) containing 0.156 wt % sulfur as determined by XRF. The solution was held at 80° C. for an addition hour before allowing the solution to cool to room temperature. The solids formed during the reaction were removed by centrifuging before concentration the solution in vacuo (60-65° C., 20-80 mm Hg) to a pale yellow liquid. The liquid was extracted with two 300 mL portions of EtOAc. The liquid was concentrated first at 60° C., 20-50 mm Hg then at 90° C., 4 mm Hg leading to 297.8 g of a pale yellow oil. Proton NMR confirmed the formation of the [BMIm] OAc which, by XRF, contained 0.026 wt % sulfur.

Example 17—Preparation of [BMIm]Propionate

To a 1 L 3-neck round bottom flask was added 400 mL of water, 62.7 g of acetic acid, and 267 g of Ba(OH)$_2$.H$_2$O. The mixture was heated to 74° C. giving a translucent solution. To this solution was added 100 g of commercial [BMIm] HSO$_4$ dropwise (1.75 h addition). The solution was held at 74-76° C. for an addition 30 min before allowing the solution to cool to room temperature and stand overnight (ca. 14 h). The solids formed during the reaction were removed by filtration before concentration the solution in vacuo which gave an oil containing solids which formed during concentration. The solids were removed centrifuging giving an amber liquid. Additional product was obtained by slurring the solids in EtOH and centrifuging. The liquids were concentrated first at 60° C., 20-50 mmHg then at 90° C., 4 mm Hg leading to 65.8 g of an amber oil. Proton NMR confirmed the formation of the [BMIm]OPr which, by XRF, contained 0.011 wt % sulfur.

Example 18—Preparation of [BMIm]Formate

To 300 mL autoclave was added 25 g of 1-butylimidazole, 45.4 g (3.75 eq) of methyl formate, and 21 mL of MeOH (2.58 eq). The autoclave was pressurized to 1035 kPa before heating the solution to 150° C. The contact solution was maintained at 150° C. for 18 h. The solution was allowed to cool to room temperature before removing the volatiles components in vacuo. Proton NMR of the crude reaction mixture revealed that 89% of the 1-butylimidazole was converted to [BMIm]formate. Purified [BMIm]formate was obtained by removal of 1-butylimidazole from the crude product by distillation.

Example 19—Conversion of [BMIm]Formate to [BMIm]Acetate Using Methyl Acetate

To 300 mL autoclave was added 25 g of [BMIm]formate, 50.3 g (5.0 eq) of methyl acetate, and 50 mL of MeOH (9 eq). The autoclave was pressurized to 1035 kPa before heating the solution to 170° C. The contact solution was maintained 170° C. for 15.3 h. The solution was allowed to cool to room temperature before removing the volatiles components in vacuo. Proton NMR of the reaction mixture revealed that 57% of the [BMIm]formate was converted to [BMIm]acetate.

Example 20—Conversion of [BMIm]Formate to [BMIm]Acetate Using Acetic Anhydride

To 25 mL single-neck round bottom flask was added 11.1 g of [BMIm]formate. Acetic anhydride (6.15 g) was added dropwise to the [BMIm]formate. Evolution of gas was noted during the addition as well as warming of the solution (47° C.). The flask was then placed in a preheated 50° C. water bath for 45 min before applying a vacuum (4 mm Hg) and heating to 80° C. to remove the volatile components. Analysis of the resulting liquid by 1H NMR indicated 100% conversion of the starting material to [BMIm]acetate.

Example 21—Conversion of [BMIm]Formate to [BMIm]Acetate Using Acetic Acid

To 300 mL autoclave was added 25 g of [BMIm]formate, 87.4 g (6.3 eq) of acetic acid, and 23.1 g of MeOH (5.3 eq). The autoclave was pressurized to 1035 kPa before heating the solution to 150° C. The contact solution was maintained 150° C. for 14 h. The solution was allowed to cool to room temperature before removing the volatiles components in vacuo. Proton NMR of the reaction mixture revealed that 41% of the [BMIm]formate was converted to [BMIm] acetate.

Example 22—Conversion of [BMIm]Acetate to [BMIm]Formate Using Methyl Formate

To 1 L autoclave was added 100.7 g of [BMIm]acetate, 152.5 g (5 eq) of methyl formate, and 200 mL of MeOH (9.7 eq). The autoclave was pressurized to 1035 kPa before heating the solution to 140° C. The contact solution was maintained 140° C. for 18 h. The solution was allowed to cool to room temperature before removing the volatiles components in vacuo. Proton NMR of the reaction mixture revealed that 100% of the [BMIm]acetate was converted to [BMIm]formate.

Example 23—Comparison of High and Low Sulfur [BMIm]OAc

23A:

To a 100 mL 3-neck round bottom flask was added 32.75 g of commercial high sulfur [BMIm]OAc (0.156 wt % sulfur) and 1.72 g of cellulose powder. This mixture was briefly homogenized at ambient temperature before the flask was placed in a preheated 80° C. oil bath. The mixture was stirred at 80° C., 2 mm Hg for 1.75 h; ca. 15 min was required to completely dissolve the cellulose. The straw colored solution was allowed to cool to room temperature and stand under vacuum overnight (ca. 14 h).

To the mechanically stirred solution was added a solution of methane sulfonic acid (MSA, 210 mg) and acetic anhydride (5.42 g, 5 eq/AGU) dropwise (23 min). At the end of the addition, the temperature of the contact mixture was 35° C. and the solution was dark amber. After 1.5 h from the start of the addition, 5.5 g of the contact mixture was removed and the product was isolated by precipitation in MeOH. The contact mixture was then heated to 50° C. (25 min heat up time) and stirred for 1.5 h before 6.5 g of solution was removed and poured into MeOH. The remaining contact solution was heated to 80° C. (25 min heat up) and stirred for 2.5 h before pouring into MeOH. All of the solids obtained by precipitation in MeOH were isolated by filtration, washed extensively with MeOH, and dried overnight at 50° C., 5 mm Hg.

23B:

An identical reaction to 23A was conducted side-by-side using 37.02 g of low sulfur [BMIm]OAc (0.025 wt % sulfur, cf. example 1), 1.95 g of cellulose, 6.14 g of acetic anhydride, and 222 mg of MSA.

The grams of product isolated and the analysis of each product is summarized below in Table 6.

TABLE 6

Yield and Properties of CA Prepared in [BMIm]OAc

| Entry | Yield (g) | DS | Mn | Mw | Mz |
|---|---|---|---|---|---|
| 23A-RT | 0.37 | 2.53 | 15123 | 54139 | 135397 |
| 23A-50° C. | 0.45 | 2.65 | 12469 | 51688 | 123527 |
| 23A-80° C. | 1.36 | 2.62 | 15828 | 85493 | 237785 |
| 23B-RT | 0.29 | 0.80 | 14499 | 65744 | 301858 |
| 23B-50° C. | 0.40 | 0.80 | 14768 | 57066 | 227833 |
| 23B-80° C. | 1.26 | 0.76 | 16100 | 70293 | 325094 |

As can be seen from Table 6, above, the DS of the CA made using the high sulfur [BMIm]OAc as solvent was higher and the molecular weight lower relative to the CA made using the low sulfur [BMIm]OAc as solvent. Despite the increased temperature and extended contact time, the DS did not increase significantly above that observed after 1.5 h contact time at room temperature regardless of which [BMIm]OAc was used as the solvent. Another notable feature of this example was the color of the solutions and products. The contact solution involving high sulfur [BMIm]OAc solvent was black at all temperatures while the contact solution involving low sulfur [BMIm]OAc solvent retained the straw color typical of these solutions prior to the addition of the anhydride. The CA solids obtained from the high sulfur [BMIm]OAc solvent were brown to black in appearance while the CA solids obtained from the low sulfur [BMIm]OAc solvent were white and provided colorless solutions upon dissolution in an appropriate solvent.

This example shows that impurities (e.g., sulfur or halides) in the high sulfur [BMIm]OAc can act as a catalyst in the esterification of cellulose dissolved in the [BMIm] OAc. However, the same impurities negatively impact the molecular weight and quality of the product in such a manner that the CA does not have practical value. When cellulose is dissolved in [BMIm]OAc containing no or little of these impurities, high-quality CA can be obtained. By introduction of an appropriate catalyst, high quality CA with the desired DS can be obtained in a predictable manner.

Example 24—Acetylation of Cellulose in High Chloride [EMIm]OAc

Cellulose (1.19 g) was dissolved in 22.65 g of commercial [EMIm]OAc which, by XRF, contained 0.463 wt % chloride following the general procedure described in Example 8 with the exception that the mixture was not homogenized prior to heating to 80° C.

To the mechanically stirred straw colored solution preheated to 80° C. was added a solution of MSA (141 mg) and acetic anhydride (3.76 g, 5 eq/AGU) dropwise (10 min). By the end of the addition, the contact mixture became dark brown-black. The contact solution was stirred for 2.5 h before pouring into $H_2O$. The resulting solids were isolated by filtration, washed extensively with $H_2O$, and dried overnight at 50° C., 5 mm Hg. This yielded 1.57 g of a brown-black CA powder. Analysis revealed that the CA had a DS of 2.21 and that the Mw was 42,206.

This example shows that [EMIm]OAc containing high levels of halides is not a suitable solvent for esterification of cellulose.

Example 25—Acetylation of Cellulose in [BMIm]Cl and [BMIm]OAc

25A:

Previously dried cellulose (13.2 g) and solid [BMIm]Cl (250.9 g, mp=70° C.) were combined in a glass jar. The glass jar was placed in a preheated 40° C. vacuum oven and heated to 80° C. over 3 h. The sample was allowed to stand under vacuum at 80° C. for ca. 14 h before the jar was removed. The sample was immediately homogenized giving a clear solution of cellulose.

To a 100 mL 3-neck round bottom flask was added 33.6 g of the cellulose solution prepared above. The flask was placed in a preheated 80° C. oil bath and a vacuum was applied (7-8 mm Hg). The solution was then stirred for 21 h while at 80° C. and under vacuum. The cellulose solution was then allowed to cool to 38° C.; the temperature could not be lowered further due to the solution viscosity. Acetic anhydride (5.3 g, 5 eq/AGU) was added dropwise over 7 min. The contact mixture was then stirred at 32-35° C. for 2 h before a small amount of the solution was removed and poured into MeOH resulting in precipitation of the cellulose acetate. The remaining contact mixture was then heated to 50° C. and held at that temperature for 1.6 h before removing a small amount of the solution which was poured into MeOH to precipitate the cellulose acetate. The remaining contact mixture was then heated to 80° C. and held at that temperature for 1.5 h before allowing the solution to cool and adding 60 mL of MeOH to precipitate the cellulose acetate. All three samples were washed extensively with MeOH then dried at 50° C., 5 mm Hg overnight.

25B:

To a 100 mL 3-neck round bottom flask was added 31.3 g of the cellulose solution prepared above. The same general protocol as used in the previous reaction was followed with the exception that $Zn(OAc)_2$ (0.05 eq/AGU) was added to the cellulose solution prior to cooling to 38° C.

25C:

To a 100 mL 3-neck round bottom flask was added 27.41 g of low sulfur [BMIm]OAc liquid (cf. example 16) and 1.44 g of cellulose. The flask was placed in a preheated 80° C. oil bath and the mixture was allowed to stir overnight (ca. 14 h) under a 2 mm Hg vacuum.

After cooling the solution to room temperature (25.1° C.), $Ac_2O$ (5 eq/AGU) was added to the cellulose solution dropwise (25 min addition). The contact mixture was stirred for 1.8 h at room temperature before removing a small portion of the solution which was poured into MeOH to precipitate the cellulose acetate. The remaining contact mixture was heated to 50° C. and maintained at that temperature for 1.5 h before removing a small portion of the solution which was poured into MeOH to precipitate the cellulose acetate. The remaining contact mixture was heated to 80° C. and maintained at that temperature for 2.5 h before cooling and pouring into MeOH. All three samples were washed extensively with MeOH then dried at 50° C., 5 mm Hg overnight.

25D:

To a 100 mL 3-neck round bottom flask was added 25.55 g of low sulfur [BMIm]OAc liquid (cf. example 16) and 1.35 g of cellulose. The flask was placed in a preheated 80° C. oil bath and the mixture was allowed to stir overnight (ca. 14 h) under a 2 mm Hg vacuum. The same general protocol as used in the previous reaction was followed with the exception that $Zn(OAc)_2$ (0.05 eq/AGU) was added to the cellulose solution prior to cooling to room temperature.

Analysis of the cellulose acetates isolated from these 4 comparative reactions (25A-25D) is summarized below in Table 7.

TABLE 7

Physical properties of CA prepared in [BMIm]Cl or [BMIm]OAc

| Entry | Solvent | Catalyst | DS | Mn | Mw | Mz |
|---|---|---|---|---|---|---|
| 25A-RT | [BMIm]Cl | none | 0.57 | 7753 | 16777 | 32019 |
| 25A-50° C. | [BMIm]Cl | none | 1.42 | 9892 | 19083 | 33019 |
| 25A-80° C. | [BMIm]Cl | none | 2.27 | 11639 | 21116 | 34138 |
| 25B-RT | [BMIm]Cl | $Zn(OAc)_2$ | 1.77 | 8921 | 19468 | 36447 |
| 25B-50° C. | [BMIm]Cl | $Zn(OAc)_2$ | 2.32 | 7652 | 18849 | 38367 |
| 25B-80° C. | [BMIm]Cl | $Zn(OAc)_2$ | 2.75 | 7149 | 18964 | 38799 |
| 25C-RT | [BMIm]OAc | none | 1.17 | 7039 | 41534 | 118265 |
| 25C-50° C. | [BMIm]OAc | none | 1.17 | 7839 | 45116 | 136055 |
| 25C-80° C. | [BMIm]OAc | none | 1.17 | 7943 | 48559 | 165491 |
| 25D-RT | [BMIm]OAc | $Zn(OAc)_2$ | 2.27 | 8478 | 47730 | 125440 |
| 25D-50° C. | [BMIm]OAc | $Zn(OAc)_2$ | 2.30 | 11017 | 53181 | 136619 |
| 25D-80° C. | [BMIm]OAc | $Zn(OAc)_2$ | 2.34 | 12096 | 56469 | 141568 |

This comparative example illustrates a number of important points. In the case of [BMIm]Cl, the DS of the cellulose acetate increases with each contact time-temperature from 0.57 to 2.27. The same trend is observed with [BMIm]Cl+ $Zn(OAc)_2$ with the exception that the DS at each contact time-temperature is higher due to the $Zn(OAc)_2$ which acts as a catalyst. In the case of [BMIm]OAc, with or without $Zn(OAc)_2$, the DS does not significantly change from that obtained at room temperature with increasing contact time-temperature; the total DS is significantly increased by the action of the $Zn(OAc)_2$. This unexpected observation indicates that acetylation of cellulose dissolved in [BMIm]OAc is much faster at lower temperatures relative to that observed in acetylation of cellulose dissolved in [BMIm]Cl. It should also be noted that a transition metal like Zn is very effective in catalyzing or promoting the acylation of cellulose dissolved in ionic liquids. Finally, it should also be noted that the molecular weights of the cellulose acetates obtained by acetylation of cellulose dissolved in [BMIm]OAc is significantly greater relative to when cellulose is dissolved in [BMIm]Cl.

Example 26—Preparation of Mixed Cellulose Esters

The following general procedure was used to prepare cellulose mixed esters. To a 100 mL 3-neck round bottom flask was added the desired amount of 1-butyl-3-methylimidazolium carboxylate. While stirring at room temperature, 5 wt % cellulose was slowly added to the ionic liquid. After the cellulose was dispersed in the ionic liquid, the flask was placed under vacuum (2-5 mm Hg) and the contact mixture was heated to 80° C. The contact solution was then stirred for ca. 2 h before adding 0.1 eg/AGU of $Zn(OAc)_2$. The contact solution was stirred for ca. 30 min before the solution was allowed to cool to room temperature and stand overnight (ca. 14 h).

The contact solution was placed under $N_2$ before the dropwise addition of 5 eq/AGU of the desired carboxylic anhydride. When the addition was complete, the flask was placed in a preheated 40° C. oil bath. The contact mixture was stirred for 5 h before the solution was allowed to cool and poured into MeOH. The resulting solids were isolated by filtration, washed extensively with MeOH, and dried in vacuo (50° C., 5 mm Hg). The products were characterized by $^1H$ NMR and the results are summarized below in Table 8.

TABLE 8

Cellulose Esters Prepared in Different Alkyl Imidazolium Carboxylates

| Entry | Ionic liquid | Anhydride | $DS_{Total}$ | $DS_{Ac}$ | $DS_{Pr}$ | $DS_{Bu}$ |
|---|---|---|---|---|---|---|
| 1 | [BMIm]OAc | $Bu_2O$ | 2.40 | 2.43 | — | 0.45 |
| 2 | [BMIm]OBu | $Ac_2O$ | 2.43 | 2.30 | — | 0.70 |
| 3 | [BMIm]OPr | $Bu_2O$ | 2.52 | — | 1.95 | 1.05 |

Note that in Table 8, above, the DS of the individual substituents have been normalized to 3.0 for comparison purposes. As this example illustrates, when cellulose is dissolved in an alkyl imidazolium carboxylate and contacted with an carboxylic anhydride different from the anion of the ionic liquid, the product is a cellulose mixed ester. That is, the cellulose substituents come from the added anhydride and from the alkyl imidazolium carboxylate. In effect, the alkyl imidazolium carboxylate is acting as an acyl donor.

Example 27—Removal of Carboxylic Acid

Figure 16:
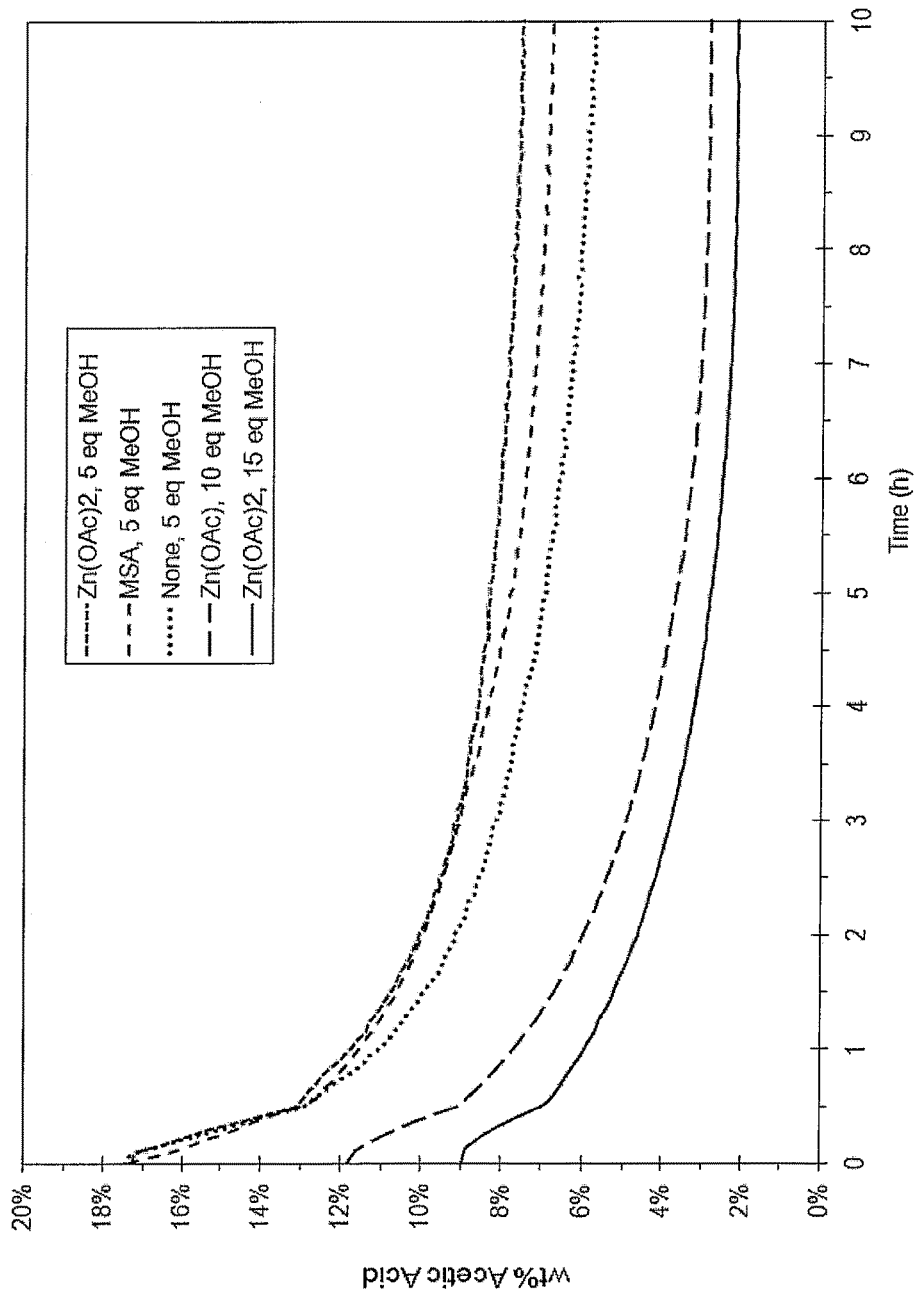
FIG. 16 is plot of weight percent acetic acid versus time as determined by infrared spectroscopy.

To each vessel of a 4 vessel Multimax high pressure reactor equipped with an in situ infrared probe was added previously dried [BMIm]OAc, 1 molar equivalent of acetic acid based on ionic liquid, different molar amounts of MeOH based on acetic acid, and optionally, a catalyst (2 mol %). The pressure in each vessel was increased to 5 bar over a 3 min period before the contact temperature was increased to 140° C. over a 25 min period. The contact mixtures were then held at 140° C. for 10-15 h and the reaction in each vessel was monitored by infrared spectroscopy. The vessels were allowed to cool to 25° C. over a 30 min period. The contents of each vessel were then concentrated invacuo to remove all volatile components before analyzing each sample by proton NMR. FIG. 16 shows a plot of wt % acetic acid versus time as determined by infrared spectroscopy; the final concentration of acetic acid was confirmed by $^1$H NMR. FIG. 16 shows that in all cases, the reactions were complete within 9-10 h. The most significant factor affecting the rates and extend of reaction was the number of molar equivalents of MeOH. The wt % acetic acid remaining in the [BMIm]OAc ranged from 7.4 wt % to 2.2 wt %.

With typical distillation techniques, it is extremely difficult to get the excess carboxylic acid concentration below 1 molar equivalent based on carboxylated ionic liquid. In the case of acetic acid in [BMIm]OAc, this corresponds to ca. 23 wt % acetic acid. This example shows that, by conversion of the acetic acid to methyl acetate which is much more easily removed, the amount of residual acetic acid can be reduced well below 23 wt %. The amount of acetic acid removed will depend upon the amount of acetic acid initially present, concentration of MeOH, contact times, and contact temperature. As shown in this example, it is not necessary to remove all of residual carboxylic acid; in many instances, it is desirable to have residual carboxylic acid.

Example 28—Solubility of Cellulose in Ionic Liquid

Samples of 1-butyl-3-methylimidazolium acetate containing different amounts of acetic acid in 2 oz jars were dried at 80° C.±° 5, ca. 3 mm Hg overnight (ca. 14 h). Examples 28-1 through 28-5 were prepared by the method of Example 27. Examples 28-6 through 28-8 were prepared by adding a known amount of acetic acid to neat [BMIm]OAc (Table). Cellulose (5 wt %, DP 335), was added to each [BMIm]OAc sample and the each sample was briefly homogenized. Each sample was transferred to a microwave reaction vessel which was then capped with an air tight lid then placed in a 48 cell microwave rotor. The rotor was placed in a Anton Paar Synthos 3000 microwave and the cellulose-[BMIm]OAc mixtures were heated to 100° C. using a 3 min ramp and held for 10 min before heating to 120° C. using a 3 min ramp and held for 5 min. Inspection of each vessel indicated that the cellulose in each example was dissolved in the [BMIm]OAc.

TABLE 9

Solubility of Cellulose in [BMIm] OAc

| Example | wt % HOAc | IL (g) | Soluble |
|---|---|---|---|
| 28-1 | 2.2 | 6.16 | y |
| 28-2 | 2.8 | 8.78 | y |
| 28-3 | 5.8 | 8.48 | y |
| 28-4 | 6.6 | 8.48 | y |
| 28-5 | 7.4 | 8.15 | y |
| 28-6 | 10.0 | 10.23 | y |
| 28-7 | 12.5 | 10.26 | y |
| 28-8 | 14.5 | 10.18 | y |

This example shows that excess residual carboxylic acid in ionic liquids can be reduced by the method of Example 27 and that the recycled ionic liquid can then be used to dissolve cellulose so that the solutions can be used for preparing cellulose esters. This example also shows that cellulose can be dissolved in an ionic liquid containing up to about 15 wt % carboxylic acid.

Example 29—Recycling of Ionic Liquid

Figure 17:
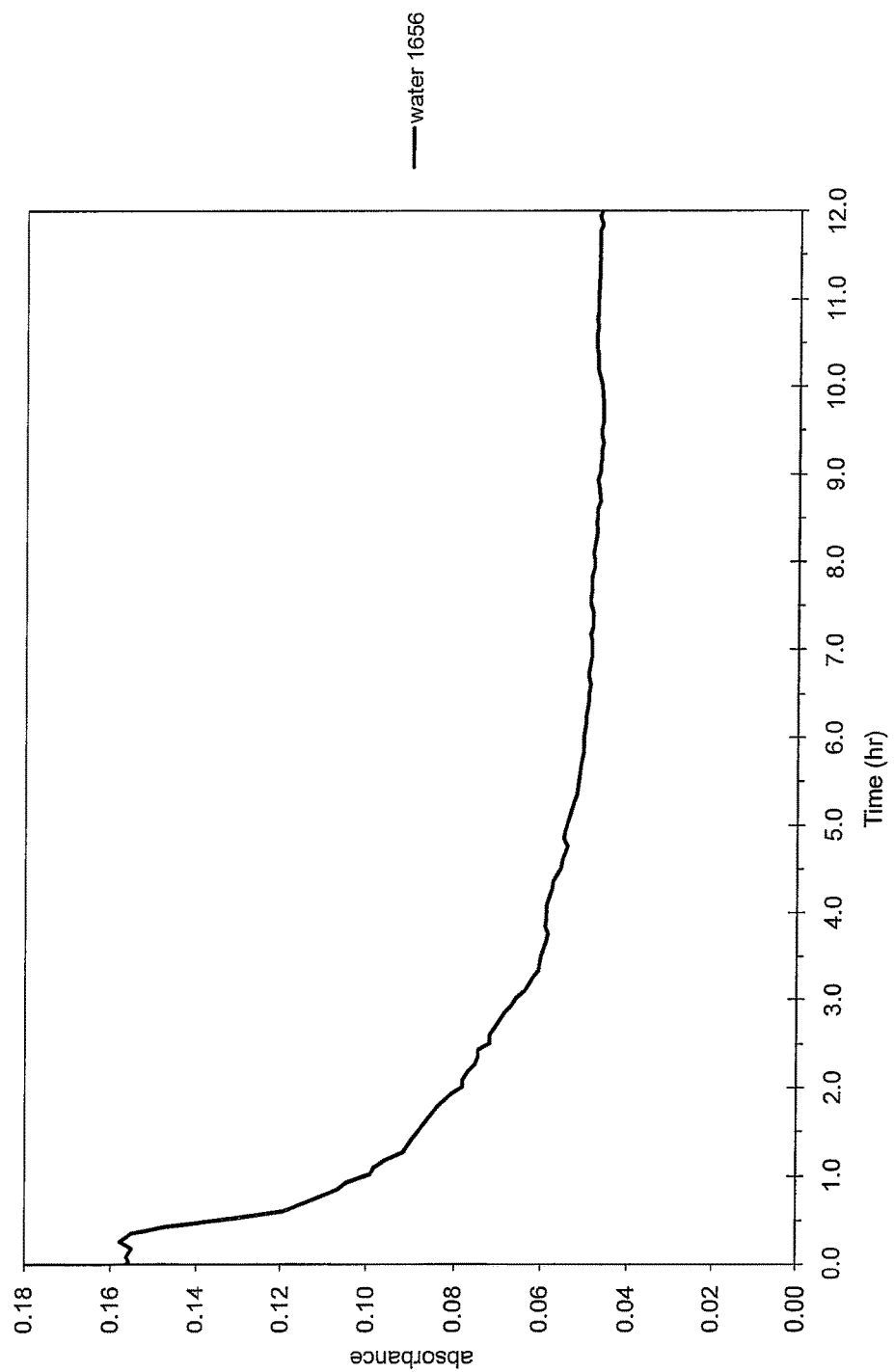
FIG. 17 is a plot of absorbance versus time showing the removal of water from 1-butyl-3-methylimidazolium acetate prior to dissolution of cellulose.

To a 500 mL flat bottom kettle was added 299.7 g of [BMIm]OAc. A 4-neck top was placed on the kettle and the kettle was fitted with a $N_2$/vacuum inlet, a React IR 4000 diamond tipped IR probe, a thermocouple, and for mechanical stirring. The kettle contents were placed under vacuum (ca. 4.5 mm Hg) and heated to 80° C. using an oil bath. The removal of water from the [BMIm]OAc was followed by infrared spectroscopy (FIG. 17). After ca. 16 h, the oil bath was removed and the kettle contents were allowed to cool to room temperature.

Figure 18:
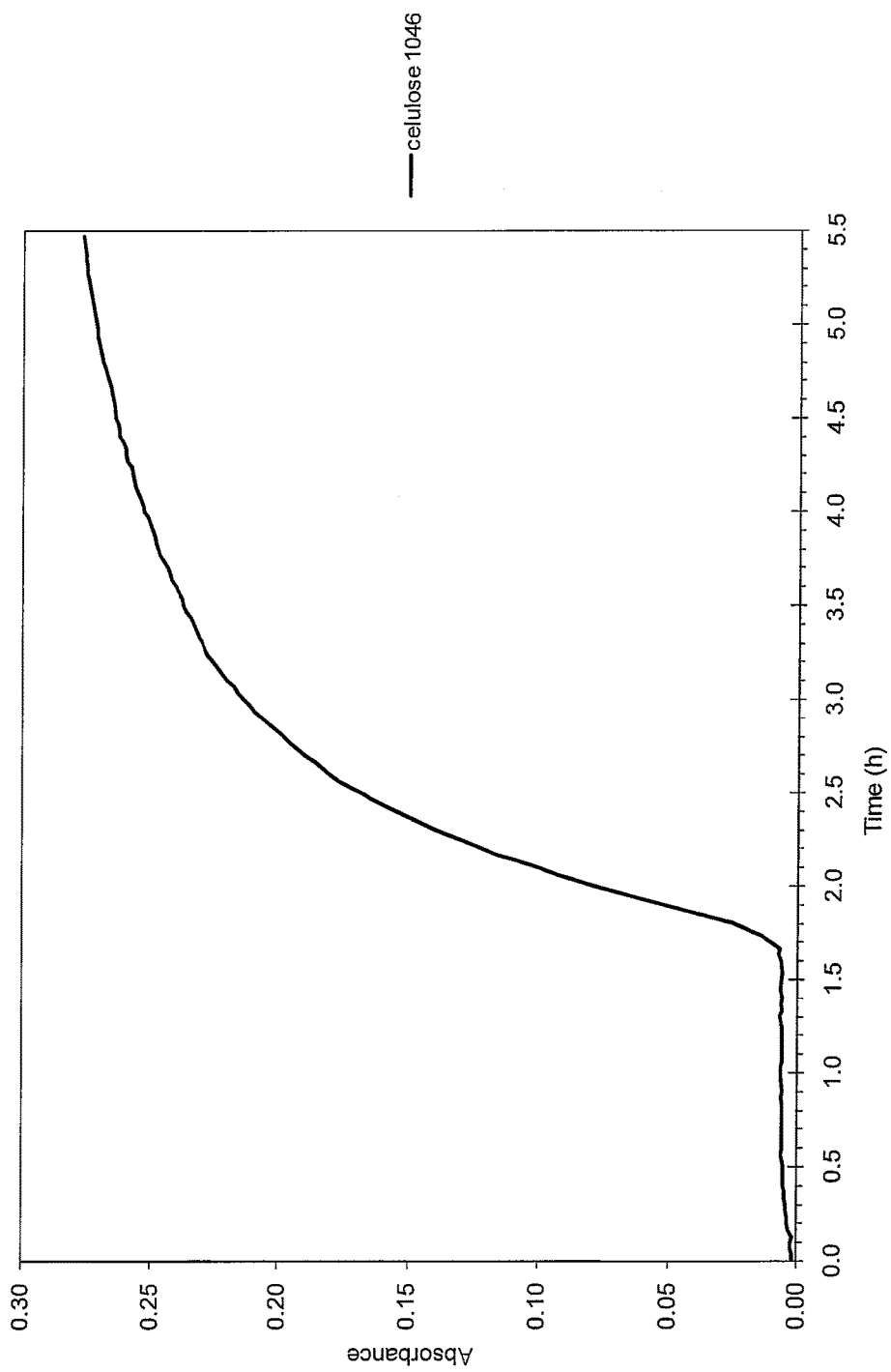
FIG. 18 is a plot of absorbance versus time showing the dissolution of 10 weight percent cellulose in 1-butyl-3-methylimidazolium acetate at room temperature.

To the ionic liquid was added 3.77 g of $Zn(OAc)_2$. The mixture was stirred for ca. 75 minutes to allow the $Zn(OAc)_2$ to dissolve before slowly adding 33.3 g (10 wt %) of previously dried cellulose (DP ca. 335) over a 26 min period. The mixture was stirred at room temperature for ca. 4 h at which time no particles or fiber were visible in the translucent solution; infrared spectroscopy indicated that all of the cellulose was dissolved (FIG. 18). The solution was heated to 80° C. By the time the temperature reached 60° C., the translucent solution was completely clear. After reaching 80° C., the solution was cooled to room temperature.

Figure 19:
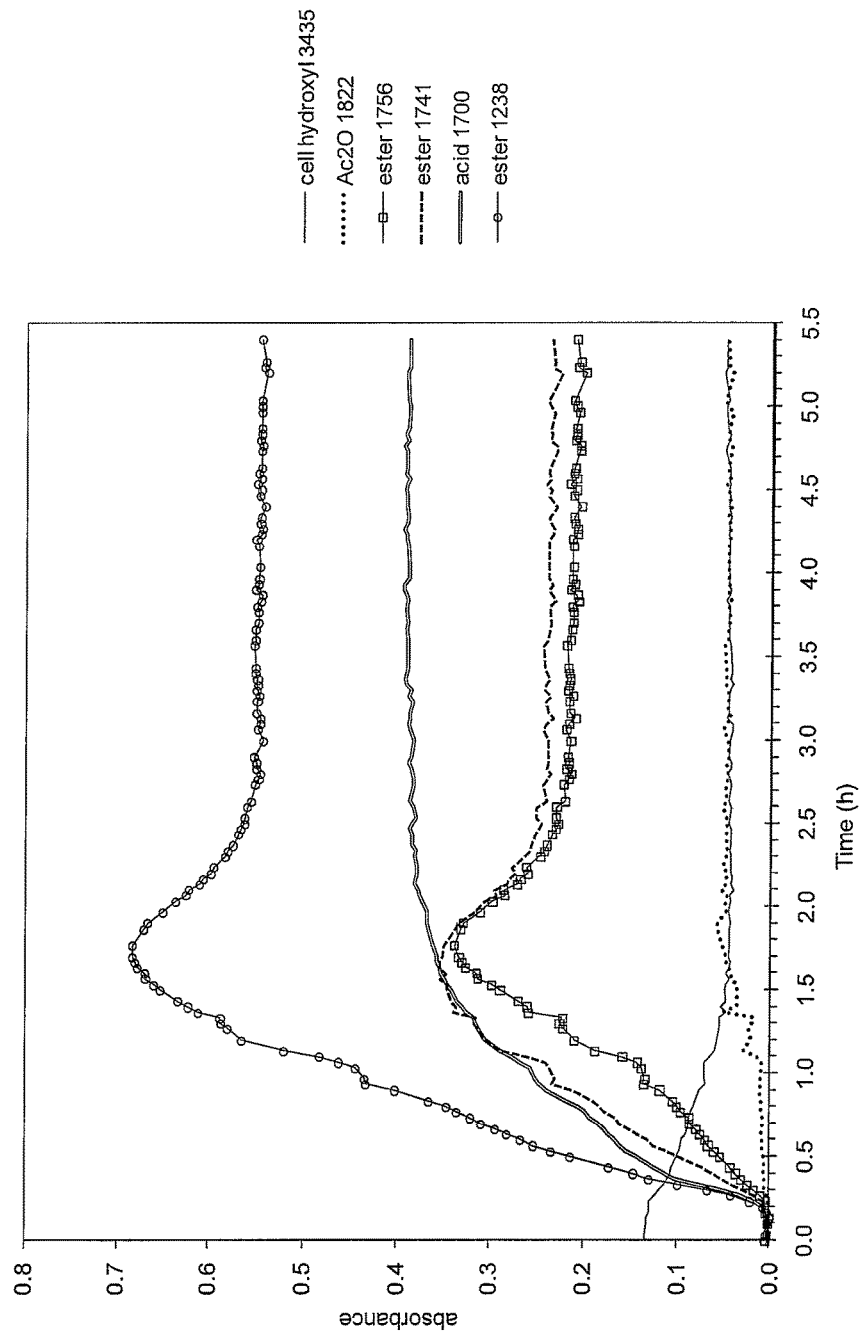
FIG. 19 is a plot of absorbance versus time showing the acetylation of cellulose dissolved in 1-butyl-3-methylimidazolium acetate with 5 molar equivalents of acetic anhydride and 0.1 molar equivalents of zinc acetate.

To the cellulose-[BMIm]OAc solution was added 104.9 g of $Ac_2O$ (5 eq) dropwise over a 70 min period. During the $Ac_2O$ addition, the contact temperature rose from an initial value of 21.4° C. to a maximum value of 44.7° C. Infrared spectroscopy indicated that the $Ac_2O$ was consumed nearly as fast as it was added (FIG. 19). When all of the $Ac_2O$ was added, the contact temperature immediately began to decline and the contact mixture went from a fluid liquid to a flaky gel. Stirring was continued for an additional 3.5 h but no changes were observed by infrared spectroscopy.

The gel was then added to 800 mL of MeOH while stirring resulting in the precipitation of a white powder. After separation by filtration, the solids were then washed 3 times with ca. 800 mL portions of MeOH then 1 time with ca. 900 mL of MeOH containing 11 wt % of 35 wt % $H_2O_2$. The solids were then dried at 40° C., 3 mm Hg resulting in 60.4 g of a white solid. Analysis by proton NMR and GPC revealed that the solid was a cellulose triacetate (DS=3.0) having a Mw of 58,725. The cellulose triacetate (13.6 wt %) was completely soluble in 90/10 $CH_2Cl_2$/MeOH from which clear films can be cast. Such films are useful in constructing liquid crystalline displays and in photographic film base.

The precipitation and wash liquids from the cellulose triacetate isolation were concentrated invacuo at 50° C. until the vacuum dropped to ca. 3 mm Hg which gave 376.6 g of a liquid. Proton NMR showed that the liquid was [BMIm]OAc containing ca. 17 wt % excess acetic acid. To a 1.8 L autoclave was added the 376.8 g of recovered [BMIm]OAc along with 483.8 g of MeOH. The pressure in autoclave was adjusted to 100 psi with $N_2$ before the vessel contents were heated to 140° C. and held for 9 h. After cooling to room temperature, the volatile components were removed invacuo which gave 299.8 g of a liquid. Proton NMR showed the liquid to be [BMIm]OAc containing 2.6 wt % excess acetic acid. When the weight of the initial [BMIm]OAc is corrected for water content, the amount of recycled [BMIm]OAc corresponds to 100% recovery.

This example shows that cellulose triacetate can rapidly be prepared from cellulose dissolved in ionic liquids. This example also shows that excess carboxylic acid can be removed from the ionic liquid and the recycled ionic liquid can be recovered in high yield. The recycled ionic liquid can then be used to dissolve cellulose so that the solutions can be used again for preparing cellulose esters.

Example 30—Anion Exchange to Form Carboxylated Ionic Liquid

Figure 20:
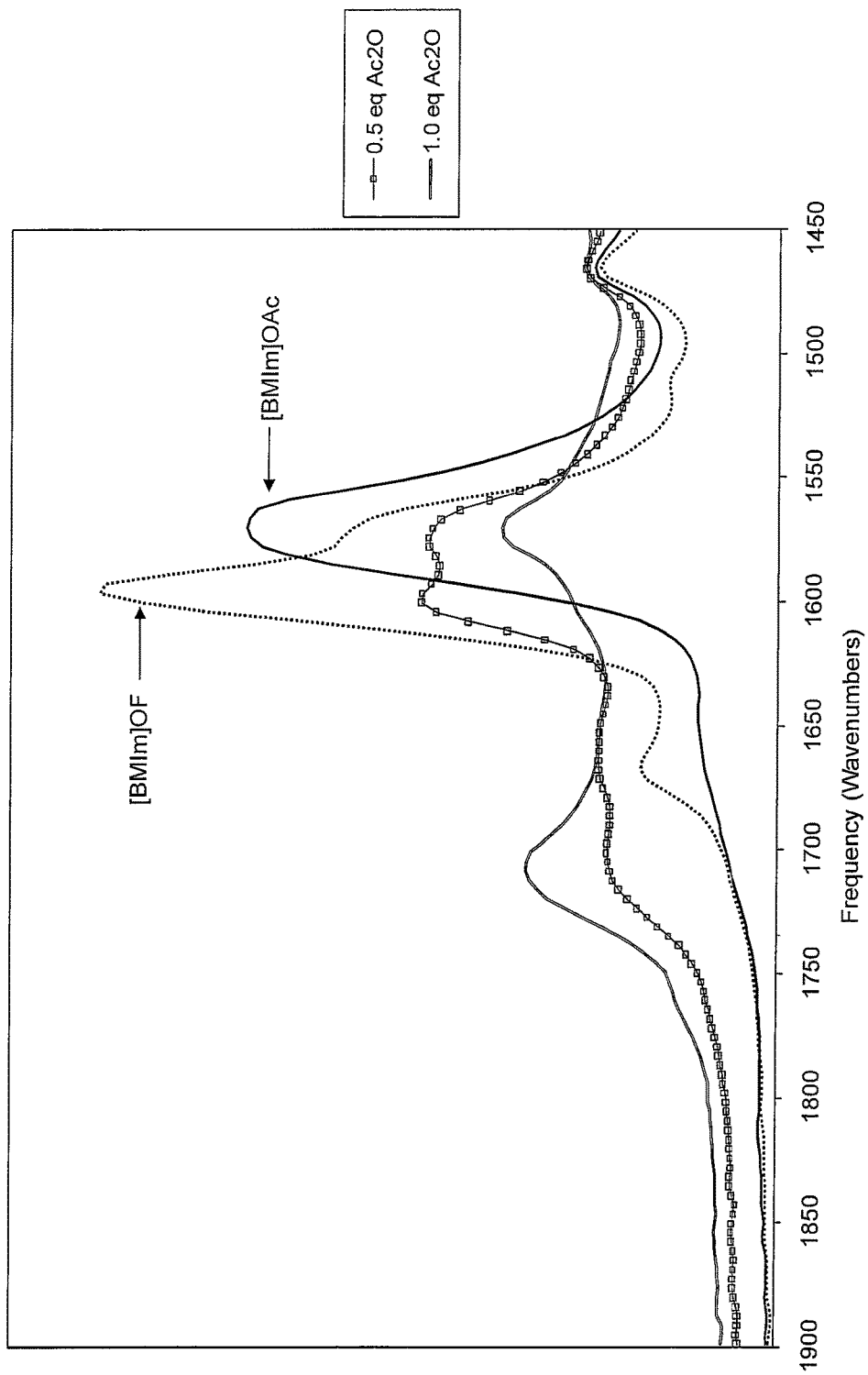
FIG. 20 is a spectral analysis showing infrared spectra of 1-butyl-3-methylimidazolium formate and 1-butyl-3-methylimidazolium acetate, a spectrum after 0.5 molar equivalents of acetic anhydride has been added to the 1-butyl-3-methylimidazolium formate, and a spectrum after another 0.5 molar equivalents of acetic anhydride has been added to the 1-butyl-3-methylimidazolium formate.
Figure 21:
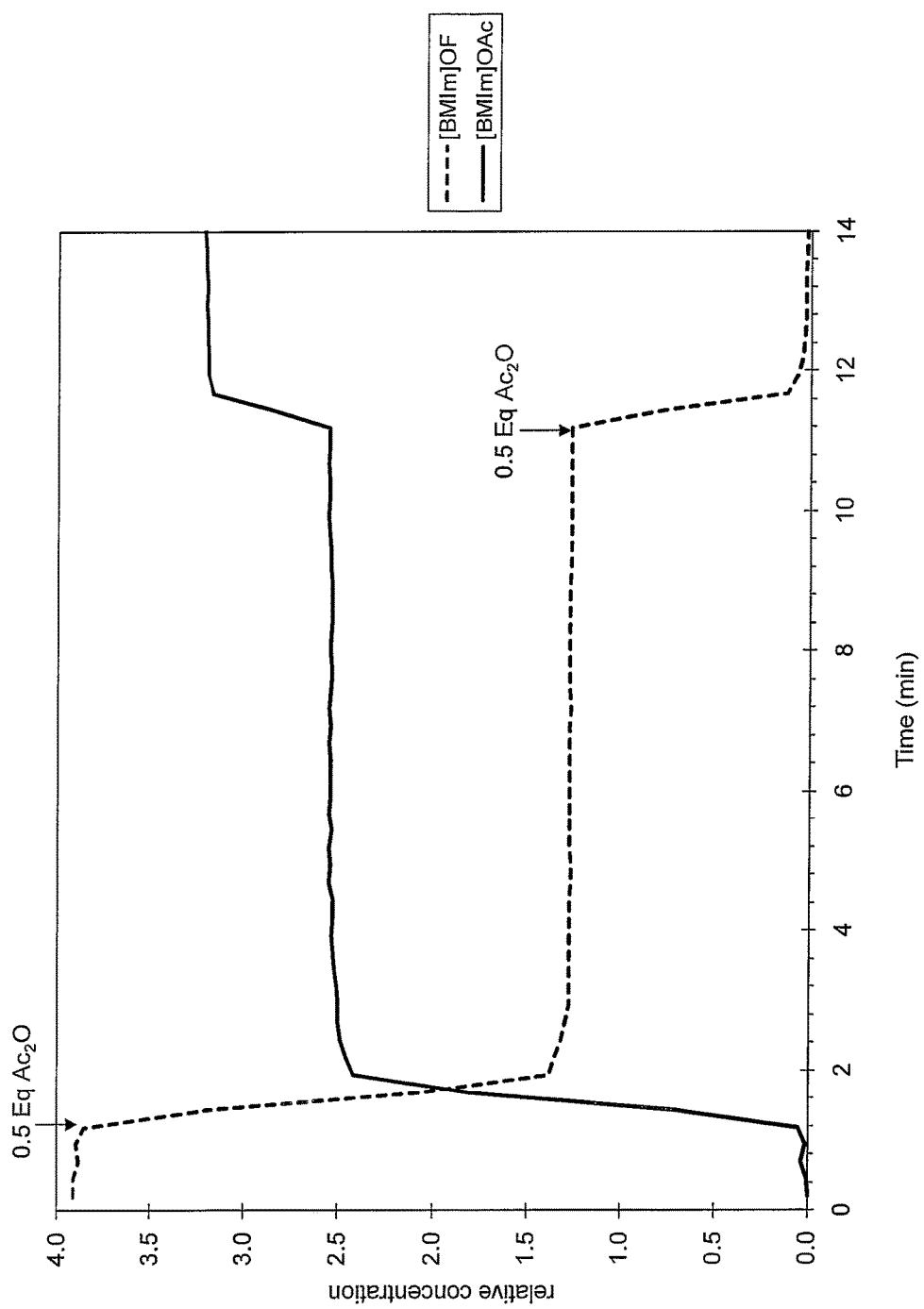
FIG. 21 is a plot of relative concentration versus time for 1-butyl-3-methylimidazolium formate and 1-butyl-3-methylimidazolium acetate upon first and second additions of 0.5 molar equivalents of acetic anhydride.

To a vial containing a small magnetic stir bar was added 4.2 g of [BMIm]formate. An iC10 diamond tipped IR probe was inserted into the vial so that the reaction could be monitored in situ by infrared spectroscopy. To the [BMIm] formate was added 0.5 eq of $Ac_2O$ in one portion. As FIGS. 20 and 21 show, 50% of the [BMIm]formate was immediately converted to [BMIm]OAc. Additional spectra were collected to allow the system to stabilize before adding another 0.5 eq of $Ac_2O$ in one portion. Infrared spectroscopy indicated that the remaining [BMIm]formate was immediately converted to [BMIm]OAc.

This example shows that [BMIm]formate is rapidly converted to [BMIm]OAc with the addition of $Ac_2O$. The reaction rate is so rapid that the [BMIm]formate can be titrated with $Ac_2O$ until no gas is evolved.

Example 31—Effect of MeOH During Anion Exchange

Figure 22:
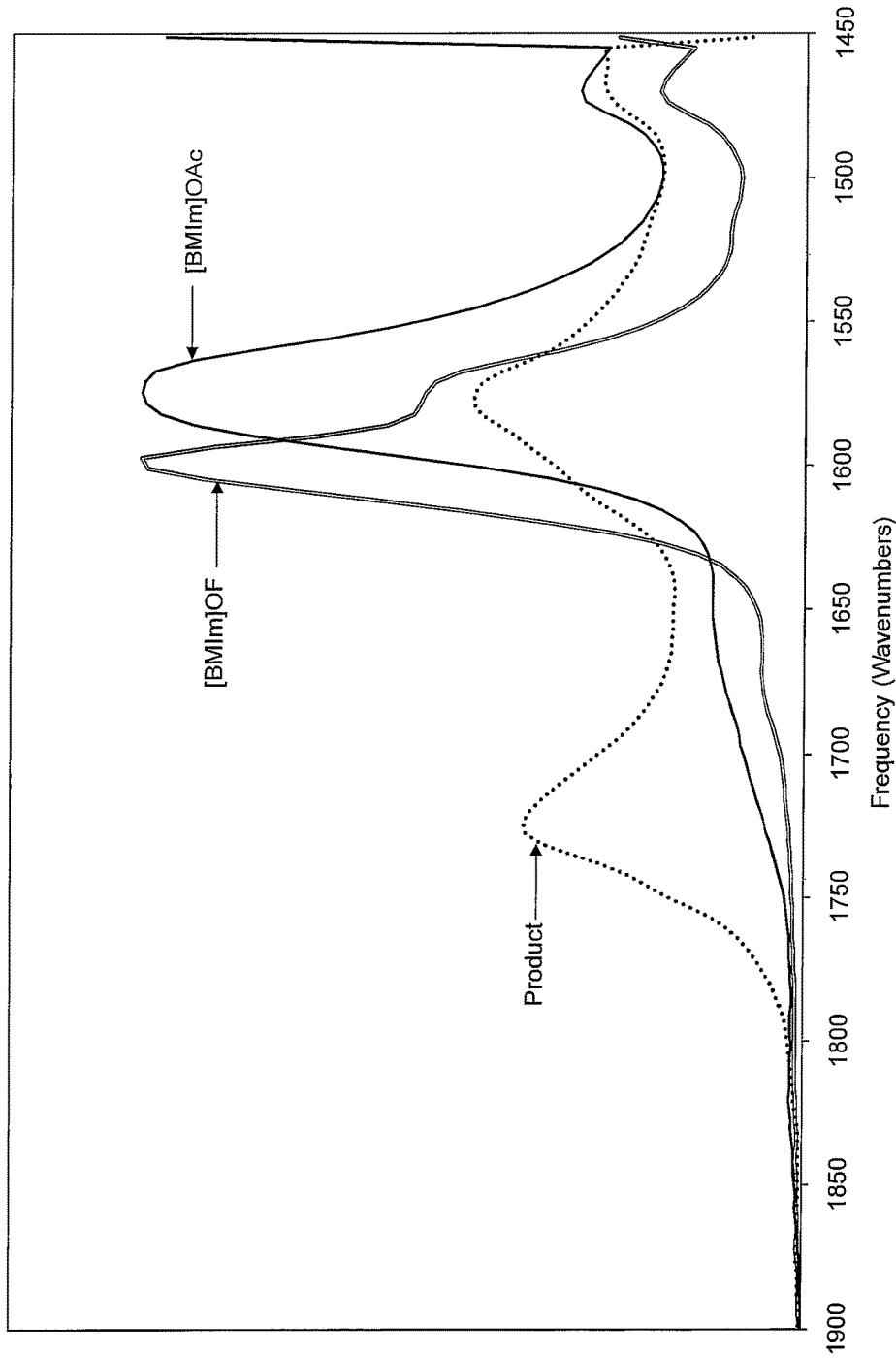
FIG. 22 is spectral analysis showing infrared spectra of 1-butyl-3-methylimidazolium formate, 1-butyl-3-methylimidazolium formate, and a spectrum after 1 equivalent of acetic anhydride has been added to the 1-butyl-3-methylimidazolium formate in the presence of 2 molar equivalents of methanol.
Figure 23:
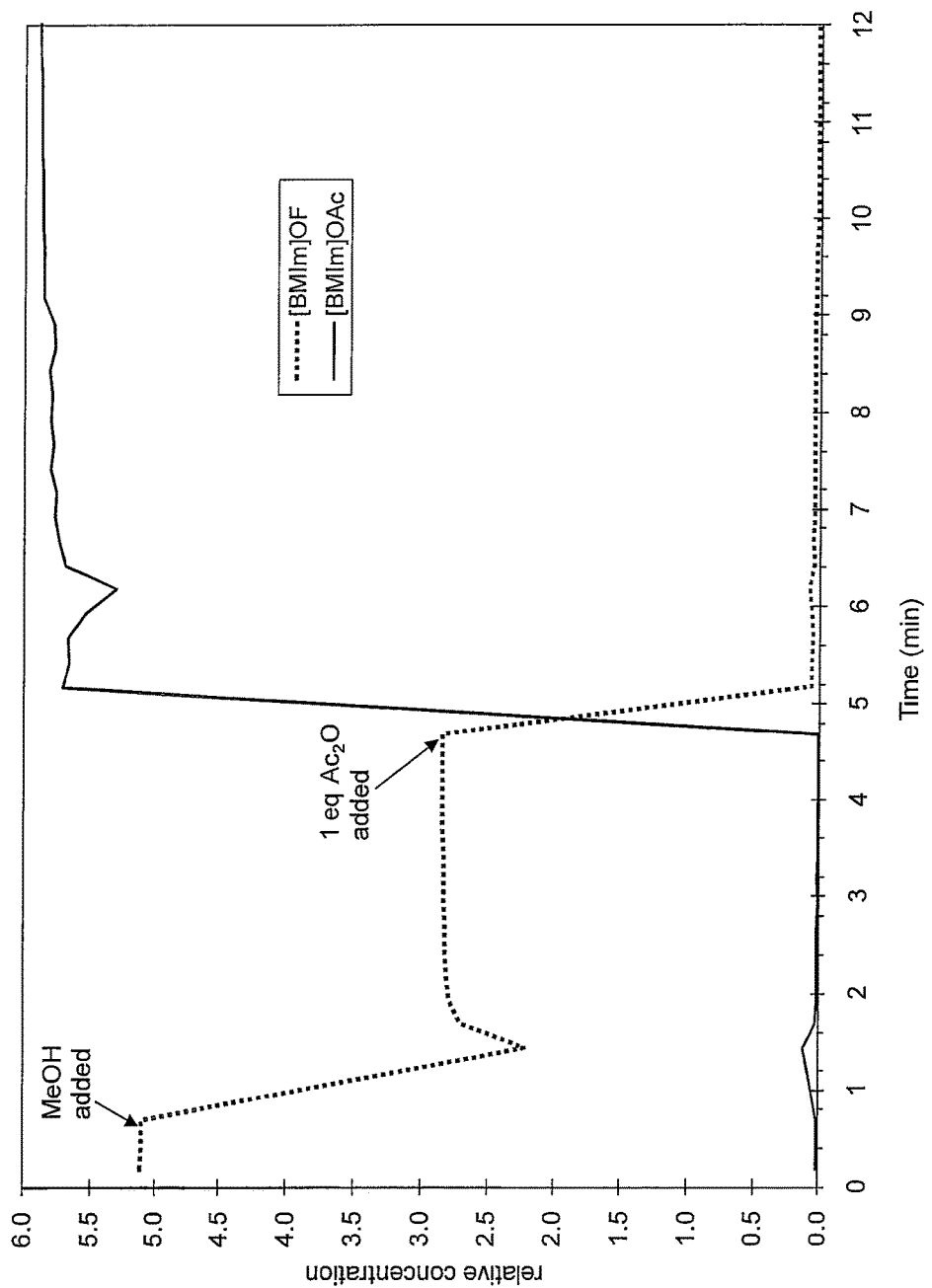
FIG. 23 is a plot of relative concentration versus time for 1-butyl-3-methylimidazolium formate and 1-butyl-3-methylimidazolium acetate upon addition of 2 molar equivalents of methanol and then upon addition of 1 equivalent of acetic anhydride.

To a vial containing a small magnetic stir bar was added 3.15 g of [BMIm]formate. An iC10 diamond tipped IR probe was inserted into the vial so that the reaction could be monitored in situ by infrared spectroscopy. To the [BMIm] formate was added 2 eq of MeOH. After the system thermally stabilized, 1 eq of $Ac_2O$ was added to the [BMIm] formate in one portion. As FIGS. 22 and 23 show, infrared spectroscopy indicated that the [BMIm]formate was immediately converted to [BMIm]OAc.

This example shows that the reaction of [BMIm]formate with $Ac_2O$ to form [BMIm]OAc is much faster than the reaction of $Ac_2O$ with MeOH to form MeOAc. Hence, it is not necessary to remove MeOH from [BMIm]formate prior to converting the [BMIm]formate to [BMIm]OAc.

Example 32—Effects of Water Modification and MSA

A 3-neck 250 mL round bottom flask, fitted with two double neck adapters giving five ports, was equipped for mechanical stirring, with a iC10 diamond tipped IR probe, and with an $N_2$/vacuum inlet. To the flask added 62.37 g of 1-butyl-3-methylimidazolium acetate.

Figure 24:
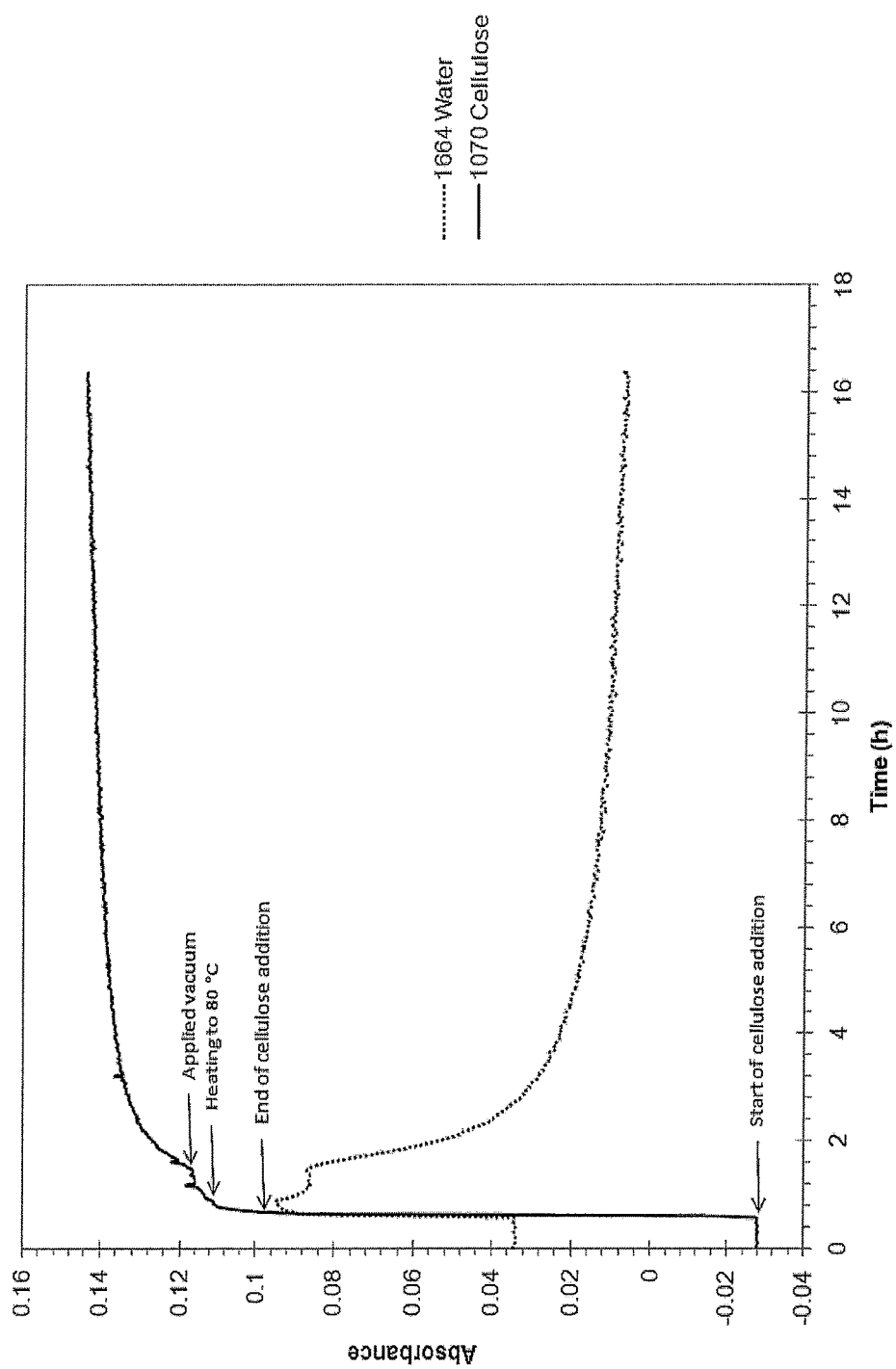
FIG. 24 is a plot of absorbance versus time showing the dissolution of cellulose in 1-butyl-3-methylimidazolium acetate at 80° C.

To 5.06 g (7.5 wt %) of cellulose (DP ca. 335) was added 20.68 g of water. After hand mixing, the cellulose was allowed to stand in the water for 65 min at 60° C. before filtering which, gave 10.78 g of a wet cellulose cake. The water wet cellulose was then added in small portions to the [BMIm]OAc (5 min addition). Within 5 min, the cellulose was well dispersed in the ionic liquid (a few small clumps were visible). The mixture was stirred for 7 min before a preheated 80° C. oil bath was raised to the flask. The mixture was then stirred for 28 min (visually, nearly all of the cellulose was dissolved) before slowly placing the flask contents under vacuum with the aid of a bleed valve (FIG. 24). After 1.5 h, the vacuum was 1.9 mm Hg. The clear mixture was then stirred overnight under vacuum at 80° C.

The clear solution was allowed to cool to room temperature 15 h 45 min from the point of cellulose addition before adding a mixture of 12.11 g (3.8 eq) of $Ac_2O$ and 600 mg of MSA dropwise (28 min addition). The maximum temperature reached during the $Ac_2O$ addition was 46° C. Eight minutes after completing the $Ac_2O$ addition, a preheated 50° C. oil bath was raised to the flask. The mixture was stirred for 16 min before 1.46 g of water was slowly added to the solution (2 min addition). The solution was then stirred for 17 min before adding an additional 0.47 g of water. The solution was then stirred for 5 h 9 min before cooling the solution to room temperature. The reaction was sampled (FIG. 25) throughout the contact period by removing 6-10 g aliquots of the reaction mixture and precipitating in 100 mL of MeOH. The solid from each aliquot was washed once with a 100 mL portion of MeOH then twice with 100 mL of MeOH containing 8 wt % of 35 wt % $H_2O_2$. The samples were then dried at 60° C., 5 mm Hg overnight.

Figure 25:
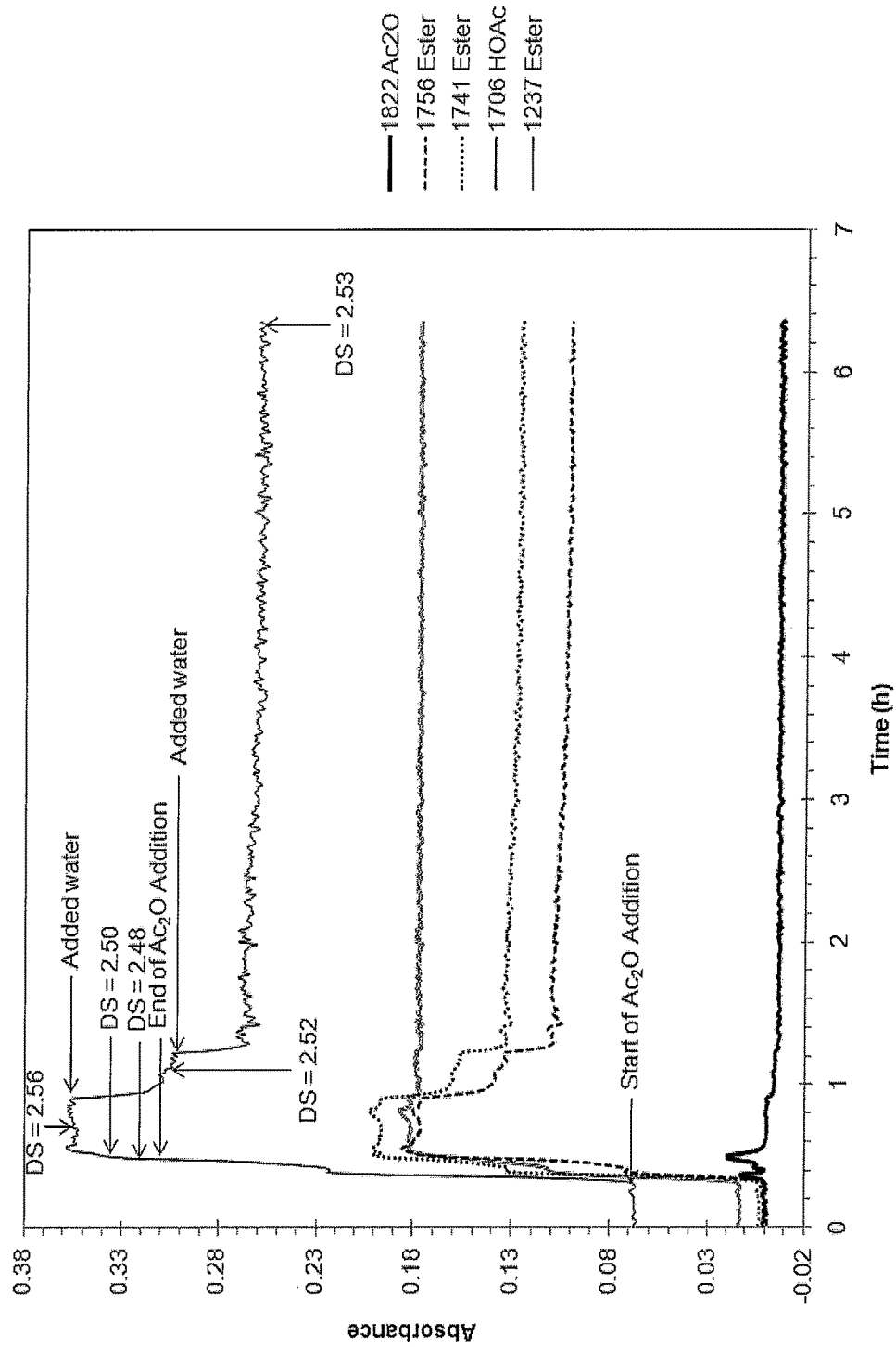
FIG. 25 is a plot of absorbance versus time showing the esterification of cellulose dissolved in 1-butyl-3-methylimidazolium acetate.
Figure 26:
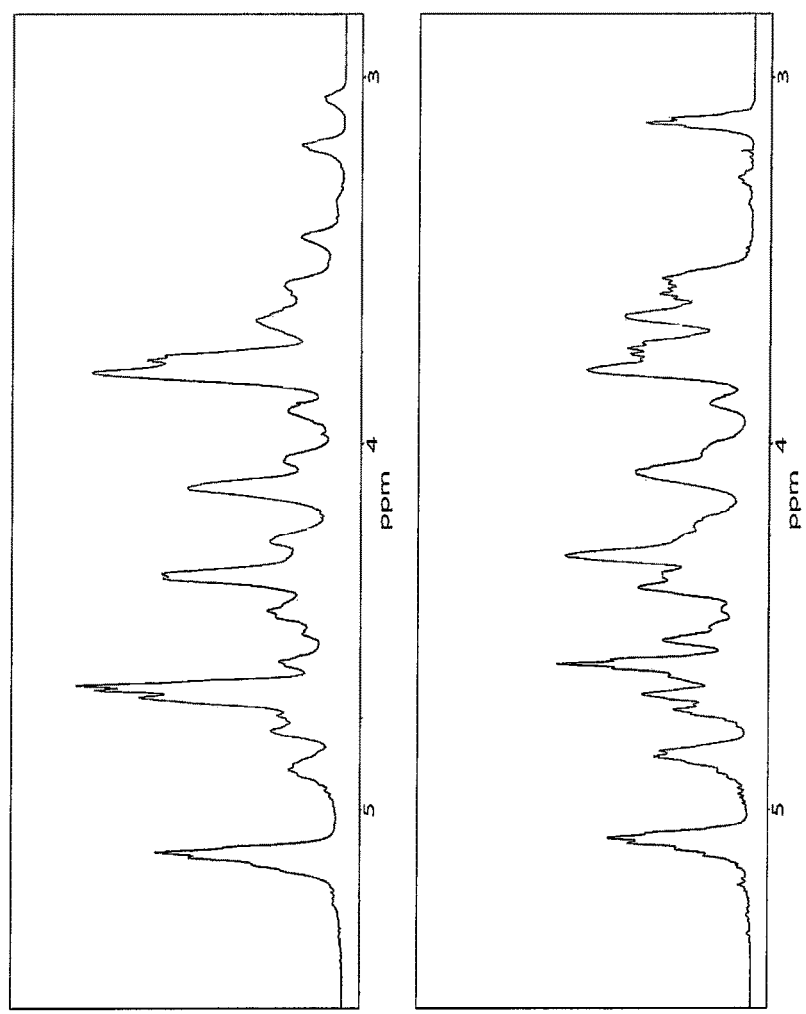
FIG. 26 is a spectral analysis showing the ring proton resonances for cellulose acetates prepared from cellulose dissolved in 1-butyl-3-methylimidazolium acetate (top spectrum), and the ring proton resonances for cellulose acetates prepared from cellulose dissolved in 1-butyl-3-methylimidazolium chloride (bottom spectrum)
Figure 27:
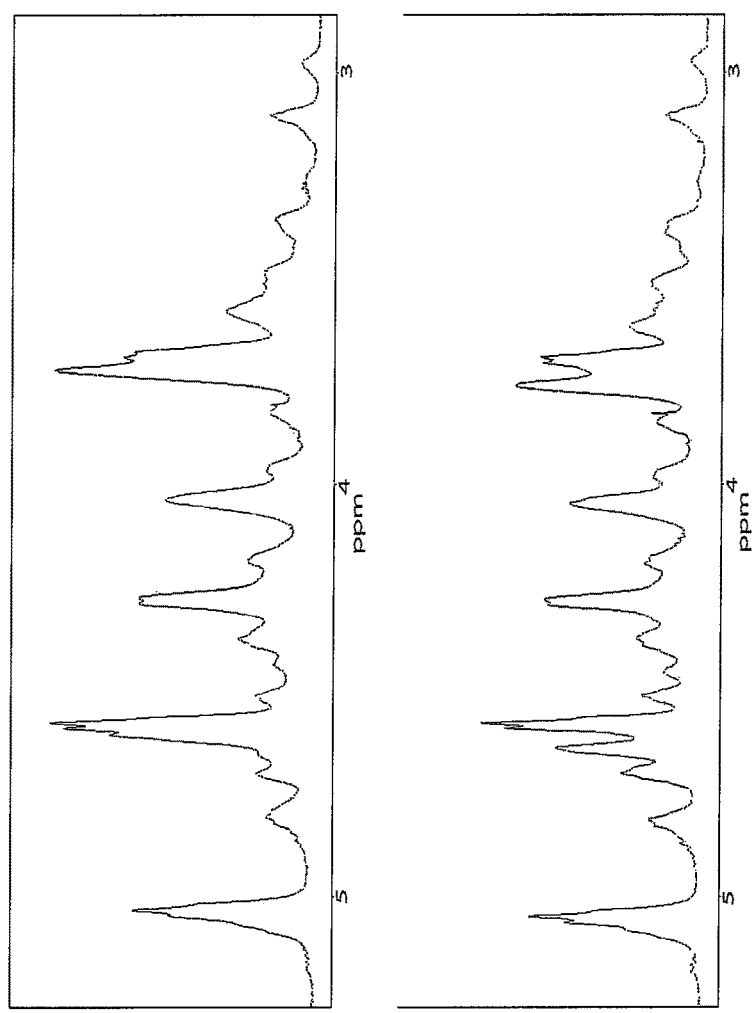
FIG. 27 is a spectral analysis showing the ring proton resonances for cellulose acetates prepared from cellulose dissolved in 1-butyl-3-methylimidazolium acetate after water addition (top spectrum) and before water addition (bottom spectrum).

This example illustrates a number of benefits of the methods employed herein. As can be seen from FIG. 24, water wet cellulose can be readily dissolved in carboxylated ionic liquid even when a significant amount of water still remains in the ionic liquid. As shown in FIG. 25, the rate of reaction in the acylation of this cellulose in a carboxylated ionic liquid is very rapid; a significant concentration of $Ac_2O$ is never observed indicating that the $Ac_2O$ is consumed as fast as it is added. The rapid rates of reaction can lead to a much different monomer distribution relative to that observed in other ionic liquids. For example, FIG. 26 compares the proton resonances of the protons attached to the anhydroglucose rings of cellulose acetates (DS=2.56) prepared from cellulose dissolved in [BMIm]OAc (top spectrum) and dissolved in [BMIm]Cl (bottom spectrum). The major resonances in the top spectrum centered near 5.04, 5.62, 4.59, 4.29, 4.04, 3.73, and 3.69 correspond to trisubstituted monomers. In the bottom spectrum, there are much less of these resonances relative to the other type of monomer resonances. This discovery is significant in that the rapid rates of reaction provide a means to produce nonrandom cellulose ester copolymers with different levels of block segments. The extent and the size of the block segments will depends upon factors such as mixing, prior water treatment or no water treatment of the cellulose, concentration and type of catalyst, contact temperature, and the like. As shown in FIG. 24, 3 samples were taken prior to the addition of water. These 3 samples ranged in DS from 2.48-2.56 and at 10 wt % in acetone, they were soluble giving slightly hazy solutions (solubility rating of 2). In contrast, the 2 samples taken after water addition (DS ca. 2.52) were insoluble in acetone (solubility rating of 6). FIG. 27 compares the ring proton resonances for cellulose acetates prepared from cellulose dissolved in [BMIm]OAc before and after addition of water. The top spectrum corresponds to a cellulose acetate after water addition (DS=2.53) and the bottom spectrum corresponds to a cellulose acetate before water addition (DS=2.56). The differences between these 2 spectra are consistent with different monomer compositions in the copolymers.

Example 33—Production of Cellulose Triacetate

To a 3-neck 100 mL round bottom flask equipped for mechanical stirring and with an $N_2$/vacuum inlet added 34.63 g of 1-ethyl-3-methylimidazolium acetate. While stirring rapidly, added 6.11 g (15 wt %) of dry cellulose powder (DP ca. 335). The flask was placed in a 90° C. oil bath and the mixture was stirred for 10 min before applying vacuum (2 mm Hg). After 50 min, the oil bath temperature was increased to 100° C. After 2 h 25 min, the oil bath was turned off and left the solution was left standing under vacuum overnight.

To the cellulose solution was added a mixture of 731 mg of MSA and 19.24 g (5 eq) of $Ac_2O$ dropwise. Initially, the solution was stirred slowly so that the solution did not bunch around the stir shaft. As the $Ac_2O$ was added, the solution viscosity dropped; after adding ca. 5 mL, the solution stirred easily and the stir rate was increased. During the addition, the solution viscosity did not increase and no localized gels were observed until the last few drops of $Ac_2O$ were added (40 min addition). At this point the entire contact mixture suddenly gelled. The contact temperature rose from 24.1° C. to 47.5° C. by the end of addition. During the addition, there was little change in the color of the solution. After the reaction gelled, 11.54 g of the reaction mixture was removed with a spatula and solids were obtained by precipitation in MeOH (Sample 1). The flask containing the remaining reaction mixture was then placed in a preheated 50° C. oil bath. After 20 min at 50° C., there was no evidence of the gel softening. Hence, the gel was allowed to cool to room temperature and 50 mL of MeOH was added to the flask. The flask contents were then dumped into 400 mL of MeOH which gave a white precipitate (Sample 2). Both fractions were processed by stirring the initial slurry for ca. 1 h before isolating the solids by filtration. The solids were washed by taking them up in 300 mL of MeOH and stirring the slurry for ca. 1 h before the solids were isolated by filtration. The solids were twice taken up in 300 mL of 12/1 MeOH/35% $H_2O_2$ and the slurry was stirred for ca. 1 h before the solids were isolated by filtration. The solids were then dried overnight at 50° C., ca. 20 mm Hg.

The combined yield for Sample 1 and 2 was 10.2 g of a white solid. Analysis by 1H NMR showed that Samples 1 and 2 were identical and that they were cellulose triacetates with a DS of 3.0. By GPC, both samples have a Mw of ca. 54,000.

This example shows that cellulose triacetate can rapidly be prepared from cellulose dissolved in [EMIm]OAc. Cellulose triacetate can be used to prepare film useful in liquid crystalline displays and photographic film base.

Example 34—Immiscible Co-Solvent (Effect on IL Viscosity)

To a 3-neck 50 mL round bottom flask equipped for mechanical stirring and with an $N_2$/vacuum inlet added 20.03 g of 1-ethyl-3-methylimidazolium acetate. While stirring rapidly, added 1.05 g of dry cellulose powder (DP ca. 335). The flask was placed under vacuum (2 mm Hg) and placed in an oil bath preheated to 90° C. After 1 h 45 min, the oil bath temperature was increased to 100° C. and stirred an additional 55 min (2 h 40 min total contact time) before allowing the solution to cool to ambient temperature while under vacuum.

To the cellulose solution was added 20 mL of methyl acetate resulting in a 2-phase reaction mixture. While stirring rapidly, a mixture of 131 mg of MSA and 4.63 g of $Ac_2O$ was added drop wise (10 min). The contact temperature increased from 23.3° C. to 35.4° C. and, at the end of the addition, the contact mixture was a single phase and the viscosity of the single phase was much less than that of the original cellulose-[EMIm]OAc solution. Twenty-five minutes after beginning the addition, the flask was placed in a preheated 50° C. oil bath. The contact mixture was stirred for 2 h at 50° C. before allowing the contact mixture to cool to ambient temperature over 50 min. The product was precipitated in 350 mL of MeOH and the slurry was stirred for ca. 1 h before the solids were isolated by filtration. The solids were washed by taking them up in 300 mL of MeOH and stirring the slurry for ca. 1 h before the solids were isolated by filtration. Twice, the solids were taken up in 300 mL of 12/1 MeOH/35% $H_2O_2$ and the slurry was stirred for ca. 1 h before the solids were isolated by filtration. The solids were then dried overnight at 50° C., ca. 20 mm Hg which gave 1.68 g of a white solid. Analysis by $^1$H NMR revealed that the solid was a cellulose acetate with a DS of 2.67. Analysis by GPC indicated that the cellulose acetate had a Mw of 51,428 and a Mw/Mn of 4.08.

This example shows that a cellulose solution in an ionic liquid can be contacted with an immiscible or sparingly soluble co-solvent without causing precipitation of the cellulose. Upon contact with an acylating reagent, the cellulose is esterified changing the solubility of the now cellulose ester-ionic liquid solution with the formerly immiscible co-solvent so that the contact mixture becomes a single phase. The resulting single phase has much lower solution viscosity than the initial cellulose-ionic liquid solution. This discovery is significant in that highly viscous cellulose solutions can be used to make cellulose esters while still maintaining the ability to mix and process the solution. The discovery also provides a means to process highly viscous cellulose-ionic liquid solutions at lower contact temperatures. The cellulose ester product can be isolated from the new single phase by conventional means. The cellulose ester product has desirable degrees of substitution, molecular weights, and solubility in solvents such as acetone, and can be readily melt processed when plasticized with plasticizers such as diethyl phthalate and the like.

Example 35—Immiscible Co-Solvent (Biphasic to Single Phase)

A 3-neck 100 mL round bottom flask containing 28.84 g of a 5 wt % cellulose solution in [BMIm]Cl was equipped for mechanical stirring and with an $N_2$/vacuum inlet. The flask was placed in a preheated 80° C. oil bath and the flask contents were placed under vacuum (ca. 7 mm Hg) for 2 h. To the solution was added 25 mL of methyl ethyl ketone that had been previously dried over 4 A molecular sieves resulting in two well defined phases. To the biphasic mixture was added 4.54 g of $Ac_2O$ while stirring vigorously. After ca. 75 min, the contact mixture appeared to be homogeneous. After 2.5 h, the contact mixture was allowed to cool to room temperature. Phase separation did not occur even when a small amount of water and methyl ethyl ketone was added to the homogeneous mixture. The product was isolated by addition of the contact mixture to 200 mL of MeOH followed by filtration to separate the solids. The solids were washed twice with MeOH and three times with water before they were dried at 50° C., ca. 5 mm Hg. Analysis by $^1$H NMR and by GPC revealed that the product was a cellulose acetate with a DS of 2.11 and Mw of 50,157.

This example shows that a cellulose solution in an ionic liquid such as [BMIm]Cl can be contacted with an immiscible or sparingly soluble co-solvent such as methyl ethyl ketone without causing precipitation of the cellulose. Upon contact with an acylating reagent, the cellulose is esterified changing the solubility of the now cellulose ester-ionic liquid solution with the formerly immiscible co-solvent so that the contact mixture became a single phase from which the cellulose ester could be isolated by precipitation with an alcohol.

Example 36—Color Measurements for Cellulose Esters Prepared from Cellulose Dissolved in Ionic Liquids Color development during esterification of cellulose dissolved in ionic liquids depend upon a number of factors. These factors include the type of ionic liquid used to dissolve the cellulose, impurities contained in the ionic liquid, type of cellulose, the presence or absence of binary components (cf. Example 3), cellulose dissolution contact time and temperature, esterification contact time and temperature, among others. Understanding those factors and the mechanism involved in color formation is the best means for preventing color formations. Even when the best practices are followed, colored product is still often obtained. Hence, a means for removing or minimizing the color is very important. In this regard, we have found that we can minimize color by contacting the cellulose ester with a bleaching agent while dissolved in ionic liquid or after separation of the cellulose ester from the ionic liquid.

color (entry 9). In this case $L^*$ and $a^*$ increased while $b^*$ decreased resulting in an $E^*$ value of 4.85. When the anion was a carboxylate, in the absence of bleaching $L^*$ and $E^*$ ranged from 46.6-74.5 and 108.6-89.9, respectively (entries 4-6). Bleaching with $H_2O_2$ after separation of the cellulose ester from the ionic liquid led to a dramatic improvement of color. $L^*$ increased while $a^*$ and $b^*$ decreased resulting in $E^*$ values of 0.9-11.2 (entries 10-16).

TABLE 10

Values of $L^*$, $a^*$, $b^*$, and $E^*$ for cellulose ester solutions before and after bleaching.

| Entry | $L^*$ | $a^*$ | $b^*$ | $E^*$ | IL-BC | CE | Bleach |
|---|---|---|---|---|---|---|---|
| 1 | 97.65 | −2.24 | 11.07 | 11.54 | [BMIm]Cl-MSA | CA | None |
| 2 | 94.28 | −1.85 | 17.83 | 18.83 | [BMIm]Cl-MSA | CA | None |
| 3 | 93.56 | −1.74 | 17.84 | 19.06 | [BMIm]Cl-MSA | CA | None |
| 4 | 46.56 | 41.45 | 77.89 | 103.19 | [BMIm]OAc-MSA | CA | None |
| 5 | 50.35 | 35.44 | 89.8 | 108.59 | [BMIm]OAc | CA | None |
| 6 | 74.52 | 12.66 | 85.28 | 89.91 | [BMIm]OAc | CAP | None |
| 7 | 96.89 | −1.44 | 10.10 | 10.68 | [BMIm]Cl-MSA | CA | $H_2O_2$ |
| 8 | 98.24 | −1.09 | 4.37 | 4.85 | [BMIm]Cl-MSA | CA | $H_2O_2$ |
| 9 | 98.37 | −1.04 | 5.69 | 6.02 | [BMIm]Cl-MSA | CA | $KMnO_4$ |
| 10 | 98.43 | −3.00 | 10.72 | 11.24 | [EMIm]OAc | CA | $H_2O_2$ |
| 11 | 98.10 | −3.06 | 10.34 | 10.95 | [BMIm]OAc | CA | $H_2O_2$ |
| 12 | 98.44 | −1.51 | 5.87 | 6.27 | [BMIm]OBu | CAB | $H_2O_2$ |
| 13 | 97.91 | −2.43 | 10.68 | 11.15 | [EMIm]OAc-MSA | CA | $H_2O_2$ |
| 14 | 99.44 | 0.00 | 0.58 | 0.87 | [BMIm]OAc—Zn(OAc)$_2$ | CA | $H_2O_2$ |
| 15 | 99.02 | 0.05 | 1.63 | 1.94 | [BMIm]OAc—Zn(OAc)$_2$ | CA | $H_2O_2$ |
| 16 | 99.32 | −0.48 | 1.98 | 2.16 | [BMIm]OPr-MSA | CP | $H_2O_2$ |

Example of a general method for bleaching cellulose esters while dissolved in ionic liquid: To a 7.5 wt % solution of cellulose dissolved in [BMIm]Cl was added a mixture of 2.9 eq Ac$_2$O and 0.1 eq MSA. After 65 minutes, in situ IR indicated that the reaction was complete. To the solution was added a bleaching agent (in this case, 0.75 wt % of a 2.25 wt % solution of KMnO$_4$ dissolved in MeOH). The mixture was stirred for 2 h before the cellulose ester was isolated by precipitation in water, washed with water, and dried. The concentration of bleaching agent and bleaching contact time depends upon the particular process.

Example of a general method for bleaching cellulose esters after separation from the ionic liquid: After completing the reaction, the cellulose ester is isolated from the ionic liquid by precipitation in a nonsolvent such as water or alcohol. The liquids are separated from the cellulose ester and, optionally, the cellulose ester can be washed further before contacting the solid product with a bleaching agent (e.g. 35 wt % aqueous $H_2O_2$). Specific examples of this process can be found in Examples 33 and 34. The concentration of bleaching agent, the number of bleaching cycles, and bleaching contact time depends upon the particular process.

Values of $L^*$, $a^*$, $b^*$, and $E^*$ for cellulose ester solutions before and after bleaching are provided in Table 10. Comparing entries 1-3 to entries 4-6 (no bleaching) it is evident that more color is created during cellulose esterification when the anion of the ionic liquid is a carboxylate relative to when the anion is a halide. When the anion was a halide, in the absence of bleaching $L^*$ and $E^*$ ranged from 93.6-97.7 and 19.1-11.5, respectively (entries 1-3). Bleaching with $H_2O_2$ after separation of the cellulose ester from the ionic liquid increased $a^*$ and decreased $b^*$ resulting in improvement of color which is reflected in a lower $E^*$ value (entries 7 and 8). Bleaching the cellulose ester while it is dissolved in the ionic liquid led to a similar improvement in color (entry 9). This example illustrates that contacting a cellulose ester with a bleaching agent while dissolved in ionic liquid or after separation of the cellulose ester from the ionic liquid can lead to very significant improvements in color.

Example 37—Viscosity of Solutions of Cellulose Dissolved in Ionic Liquids Containing Miscible Cosolvents Solutions of cellulose dissolved in [BMIm]Cl containing different levels of acetic acid were prepared by the following general procedure: To a 3-neck 50 mL round bottom flask equipped for mechanical stirring and with a N$_2$/vacuum inlet was added [BMIm]Cl. The flask contents were heated to 80° C. and placed under vacuum (0.8 mm Hg). After 1.7 h, 5 wt % acetic acid was added to the [BMIm]Cl before allowing the solution to cool to room temperature. Cellulose (5 wt %) was added to the solution before heating the mixture to 80° C. The mixture was stirred until a homogeneous solution was obtained (ca. 80 min), The solution was then cooled to room temperature.

Figure 28:
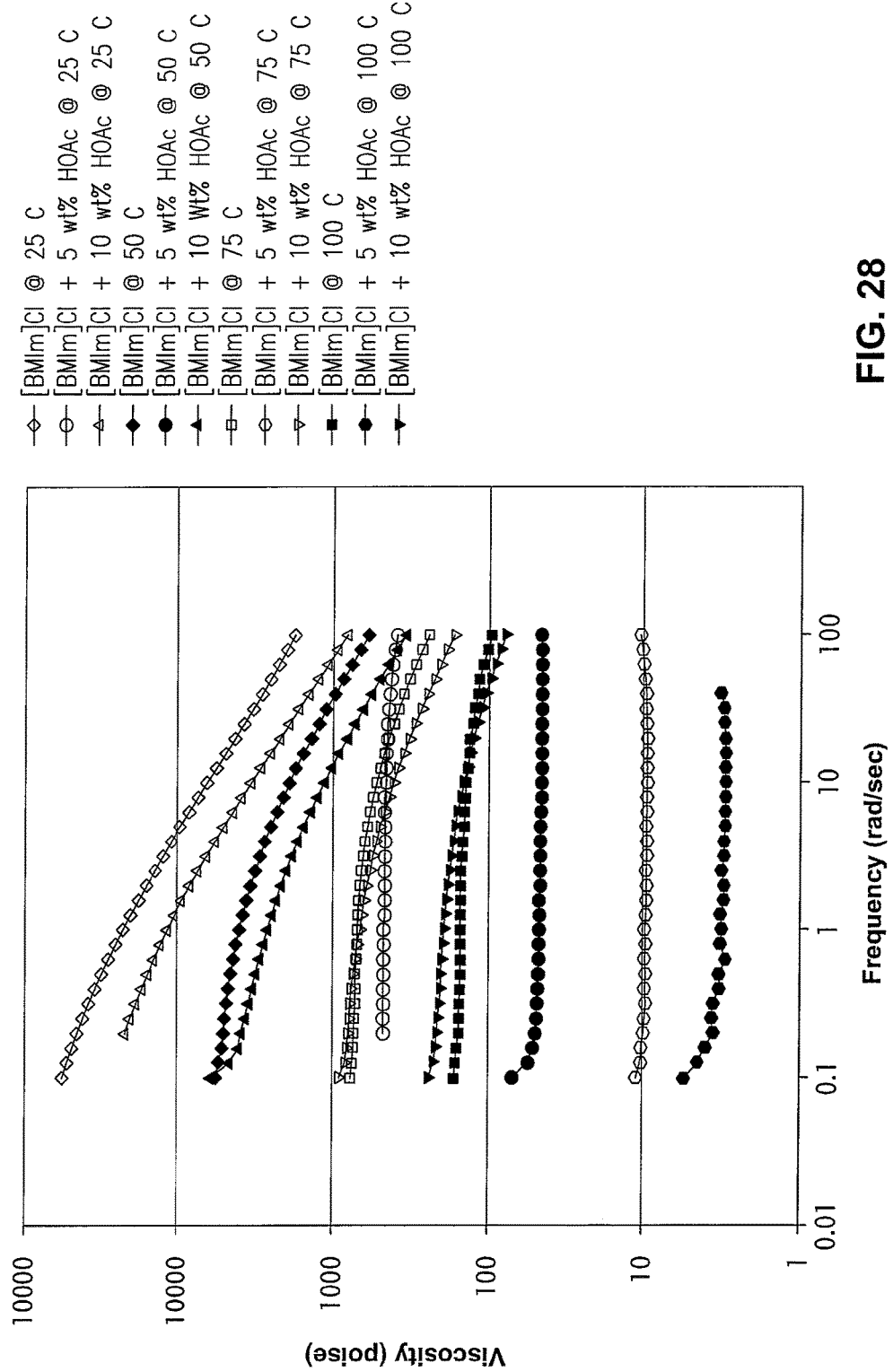
FIG. 28 compares the viscosities of solutions of cellulose (5 wt %) dissolved in [BMIm]Cl, [BMIm]Cl+5 wt % acetic acid, and [BMIm]Cl+10 wt % acetic acid.

FIG. 28 compares the viscosities of cellulose solutions containing no acetic acid, 5 wt % acetic acid, and 10 wt % acetic acid at 25, 50, 75, 100° C. The viscosity of the cellulose-[BMIm]Cl-5 wt % acetic acid solution is significantly less than that of cellulose-[BMIm]Cl at all temperatures. For example, at 25° C. and 0.2 rad/sec the viscosity of the cellulose-[BMIm]Cl-5 wt % acetic acid solution is 466 poise versus 44,660 poise for the cellulose-[BMIm]Cl solution. Comparing the viscosities of the cellulose-[BMIm]Cl-10 wt % acetic acid solution to the cellulose-[BMIm]Cl-5 wt % acetic acid and cellulose-[BMIm]Cl solutions at 25° C., it is evident that the viscosity of the cellulose-[BMIm]Cl-10 wt % acetic acid solution is less than that of the cellulose-[BMIm]Cl solution but greater than that of the cellulose-[BMIm]Cl-5 wt % acetic acid solution. At 25° C. and 0.2 rad/sec, the viscosities of the cellulose-[BMIm]Cl-10 wt % acetic acid, cellulose-[BMIm]Cl-5 wt % acetic acid, and cellulose-[BMIm]Cl solutions are 22,470, 466, and 44,660 poise, respectively. With increasing temperature, the differences in the viscosities between the cellulose-[BMIm]Cl-10 wt % acetic acid and cellulose-[BMIm]Cl solutions diminish and the observed viscosities depend upon the shear rate.

This example shows that the viscosity of a cellulose-ionic liquid solution can be dramatically altered by adding a miscible cosolvent such as a carboxylic acid to the solution. The viscosity drops with increasing miscible cosolvent reaching a minimum before increasing again as addition cosolvent is added.

Example 38—Viscosity of Solutions of Cellulose Dissolved in Ionic Liquids Containing Immiscible Cosolvents To determine the impact of an immiscible cosolvent which, forms two layers with the initial cellulose-ionic liquid solution, on solution viscosity it is necessary to convert the cellulose to a cellulose ester prior to making the viscosity measurement.

To a 3-neck 100 mL round bottom flask equipped for mechanical stirring and with an $N_2$/vacuum inlet was added 33.18 g of 1-butyl-3-methylimidazolium chloride. While stirring rapidly, added 1.75 g of dry cellulose (5 wt %). The flask was placed under vacuum (2 mm Hg) and placed in an oil bath preheated to 80° C. After 30 min in the oil bath all of the cellulose was dissolved. The oil bath and stirring was turned off and the solution was left under vacuum overnight.

To the cellulose solution was added 30 mL of methyl ethyl ketone resulting in a 2-phase reaction mixture. While stirring rapidly, added a mixture of 104 mg of MSA and 5.51 g of $Ac_2O$ dropwise (3 min). At the end of the addition, the reaction mixture was two phases. After stirring for ca. 70 min from the start of addition, the reaction mixture was a single phase; the viscosity of the phase was much less than that of the original cellulose solution. Stirring was continued for an additional 150 min before 10.9 g of the solution was removed for viscosity measurements. The remaining solution was then cooled to room temperature and the product was isolated by precipitating in 350 mL of MeOH. The slurry was stirred for ca. 1 h before the solids were isolated by filtration. The solids were washed 4 times with 250 mL of MeOH. The solids were then dried overnight at 50° C., 5 mm Hg which gave 1.66 g of a white solid. Analysis revealed that the solid was the expected cellulose acetate. A second reaction was conducted in the same fashion except that the cosolvent was omitted. Again, a sample was removed for viscosity measurements just prior to precipitation of the cellulose acetate.

Figure 29:
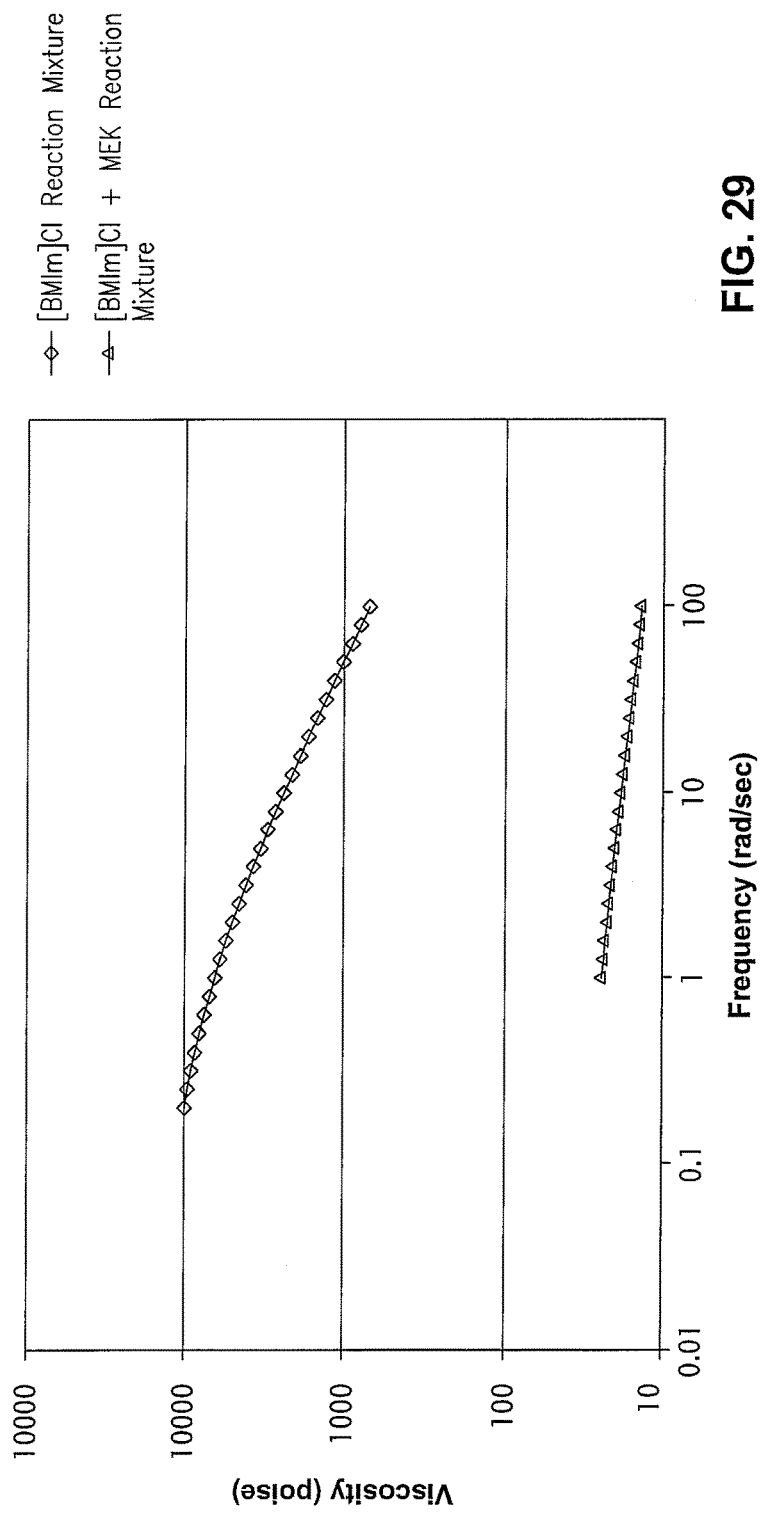
FIG. 29 compares the viscosities of solutions of cellulose contact mixtures without a cosolvent and with methyl ethyl ketone as a cosolvent.

FIG. 29 compares the solution viscosity of the contact mixtures with and without cosolvents at 25° C. Inclusion of a cosolvent dramatically reduces the viscosity of the solution. For example at 25° C. and 1 rad/sec, inclusion of methyl ethyl ketone resulted in a solution with a viscosity of 24.6 poise versus 6392 poise for the solution without methyl ethyl ketone.

Example 39—Impact of Miscible Cosolvents on Reaction Rates and Total DS

A 3-neck 100 mL round bottom flask was equipped with a double neck adapter giving four ports, an iC10 diamond tipped IR probe, for mechanical stirring, and a $N_2$/vacuum inlet. To the flask was added 50.15 g of 1-butyl-3-methylimidazolium propionate ([BMIm]OPr). While stirring rapidly, cellulose (4.07 g, 7.5 wt %) was added to the [BMIm]OPr at room temperature. Vacuum was applied with the aid of a bleed valve. After reaching 0.6 mm Hg, a preheated 80° C. oil bath was raised to the flask. A clear solution was obtained 8 min after raising the oil bath. Stirring was continued for an additional 2.8 h before the solution was allowed to cool to room temperature and stand under $N_2$ for 12 h.

To the cellulose solution at room temperature was added a mixture of propionic anhydride (12.09 g, 3.7 eq) and MSA (482 mg, 0.2 eq) dropwise (20 min). During the course of the reaction, aliquots were removed and the product was isolated by precipitation in 200 mL of MeOH and filtering. The reaction was complete 20 min after the end of addition. The experiment was terminated and the remaining reaction mixture was processed as the aliquots. The solid from each sample was washed 3 times with 200 mL portions of MeOH then 1 time with 250 mL of MeOH containing 8 wt % of 35 wt % $H_2O_2$. The white solids were then dried at 60° C., 5 mm Hg.

A second experiment was conducted following the same procedure. The only difference was that the [BMIm]OPr contained 11.9 wt % propionic acid as a miscible cosolvent.

Figure 30:
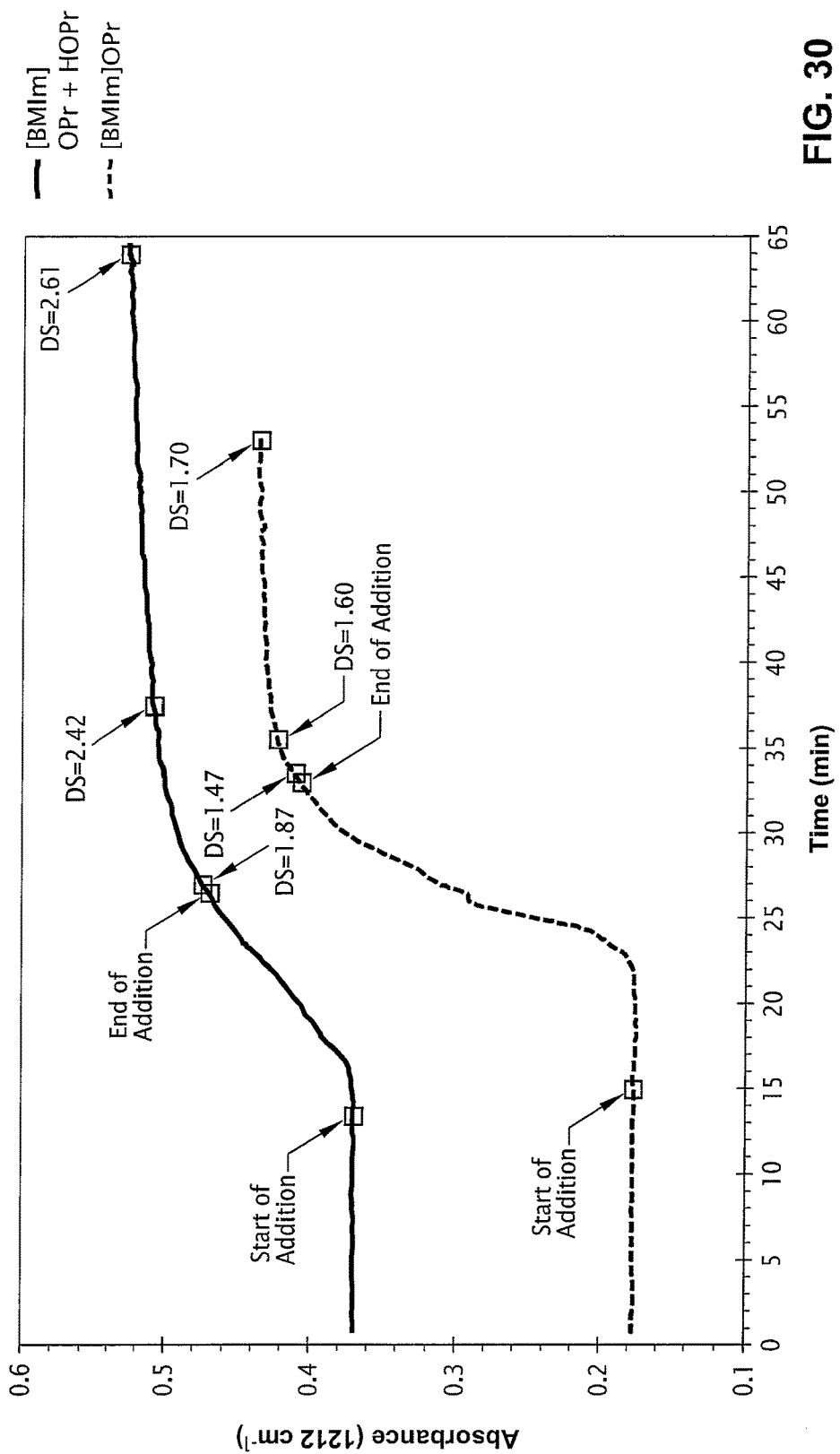
FIG. 30 shows a plot of absorbance for an infrared band at 1212 cm$^{-1}$ (propionate ester and propionic acid) versus contact time during esterification (3.7 eq propionic anhydride) of cellulose dissolved either in [BMIm]OPr or [BMIm]OPr+11.9 wt % propionic acid.

FIG. 30 shows a plot of absorbance for a band at 1212 $cm^{-1}$ (propionate ester and propionic acid) versus contact time. The DS indicated in FIG. 30 correspond to the DS values for the samples obtained in each experiment. Relative to the reaction of cellulose dissolved in [BMIm]OPr (no propionic acid), the reaction rate of cellulose dissolved in [BMIm]OPr+11.9 wt % propionic acid is slower and the DS of each sample is higher than the corresponding sample in the other experiment. Thus, this example shows in addition to impacting solution viscosity, a cosolvent can also have a dramatic impact on reaction rates and total DS obtained.

Example 40—Regioselective Esterification of Cellulose Dissolved in Ionic Liquids by the Controlled Addition of Anhydrides Series 1: A 3-neck 100 mL round bottom flask which contained a solution 4.9 g (7.5 wt %) of cellulose dissolved in [BMIm]Cl was equipped for mechanical stirring, with an iC10 diamond tipped IR probe, and with an $N_2$/vacuum inlet. The flask contents were heated to 80° C. before adding mixture of 5.9 g $Pr_2O$ (1.5 eq) and 0.29 g MSA (0.1 eq) to the cellulose solution (4 min addition). The consumption of anhydride and the production of cellulose ester and carboxylic acid was followed in situ using infrared spectroscopy. Forty minutes after the start of the $Pr_2O$ addition, 4.66 g of $Ac_2O$ (1.5 eq) was added to the contact mixture (2 min addition). The contact mixture was stirred for an additional 2 h at 80° C. before adding 1 g of n-propanol to quench the remaining anhydride. During the course and at the end of the contact period, the contact mixture was sampled by removing 6-10 g aliquots of the contact mixture and cellulose ester was obtained by precipitation in aqueous methanol. The solid from each aliquot was washed 4× with aqueous methanol then dried at 60° C., 5 mm Hg.

Figure 31:
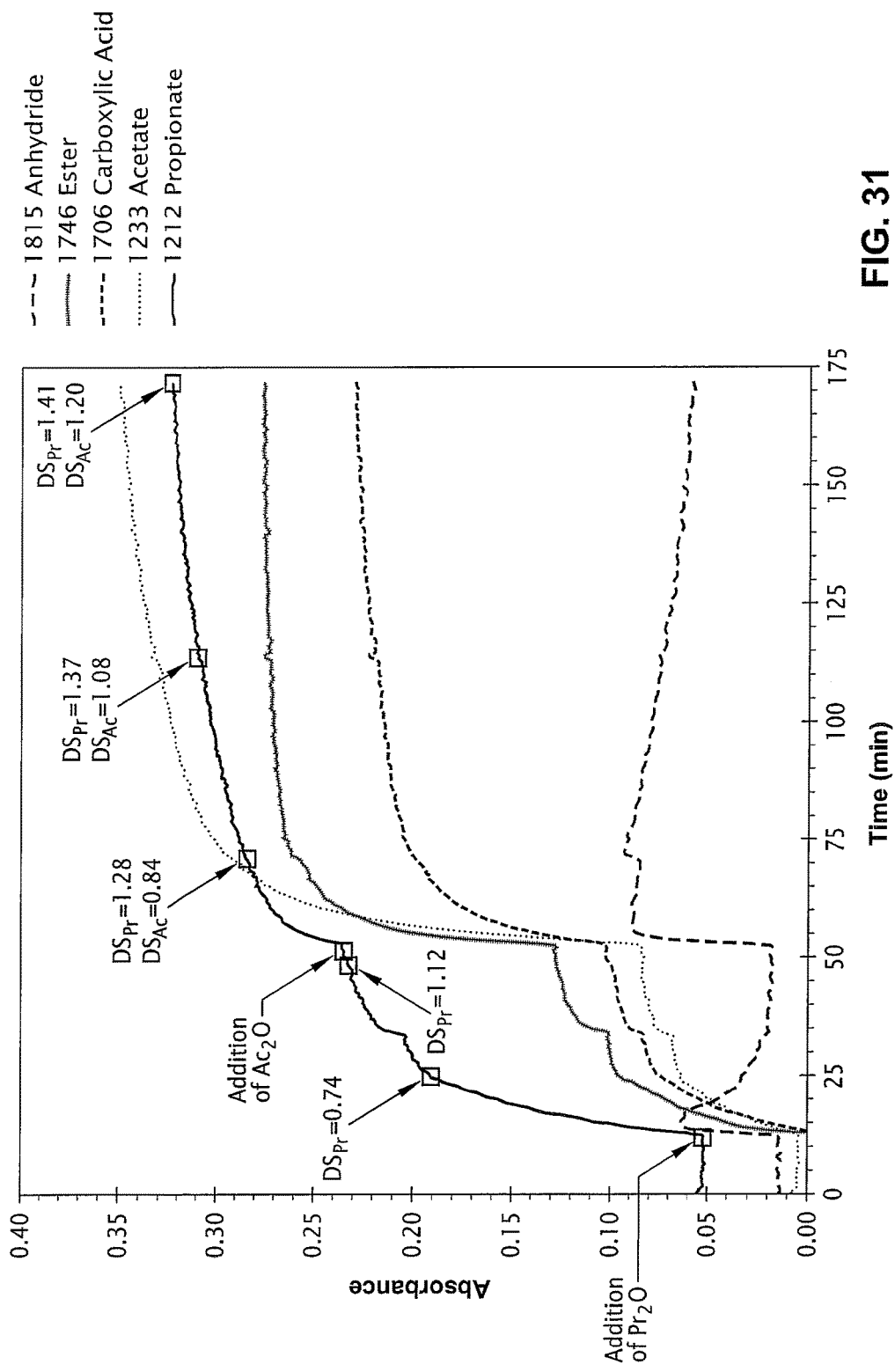
FIG. 31 shows a plot of absorbance versus time for a staged addition of Pr$_2$O (1$^{st}$) and Ac$_2$O (2$^{nd}$) illustrating the esterification cellulose (1756, 1233, 1212 cm$^{-1}$), the consumption of anhydride (1815 cm$^{-1}$), and the coproduction of carboxylic acid (1706 cm$^{-1}$) during the experiment.
Figure 32E:
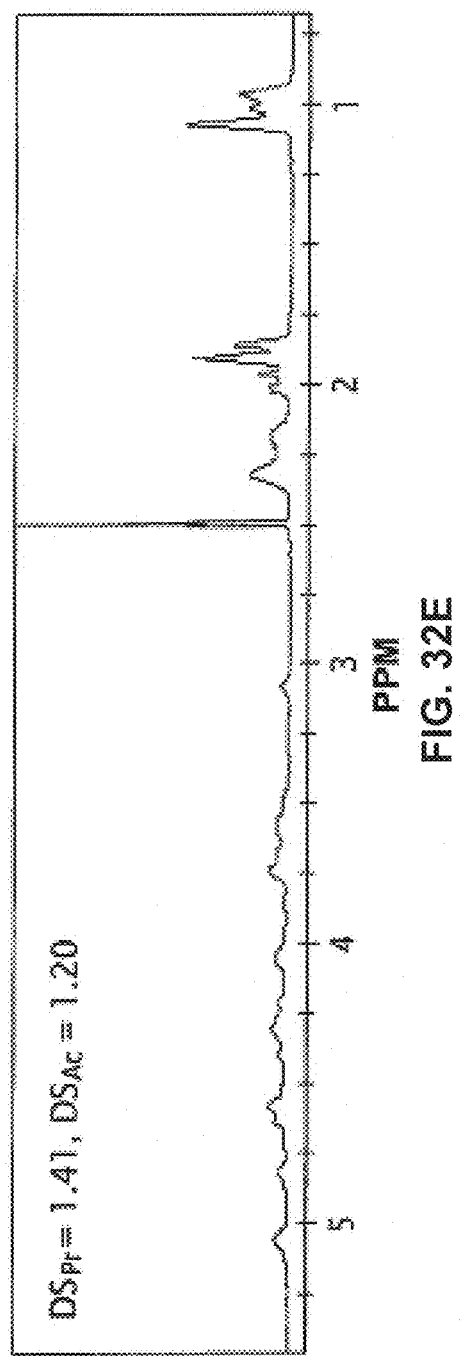

FIG. 31 is a plot of absorbance versus time for series 1, and it illustrates the esterification of cellulose (1756, 1233, 1212 cm$^{-1}$), the consumption of anhydride (1815 cm$^{-1}$), and the coproduction of carboxylic acid (1706 cm$^{-1}$) during the experiment. The DS values shown in FIG. 31 were determined by proton NMR spectroscopy and correspond to the samples removed during the course of the contact period. The change in the acetyl methyl (centered near 1.9 ppm) and propionyl methyl (centered near 1.0 ppm) resonances (FIGS. 32A-32C) clearly indicated a nonrandom distribution of the acyl substituents. This finding is surprising in that cellulose esters prepared by conventional processes typically have a random distribution of acyl substituents. That is, the relative degree of substitution at the C6, C3, and C2 anhydroglucose monomer is close to a 1:1:1 ratio.

Series 2: Following the general procedure of series 1, cellulose dissolved in [BMIm]Cl was esterified by first adding a mixture of 1.5 eq Ac$_2$O and 0.1 eq MSA. Twenty minutes after adding the Ac$_2$O, 1.5 eq Pr$_2$O was added to the contact mixture. The contact mixture was stirred for an additional 7 h at 80° C. As with series 1, during the course and at the end of the contact period, the contact mixture was sampled by removing 6-10 g aliquots of the contact mixture and cellulose ester was obtained by precipitation in aqueous methanol. As shown in FIG. 32D, proton NMR again indicated a nonrandom distribution of the acyl substituents different from that obtained with series 1.

Series 3: Following the general procedure of series 1, cellulose dissolved in [BMIm]Cl was esterified by adding a mixture of 1.5 eq Ac$_2$O, 1.5 eq Pr$_2$O, and 0.1 eq MSA. The contact time was 2 h 5 min. As with series 1 and 2, during the course and at the end of the contact period, the contact mixture was sampled by removing 6-10 g aliquots of the contact mixture, and cellulose ester was obtained by precipitation in aqueous methanol. As shown in FIG. 32E, proton NMR again indicated a nonrandom distribution of the acyl substituents different from that obtained with series 1 and 2.

Figure 33A:
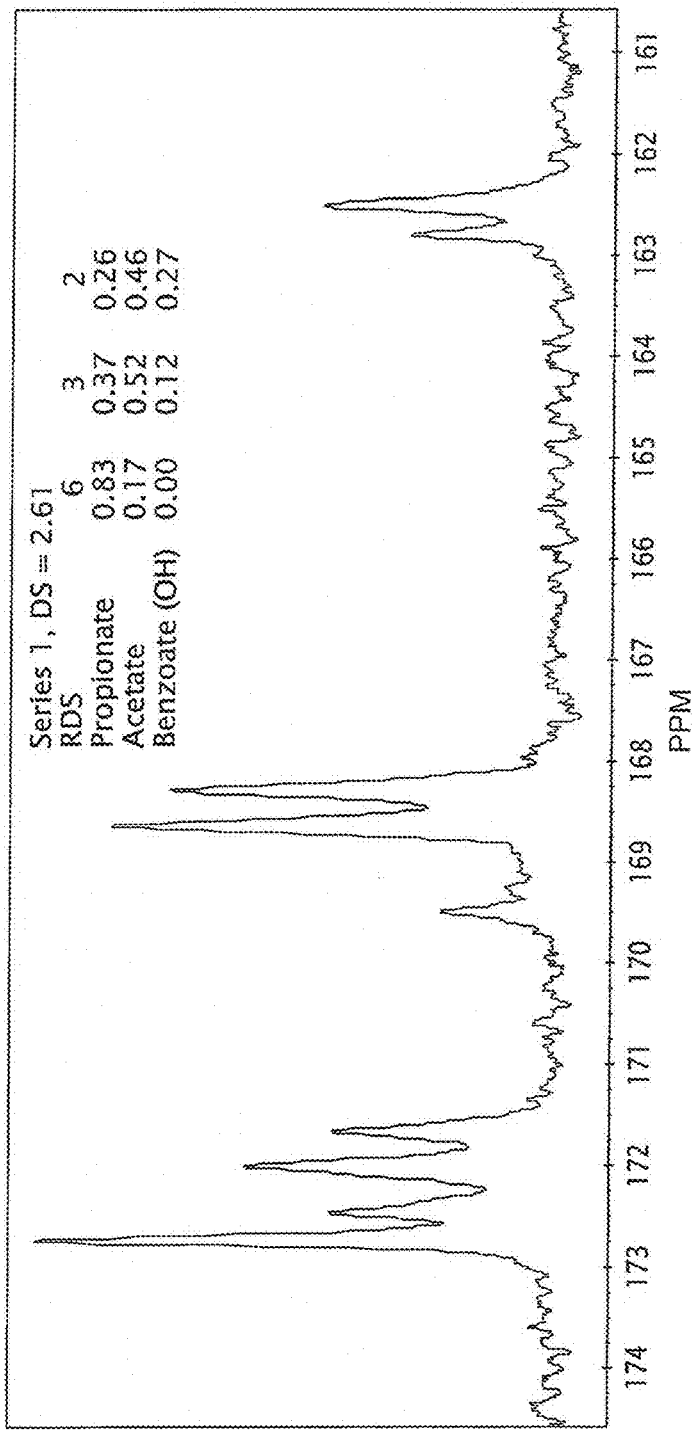
FIGS. 33A-33C show the carbonyl region in the $^{13}$C NMR spectra of a sample following the staged addition of Pr$_2$O (1$^{st}$) and Ac$_2$O (2$^{nd}$) [series 1], following the staged addition of Ac$_2$O (1$^{st}$) and Pr$_2$O (2$^{nd}$) [series 2], and following the mixed addition of Pr$_2$O and Ac$_2$O [series 3].
Figure 33B:
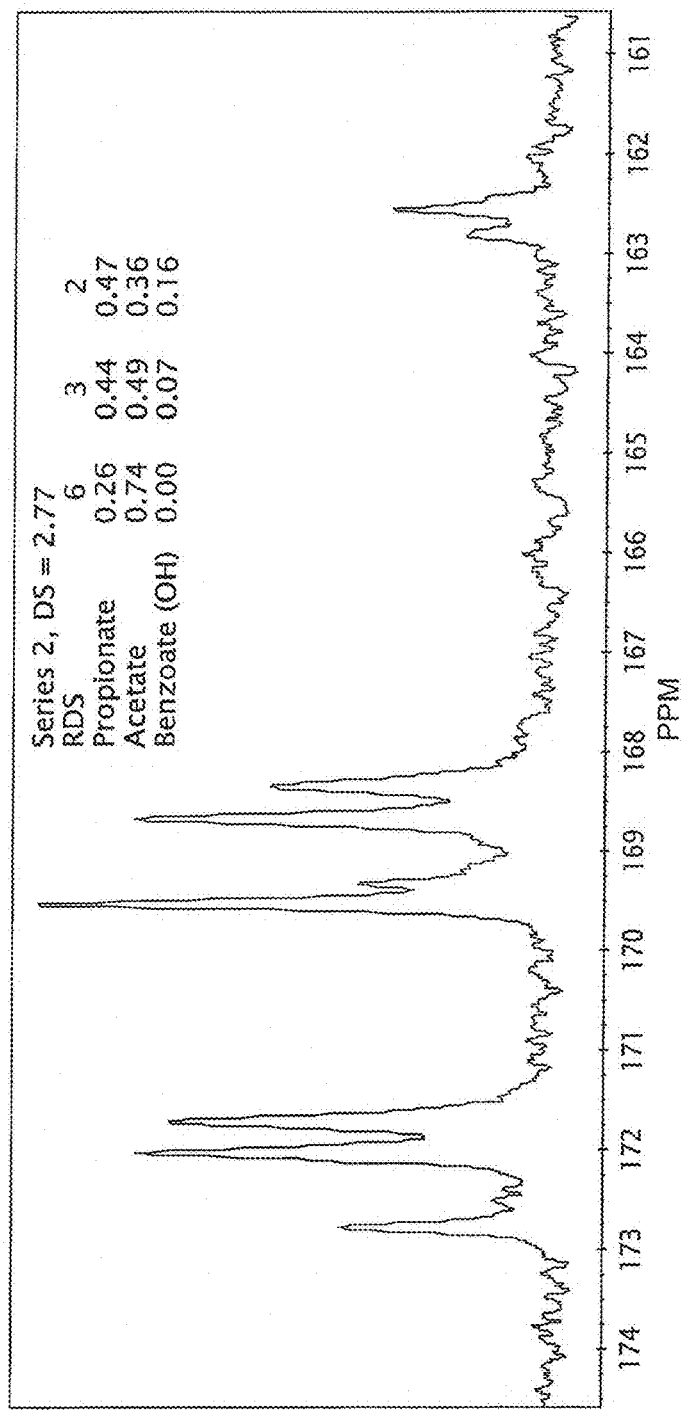
Figure 33C:
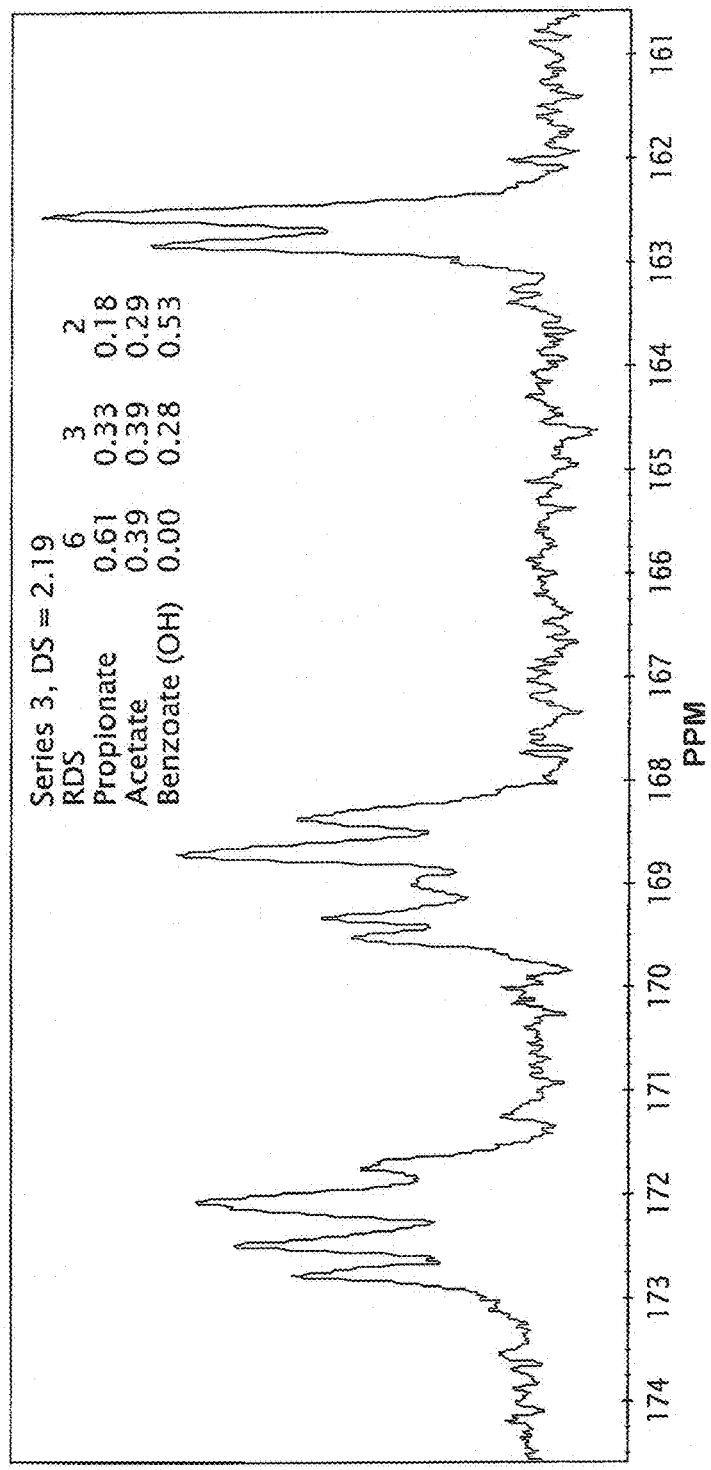

In order to measure the differences in RDS obtained by the different order of anhydride additions, selected aliquots (400 mg each) from each sample series was dissolved in pyridine and contacted with p-nitrobenzoyl chloride (1 g) at 70° C. for ca. 23 h before precipitating and washing with EtOH. This process converted the cellulose acetate propionate esters to fully substituted cellulose acetate propionate p-nitrobenzoate esters. These samples were then analyzed by carbon 13 NMR, and the RDS could be determined by integration of the carbonyl resonances. The position of the p-nitrobenzoate esters indicate the location of the hydroxyls in the cellulose acetate propionate. FIGS. 33A-33C compare the carbonyl region in the $^{13}$C NMR spectra of a sample from each series having a similar DS; the RDS for each sample is given in the Figure.

Examination of the RDS for each series shows that in each case the order of reactivity is $C_6$>>$C_3$>$C_2$. For example, for series 1 in which the propionate was added first, RDS $C_6$=1.00, RDS $C_3$=0.89, and RDS $C_2$=0.73. In terms of acetate versus propionate selectivity, the RDS$_{Pr}$ at $C_6$ was 0.78 and the RDS$_{Ac}$ at $C_6$ was 0.26. Comparing the RDS for acetate versus propionate at $C_3$ and $C_2$, it is evident that that there is more acetate than propionate at $C_3$ (0.50 versus 0.39) and $C_2$ (0.47 versus 0.26). That is, placement of the acyl substituents was regioselective leading to a cellulose acetate propionate enriched in 6-propionyl-2,3-diacetyl cellulose. In series 1, the propionate carbonyl $C_6/C_2$ and $C_6/C_2$ ratios were large (2.0 and 3.0, respectively) as were the propionate carbonyl $C_6/C_3$*DS (2.8) and $C_6/C_2$*DS (4.2) values. In the case of series 2 in which the Ac$_2$O was added first, RDS $C_6$=1.00, RDS $C_3$=0.93, RDS $C_2$=0.86. In terms of acetate versus propionate selectivity, the RDS$_{Pr}$ at $C_6$ was 0.25 and the RDS$_{Ac}$ at $C_6$ was 0.75 opposite from that observed with series 1. In series 2, the acetate carbonyl $C_6/C_2$ and $C_6/C_2$ ratios were large (1.5 and 2.0, respectively) as were the acetate carbonyl $C_6/C_3$*DS (2.3) and $C_6/C_2$*DS (3.1) values. In the case of Series 3, in which the Ac$_2$O and the Pr$_2$O were added as a mixture, regioselectivity was still observed; RDS $C_6$=1.00, RDS $C_3$=0.68, RDS $C_2$=0.50. In terms of acetate versus propionate selectivity, the RDS$_{Pr}$ at $C_6$ was 0.56 and the RDS$_{Ac}$ at $C_6$ was 0.44. At $C_3$, the RDS for propionate and acetate were roughly equivalent. At $C_2$, the RDS$_{Pr}$ was 0.20 and the RDS$_{Ac}$ was 0.30. In series 3, the propionate carbonyl $C_6/C_2$ and $C_6/C_2$ ratios were large (1.6 and 2.8, respectively) as were the propionate carbonyl $C_6/C_3$*DS (1.7) and $C_6/C_2$*DS (3.1) values.

Figure 34:
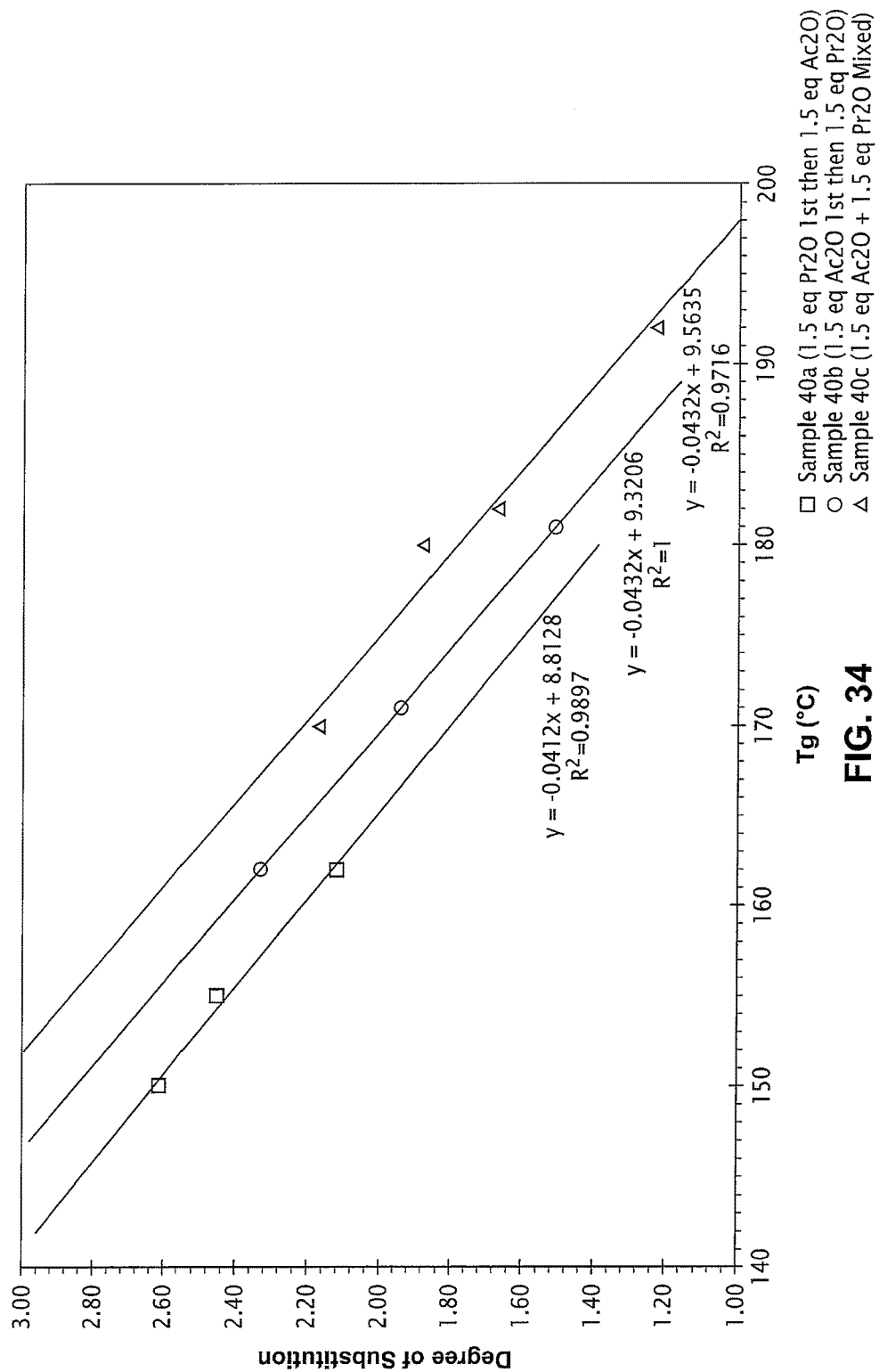
FIG. 34 shows a plot of DS versus glass transition temperature (Tg) for the cellulose acetate propionates prepared by staged addition of Pr$_2$O (1$^{st}$) and Ac$_2$O (2$^{nd}$) [series 1], by staged addition of Ac$_2$O (1$^{st}$) and Pr$_2$O (2$^{nd}$) [series 2], and by mixed addition of Pr$_2$O and Ac$_2$O [series 3].
Figure 35:
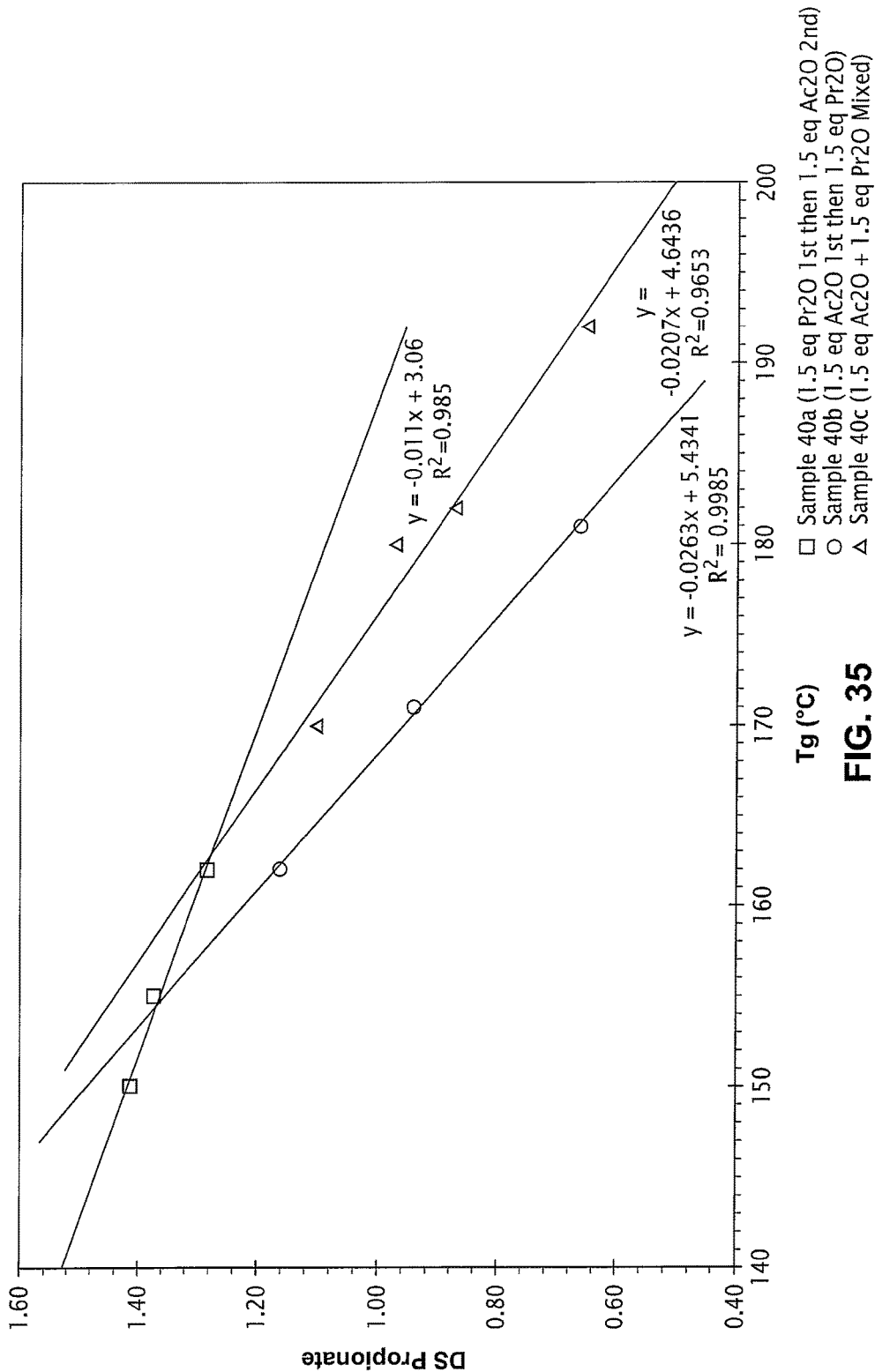
FIG. 35 shows a plot of DS propionate versus glass transition temperature (Tg) for the cellulose acetate propionates prepared by staged addition of Pr$_2$O (1$^{st}$) and Ac$_2$O (2$^{nd}$) [series 1], by staged addition of Ac$_2$O (1$^{st}$) and Pr$_2$O (2$^{nd}$) [series 2], and by mixed addition of Pr$_2$O and Ac$_2$O [series 3].

Regioselective placement of substituents in a cellulose ester leads to polymers with different physical properties in a fashion analogous to classical random copolymers versus block copolymers. As an example, FIG. 34 shows a plot of DS versus glass transition temperature (Tg) for the polymers prepared in series 1-3. At a given DS, the Tg for series 1 is shifted 5° C. lower relative to series 2. In turn, the Tg for series 2 is shifted 5° C. lower relative to series 3. That is, the Tg can be shifted as much as 10° C. at a constant DS by controlling the placement of the acyl substituents. FIG. 35 shows a plot of DS$_{Pr}$ versus Tg for the same series 1-3. The slope of the lines for series 2 and 3 are similar and are ca. twice that of series 1. This means that when the propionate substituent is located predominately at C6, small changes in DS$_{Pr}$ will result in large changes in Tg. This illustrates that these new cellulose ester compositions surprisingly leads to polymers having different and novel physical properties relative to conventional cellulose ester that impacts their use in many applications.

Example 41.—Casting of Film and Film Optical Measurements Using Cellulose Esters Containing a Minor Amount (DS≤0.2) of a Second Acyl Group Cellulose esters that are essentially 6,3- and 6,2-regioselectively substituted (high $C_6$ RDS, Examples 41.1-41.3) were prepared according to the methods of the present invention in Examples 1-3. Commercial (Comparative examples 41.6 and 41.7) cellulose esters available from Eastman Chemical Company, were produced by the general procedures described in US 2009/0096962 and US 2009/0050842. Comparative examples 41.4 and 41.5 were prepared as described in US 2005/0192434. The cellulose esters in examples 41.4 and 41.5 are essentially 2,3-regioselectively substituted and differs from the examples of the present invention in that they have a low RDS at $C_6$ while the cellulose esters of the present invention have a high RDS at $C_6$. The ring RDS was determined for each sample before film was cast and the film optical properties determined. The results are summarized in Table 11.

TABLE 11

The degree of substitution, relative degree of substitution, and out-of-plane retardation (nm) for compensation film for cellulose esters containing a minor amount (DS ≤ 0.2) of a second acyl group prepared by the methods of the present invention versus comparative (C) cellulose esters.

| Example | IL | DS | $DS_{Pr}$ | $DS_{Ac}$ | RDS $C_6$ | RDS $C_3$ | RDS $C_2$ | $R_{th}$ (589) |
|---|---|---|---|---|---|---|---|---|
| 41.1 | [EMIm]OAc | 2.81 | 0.00 | 2.81 | 1.00 | 0.86 | 0.95 | −55.9 |
| 41.2 | [BMIm]OPr | 2.81 | 2.77 | 0.04 | 1.00 | 0.86 | 0.95 | 36.1 |
| 41.3 | [BMIm]OPr | 1.68 | 1.65 | 0.03 | 0.85 | 0.42 | 0.41 | −342.5 |
| 41.4 | (C) | 1.99 | 1.94 | 0.05 | 0.36 | 0.80 | 0.83 | −80.2 |
| 41.5 | (C) | 1.53 | 1.48 | 0.05 | 0.24 | 0.63 | 0.66 | −119.0 |
| 41.6 | (C) | 2.73 | 2.69 | 0.04 | 0.83 | 0.98 | 0.90 | −29.2 |
| 41.7 | (C) | 1.93 | 1.77 | 0.16 | 0.56 | 0.71 | 0.66 | −209.9 |

Examples 41.1 and 41.2 are essentially identical except that Example 41.1 was a cellulose acetate, and Example 41.2 was a cellulose propionate. As shown in Table 11, the cellulose propionate had a higher $R_{th}$ (+36 nm) relative to the cellulose acetate (−56 nm). Comparing the values of $R_{th}$ for the low DS 6,3-, 6,2-cellulose propionate (Example 41.3, DS=1.68, $C_6/C_3$=2.0, $C_6/C_2$=2.1, DS*$C_6/C_3$=3.4, DS*$C_6/C_2$=3.5) to the two 2,3-cellulose propionates (Example 41.4, DS=1.99 $C_6/C_3$=0.45, $C_6/C_2$=0.43, DS*$C_6/C_3$=0.9, DS*$C_6/C_2$=0.9 and Example 41.5, DS=1.53, $C_6/C_3$=0.38, $C_6/C_2$=0.36, DS*$C_6/C_3$=0.6, DS*$C_6/C_2$=0.6) it was evident that the 6,3-, 6,2-cellulose propionate provided a much more negative $R_{th}$ value (−343 nm versus −80 and −119 nm) even though the cellulose esters have similar DS values. Similarly, comparison of the $R_{th}$ value for Example 41.3 to the $R_{th}$ value for Example 41.7 (DS=1.93, $C_6/C_3$=0.79, $C_6/C_2$=0.85, DS*$C_6/C_3$=1.5, DS*$C_6/C_2$=1.6) revealed that the regioselectively substituted cellulose propionate had a much lower $R_{th}$ value (−343 nm versus −210 nm). Comparison of the $R_{th}$ value for the high DS regioselectively substituted cellulose propionate (Example 41.2, DS=2.81, $C_6/C_3$=1.16, $C_6/C_2$=1.05, DS*$C_6/C_3$=3.3, DS*$C_6/C_2$=3.0) to the $R_{th}$ value for the high DS conventional cellulose propionate (Example 41.6, DS=2.73, $C_6/C_3$=0.85, $C_6/C_2$=0.92, DS*$C_6/C_3$=2.3, DS*$C_6/C_2$=2.3) revealed that the regioselectively substituted cellulose propionate has a much higher $R_{th}$ (+36 nm) than the conventional cellulose propionate (−29 nm).

This example illustrated several important aspects of the present invention. As the comparison of Examples 41.1 and 41.2 demonstrated, a propionate substituent increased $R_{th}$ more that an acetate substituent at an equivalent DS and substitution pattern. As expected, the total hydroxyl DS had a significant influence on the $R_{th}$ values regardless of the substitution pattern. However, the regioselectively substituted cellulose esters of the present invention provided for a much wider range of $R_{th}$ relative to other substitution patterns. At the lower DS range, $R_{th}$ was much more negative for the regioselectively substituted cellulose esters relative to conventional cellulose esters. At higher DS range, $R_{th}$ was less negative and even positive for the regioselectively substituted cellulose esters relative to other cellulose esters.

Example 42.—Casting of Film and Film Optical Measurements Using Cellulose Esters Containing a Second Acyl Group (DS≥0.2)

Regioselectively substituted cellulose acetate propionates (Examples 42.1-42.6) were prepared according to the methods of the present invention (high C6 RDS) in Examples 1-6. Comparative example 42.7 cellulose ester was a cellulose acetate propionate that was prepared by the general procedures described in US 2009/0096962 and US 2009/0050842 and is available from Eastman Chemical Company. The ring and carbonyl RDS were determined for each sample before film was cast, and the film optical properties were determined. Table 12 provides the ring RDS versus $R_{th}$, Table 13 provides the carbonyl RDS versus $R_{th}$, and Table 14 provides the propionate and acetate ratios of $C_6/C_3$ and $C_6/C_2$ as well as $C_6/C_3$*DS and $C_6/C_2$*DS.

TABLE 12

The degree of substitution, relative degree of substitution, and out-of-plane retardation (nm) for compensation film for cellulose esters containing a second acyl group (DS ≥ 0.2) prepared by the methods of the present invention from cellulose dissolved in [BMIm]Cl versus comparative (C) cellulose esters.

| Example | DS | $DS_{Pr}$ | $DS_{Ac}$ | RDS $C_6$ | RDS $C_3$ | RDS $C_2$ | $R_{th}$ (589) |
|---|---|---|---|---|---|---|---|
| 42.1 | 1.99 | 1.15 | 0.85 | 1.00 | 0.62 | 0.42 | −109.5 |
| 42.2 | 2.14 | 0.90 | 1.24 | 1.00 | 0.69 | 0.48 | −54.2 |
| 42.3 | 2.34 | 0.99 | 1.35 | 1.00 | 0.77 | 0.60 | −137.2 |
| 42.4 | 2.61 | 1.41 | 1.20 | 1.00 | 0.89 | 0.73 | −17.4 |
| 42.5 | 2.77 | 1.25 | 1.52 | 1.00 | 0.93 | 0.86 | −33.7 |
| 42.6 | 2.17 | 1.10 | 1.07 | 1.00 | 0.68 | 0.50 | −156.9 |
| 42.7 (C) | 2.47 | 0.88 | 1.59 | 0.75 | 0.90 | 0.82 | −161.7 |

TABLE 13

The degree of substitution, carbonyl carbon relative degree of substitution, and out-of-plane retardation (nm) for compensation film for cellulose propionates prepared from cellulose dissolved in [BMIm]Cl by the methods of the present invention versus comparative (C) cellulose esters.

| Example | DS | $DS_{Pr}$ | $DS_{Ac}$ | Pr $C_6$ | Pr $C_3$ | Pr $C_2$ | Ac $C_6$ | Ac $C_3$ | Ac $C_2$ | $R_{th}$ (589) |
|---|---|---|---|---|---|---|---|---|---|---|
| 42.1 | 1.99 | 1.15 | 0.85 | 0.52 | 0.39 | 0.24 | 0.48 | 0.23 | 0.18 | −109.5 |
| 42.2 | 2.14 | 0.90 | 1.24 | 0.48 | 0.28 | 0.14 | 0.52 | 0.41 | 0.34 | −54.2 |
| 42.3 | 2.34 | 0.99 | 1.35 | 0.56 | 0.28 | 0.18 | 0.44 | 0.49 | 0.42 | −137.2 |

TABLE 13-continued

The degree of substitution, carbonyl carbon relative degree of substitution, and out-of-plane retardation (nm) for compensation film for cellulose propionates prepared from cellulose dissolved in [BMIm]Cl by the methods of the present invention versus comparative (C) cellulose esters.

| Example | DS | $DS_{Pr}$ | $DS_{Ac}$ | Pr $C_6$ | Pr $C_3$ | Pr $C_2$ | Ac $C_6$ | Ac $C_3$ | Ac $C_2$ | $R_{th}$ (589) |
|---|---|---|---|---|---|---|---|---|---|---|
| 42.4 | 2.61 | 1.41 | 1.20 | 0.78 | 0.39 | 0.26 | 0.22 | 0.50 | 0.47 | −17.4 |
| 42.5 | 2.77 | 1.25 | 1.52 | 0.25 | 0.44 | 0.49 | 0.75 | 0.49 | 0.37 | −33.7 |
| 42.6 | 2.17 | 1.10 | 1.07 | 0.56 | 0.36 | 0.20 | 0.44 | 0.32 | 0.30 | −156.9 |
| 42.7 (C) | 2.47 | 0.88 | 1.59 | 0.29 | 0.26 | 0.31 | 0.52 | 0.53 | 0.53 | −161.7 |

TABLE 14

The ratios of $C_6/C_3$ and $C_6/C_2$ as well as $C_6/C_3$*DS and $C_6/C_2$*DS products for propionate and acetate and the corresponding Rth values (nm) for compensation film for cellulose acetate propionates prepared from cellulose dissolved in [BMIm]Cl by the methods of the present invention versus comparative (C) cellulose esters.

| Example | Pr $C_6/C_3$ | Pr $C_6/C_2$ | $C_6/C_3$* $DS_{Pr}$ | $C_6/C_2$* $DS_{Pr}$ | Ac $C_6/C_3$ | Ac $C_6/C_2$ | $C_6/C_3$* $DS_{Ac}$ | $C_6/C_2$* $DS_{Ac}$ | $R_{th}$ (589) |
|---|---|---|---|---|---|---|---|---|---|
| 42.1 | 1.33 | 2.17 | 1.53 | 2.49 | 2.09 | 2.67 | 1.77 | 2.27 | −109.5 |
| 42.2 | 1.71 | 3.43 | 1.54 | 3.09 | 1.27 | 1.53 | 1.57 | 1.90 | −54.2 |
| 42.3 | 2.00 | 3.11 | 1.98 | 3.08 | 0.90 | 1.05 | 1.21 | 1.41 | −137.2 |
| 42.4 | 2.00 | 3.00 | 2.82 | 4.23 | 0.44 | 0.47 | 0.53 | 0.56 | −17.4 |
| 42.5 | 0.57 | 0.51 | 0.71 | 0.64 | 1.53 | 2.03 | 2.33 | 3.08 | −33.7 |
| 42.6 | 1.56 | 2.80 | 1.71 | 3.08 | 1.38 | 1.47 | 1.47 | 1.57 | −156.9 |
| 42.7 (C) | 1.12 | 0.94 | 0.98 | 0.82 | 0.98 | 0.98 | 1.56 | 1.56 | −161.7 |

Upon comparing Examples 42.1-42.6 to Example 42.7 (Table 12), it is evident that the regioselectively substituted cellulose acetate propionates gave $R_{th}$ values that were less negative than that provided by the conventional cellulose acetate propionate regardless of $DS_{OH}$. As an illustration, Example 42.3 had a slightly lower DS relative to Example 42.7, but the $R_{th}$ value of Example 42.3 ($R_{th}$=−137 nm) was still less negative than Example 42.7 ($R_{th}$=−162 nm). Even upon further reduction in total DS (increasing $DS_{OH}$, Examples 42.1, 42.2, and 42.6), the $R_{th}$ values for the regioselectively substituted cellulose acetate propionates were still less negative.

As Table 12 shows, Examples 42.1-42.6 had high ring RDS $C_6/C_3$ and $C_6/C_2$ ratios but there was variation in $R_{th}$ at similar total DS values. As an illustration, Examples 42.6 and 42.2 had similar DS values but significantly different $R_{th}$ values (−157 nm versus −54 nm). Upon examination of the carbonyl RDS $C_6/C_3$ and $C_6/C_2$ ratios for these two Examples, it was evident that Example 42.2 ($R_{th}$=−54 nm) had a much higher $C_6/C_3$ and $C_6/C_2$ Pr RDS than did Example 42.6. Similarly, Example 42.4 had a lower DS (2.61) than did Example 42.5 (2.77), but yet the $R_{th}$ value for Example 42.4 (−17 nm) was less negative than Example 42.5 (−34 nm). Again, examination of the carbonyl RDS $C_6/C_3$ and $C_6/C_2$ ratios for these two Examples revealed that Example 42.4 had a much higher $C_6/C_3$ and $C_6/C_2$ Pr RDS than did Example 42.5. That is, having propionate at $C_6$ with a high $C_6/C_3$ and $C_6/C_2$ Pr RDS ratios had a significant influence on $R_{th}$.

In Example 41 (single acyl substituent), it was shown that a propionate substituent increased $R_{th}$ more that an acetate substituent at an equivalent DS and substitution pattern and that the total hydroxyl DS had a significant influence on the $R_{th}$ values. The regioselectively substituted cellulose esters provided for a much wider range of $R_{th}$ relative to other substitution patterns. The present Example illustrated the influence that a second acyl group can have on $R_{th}$ values. That is, for regioselectively substituted cellulose esters of the present invention, the combination of acetyl and propionyl substituents led to a narrower and less negative $R_{th}$ range relative to conventional cellulose esters. Higher propionate DS and high $C_6/C_3$ and $C_6/C_2$ Pr RDS ratios at equivalent total DS served to further modify $R_{th}$.

That which is claimed is:

1. A cellulose ester comprising at least two different acyl groups, wherein at least one of said acyl groups comprises an aromatic compound, wherein said cellulose ester is regioselectively substituted with a RDS ratio of C6>C2>C3; wherein said regioselectively substituted cellulose ester is a mixed cellulose ester having at least two different acyl substituents; wherein said regioselectively substituted cellulose ester has a carbonyl RDS ratio of at least one acyl substituent for $C_6/C_3$ or $C_6/C_2$ of at least 1.3.

2. The cellulose ester of claim 1, wherein said aromatic compound comprises a benzoate or a substituted benzoate.

3. The cellulose ester of claim 1, wherein said aromatic compound comprises a benzoate.

4. The cellulose ester of claim 1, wherein the degree of substitution of said aromatic compound is greater at the C2 and C3 positions relative to the C6 position.

5. The cellulose ester of claim 1, wherein at least one of said acyl groups comprises acetate or propionate.

6. The cellulose ester of claim 1, wherein said cellulose ester has a degree of substitution from 1.6 to 2.9.

7. The cellulose ester of claim 1, wherein the ring RDS ratio of said cellulose ester for C6/C3 or C6/C2 is at least 1.05.

8. The cellulose ester of claim 1, wherein the molar ratio of said two different acyl groups is in the range of from about 1:10 to 10:1.

9. The cellulose ester of claim 1, wherein the molar ratio of said two different acyl groups is in the range of from about 3:7 to 7:3.

10. The cellulose ester of claim 1, wherein said cellulose ester is derived from a cellulose having an α-cellulose content of at least about 95 percent by weight.

11. The cellulose ester of claim 1, wherein said cellulose ester has a degree of polymerization in the range of from 5 to 1,000.

12. The cellulose ester of claim 1, wherein said cellulose ester has a polydispersity (Mw/Mn) in the range of from 1.3 to about 7.

13. A coating comprising said cellulose ester of claim 1.

14. A film comprising said cellulose ester of claim 1.

15. The film of claim 14, wherein said film comprises a compensation film.

16. The film of claim 15, wherein said film comprises a +C plate, a −C plate, a +A plate, or −A plate.

17. The film of claim 14, wherein said film has an Rth in the range of −160 to +270 nm.

* * * * *